United States Patent

Rupprecht et al.

Patent Number: 5,550,233
Date of Patent: Aug. 27, 1996

[54] ARYL, ALKYL, ALKENYL AND ALKYNYLMACROLIDES HAVING IMMUNOSUPPRESSIVE ACTIVITY

[75] Inventors: Kathleen M. Rupprecht; Robert K. Baker, both of Cranford; Hyun O. Ok; William H. Parsons, both of Edison, all of N.J.

[73] Assignee: Merck & Co., Inc., Rahway, N.J.

[21] Appl. No.: 263,298

[22] Filed: Jun. 21, 1994

[51] Int. Cl.$^6$ .................................. C07D 498/16
[52] U.S. Cl. .......................... 540/456; 540/450
[58] Field of Search ...................... 540/456, 450

[56] References Cited

FOREIGN PATENT DOCUMENTS

| | | |
|---|---|---|
| 0427680A1 | 5/1991 | European Pat. Off. . |
| 2244991 | 12/1991 | United Kingdom . |
| 2245891 | 1/1992 | United Kingdom . |

*Primary Examiner*—John M. Ford
*Assistant Examiner*—Pavanaram K. Sripada
*Attorney, Agent, or Firm*—J. Eric Thies; David L. Rose

[57] ABSTRACT

Aryl, alkyl, alkenyl and alkynyl macrolides of the general structural Formula I:

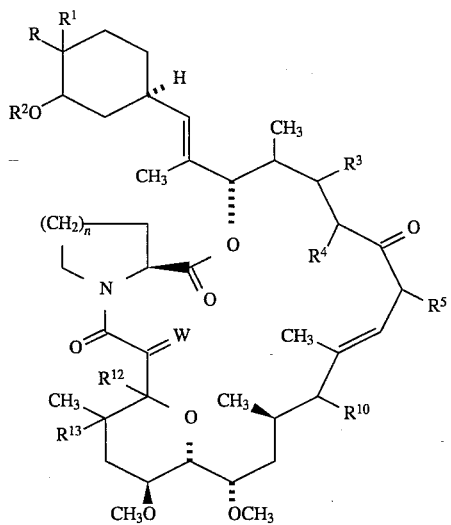

have been prepared from suitable precursors by oxidation and alkylation at C-4" of the cyclohexyl ring. These macrolide immunosuppressants are useful in a mammalian host for the treatment of autoimmune diseases, infectious diseases and/or the prevention of rejection of foreign organ transplants and/or related afflictions, diseases and illnesses.

13 Claims, No Drawings

ARYL, ALKYL, ALKENYL AND ALKYNYLMACROLIDES HAVING IMMUNOSUPPRESSIVE ACTIVITY

SUMMARY OF THE INVENTION

The present invention is related to aryl, alkyl, alkenyl and alkynylmacrolides which are useful in a mammalian subject for the treatment of autoimmune diseases (such as juvenile-onset or recent-onset diabetes mellitus, multiple sclerosis, and rheumatoid arthritis, liver disease, posterior uveitis, allergic encephalomyelitis, and glomerulonephritis), immunodepression, infectious diseases and/or the prevention of rejection of foreign organ transplants, (e.g. bone marrow, kidney, liver, heart, skin, small-bowel, and pancreatic islet-cell transplants, including xeno transplants), the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus or Alopecia arecata), male pattern alopecia, alopecia senilis, reversible obstructive airways disease, particularly asthma, inflammation of mucosa and blood vessels, cytomegalovirus infection, multidrug resistance, idiopathic thromboytopenic purpura, Behcet's syndrome, conjunctivitis, Crohn's disease, Mooren's ulcer, uveitis, servere intraocular inflammation and/or hepatic injury associated with ischemia. The present compounds are further useful in combination with a 5α-reductase inhibitor, a cyclosporin, a potassium channel opener or a phospholipid in a mammalian host for the treatment of baldness, especially male pattern alopecia, female pattern alopecia, alopecia senilis, or alopecia areata. In addition, some of the compounds of this invention may have antagonistic properties and so have utility in the reversal of immunosuppressive activity and/or diminishing the toxicity of other immunosuppressive agents.

More particularly, this invention relates to compounds of the general structural Formula I:

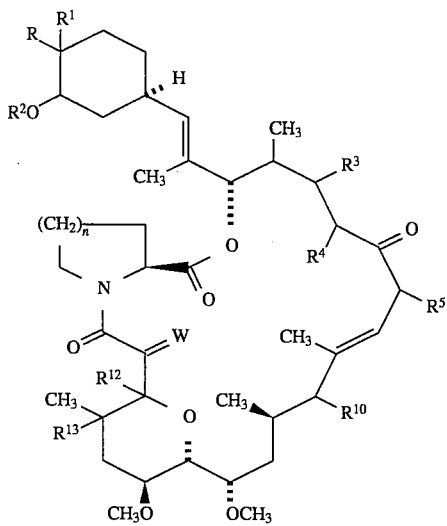

wherein R, $R^1$, $R^2$, $R^3$, $R^4$, $R^5$, $R^{10}$, $R^{11}$, $R^{12}$, $R^{13}$ W and n are hereinafter defined.

This invention also relates to pharmaceutical compositions containing the compounds and to a method of use of the present compounds and other agents for the treatment of and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO publication No. 0,184,162 and PBJ Disclosure 63-17884) and publications (*J. Am. Chem. Soc.*, 1987, 109, 5031 and *J. Antibiotics* 1987, 40, 1249) disclose 17-allyl-1,14-dihydroxy-12-[2'-(4"-hydroxy- 3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3, 10,16-tetraone (FR-900506) (FK-506) (L-679,934), 17-ethyl-1,14 -dihydroxy-12-[2'-(4"-hydroxy-3"-methoxy-cyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (FR-900520) and related compounds which are the starting materials for the preparation of the compounds described. The synthetic preparation of the aforementioned starting material (FR-900506) has been reported (*J. Am. Chem. Soc.*, 1989, 111, 1157). A Sandoz U.S. patent (U.S. Pat. No. 5,011,844) and European patent application (EPO Publication No. 0,356,399) disclose stereoisomers of FR-900506 and derivatives at the 17-position. Fisons European and WIPO patent applications (EPO Publication No. 0,323,042 and PCT Publication No. W089/05304) disclose various derivatives of FR-900506, FR-900520 and related compounds. A Sandoz European patent application (EPO Publication No. 0,437,680) discloses chloro, bromo, iodo and azido derivatives of FR-900506, FR-900520 and related compounds. A Merck-European patent application (EPO Publication No. 0,428, 365) discloses various amino derivatives. of FR-900506, FR-900520 and related compounds. A Fujisawa UK patent application (UK Publication No. GB2,245,891A) discloses various aryl(lower alkyl) and heteroaryl derivatives of FR-900506, FR-900520 and related compounds. Merck U.S. Pat. Nos. 5,247,076, 5,250,678 and 5,252,732 disclose various aryl and heteroaryl derivatives of FR-900506, FR-900520 and related compounds. Merck U.S. Pat. No. 5,284,877 discloses C-17 alkyl and alkenyl derivatives of FR-900506, FR-900520 and related compounds.

Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons World patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., *Clinical exp. Immunol.*, 1990, 82, 456–461; N. Inamura, et al., *Clin. Immunol Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmul. Vis. Sci.*, 1988, 29, 1265–71), hepatic injury associated with ischemia (M. Sakr, et al., *Life Sci.,* 1990, 47, 687–91) allergic encephalomyelitis (K, Deguchi, et al., *Brain Nerve,* 1990, 42, 391–97), glomerulonephritis (J. McCauley, et al., *Lancet,* 1990, 335, 674), systemic lupus erythematosus (K. Takabayashi, et al., *Clin Immunol. Immunopathol.,* 1989, 51, 110–117), multidrug resistance (M. Naito, et al., *Cancer Chemother. Pharmacol.,* 1992, 29, 195–200), inflammation of mucosa and blood vessels (PCT Publication WO 91/17754), cytomegalovirus infection (UK Publication GB 2,247,620A), and idiopathic thrombocytopenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, type 2 adult onset diabetes, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, tacrolimus, FR-900506, FK-506,

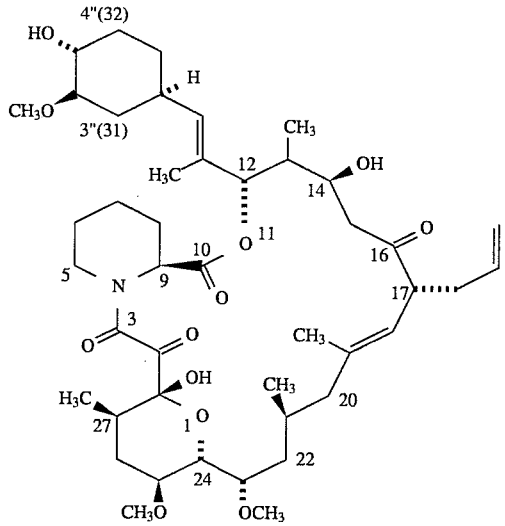

(17-allyl-1,14-dihydroxy-12-[2'-(4"-hydroxy-3"-methoxy-cyclohexyl)- 1'-methylvinyl]-23,25-dimethoxy-13,19,21, 27-tetramethyl-11,28-dioxa- 4-azatricyclo-[22.3.10$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.,* 1987, 109, 5031, and U.S. Pat. No. 4,894.366, issued Jan. 16, 1990) have been shown to possess exceptional immunosuppressive activity. Fujisawa United States patents (U.S. Pat. No.4,929,611, issued May 29, 1990 and U.S. Pat. No. 4,956,352, issued Sep. 11, 1990) disclose the use of FK-506-type compounds in treating resistance to transplantation. In particular, the compound FR- 900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthritis (C. Arita, et al., *Clinical exp. Immunol.,* 1990, 82, 456–461; N. Inamura, et al., *Clin. Immunol. Immunopathol.* 1988, 46, 82–90), recent-onset diabetes (N. Murase, et al., *Diabetes,* 1990, 39, 1584–86; N. Murase, et al., *Lancet,* 1990, 336, 373–74), posterior uveitis (H. Kawashima, *Invest. Ophthalmol. Vis. Sci.,* 1988, 29, 1265–71), hepatic injury associated with ischemia (M. Sakr, et al., *Life Sci.,* 1990, 47, 687–91) allergic encephalomyelitis (K, Deguchi, et al., *Brain Nerve,* 1990, 42, 391–97), glomerulonephritis (J. McCauley, et al., *Lancet,* 1990, 335,674), systemic lupus erythematosus (K. Takabayashi, et al., *Clin. Immunol. Immunopathol.,* 1989, 51, 110–117) multidrug resistance (M. Naito, et al., *Cancer Chemother. Pharmacol.,* 1992, 29, 195–200), inflammation of mucosa and blood vessels (PCT Publication WO 92/17754), cytomegalovirus infection (UK Publication GB 2,247,620A), and idiopathic thrombocytopenic purpura and Basedow's disease (PCT Publication WO 91/19495).

DETAILED DESCRIPTION OF THE INVENTION

A. Scope of the Invention

The novel compound of this invention has structural Formula I:

[Chemical structure of Formula I showing a macrocyclic compound with substituents R, R$^1$, R$^2$O, H, CH$_3$, R$^3$, R$^4$, R$^5$, (CH$_2$)$_n$, N, W, R$^{10}$, R$^{12}$, R$^{13}$, CH$_3$O, OCH$_3$, and O groups]

or a pharmaceutically acceptable salt thereof, wherein:
R is selected from:
(1) $C_{1-10}$alkyl
(2) substituted $C_{1-10}$alkyl wherein the alkyl is substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) -OCO-$C_{1-6}$alkyl
(o) -NR$^6$R$^7$, wherein R$^6$ and R$^7$ are independently selected from:
  (i) hydrogen,
  (ii) $C_{1-10}$alkyl unsubstituted or substituted with one or more of the substituent(s) selected from:
    (a') aryl, which is unsubstituted or substituted with X, Y and Z,
    (b') heteroaryl, which is unsubstituted or substituted with X, Y and Z,
    (c')-OH,
    (d') $C_{1-6}$alkoxy,
    (e') -CO$_2$H,
    (f') -CO$_2$-$C_{1-6}$alkyl,
    (g') -$C_{3-7}$cycloalkyl, and
    (h') -OR$^{11}$,
  (iii) $C_{3-10}$alkenyl unsubstituted or substituted with one or more of the substituent(s) selected from:
    (a') aryl, which is unsubstituted or substituted with X, Y and Z,
    (b') heteroaryl, which is unsubstituted or substituted with X, Y and Z,
    (c') -OH,
    (d') $C_{1-6}$alkoxy,
    (e') -CO$_2$H,
    (f') -CO$_2$-$C_{1-6}$alkyl,
    (g') -$C_{3-7}$cycloalkyl, and
    (h') -OR$^{11}$,
  (iv) or where R$^6$ and R$^7$ and the N to which they are attached may form an unsubstituted or substituted 3–7-membered heterocyclic ring which may include one or two additional heteroatoms independently selected from the group consisting of O, S(O)$_p$, NR$^{14}$, wherein R$^{14}$ is hydrogen or $C_{1-6}$ alkyl unsubstituted or substituted by phenyl, and p is 0, 1 or 2, such as morpholine, thiomorpholine, pipeddine, or piperizine,
(p) -NR$^6$CO-$C_{1-6}$alkyl-R$^7$,
(q) -NR$^6$CO$_2$-$C_{1-6}$alkyl-R$^7$,
(r) -NR$^6$CONR$^6$R$^7$,
(s) -OCONR$^6$R$^7$,
(t) -COOR$^6$,
(u) -CHO,
(v) -OR$^{11}$, and
(w) -S(O)$_p$-$C_{1-6}$alkyl;
(3) substituted or unsubstituted $C_{1-10}$alkyl wherein one or more of the alkyl carbons is replaced by a group selected from: -NR$^6$-, -O-, -S(O)$_p$-, -CO$_2$-, -O$_2$C-, -CONR$^6$-, -NR$^6$CO-, and -NR$^6$CONR$^7$-, and the alkyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z, aryl-$C_{1-3}$alkoxy,
(k) substituted aryl-$C_{1-3}$alkoxy, in which the substituents on aryl are X, Y and Z,
(l) hydroxy,
(m) oxo
(n) -OCO-$C_{1-6}$alkyl,
(o) -NR$^6$R$^7$, wherein R$^6$ and R$^7$ are defined above,
(p) -NR$^6$CO-$C_{1-6}$alkyl-R$^7$,
(q) -NR$^6$CO$_2$-$C_{1-6}$alkyl-R$^7$,
(r) -NR$^6$CONR$^6$R$^7$,
(s) -OCONR$^6$R$^7$,
(t) -COOR$^6$,
(u) -CHO,
(v) -OR$^{11}$, and
(w) -S(O)$_p$-$C_{1-6}$alkyl;
(4) $C_{1-10}$alkenyl wherein alkenyl contains one to four double bonds;
(5) substiuted $C_{1-10}$alkenyl wherein the alkenyl contains one to four double bonds and the alkyl or alkenyl may be substituted with one or more of the substituent(s) selected from:
(a) aryl,
(b) substituted aryl in which the substituents are X, Y and Z, (c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) -OCO-$C_{1-6}$alkyl
(o) -NR$^6$R$^7$, wherein R$^6$ and R$^7$ are as defined above,
(p) -NR$^6$CO-$C_{1-6}$alkyl-R$^7$,
(q) -NR$^6$CO$_2$-$C_{1-6}$alkyl-R$^7$,
(r) -NR$^6$CONR$^6$R$^7$,
(s) -OCONR$^6$R$^7$,
(t) -COOR$^6$,
(u) -CHO,
(v) -OR$^{11}$, and
(w) -S(O)$_p$-$C_{1-6}$alkyl;

(6) $C_{2-10}$alkenyl wherein alkenyl contains one to four double bonds and wherein one or more of the alkyl carbons is replaced by a group selected from: -NR$^6$-, -O-, -S(O)$_p$-, -CO$_2$-, -O$_2$C-, -CONR$^6$-, -NR$^6$CO-, and -NR$^6$CONR$^7$-;

(7) substituted $C_{2-10}$alkenyl wherein alkenyl contains one to four double bonds and wherein one or more of the alkyl carbons may be replaced by a group selected from: -NR$^6$-, -O-, -S(O)$_p$-, -CO$_2$-, -O$_2$C-, -CONR$^6$-, -NR$^6$CO-, and -NR$^6$CONR$^7$, and the alkyl or alkenyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) -OCO-$C_{1-6}$alkyl,
(o) -NR$^6$R$^7$, wherein R$^6$ and R$^7$ are as defined above,
(P) -NR$^6$CO-$C_{1-6}$alkyl-R$^7$,
(q) -NR$^6$CO$_2$-$C_{1-6}$alkyl-R$^7$,
(r) -NR$^6$CONR$^6$R$^7$,
(s) -OCONR$^6$R$^7$,
(t) -COOR$^6$,
(u) -CHO,
(v) -OR$^{11}$, and
(w) -S(O)$_p$-$C_{1-6}$alkyl;

(8) $C_{2-10}$alkynyl wherein the alkynyl contains one to four double bonds;

(9) substituted $C_{2-10}$alkynyl wherein the alkynyl contains one to four double bonds and the alkyl or alkynyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo
(n) -OCOO-$C_{1-6}$alkyl,
(o) -NR$^6$R$^7$, wherein R$^6$ and R$^7$ are as defined above,
(p) -NR$^6$CO-$C_{1-6}$alkyl-R$^7$,
(q) -NR$^6$CO$_2$-$C_{1-6}$alkyl-R$^7$,
(r) -NR$^6$CONR$^6$R$^7$,
(s) -OCONR$^6$R$^7$,
(t) -COOR$^6$,
(u) -CHO,
(v) -OR$^{11}$, and
(w) -S(O)$_p$-$C_{1-6}$alkyl;

(10) $C_{2-10}$alkynyl wherein alkynyl contains one to four double bonds and wherein one or more of the alkyl carbons is replaced by a group selected from: -NR$^6$-, -O-, -S(O)$_p$-, -CO$_2$-, -O$_2$C-, -CONR$^6$-, -NR$^6$CO-, and -NR$^6$CONR$^7$-;

(11) substituted $C_{2-10}$alkynyl wherein alkynyl contains one to four double bonds and wherein one or more of the alkyl carbons may be replaced by a group selected from: -NR$^6$-, -O-, -S(O)$_p$-, -CO$_2$-, -O$_2$C-, -CONR$^6$-, -NR$^6$CO-, and -NR$^6$CONR$^7$, and the alkyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) -OCO-$C_{1-6}$alkyl
(o) -NR$^6$R$^7$, wherein R$^6$ and R$^7$ are as defined above,
(p) -NR$^6$CO-$C_{1-6}$alkyl-R$^7$,
(q) -NR$^6$CO$_2$-$C_{1-6}$alkyl-R$^7$,
(r) -NR$^6$CONR$^6$R$^7$,
(s) -OCONR$^6$R$^7$,
(t) -COOR$^6$,
(u) -CHO,
(v) -OR$^{11}$, and
(w) -S(O)$_p$-$C_{1-6}$alkyl;
(12) aryl
(13) heteroaryl;
(14) substituted aryl in which the substituents are X, Y and Z;

(15) substituted heteroaryl in which the substituents are X, Y and Z;

$R^1$ is selected from:
(1) hydrogen,
(2) hydroxy,
(3) $C_{1-6}$alkoxy,
(4) aryl-$C_{1-3}$alkoxy,
(5) substituted aryl-$C_{1-3}$alkoxy, in which the substituents on aryl are X, Y and Z,
(6) unsubstituted or substituted aryloxy, in which the substituents on aryl are X, Y and Z,
(7) heteroaryl-$C_{1-3}$alkoxy,
(8) substituted heteroaryl-$C_{1-3}$alkoxy, in which the substituents on heteroaryl are X, Y and Z,
(9) unsubstituted or substituted heteroaryloxy, in which the substituents on aryl are X, Y and Z,
(10) -OCO-$C_{1-6}$alkyl, -OCONR$^6$R$^7$, and
(12) -OR$^{11}$, and $R^2$ is selected from:
(1) hydrogen;
(2) $C_{1-10}$alkyl;
(3) substituted-$C_{1-10}$alkyl in which one or more substituent(s) is(are) selected from:
(a) hydroxy,
(b) oxo,
(c) $C_{1-6}$alkoxy,
(d) aryl-$C_{1-3}$alkoxy,
(e) substituted aryl-$C_{1-3}$alkoxy, in which the substituents on aryl are X, Y and Z,
(f) unsubstituted or substituted aryloxy, in which the substituents on aryl are X, Y and Z,
(g) -OCO-$C_{1-6}$alkyl,
(h) -NR$^6$R$^7$, wherein $R^6$ and $R^7$ are as defined above
(i) -NR$^6$CO-$C_{1-6}$alkyl-R$^7$, wherein $R^6$ and $R^7$ are as defined above,
(j) -COOR$^6$, wherein $R^6$ is as defined above,
(k) -CHO,
(l) -OR$^{11}$,
(m) -S(O)$_p$-$C_{1-6}$alkyl;
(4) $C_{3-10}$alkenyl;
(5) substituted $C_{3-10}$alkenyl in which one or more substituent(s) is(are) selected from:
(a) hydroxy,
(b) oxo,
(c) $C_{1-6}$alkoxy,
(d) aryl-$C_{1-3}$alkoxy,
(e) substituted aryl-$C_{1-3}$alkoxy, in which the substituents on aryl are X, Y and Z,
(f) unsubstituted or substituted aryloxy, in which the substituents on aryl are X, Y and Z,
(g) -OCO-$C_{1-6}$alkyl,
(h) -NR$^6$R$^7$, wherein $R^6$ and $R^7$ are as defined above
(i) -NR$^6$CO-$C_{1-6}$alkyl-R$^7$, wherein $R^6$ and $R^7$ are as defined above,
(j) -COOR$^6$, wherein $R^6$ is as defined above,
(k) -CHO,
(l) -OR$^{11}$,
(m) -S(O)$_p$-$C_{1-6}$alkyl;
(6) $C_{3-10}$alkynyl;
(7) substituted $C_{3-10}$alkynyl in which one or more substituent(s) is(are) selected from:
(a) hydroxy,
(b) oxo,
(c) $C_{1-6}$alkoxy,
(d) aryl-$C_{1-3}$alkoxy,
(e) substituted aryl-$C_{1-3}$alkoxy, in which the substituents on aryl are X, Y and Z,
(f) unsubstituted or substituted aryloxy, in which the substituents on aryl are X, Y and Z,
(g) -OCO-$C_{1-6}$alkyl,
(h) -NR$^6$R$^7$, wherein $R^6$ and $R^7$ are as defined above
(i) -NR$^6$CO-$C_{1-6}$alkyl-R$^7$, wherein $R^6$ and $R^7$ are as defined above.
(j) -COOR$^6$, wherein $R^6$ is as defined above,
(k) -CHO,
(l) -OR$^{11}$,
(m) -S(O)$_p$-$C_{1-6}$alkyl;

$R^3$ is hydrogen, hydroxy, -OR$^{11}$, or $C_{1-6}$alkoxy;
$R^4$ is hydrogen, or $R^3$ and $R^4$ taken together form a double bond;
$R^5$ is methyl, ethyl, propyl or allyl;
$R^{10}$ is hydrogen, hydroxy, -OR$^{11}$ or fluoro;
$R^{11}$ is selected from:
(a) -PO(OH)O-M+, wherein M+ is a positively charged inorganic or organic counterion,
(b) -SO$_3$-M+,
(c) -CO(CH$_2$)$_q$CO$_2$-M+, wherein q is 1–3, and
(d) -CO-$C_{1-6}$alkyl-NR$^6$R$^7$, wherein $R^6$ and $R^7$ are as defined above and the alkyl is unsubstituted or substituted with one or more substituents selected from:
(i) hydroxy,
(ii) $C_{1-6}$alkoxy,
(iii) -NR$^{16}$R$^{17}$, wherein $R^{16}$ and $R^{17}$ are independently selected from:
(a') hydrogen, and
(b') $C_{1-6}$alkyl,
(iv) -COOR$^6$, wherein $R^6$ is as defined above,
(v) phenyl,
(iv) substituted phenyl in which the substituents are X, Y and Z,
(vii) heteroaryl,
(viii) -SH, and
(ix) -S-$C_{1-6}$alkyl;

$R^{12}$ is OH, H, or $R^{12}$ and $R^{13}$ taken together form a double bond;
W is O, (H, OH) or (H, H);
X, Y and Z independently are selected from:
(a) hydrogen,
(b) $C_{1-10}$alkyl, unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) -OR$^6$,
(vii) -OR$^{11}$,
(viii) -OCOR$^6$,
(ix) -OCO$_2$R$^6$,
(x) -NR$^6$R$^7$,
(xi) -CHO,
(xii) -NR$^6$COC$_{1-6}$alkyl-R$^7$,
(xiii) -NR$^6$CO$_2$C$_{1-6}$alkyl-R$^7$,
(xiv) -NR$^6$CONR$^6$R$^7$,
(xv) -OCONR$^6$R$^7$,
(xvi) -CONR$^6$R$^7$, (c) $C_{1-10}$alkyl wherein one or more of the alkyl carbons is replaced by a group selected from -$NR^6$- -O-, -$S(O)_p$-, -$CO_2$-, -$O_2C$-, -$CONR^6$-, -$NR^6CO$-, -$NR^6CONR^7$-, -CO-, -CH(OH)-, alkenyl or alkynyl and the alkyl may be unsubstituted or substituted with one or more substituents selected from:
  (i) aryl,
  (ii) substituted aryl in which the substituents are X', Y' and Z',
  (iii) heteroaryl,
  (iv) substituted heteroaryl in which the substituents are X', Y', and Z',
  (v) unsubstituted or substituted aryloxy, in which the substituents on aryl are X', Y', and Z',
  (vi) -$OR^6$,
  (vii) -$OR^{11}$,
  (viii) -$OCOR^6$,
  (ix) -$OCO_2R^6$,
  (x) -$NR^6R^7$,
  (xi) -CHO
  (xii) -$NR^6COC_{1-6}$alkyl-$R^7$,
  (xiii) -$NR^6CO_2C_{1-6}$alkyl-$R^7$,
  (xiv) -$NR^6CONR^6R^7$,
  (xv) -$OCONR^6R^7$,
  (xvi) -$CONR^6R^7$,
(d) aryl,
(e) substituted aryl wherein the substituents are X', Y' or Z',
(f) heteroaryl,
(g) substituted heteroaryl wherein the substituents are X', Y' or Z',
(h) substituted and unsubstituted aryloxy wherein the substitutents are X', Y', or Z',
  (i) substituted and unsubstituted heteroaryloxy wherein the substitutents are X', Y', or Z',
(j) -NO2,
(k) halogen,
(l) -$NR^6R^7$,
(m) -CN,
(n) -CHO,
(o) -$CF_3$,
(p) -$SR^8$, wherein $R^8$ is hydrogen, $C_{1-6}$alkyl, trifluoromethyl, or phenyl,
(q) -$SOR^8$,
(r) -$SO_2R^8$,
(s) -$CONR^6R^7$,
(t) $R^9O(CH_2)_m$- wherein $R^9$ is hydrogen, $C_{1-6}$alkyl, hydroxy-$C_{2-3}$alkyl, -$CF_3$, phenyl, $R^{11}$ or naphthyl and m is 0, 1, 2, or 3,
(u) -$CH(OR^{12})(OR^{13})$, wherein $R^{12}$ and $R^{13}$ are $C_{1-3}$ alkyl or taken together form an ethyl or propyl bridge,
(v) $R^9CO(CH_2)_m$- wherein $R^9$ and m are as defined above,
(w) $R^9O_2C(CH_2)_m$- wherein $R^9$ and m are as defined above, and
(x) -$R^{11}$; or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;
X', Y' and Z' independently are selected from:
(a) hydrogen,
(b) $C_{1-7}$alkyl,
(c) $C_{2-6}$alkenyl,
(d) halogen,
(e) -$NO_2$,
(f) $NR^6R^7$, wherein $R^6$, and $R^7$ are as defined above,
(g) -CN,
(h) -CHO,
(i) -$CF_3$,
(j) -$SR^8$, wherein $R^8$ is hydrogen, $C_{1-6}$alkyl, trifluoromethyl, or phenyl,
(k) -$SOR^8$, wherein $R^8$ is as defined above,
(l) -$SO_2R^8$, wherein $R^8$ is as defined above,
(m) -$CONR^6R^7$, wherein $R^6$ and $R^7$ are as defined above,
(n) $R^9O(CH_2)_m$- wherein $R^9$ and m are as defined above,
(o) -$CH(OR^{12})(OR^{13})$, wherein $R^{12}$ and $R^{13}$ are as defined above,
(p) $R^9CO(CH_2)_m$- wherein $R^9$ and m are as defined above,
(q) $R^9O_2C(CH_2)_m$-wherein $R^9$ and m are as defined above, and
(r) -$R^{11}$;
n is 1 or 2.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, $R^6$, $R^7$, $R^8$, $R^9$, $R^{10}$, $R^{11}$, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, secoand tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkanoyl" is intended to include those alkylcarbonyl groups of specified number of carbon atoms, which are exemplified by formyl, acetyl, propanoyl and butyryl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

The heteroaryl group as used herein includes acridine, carbazole, cinnoline, dibenzofuran, dibenzothiophene, quinoxaline, pyrrazole, indole, imidazole, benzimidazole, benzotriazole, furan, benzofuran, quinoline, isoquinoline, pyrazine, pyridazine, pyridine, pyrimidine, pyrrole which are optionally substituted.

In the compounds of Formula I the heteroaryl group may be optionally substituted with X, Y and Z at any available carbon atom or nitrogen atom (if present), but compounds bearing certain of X, Y and Z directly substituted to a nitrogen atom of the heteroaryl ring may be relatively unstable and are not preferred.

The aryl or aromatic group includes phenyl or naphthyl which are optionally substituted by from one- to three-members independently selected from the group consisting of: alkyl, alkenyl, halogen, carboxyl, CHO, amino, mono-alkylamino, di-alkylamino, aminoalkyl, mono-alkylaminoalkyl, di-alkylaminoalkyl, alkylthio, alkylsulfinyl, alkysulfonyl, trifluoromethyl, amido, mono-alkylamido, dialkylamido, hydroxy, hydroxyalkyl, $R^{11}$O-alkyl, alkoxy, alkoxyalkyl, formamido, alkyl-$CO_2$-, formamidoalkyl, alkyl-$CO_2$-alkyl-, carboxyl, alkyl-$CO_2$H, alkyl-$O_2$C-, alkyl-$O_2$C-alkyl-, and $OR^{11}$.

In the present invention it is preferred that in compounds of Formula I:
R is selected from:
(1) substituted $C_{2-6}$alkyl wherein the alkyl is substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) hydroxy,
(g) oxo, and
(h) -$OR^{11}$;
(2) substituted or unsubstituted $C_{2-6}$alkyl wherein one or more of the alkyl carbons is replaced by a group selected from: -$NR^6$-, -O-, -S(O)$_p$-, -$CO_2$-, -$O_2$C-, -$CONR^6$-, -$NR^6$CO-, and -$NR^6CONR^7$-, and the alkyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) hydroxy,
(g) oxo, and
(h) -$OR^{11}$;
(3) subsituted $C_{3-6}$alkenyl wherein the alkenyl contains one to two double bonds and the alkyl or alkenyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) hydroxy,
(g) oxo, and
(h) -$OR^{11}$.

In the compound of Formula I it is also preferred that:
$R^1$ is selected from:
(1) hydrogen,
(2) hydroxy,
(3) $C_{1-6}$alkoxy, and
(4) -$OR^{11}$.

In the compound of Formula I it is also preferred that:
$R^2$ is selected from:
(1) hydrogen,
(2) methyl,
(3) ethyl,
(4) propyl,
(5) allyl,
(6) $R^{11}$,
(7) -$C_{2-3}$alkyl-OH; and
(8) -$C_{2-3}$alkyl-$OR^{11}$;
$R^3$ is selected from:
(1) hydrogen,
(2) hydroxy,
(3) -$OR^{11}$, or
$R^3$ and $R^4$ taken together form a double bond;
$R^{10}$ is hydrogen, hydroxy, fluoro, or-$OR^{11}$;
$R^{12}$ is hydroxy, hydrogen or with $R^{13}$ forms a double bond;
W is O or (H,H); and
n is 2.

In the compound of Formula I it is even more preferred that:
R is selected from:

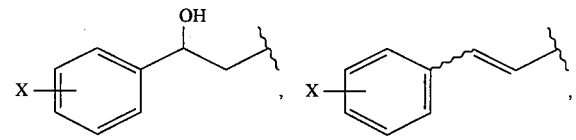

wherein X is selected from: H, 3-$CH_3$, 3-F, 4-$CH_3$S, 4-$CF_3$, 3,5-$(CH_3)_2$, 3-$NO_3$, 3-OCH3, 4-OCH3, 4-$OCH_2$Ph, 4-$OCH_2$Ph(4-$OCH_3$), 3-HOPh,

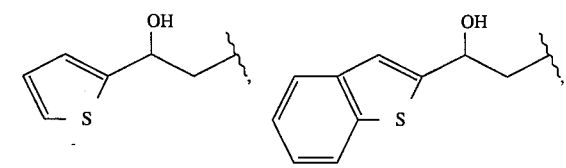

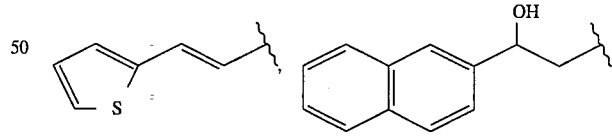

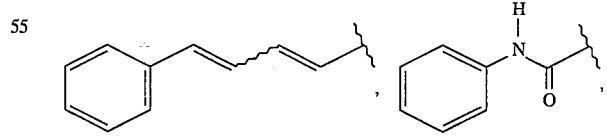

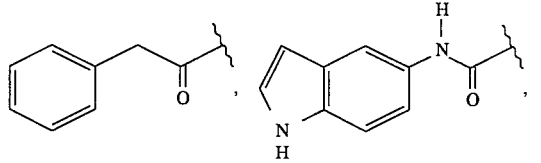

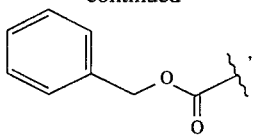

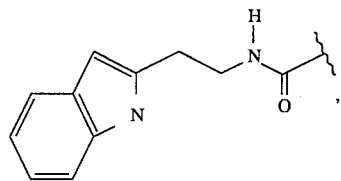

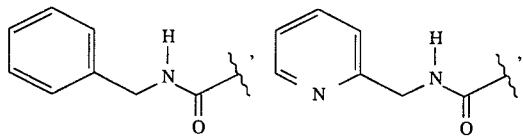

—CH$_3$, —CH=CH$_2$, —CH$_2$—CH=CH$_2$,

—CH$_2$CH$_2$—CH=CH$_2$, -phenyl, —CH$_2$-phenyl, —CHO,

—CH$_2$CHO, —CH$_2$CH$_2$CHO, —CH$_2$OH, —CH(OH)CH$_2$OH,

—CH$_2$CH(OH)CH$_2$OH, and —CH$_2$CH$_2$CH(OH)CH$_2$OH.

The term "heteroaryl" as utilized herein is intended to include the following heteroaromatic groups which may include X, Y and Z substitution as indicated and wherein Q is -N(X)-, -O-, -S-, -SO, or -SO$_2$-:

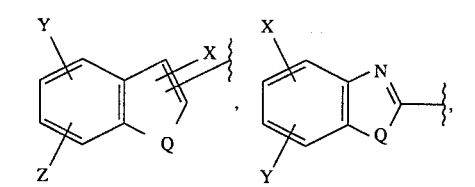

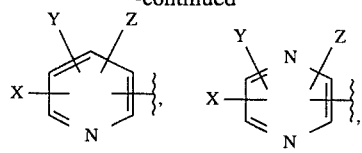

(Pyridine)   (Pyrazine)

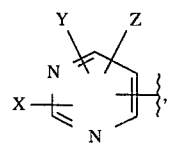

(Pyrimidine)

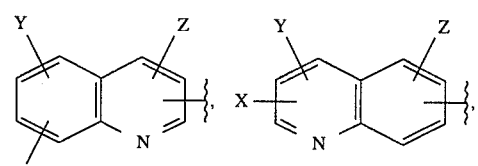

(Quinoline)

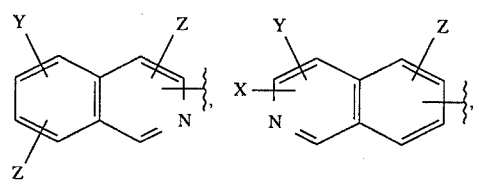

(Isoquinoline)

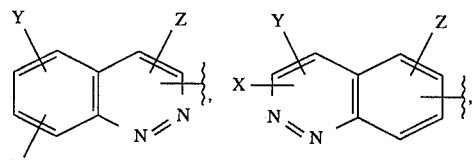

(Cinnoline)

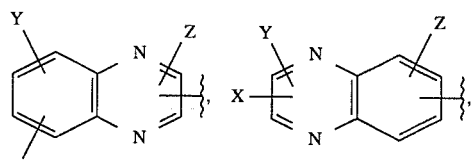

(Quinoxaline)

In the compound of Formula I it is preferred that the heteroaryl is selected from the group consisting of:

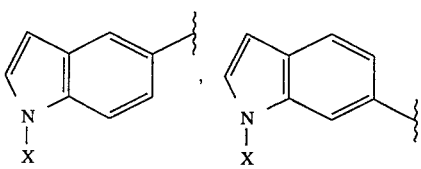

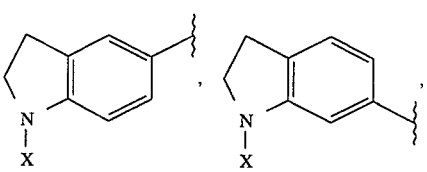

(Pyridazine)

17
-continued
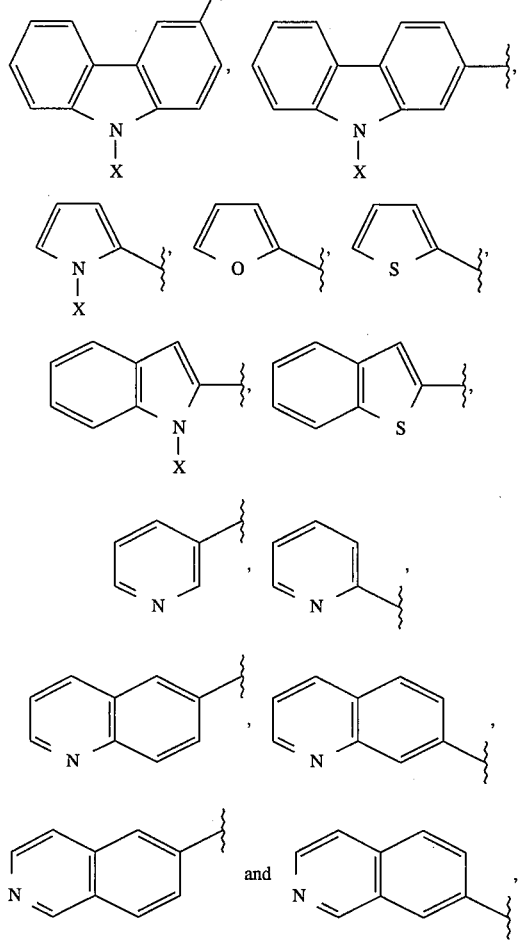
wherein X is as defined above.
Representative compounds of the present invention include the compounds of formula 1–4:
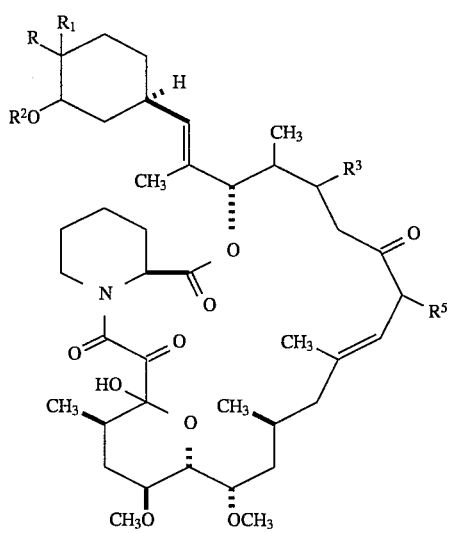
18
-continued
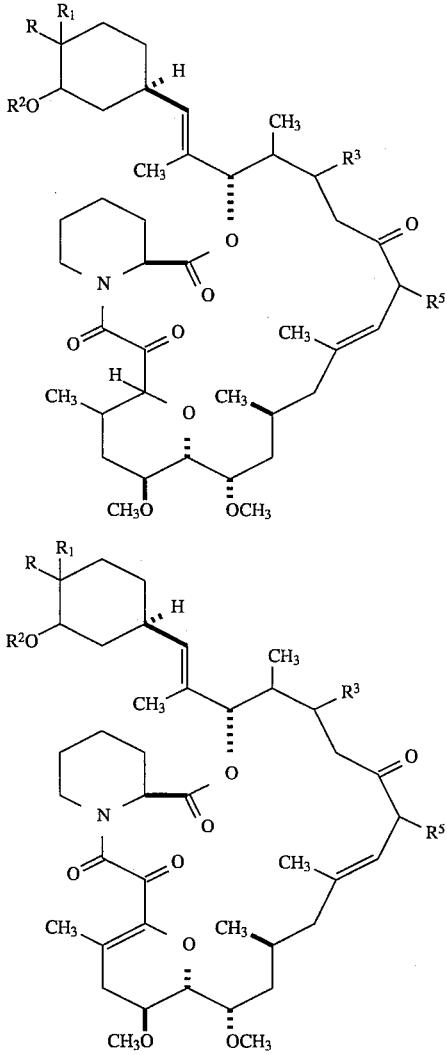
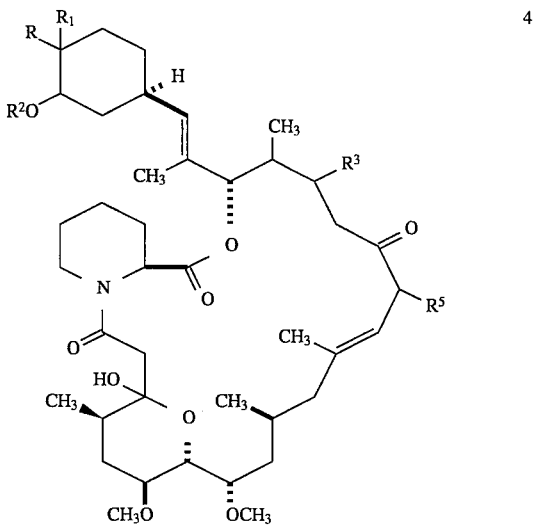
wherein for each of formula 1–4 the definitions of R, $R^1$, $R^3$ and $R^5$ are selected from the following groups of substituents:

-continued

| R | R¹ | R² | R³ | R⁵ |
|---|---|---|---|---|
| 4-HO₂C-phenyl | OH | CH₃ | OH | ethyl |
| 4-H₂NCO-phenyl | OH | CH₃ | OH | ethyl |
| 4-HO-phenyl | OH | CH₃ | OH | ethyl |
| 4-Cl-phenyl | OH | CH₃ | OH | ethyl |
| 4-(CH₃)₂N-phenyl | OH | CH₃ | OH | ethyl |
| 3-HO₂C-phenyl | OH | CH₃ | OH | ethyl |
| 3-H₂NCO-phenyl | OH | CH₃ | OH | ethyl |
| 3-HO-phenyl | OH | CH₃ | OH | ethyl |
| 3-Cl-phenyl | OH | CH₃ | OH | ethyl |
| 3-(CH₃)₂N-phenyl | OH | CH₃ | OH | ethyl |
| 2-HO₂C-phenyl | OH | CH₃ | OH | ethyl |
| 2-H₂NCO-phenyl | OH | CH₃ | OH | ethyl |
| 2-HO-phenyl | OH | CH₃ | OH | ethyl |
| 2-Cl-phenyl | OH | CH₃ | OH | ethyl |
| 2-(CH₃)₂N-phenyl | OH | CH₃ | OH | ethyl |
| 4-pyridyl | OH | CH₃ | OH | ethyl |
| 3-pyridyl | OH | CH₃ | OH | ethyl |
| 2-pyridyl | OH | CH₃ | OH | ethyl |
| 2-O₂N-phenyl | OH | CH₃ | OH | ethyl |
| 3-O₂N-phenyl | OH | CH₃ | OH | ethyl |
| 4-O₂N-phenyl | OH | CH₃ | OH | ethyl |
| 2-F-phenyl | OH | CH₃ | OH | ethyl |
| 3-F-phenyl | OH | CH₃ | OH | ethyl |
| 4-F-phenyl | OH | CH₃ | OH | ethyl |
| 2-F₃C-phenyl | OH | CH₃ | OH | ethyl |
| 3-F₃C-phenyl | OH | CH₃ | OH | ethyl |
| 4-F₃C-phenyl | OH | CH₃ | OH | ethyl |
| 4-HO₂C-phenyl | OH | CH₃ | H | ethyl |
| 4-H₂NCO-phenyl | OH | CH₃ | H | ethyl |
| 4-HO-phenyl | OH | CH₃ | H | ethyl |
| 4-Cl-phenyl | OH | CH₃ | H | ethyl |
| 4-(CH₃)₂N-phenyl | OH | CH₃ | H | ethyl |
| 3-HO₂C-phenyl | OH | CH₃ | H | ethyl |
| 3-H₂NCO-phenyl | OH | CH₃ | H | ethyl |
| 3-HO-phenyl | OH | CH₃ | H | ethyl |
| 3-Cl-phenyl | OH | CH₃ | H | ethyl |
| 3-(CH₃)₂N-phenyl | OH | CH₃ | H | ethyl |
| 2-HO₂C-phenyl | OH | CH₃ | H | ethyl |
| 2-H₂NCO-phenyl | OH | CH₃ | H | ethyl |
| 2-HO-phenyl | OH | CH₃ | H | ethyl |
| 2-Cl-phenyl | OH | CH₃ | H | ethyl |
| 2-(CH₃)₂N-phenyl | OH | CH₃ | H | ethyl |
| 4-pyridyl | OH | CH₃ | H | ethyl |
| 3-pyridyl | OH | CH₃ | H | ethyl |
| 2-pyridyl | OH | CH₃ | H | ethyl |
| 2-O₂N-phenyl | OH | CH₃ | H | ethyl |
| 3-O₂N-phenyl | OH | CH₃ | H | ethyl |
| 4-O₂N-phenyl | OH | CH₃ | H | ethyl |
| 2-F-phenyl | OH | CH₃ | H | ethyl |
| 3-F-phenyl | OH | CH₃ | H | ethyl |
| 4-F-phenyl | OH | CH₃ | H | ethyl |
| 2-F₃C-phenyl | OH | CH₃ | H | ethyl |
| 3-F₃C-phenyl | OH | CH₃ | H | ethyl |
| 4-F₃C-phenyl | OH | CH₃ | H | ethyl |
| 3-(CH₃)₂N-phenyl | OH | CH₃ | OH | allyl |
| 2-HO₂C-phenyl | OH | CH₃ | OH | allyl |
| 2-H₂NCO-phenyl | OH | CH₃ | OH | allyl |
| 2-HO-phenyl | OH | CH₃ | OH | allyl |
| 2-Cl-phenyl | OH | CH₃ | OH | allyl |
| 2-(CH₃)₂N-phenyl | OH | CH₃ | OH | allyl |
| 4-pyridyl | OH | CH₃ | OH | allyl |
| 3-pyridyl | OH | CH₃ | OH | allyl |
| 2-pyridyl | OH | CH₃ | OH | allyl |
| 2-O₂N-phenyl | OH | CH₃ | OH | allyl |
| 3-O₂N-phenyl | OH | CH₃ | OH | allyl |
| 4-O₂N-phenyl | OH | CH₃ | OH | alyl |
| 2-F-phenyl | OH | CH₃ | OH | allyl |
| 3-F-phenyl | OH | CH₃ | OH | allyl |
| 4-F-phenyl | OH | CH₃ | OH | allyl |
| 2-F₃C-phenyl | OH | CH₃ | OH | allyl |
| 3-F₃C-phenyl | OH | CH₃ | OH | allyl |
| 4-F₃C-phenyl | OH | CH₃ | OH | allyl |
| CH₃ | OH | CH₃ | H | ethyl |
| CH₃CH₂ | OH | CH₃ | H | ethyl |
| CH₃CH₂CH₂ | OH | CH₃ | H | ethyl |
| (CH₃)₂CH | OH | CH₃ | H | ethyl |
| HO₂CCH₂CH₂ | OH | CH₃ | H | ethyl |
| H₂NCOCH₂CH₂ | OH | CH₃ | H | ethyl |
| HOCH₂CH₂ | OH | CH₃ | H | ethyl |
| HOCH₂CH₂CH₂ | OH | CH₃ | H | ethyl |
| CH₃ | OH | H | OH | ethyl |
| CH₃CH₂ | OH | H | OH | ethyl |
| CH₃CH₂CH₂ | OH | H | OH | ethyl |
| (CH₃)₂CH | OH | H | OH | ethyl |
| HO₂CCH₂CH₂ | OH | H | OH | ethyl |
| H₂NCOCH₂CH₂ | OH | H | OH | ethyl |
| HOCH₂CH₂ | OH | H | OH | ethyl |
| HOCH₂CH₂CH₂ | OH | H | OH | ethyl |
| 4-HO₂C-phenyl | H | CH₃ | OH | ethyl |
| 4-H₂NCO-phenyl | H | CH₃ | OH | ethyl |
| 4-HO-phenyl | H | CH₃ | OH | ethyl |
| 4-Cl-phenyl | H | CH₃ | OH | ethyl |
| 4-(CH₃)₂N-phenyl | H | CH₃ | OH | ethyl |
| 3-HO₂C-phenyl | H | CH₃ | OH | ethyl |
| 3-H₂NCO-phenyl | H | CH₃ | OH | ethyl |
| 3-HO-phenyl | H | CH₃ | OH | ethyl |
| 3-Cl-phenyl | H | CH₃ | OH | ethyl |
| 3-(CH₃)₂N-phenyl | H | CH₃ | OH | ethyl |
| 2-HO₂C-phenyl | H | CH₃ | OH | ethyl |
| 2-H₂NCO-phenyl | H | CH₃ | OH | ethyl |
| 2-HO-phenyl | H | CH₃ | OH | ethyl |
| 2-Cl-phenyl | H | CH₃ | OH | ethyl |
| 2-(CH₃)₂N-phenyl | H | CH₃ | OH | ethyl |
| 4-pyridyl | H | CH₃ | OH | ethyl |
| 3-pyridyl | H | CH₃ | OH | ethyl |
| 2-pyridyl | H | CH₃ | OH | ethyl |
| 2-O₂N-phenyl | H | CH₃ | OH | ethyl |
| 3-O₂N-phenyl | H | CH₃ | OH | ethyl |
| 4-O₂N-phenyl | H | CH₃ | OH | ethyl |
| 2-F-phenyl | H | CH₃ | OH | ethyl |
| 3-F-phenyl | H | CH₃ | OH | ethyl |
| 4-F-phenyl | H | CH₃ | OH | ethyl |
| 2-F₃C-phenyl | H | CH₃ | OH | ethyl |
| 3-F₃C-phenyl | H | CH₃ | OH | ethyl |
| 4-F₃C-phenyl | H | CH₃ | OH | ethyl |
| 3-Cl-phenyl | H | CH₃ | H | ethyl |
| 3-(CH₃)₂N-phenyl | H | CH₃ | H | ethyl |
| 2-HO₂C-phenyl | H | CH₃ | H | ethyl |
| 2-H₂NCO-phenyl | H | CH₃ | H | ethyl |
| 2-HO-phenyl | H | CH₃ | H | ethyl |
| 2-Cl-phenyl | H | CH₃ | H | ethyl |
| 2-(CH₃)₂N-phenyl | H | CH₃ | H | ethyl |
| 4-pyridyl | H | CH₃ | H | ethyl |
| 3-pyridyl | H | CH₃ | H | ethyl |
| 2-pyridyl | H | CH₃ | H | ethyl |
| 2-O₂N-phenyl | H | CH₃ | H | ethyl |
| 3-O₂N-phenyl | H | CH₃ | H | ethyl |
| 4-O₂N-phenyl | H | CH₃ | H | ethyl |
| 2-F-phenyl | H | CH₃ | H | ethyl |
| 3-F-phenyl | H | CH₃ | H | ethyl |
| 4-F-phenyl | H | CH₃ | H | ethyl |
| 2-F₃C-phenyl | H | CH₃ | H | ethyl |
| 3-F₃C-phenyl | H | CH₃ | H | ethyl |
| 4-F₃C-phenyl | H | CH₃ | H | ethyl |
| 3-Cl-phenyl | H | CH₃ | OH | allyl |
| 3-(CH₃)₂N-phenyl | H | CH₃ | OH | allyl |
| 2-HO₂C-phenyl | H | CH₃ | OH | allyl |
| 2-H₂NCO-phenyl | H | CH₃ | OH | allyl |
| 2-HO-phenyl | H | CH₃ | OH | allyl |
| 2-Cl-phenyl | H | CH₃ | OH | allyl |
| 2-(CH₃)₂N-phenyl | H | CH₃ | OH | allyl |
| 4-pyridyl | H | CH₃ | OH | allyl |
| 3-pyridyl | H | CH₃ | OH | allyl |
| 2-pyridyl | H | CH₃ | OH | allyl |
| 2-O₂N-phenyl | H | CH₃ | OH | allyl |
| 3-O₂N-phenyl | H | CH₃ | OH | allyl |
| 4-O₂N-phenyl | H | CH₃ | OH | allyl |
| 2-F-phenyl | H | CH₃ | OH | allyl |
| 3-F-phenyl | H | CH₃ | OH | allyl |
| 4-F-phenyl | H | CH₃ | OH | allyl |
| 2-F₃C-phenyl | H | CH₃ | OH | allyl |
| 3-F₃C-phenyl | H | CH₃ | OH | allyl |
| 4-F₃C-phenyl | H | CH₃ | OH | allyl |
| CH₃ | H | CH₃ | H | ethyl |
| CH₃CH₂ | H | CH₃ | H | ethyl |
| CH₃CH₂CH₂ | H | CH₃ | H | ethyl |

-continued

| R | $R^1$ | $R^2$ | $R^3$ | $R^5$ |
|---|---|---|---|---|
| $(CH_3)_2CH$ | H | $CH_3$ | H | ethyl |
| $HO_2CCH_2CH_2$ | H | $CH_3$ | H | ethyl |
| $H_2NCOCH_2CH_2$ | H | $CH_3$ | H | ethyl |
| $HOCH_2CH_2$ | H | $CH_3$ | H | ethyl |
| $HOCH_2CH_2CH_2$ | H | $CH_3$ | H | ethyl |
| $CH_3$ | H | H | OH | ethyl |
| $CH_3CH_2$ | H | H | OH | ethyl |
| $CH_3CH_2CH_2$ | H | H | OH | ethyl |
| $(CH_3)_2CH$ | H | H | OH | ethyl |
| $HO_2CCH_2CH_2$ | H | H | OH | ethyl |
| $H_2NCOCH_2CH_2$ | H | H | OH | ethyl |
| $HOCH_2CH_2$ | H | H | OH | ethyl |
| $HOCH_2CH_2CH_2$ | H | H | OH | ethyl. |

Representative compounds of the present invention include the compounds identified as follows:

17-Ethyl-1,14-dihydroxy-12-[2'-(4"-hydroxy-4"-methyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-hydroxy-4 "-methyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4 "-hydroxy-4"-methyl-3"-methoxycyclo-hexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-hydroxy-4"-phenyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-hydroxy-4"-phenyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-hydroxy-4"-phenyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-hydroxy-4"-benzyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-hydroxy-4"-benzyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-hydroxy-4"-benzyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-hydroxy-4"-(indol-5-yl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-enc- 2,3,10,16-tetraone;

17-Ethyl-1-hydroxy-12-[2'-(4"-hydroxy-4"-(indol-5-yl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-hydroxy-4"-(indol-5-yl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-hydroxy-4"-(indol-5-ylmethyl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxo-12-[2'-(4"-hydroxy-4"-(indol-5-ylmethyl)-3"-methoxycyclohexyl)-1'-methylvinyl]-23,25-dimethoxy-13,19,21.27 -tetramethyl-11,28-dioxa-4-azatricyclo-[22.3.1.0$^{4,9}$]octacos-18-ene-2,3,10,16-tetraone;

17-Allyl-1,14-dihydroxy-12-[2'-(4"-hydroxy-4"-(indol-5-ylmethyl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-hydroxy-4"-(2-propen-1-yl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-hydroxy-4"-(2-propen-1-yl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-hydroxy-4"-(2-propen-1-yl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-hydroxy-4"-(3-phenyl-2-propen-1 -yl)-3"-methoxycyclohexyl)-1'-methylvinyl]-23,25-dimethoxy- 13,19,21,27-tetramethyl-11,28-dioxa-4-azatricyclo-[22.3.1.0$^{4,9}$]octacos- 18-ene-2,3,10,16-tetraone;

17-Ethyl-1-hydroxy-12-[2'-(4"-hydroxy-4"-(3-phenyl-2-propen-1-yl)- 3"-methoxycyclohexyl)-1'-methylvinyl-1-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-hydroxy-4"-(3-phenyl-2-propen-1 -yl)-3"-methoxycyclohexyl)-1'-methylvinyl]-23,25-dimethoxy- 13,19,21,27-tetramethyl-11,28-dioxa-4-azatricyclo-[22.3.1.0$^{4,9}$]octacos- 18-ene-2,3,10,16-tetraone;

17-Ethyl-1,14-dihydroxy-12-[2'-(4"-hydroxy-4"-[3-(4-methoxyphenyl)- 2-propen-1-yl]-3"-methoxycyclohexyl)-1'-methylvinyl]-23,25 -dimethoxy-13,19,21,27-tetramethyl-11,28-dioxa-4-azatricyclo-[2.3.1.0$^{4,9}$] octacos-18-ene-2,3,10,16-tetraone;

17-Ethyl-1-hydroxy-12-[2'-(4"-hydroxy-4"-[3-(4-methoxyphenyl)-2 -propen-1-yl]-3"-methoxycyclohexyl)-1'-methylvinyl]-23,25-dimethoxy- 13,19,21,27-tetramethyl-11,28-dioxa-4-azatricyclo-[22.3.1.0$^{4,9}$]octacos- 18-ene-2,3,10,16-tetraone;

17-Allyl-1,14-dihydroxy-12-[2'-(4"-hydroxy-4"-[3-(4-methoxyphenyl)- 2-propen-1-yl]-3"-methoxycyclohexyl)-1'-methylvinyl]-23,25 -dimethoxy-13,19,21,27-tetramethyl-11,28-dioxa-4-azatricyclo-[22.3.1.0$^{4,9}$] octacos-18-ene-2,3,10,16-tetraone;

17-Ethyl-1,14-dihydroxy-12-[2'-(4"-hydroxy-4"-[3-(3-methoxyphenyl)- 2-propen-1-yl]-3"-methoxycyclohexyl)-1'-methylvinyl]-23,25 -dimethoxy-13,19,21,27-tetramethyl-11,28-dioxa-4-azatricyclo- [22.3.1.0$^{4,9}$] octacos-18-ene-2,3,10,16-tetraone;

17-Ethyl-1-hydroxy-12-[2'-(4"-hydroxy-4"-[3-(3-methoxyphenyl)-2 -propen-1-yl]-3"-methoxycyclohexyl)-1'-methylvinyl]-23,25-dimethoxy- 13,19,21,27-tetramethyl-11,28-dioxa-4-azatricyclo-[22.3.1.0$^{4,9}$]octacos- 18-ene-2,3,10,16-tetraone;

17-Allyl-1,14-dihydroxy-12-[2'-(4"-hydroxy-4"-[3-(3-methoxyphenyl)-2-propen-1-yl]-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-hydroxy-4"-[3-(3,5-dimethoxyphenyl)-2-propen-1-yl]-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-hydroxy-4"-[3-(3,5-dimethoxyphenyl)-2-propen-1-yl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4"-hydroxy-4"-[3-(3,5-dimethoxyphenyl)-2-propen-1-yl]-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

or a pharmaceutically acceptable salt thereof.

Representative compounds of the present invention include the compounds of formula 5–12:

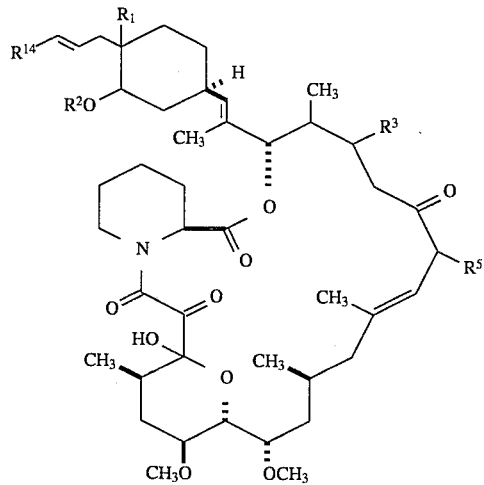

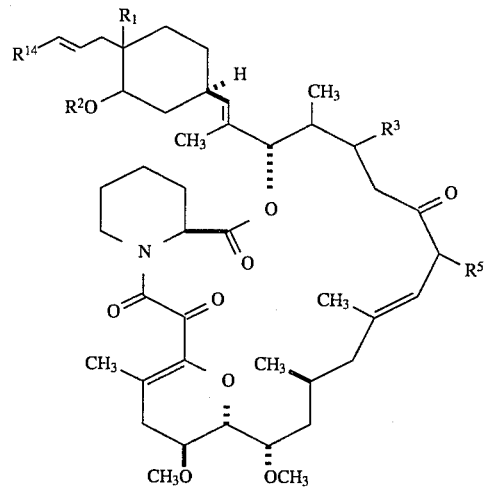

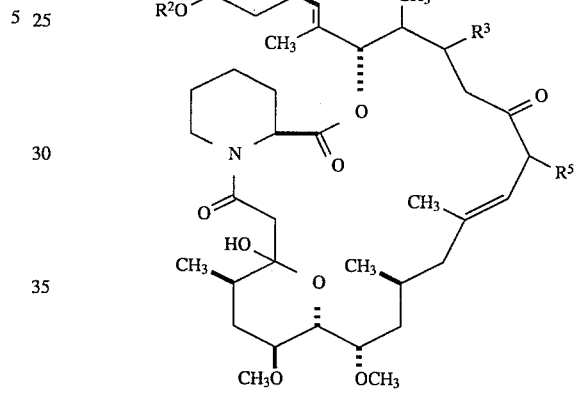

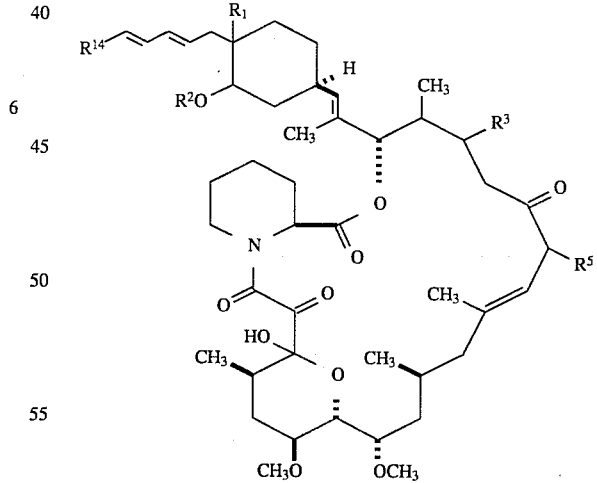

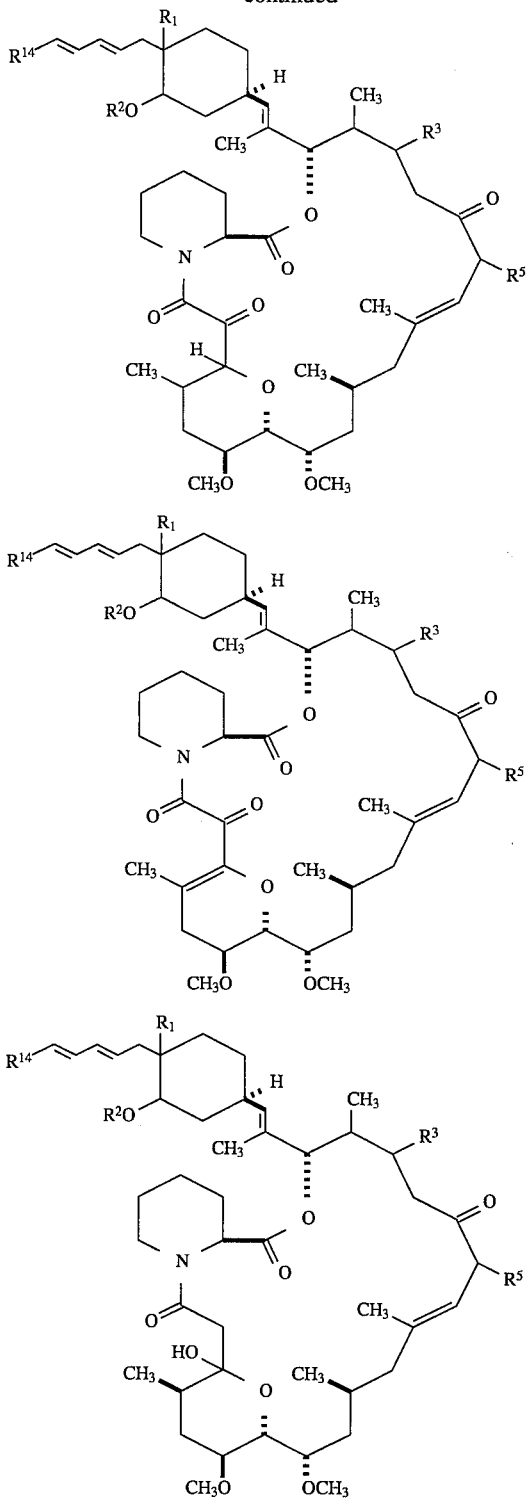

wherein for each of formula 5–12 the definitions of $R^1$, $R^3$, $R^5$, and $R^{14}$ are selected from the following groups of substituents:

| $R^{14}$ | $R^1$ | $R^2$ | $R^3$ | $R^5$ |
|---|---|---|---|---|
| 4-HO$_2$C-phenyl | OH | CH$_3$ | OH | ethyl |
| 4-H$_2$NCO-phenyl | OH | CH$_3$ | OH | ethyl |
| 4-HO-phenyl | OH | CH$_3$ | OH | ethyl |
| 4-Cl-phenyl | OH | CH$_3$ | OH | ethyl |
| 3-(CH$_3$)$_2$N-phenyl | OH | CH$_3$ | OH | ethyl |
| 3-HO$_2$C-phenyl | OH | CH$_3$ | OH | ethyl |
| 3-H$_2$NCO-phenyl | OH | CH$_3$ | OH | ethyl |
| 3-HO-phenyl | OH | CH$_3$ | OH | ethyl |
| 3-Cl-phenyl | OH | CH$_3$ | OH | ethyl |
| 2-(CH$_3$)$_2$N-phenyl | OH | CH$_3$ | OH | ethyl |
| 2-HO$_2$C-phenyl | OH | CH$_3$ | OH | ethyl |
| 2-H$_2$NCO-phenyl | OH | CH$_3$ | OH | ethyl |
| 2-HO-phenyl | OH | CH$_3$ | OH | ethyl |
| 2-Cl-phenyl | OH | CH$_3$ | OH | ethyl |
| 2-(CH$_3$)$_2$N-phenyl | OH | CH$_3$ | OH | ethyl |
| 4-pyridyl | OH | CH$_3$ | OH | ethyl |
| 3-pyridyl | OH | CH$_3$ | OH | ethyl |
| 2-pyridyl | OH | CH$_3$ | OH | ethyl |
| 2-O$_2$N-phenyl | OH | CH$_3$ | OH | ethyl |
| 3-O$_2$N-phenyl | OH | CH$_3$ | OH | ethyl |
| 4-O$_2$N-phenyl | OH | CH$_3$ | OH | ethyl |
| 2-F-phenyl | OH | CH$_3$ | OH | ethyl |
| 3-F-phenyl | OH | CH$_3$ | OH | ethyl |
| 4-F-phenyl | OH | CH$_3$ | OH | ethyl |
| 2-F$_3$C-phenyl | OH | CH$_3$ | OH | ethyl |
| 3-F$_3$C-phenyl | OH | CH$_3$ | OH | ethyl |
| 4-F$_3$C-phenyl | OH | CH$_3$ | OH | ethyl |
| 4-HO$_2$C-phenyl | OH | CH$_3$ | H | ethyl |
| 4-H$_2$NCO-phenyl | OH | CH$_3$ | H | ethyl |
| 4-HO-phenyl | OH | CH$_3$ | H | ethyl |
| 4-Cl-phenyl | OH | CH$_3$ | H | ethyl |
| 4-(CH$_3$)$_2$N-phenyl | OH | CH$_3$ | H | ethyl |
| 3-HO$_2$C-phenyl | OH | CH$_3$ | H | ethyl |
| 3-H$_2$NCO-phenyl | OH | CH$_3$ | H | ethyl |
| 3-HO-phenyl | OH | CH$_3$ | H | ethyl |
| 3-Cl-phenyl | OH | CH$_3$ | H | ethyl |
| 3-(CH$_3$)$_2$N-phenyl | OH | CH$_3$ | H | ethyl |
| 2-HO$_2$C-phenyl | OH | CH$_3$ | H | ethyl |
| 2-H$_2$NCO-phenyl | OH | CH$_3$ | H | ethyl |
| 2-HO-phenyl | OH | CH$_3$ | H | ethyl |
| 2-Cl-phenyl | OH | CH$_3$ | H | ethyl |
| 2-(CH$_3$)$_2$N-phenyl | OH | CH$_3$ | H | ethyl |
| 4-pyridyl | OH | CH$_3$ | H | ethyl |
| 3-pyridyl | OH | CH$_3$ | H | ethyl |
| 2-pyridyl | OH | CH$_3$ | H | ethyl |
| 2-O$_2$N-phenyl | OH | CH$_3$ | H | ethyl |
| 3-O$_2$N-phenyl | OH | CH$_3$ | H | ethyl |
| 4-O$_2$N-phenyl | OH | CH$_3$ | H | ethyl |
| 2-F-phenyl | OH | CH$_3$ | H | ethyl |
| 3-F-phenyl | OH | CH$_3$ | H | ethyl |
| 4-F-phenyl | OH | CH$_3$ | H | ethyl |
| 2-F$_3$C-phenyl | OH | CH$_3$ | H | ethyl |
| 3-F$_3$C-phenyl | OH | CH$_3$ | H | ethyl |
| 4-F$_3$C-phenyl | OH | CH$_3$ | H | ethyl |
| 3-(CH$_3$)$_2$N-phenyl | OH | CH$_3$ | OH | allyl |
| 2-HO$_2$C-phenyl | OH | CH$_3$ | OH | allyl |
| 2-H$_2$NCO-phenyl | OH | CH$_3$ | OH | allyl |
| 2-HO-phenyl | OH | CH$_3$ | OH | allyl |
| 2-Cl-phenyl | OH | CH$_3$ | OH | allyl |
| 2-(CH$_3$)$_2$N-phenyl | OH | CH$_3$ | OH | allyl |
| 4-pyridyl | OH | CH$_3$ | OH | allyl |
| 3-pyridyl | OH | CH$_3$ | OH | allyl |
| 2-pyridyl | OH | CH$_3$ | OH | allyl |
| 2-O$_2$N-phenyl | OH | CH$_3$ | OH | allyl |
| 3-O$_2$N-phenyl | OH | CH$_3$ | OH | allyl |
| 4-O$_2$N-phenyl | OH | CH$_3$ | OH | allyl |
| 2-F-phenyl | OH | CH$_3$ | OH | allyl |
| 3-F-phenyl | OH | CH$_3$ | OH | allyl |
| 4-F-phenyl | OH | CH$_3$ | OH | allyl |
| 2-F$_3$C-phenyl | OH | CH$_3$ | OH | allyl |
| 3-F$_3$C-phenyl | OH | CH$_3$ | OH | allyl |
| 4-F$_3$C-phenyl | OH | CH$_3$ | OH | allyl |
| CH$_3$ | OH | CH$_3$ | H | ethyl |
| CH$_3$CH$_2$ | OH | CH$_3$ | H | ethyl |
| CH$_3$CH$_2$CH$_2$ | OH | CH$_3$ | H | ethyl |
| (CH$_3$)$_2$CH | OH | CH$_3$ | H | ethyl |
| HO$_2$CCH$_2$CH$_2$ | OH | CH$_3$ | H | ethyl |
| H$_2$NCOCH$_2$CH$_2$ | OH | CH$_3$ | H | ethyl |
| HOCH$_2$CH$_2$ | OH | CH$_3$ | H | ethyl |
| HOCH$_2$CH$_2$CH$_2$ | OH | CH$_3$ | H | ethyl |
| CH$_3$ | OH | H | OH | ethyl |
| CH$_3$CH$_2$ | OH | H | OH | ethyl |

-continued

| R$^{14}$ | R$^1$ | R$^2$ | R$^3$ | R$^5$ |
|---|---|---|---|---|
| CH$_3$CH$_2$CH$_2$ | OH | H | OH | ethyl |
| (CH$_3$)$_2$CH | OH | H | OH | ethyl |
| HO$_2$CCH$_2$CH$_2$ | OH | H | OH | ethyl |
| H$_2$NCOCH$_2$CH$_2$ | OH | H | OH | ethyl |
| HOCH$_2$CH$_2$ | OH | H | OH | ethyl |
| HOCH$_2$CH$_2$CH$_2$ | OH | H | OH | ethyl |
| 4-HO$_2$C-phenyl | H | CH$_3$ | OH | ethyl |
| 4-H$_2$NCO-phenyl | H | CH$_3$ | OH | ethyl |
| 4-HO-phenyl | H | CH$_3$ | OH | ethyl |
| 4-Cl-phenyl | H | CH$_3$ | OH | ethyl |
| 4-(CH$_3$)$_2$N-phenyl | H | CH$_3$ | OH | ethyl |
| 3-HO$_2$C-phenyl | H | CH$_3$ | OH | ethyl |
| 3-H$_2$NCO-phenyl | H | CH$_3$ | OH | ethyl |
| 3-HO-phenyl | H | CH$_3$ | OH | ethyl |
| 3-Cl-phenyl | H | CH$_3$ | OH | ethyl |
| 3-(CH$_3$)$_2$N-phenyl | H | CH$_3$ | OH | ethyl |
| 2-HO$_2$C-phenyl | H | CH$_3$ | OH | ethyl |
| 2-H$_2$NCO-phenyl | H | CH$_3$ | OH | ethyl |
| 2-HO-phenyl | H | CH$_3$ | OH | ethyl |
| 2-Cl-phenyl | H | CH$_3$ | OH | ethyl |
| 2-(CH$_3$)$_2$N-phenyl | H | CH$_3$ | OH | ethyl |
| 4-pyridyl | H | CH$_3$ | OH | ethyl |
| 3-pyridyl | H | CH$_3$ | OH | ethyl |
| 2-pyridyl | H | CH$_3$ | OH | ethyl |
| 2-O$_2$N-phenyl | H | CH$_3$ | OH | ethyl |
| 3-O$_2$N-phenyl | H | CH$_3$ | OH | ethyl |
| 4-O$_2$N-phenyl | H | CH$_3$ | OH | ethyl |
| 2-F-phenyl | H | CH$_3$ | OH | ethyl |
| 3-F-phenyl | H | CH$_3$ | OH | ethyl |
| 4-F-phenyl | H | CH$_3$ | OH | ethyl |
| 2-F$_3$C-phenyl | H | CH$_3$ | OH | ethyl |
| 3-F$_3$C-phenyl | H | CH$_3$ | OH | ethyl |
| 4-F$_3$C-phenyl | H | CH$_3$ | OH | ethyl |
| 3-Cl-phenyl | H | CH$_3$ | H | ethyl |
| 3-(CH$_3$)$_2$N-phenyl | H | CH$_3$ | H | ethyl |
| 2-HO$_2$C-phenyl | H | CH$_3$ | H | ethyl |
| 2-H$_2$NCO-phenyl | H | CH$_3$ | H | ethyl |
| 2-HO-phenyl | H | CH$_3$ | H | ethyl |
| 2-Cl-phenyl | H | CH$_3$ | H | ethyl |
| 2-(CH$_3$)$_2$N-phenyl | H | CH$_3$ | H | ethyl |
| 4-pyridyl | H | CH$_3$ | H | ethyl |
| 3-pyridyl | H | CH$_3$ | H | ethyl |
| 2-pyridyl | H | CH$_3$ | H | ethyl |
| 2-O$_2$N-phenyl | H | CH$_3$ | H | ethyl |
| 3-O$_2$N-phenyl | H | CH$_3$ | H | ethyl |
| 4-O$_2$N-phenyl | H | CH$_3$ | H | ethyl |
| 2-F-phenyl | H | CH$_3$ | H | ethyl |
| 3-F-phenyl | H | CH$_3$ | H | ethyl |
| 4-F-phenyl | H | CH$_3$ | H | ethyl |
| 2-F$_3$C-phenyl | H | CH$_3$ | H | ethyl |
| 3-F$_3$C-phenyl | H | CH$_3$ | H | ethyl |
| 4-F$_3$C-phenyl | H | CH$_3$ | H | ethyl |
| 3-Cl-phenyl | H | CH$_3$ | OH | allyl |
| 3-(CH$_3$)$_2$N-phenyl | H | CH$_3$ | OH | allyl |
| 1-HO$_2$C-phenyl | H | CH$_3$ | OH | allyl |
| 2-H$_2$NCO-phenyl | H | CH$_3$ | OH | allyl |
| 2-HO-phenyl | H | CH$_3$ | OH | allyl |
| 2-Cl-phenyl | H | CH$_3$ | OH | allyl |
| 2-(CH$_3$)$_2$N-phenyl | H | CH$_3$ | OH | allyl |
| 4-pyridyl | H | CH$_3$ | OH | allyl |
| 3-pyridyl | H | CH$_3$ | OH | allyl |
| 2-pyridyl | H | CH$_3$ | OH | allyl |
| 2-O$_2$N-phenyl | H | CH$_3$ | OH | allyl |
| 3-O$_2$N-phenyl | H | CH$_3$ | OH | allyl |
| 4-O$_2$N-phenyl | H | CH$_3$ | OH | allyl |
| 2-F-phenyl | H | CH$_3$ | OH | allyl |
| 3-F-phenyl | H | CH$_3$ | OH | allyl |
| 4-F-phenyl | H | CH$_3$ | OH | allyl |
| 2-F$_3$C-phenyl | H | CH$_3$ | OH | allyl |
| 3-F$_3$C-phenyl | H | CH$_3$ | OH | allyl |
| 4-F$_3$C-phenyl | H | CH$_3$ | OH | allyl |
| CH$_3$ | H | CH$_3$ | H | ethyl |
| CH$_3$CH$_2$ | H | CH$_3$ | H | ethyl |
| CH$_3$CH$_2$CH$_2$ | H | CH$_3$ | H | ethyl |
| (CH$_3$)$_2$CH | H | CH$_3$ | H | ethyl |
| HO$_2$CCH$_2$CH$_2$ | H | CH$_3$ | H | ethyl |
| H$_2$NCOCH$_2$CH$_2$ | H | CH$_3$ | H | ethyl |
| HOCH$_2$CH$_2$ | H | CH$_3$ | H | ethyl |

-continued

| R$^{14}$ | R$^1$ | R$^2$ | R$^3$ | R$^5$ |
|---|---|---|---|---|
| HOCH$_2$CH$_2$CH$_2$ | H | CH$_3$ | H | ethyl |
| CH$_3$ | H | H | OH | ethyl |
| CH$_3$CH$_2$ | H | H | OH | ethyl |
| CH$_3$CH$_2$CH$_2$ | H | H | OH | ethyl |
| (CH$_3$)$_2$CH | H | H | OH | ethyl |
| HO$_2$CCH$_2$CH$_2$ | H | H | OH | ethyl |
| H$_2$NCOCH$_2$CH$_2$ | H | H | OH | ethyl |
| HOCH$_2$CH$_2$ | H | H | OH | ethyl |
| HOCH$_2$CH$_2$CH$_2$ | H | H | OH | ethyl. |

Representative compounds of the present invention include the compounds identified as follows:

17-Ethyl-1,14-dihydroxy-12-[2'-(4"-hydroxy-4"-(penta-2,4-dien-1-yl)- 3"-methoxycyclohexyl)-1'-methylvinyl]-23, 25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-hydroxy-4"-(penta-2,4-dien-1-yl)-3" -methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-hydroxy-4"-(penta-2,4-dien-1-yl)- 3"-methoxycyclohexyl)-1'-methylvinyl]-23, 25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-hydroxy-4"-(5-phenyl-penta-2,4 -dien-1-yl)-3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10,16-tetraone;

17-Ethyl-1-hydroxy-12-[2'-(4"-hydroxy-4"-(5-phenyl-penta-2,4-dien-1 -yl)-3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10,16-tetraone;

17-Allyl-1,14-dihydroxy-12-[2'-(4"-hydroxy-4"-(5-phenyl-penta-2,4 -dien-1-yl)-3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10,16-tetraone;

17-Ethyl-1,14-dihydroxy-12-[2'-(4"-hydroxy-4"-[5-(4-methoxy, phenyl)-penta-2,4-dien-1-yl]-3"-methoxycyclohexyl)-1'-methylvinyl]- 23,25-dimethoxy-13,19,21,27-tetramethyl-11,28-dioxa-4-azatricyclo-[22.3.1.0$^{4,9}$] octacos-18-ene-2,3,10,16-tetraone;

17-Ethyl-1-hydroxy-12-[2'-(4"-hydroxy-4"-[5-(4-methoxyphenyl)-penta- 2,4-dien-1-yl]-3"-methoxycyclohexyl)- 1'-methylvinyl]-23,25 -dimethoxy-13,19,21,27-tetramethyl-11,28-dioxa-4-azatricyclo- [2.3.1.0$^{4,9}$]octacos-18-ene-2,3,10,16-tetraone;

17-Allyl-1,14-dihydroxy-12-[2'-(4"-hydroxy-4"-[5-(4-methoxy-phenyl)-penta- 2,4-dien-1-yl]-3"-methoxycyclohexyl)-1'-methylvinyl]- 23,25-dimethoxy-13,19,21, 27-tetramethyl-11,28-dioxa-4-azatricyclo- [22.3.1.0$^{4,9}$] octacos-18-ene-2,3,10,16-tetraone;

17-Ethyl-1,14-dihydroxy-12-[2'-(4"-hydroxy-4"-[5-(3-methoxy-phenyl)-penta- 2,4-dien-1-yl]-3"-methoxycyclohexyl)-1'-methylvinyl]- 23,25-dimethoxy-13,19,21, 27-tetramethyl-11,28-dioxa-4-azatricyclo- [22.3.1.0$^{4,9}$] octacos-18-ene-2,3,10,16-tetraone;

17-Ethyl-1-hydroxy-12-[2'-(4"-hydroxy-4"-[5-(3-methoxyphenyl)-penta- 2,4-dien-1-yl]-3"-methoxycyclohexyl)- 1'-methylvinyl]-23,25-dimethoxy- 13,19,21,27-tetramethyl-11,28-dioxa-4-azatricyclo- 22.3.1.0$^{4,9}$]octacos-18-ene-2,3,10,16-tetraone;

17-Allyl-1,14-dihydroxy-12-[2'-(4"-hydroxy-4"-[5-(3-methoxy-phenyl)-penta-2,4-dien-1-yl]-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10, 16-tetraone;

17-Ethyl-1,14-dihydroxy-12-[2'-(4"-hydroxy-4"-[5-(3,5-dimethoxy-phenyl)-penta-2,4-dien-1-yl]-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3, 10, 16-tetraone;

17-Ethyl-1-hydroxy-12-[2'-(4"-hydroxy-4"-[5-(3,5-dimethoxyphenyl)-penta-2,4-dien-1-yl]-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Allyl-1,14-dihydroxy-12-[2'-(4"-hydroxy-4"-[5-(3,5-dimethoxy-phenyl)-penta-2,4-dien-1-yl]-3"-methoxycyclohexyl)-1'-methylvinyl]-23,25-dimethoxy-13,19,21,27-tetramethyl-11,28-dioxa-4-azatricycl-[22.3.1.0$^{4,9}$]octacos-18-ene-2,3,10,16-tetraone;

or a pharmaceutically acceptable salt thereof.

Representative compounds of the present invention include the compounds of formula 13–16:

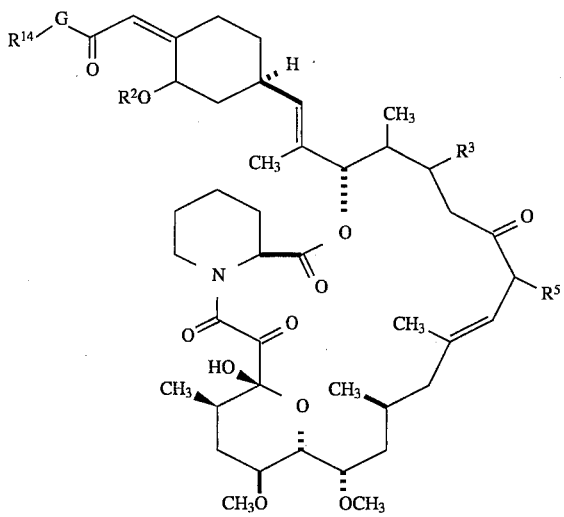

13

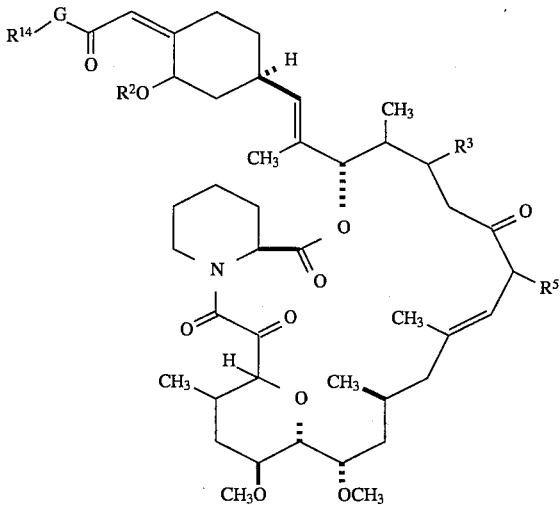

14

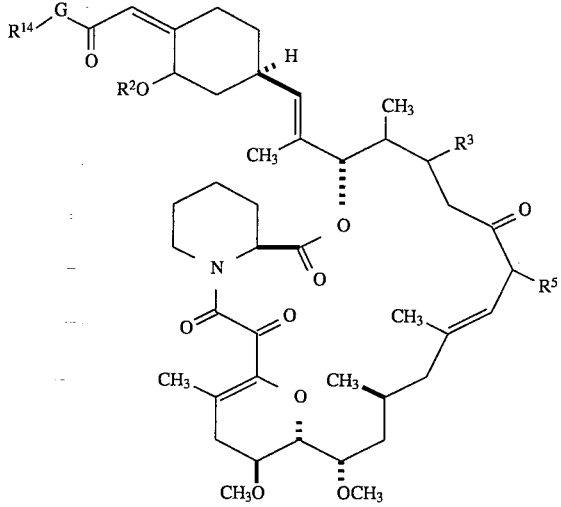

15

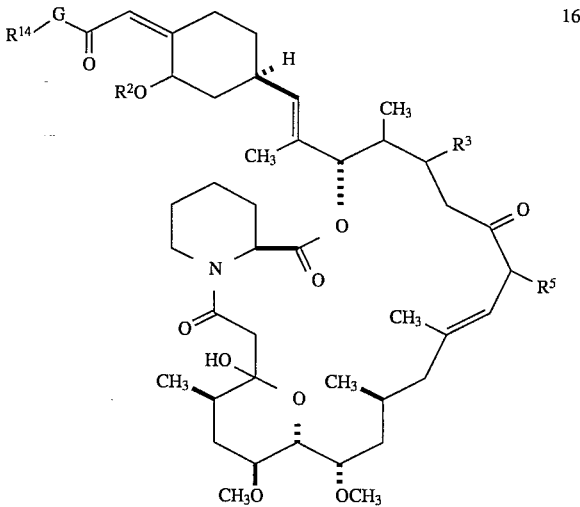

16 wherein for each of formula 13–16 the definitions of $R^{14}$, G, $R^2$, $R^3$ and $R^5$ are selected from the following groups of substituents:

| $R^{14}$ | G | $R^2$ | $R^3$ | $R^5$ |
|---|---|---|---|---|
| 4-HO$_2$C-phenyl | O | CH$_3$ | OH | ethyl |
| 4-H$_2$NCO-phenyl | O | CH$_3$ | OH | ethyl |
| 4-HO-phenyl | O | CH$_3$ | OH | ethyl |
| 4-Cl-phenyl | O | CH$_3$ | OH | ethyl |
| 4-(CH$_3$)$_2$N-phenyl | O | CH$_3$ | OH | ethyl |
| 3-HO$_2$C-phenyl | O | CH$_3$ | OH | ethyl |
| 3-H$_2$NCO-phenyl | O | CH$_3$ | OH | ethyl |
| 3-HO-phenyl | O | CH$_3$ | OH | ethyl |
| 3-Cl-phenyl | O | CH$_3$ | OH | ethyl |
| 3-(CH$_3$)$_2$N-phenyl | O | CH$_3$ | OH | ethyl |
| 2-HO$_2$C-phenyl | O | CH$_3$ | OH | ethyl |
| 2-H$_2$NCO-phenyl | O | CH$_3$ | OH | ethyl |
| 2-HO-phenyl | O | CH$_3$ | OH | ethyl |
| 2-Cl-phenyl | O | CH$_3$ | OH | ethyl |
| 2-(CH$_3$)$_2$N-phenyl | O | CH$_3$ | OH | ethyl |
| 4-pyridylmethyl | O | CH$_3$ | OH | ethyl |
| 3-pyridylmethyl | O | CH$_3$ | OH | ethyl |
| 2-pyridylmethyl | O | CH$_3$ | OH | ethyl |
| 2-O$_2$N-phenyl | O | CH$_3$ | OH | ethyl |
| 3-O$_2$N-phenyl | O | CH$_3$ | OH | ethyl |
| 4-O$_2$N-phenyl | O | CH$_3$ | OH | ethyl |
| 2-F-phenyl | O | CH$_3$ | OH | ethyl |
| 3-F-phenyl | O | CH$_3$ | OH | ethyl |
| 4-F-phenyl | O | CH$_3$ | OH | ethyl |
| 2-F$_3$C-phenyl | O | CH$_3$ | OH | ethyl |

| R14 | G | R2 | R3 | R5 |
|---|---|---|---|---|
| 3-F3C-phenyl | O | CH3 | OH | ethyl |
| 4-F3C-phenyl | O | CH3 | OH | ethyl |
| 3-Cl-phenyl | O | CH3 | H | ethyl |
| 3-(CH3)2N-phenyl | O | CH3 | H | ethyl |
| 2-HO2C-phenyl | O | CH3 | H | ethyl |
| 2-H2NCO-phenyl | O | CH3 | H | ethyl |
| 2-HO-phenyl | O | CH3 | H | ethyl |
| 2-Cl-phenyl | O | CH3 | H | ethyl |
| 2-(CH3)2N-phenyl | O | CH3 | H | ethyl |
| 4-pyridylmethyl | O | CH3 | H | ethyl |
| 3-pyridylmethyl | O | CH3 | H | ethyl |
| 2-pyridylmethyl | O | CH3 | H | ethyl |
| 2-O2N-phenyl | O | CH3 | H | ethyl |
| 3-O2N-phenyl | O | CH3 | H | ethyl |
| 4-O2N-phenyl | O | CH3 | H | ethyl |
| 2-F-phenyl | O | CH3 | H | ethyl |
| 3-F-phenyl | O | CH3 | H | ethyl |
| 4-F-phenyl | O | CH3 | H | ethyl |
| 2-F3C-phenyl | O | CH3 | H | ethyl |
| 3-F3C-phenyl | O | CH3 | H | ethyl |
| 4-F3C-phenyl | O | CH3 | H | ethyl |
| 3-Cl-phenyl | O | CH3 | OH | allyl |
| 3-(CH3)2N-phenyl | O | CH3 | OH | allyl |
| 2-HO2C-phenyl | O | CH3 | OH | allyl |
| 2-H2NCO-phenyl | O | CH3 | OH | allyl |
| 2-HO-phenyl | O | CH3 | OH | allyl |
| 2-Cl-phenyl | O | CH3 | OH | allyl |
| 2-(CH3)2N-phenyl | O | CH3 | OH | allyl |
| 4-pyridylmethyl | O | CH3 | OH | allyl |
| 3-pyridylmethyl | O | CH3 | OH | allyl |
| 2-pyridylmethyl | O | CH3 | OH | allyl |
| 2-O2N-phenyl | O | CH3 | OH | allyl |
| 3-O2N-phenyl | O | CH3 | OH | allyl |
| 4-O2N-phenyl | O | CH3 | OH | allyl |
| 2-F-phenyl | O | CH3 | OH | allyl |
| 3-F-phenyl | O | CH3 | OH | allyl |
| 4-F-phenyl | O | CH3 | OH | allyl |
| 2-F3C-phenyl | O | CH3 | OH | allyl |
| 3-F3C-phenyl | O | CH3 | OH | allyl |
| 4-F3C-phenyl | O | CH3 | OH | allyl |
| CH3CH2 | O | CH3 | H | ethyl |
| CH3CH2CH2 | O | CH3 | H | ethyl |
| (CH3)2CH | O | CH3 | H | ethyl |
| HO2CCH2CH2 | O | CH3 | H | ethyl |
| H2NCOCH2CH2 | O | CH3 | H | ethyl |
| HOCH2CH2 | O | CH3 | H | ethyl |
| HOCH2CH2CH2 | O | CH3 | H | ethyl |
| CH3 | O | H | OH | ethyl |
| CH3O2 | O | H | OH | ethyl |
| CH3CH2CH2 | O | H | OH | ethyl |
| (CH3)2CH | O | H | OH | ethyl |
| HO2CCH2CH2 | O | H | OH | ethyl |
| H2NCOCH2CH2 | O | H | OH | ethyl |
| HOCH2CH2 | O | H | OH | ethyl |
| HOCH2CH2CH2 | O | H | OH | ethyl |
| 4-HO2C-phenyl | NH | CH3 | OH | ethyl |
| 4-H2NCO-phenyl | NH | CH3 | OH | ethyl |
| 4-HO-phenyl | NH | CH3 | OH | ethyl |
| 4-Cl-phenyl | NH | CH3 | OH | ethyl |
| 4-(CH3)2N-phenyl | NH | CH3 | OH | ethyl |
| 3-HO2C-phenyl | NH | CH3 | OH | ethyl |
| 3-H2NCO-phenyl | NH | CH3 | OH | ethyl |
| 3-HO-phenyl | NH | CH3 | OH | ethyl |
| 3-Cl-phenyl | NH | CH3 | OH | ethyl |
| 3-(CH3)2N-phenyl | NH | CH3 | OH | ethyl |
| 2-HO2C-phenyl | NH | CH3 | OH | ethyl |
| 2-H2NCO-phenyl | NH | CH3 | OH | ethyl |
| 2-HO-phenyl | NH | CH3 | OH | ethyl |
| 2-Cl-phenyl | NH | CH3 | OH | ethyl |
| 2-(CH3)2N-phenyl | NH | CH3 | OH | ethyl |
| 4-pyridylmethyl | NH | CH3 | OH | ethyl |
| 3-pyridylmethyl | NH | CH3 | OH | ethyl |
| 2-pyridylmethyl | NH | CH3 | OH | ethyl |
| 2-O2N-phenyl | NH | CH3 | OH | ethyl |
| 3-O2N-phenyl | NH | CH3 | OH | ethyl |
| 4-O2N-phenyl | NH | CH3 | OH | ethyl |
| 1-F-phenyl | NH | CH3 | OH | ethyl |
| 3-F-phenyl | NH | CH3 | OH | ethyl |
| 4-F-phenyl | NH | CH3 | OH | ethyl |
| 1-F3C-phenyl | NH | CH3 | OH | ethyl |
| 3-F3C-phenyl | NH | CH3 | OH | ethyl |
| 4-F3C-phenyl | NH | CH3 | OH | ethyl |
| 3-Cl-phenyl | NH | CH3 | H | ethyl |
| 3-(CH3)2N-phenyl | NH | CH3 | H | ethyl |
| 2-HO2C-phenyl | NH | CH3 | H | ethyl |
| 2-H2NCO-phenyl | NH | CH3 | H | ethyl |
| 2-HO-phenyl | NH | CH3 | H | ethyl |
| 2-Cl-phenyl | NH | CH3 | H | ethyl |
| 2-(CH3)2N-phenyl | NH | CH3 | H | ethyl |
| 4-pyridylmethyl | NH | CH3 | H | ethyl |
| 3-pyridylmethyl | NH | CH3 | H | ethyl |
| 2-pyridylmethyl | NH | CH3 | H | ethyl |
| 2-O2N-phenyl | NH | CH3 | H | ethyl |
| 3-O2N-phenyl | NH | CH3 | H | ethyl |
| 4-O2N-phenyl | mi | CH3 | H | ethyl |
| 2-F-phenyl | NH | CH3 | H | ethyl |
| 3-F-phenyl | NH | CH3 | H | ethyl |
| 4-F-phenyl | NH | CH3 | H | ethyl |
| 2-F3C-phenyl | NH | CH3 | H | ethyl |
| 3-F3C-phenyl | NH | CH3 | H | ethyl |
| 4-F3C-phenyl | NH | CH3 | H | ethyl |
| 3-Cl-phenyl | NH | CH3 | OH | allyl |
| 3-(CH3)2N-phenyl | NH | CH3 | OH | allyl |
| 2-HO2C-phenyl | NH | CH3 | OH | allyl |
| 2-H2NCO-phenyl | NH | CH3 | OH | allyl |
| 2-HO-phenyl | NH | CH3 | OH | allyl |
| 2-Cl-phenyl | NH | CH3 | OH | allyl |
| 2-(CH3)2N-phenyl | NH | CH3 | OH | allyl |
| 4-pyridylmethyl | NH | CH3 | OH | allyl |
| 3-pyridylmethyl | NH | CH3 | OH | allyl |
| 2-pyridylmethyl | NH | CH3 | OH | allyl |
| CH3CH2 | NH | CH3 | OH | ethyl |
| CH3CH2CH2 | NH | CH3 | OH | ethyl |
| (CH3)2CH | NH | CH3 | OH | ethyl |
| HO2CCH2CH2 | NH | CH3 | OH | ethyl |
| H2NCOCH2CH2 | NH | CH3 | OH | ethyl |
| HOCH2CH2 | NH | CH3 | OH | ethyl |
| HOCH2CH2CH2 | NH | CH3 | OH | ethyl |
| CH3 | NH | CH3 | H | ethyl |
| CH3CH2 | NH | CH3 | H | ethyl |
| CH3CH2CH2 | NH | CH3 | H | ethyl |
| (CH3)2CH | NH | CH3 | H | ethyl |
| HO2CCH2CH2 | NH | CH3 | H | ethyl |
| H2NCOH2CH2 | NH | CH3 | H | ethyl |
| HOCH2CH2 | NH | CH3 | H | ethyl |
| HOCH2CH2CH2 | NH | CH3 | H | ethyl |
| CH3 | NH | H | OH | ethyl |
| CH3CH2 | NH | H | OH | ethyl |
| CH3CH2CH2 | NH | H | OH | ethyl |
| (CH3)2CH | NH | H | OH | ethyl |
| HO2CCH2CH2 | NH | H | OH | ethyl |
| H2NCOCH2CH2 | NH | H | OH | ethyl |
| HOCH2CH2 | NH | H | OH | ethyl |
| HOCH2CH2CH2 | NH | H | OH | ethyl |

Representative compounds of the present invention include the compounds identified as follows:

17-Ethyl-1,14odihydroxy-12-[2'-(4"-(2-carboxymethylidene)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-(2-carboxymethylidene)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-(2-carboxymethylidene)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-(2-methoxycarbonylmethylidene- 3"-methoxycyclohexyl)-1'-methylvinyl]-23, 25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-(2-methoxycarbonylmethylidene)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-(2-methoxycarbonyl methylidene)- 3"-methoxycyclohexyl)-1'-methylvinyl]-23,25-dimethoxy-13,19,21,27-tetramethyl- 11,28-dioxa-4-azatricyclo-[22.3.1.0$^{4,9}$]octacos-18-ene- 2,3,10,16-tetraone;

17-Ethyl-1,14-dihydroxy-12-[2'-(4"-(2-benzyloxycarbonyl-methylidene)- 3"-methoxycyclohexyl)-1'-methylvinyl]-23,25-dimethoxy- 13,19,21,27-tetramethyl-11,28-dioxa-4-azatricyclo-[22.3.1.0$^{4,9}$]octacos- 18-ene-2,3,10,16-tetraone;

17-Ethyl-1-hydroxy-12-[2'-(4"-hydroxy-4"-(2-benzyloxycarbonyl-methylidene)- 3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10,16-tetraone;

17-Allyl-1,14-dihydroxy-12-[2'-(4"-hydroxy-4"-(2-benzyloxycarbonyl-methylidene)- 3"-methoxycyclohexyl)-1'-methylvinyl]-23,25-dimethoxy- 13,19,21,27-tetramethyl-11,28-dioxa-4-azatricyclo-[22.3.1.0$^{4,9}$]octacos- 18-ene-2, 3,10,16-tetraone;

17-Ethyl-1,14-dihydroxy-12-[2'-(4"-hydroxy-4"-(2-benzylamino-carbonylmethylidene)- 3"-methoxycyclohexyl)-1'-methylvinyl]-23,25-dimethoxy- 13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-hydroxy-4"-(2-benzylaminocarbonyl-methylidene)- 3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10,16-tetraone;

17-Allyl-1,14-dihydroxy-12-[2'-(4"-hydroxy-4"-(2-benzylamino-carbonylmethylidene)- 3"-methoxycyclohexyl)-1'-methylvinyl]-23,25-dimethoxy- 13,19,24,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2-carboxymethylidene)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-(2-carboxymethylenyl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-(2-carboxymethylenyl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$ octacos-18-ene- 2,3,10,16-tetraone;

17-Ethyl-1,14-dihydroxy-12-[2'-(4"-(2-methoxycarbonylmethylenyl-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-(2-methoxycarbonylmethylenyl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-(2-methoxycarbonylmethylenyl)- 3"-methoxycyclohexyl)-1'-methylvinyl]-23, 25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-(2-benzyloxycarbonyl methylenyl)- 3"-methoxycyclohexyl)-1'-methylvinyl]-23, 25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-hydroxy-4"-(2-benzyloxycarbonyl-methylenyl)- 3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10, 16-tetraone;

17-Allyl-1,14-dihydroxy-12-[2'-(4"-hydroxy-4"-(2-benzyloxycarbonylmethylenyl)- 3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10,16-tetraone;

17-Ethyl-1,14-dihydroxy-12-[2'-(4"-hydroxy-4"-(2-benzylamino-carbonylmethylenyl)- 3"-methoxycyclohexyl)-1'-methylvinyl]-23,25-dimethoxy- 13,19,21,27-tetramethyl-11,28-dioxa-4-azatricyclo- [22.3.1.0$^{4,9}$]octacos-18-ene-2, 3,10,16-tetraone;

17-Ethyl-1-hydroxy-12-[2'-(4"-hydroxy-4"-(2-benzylaminocarbonyl-methylenyl)- 3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10,16-tetraone;

17-Allyl-1,14-dihydroxy-12-[2'-(4"-hydroxy-4"-(2-benzylamino-carbonylmethylenyl)- 3"-methoxycyclohexyl)-1'-methylvinyl]-23,25 -dimethoxy-13,19,21,27-tetramethyl-11,28-dioxa-4-azatricyclo-[22.3.1.0$^{4,9}$]octacos-18-ene-2, 3,10,16-tetraone;

or a pharmaceutically acceptable salt thereof.

Representative compounds of the present invention include the compounds of formula 17–19:

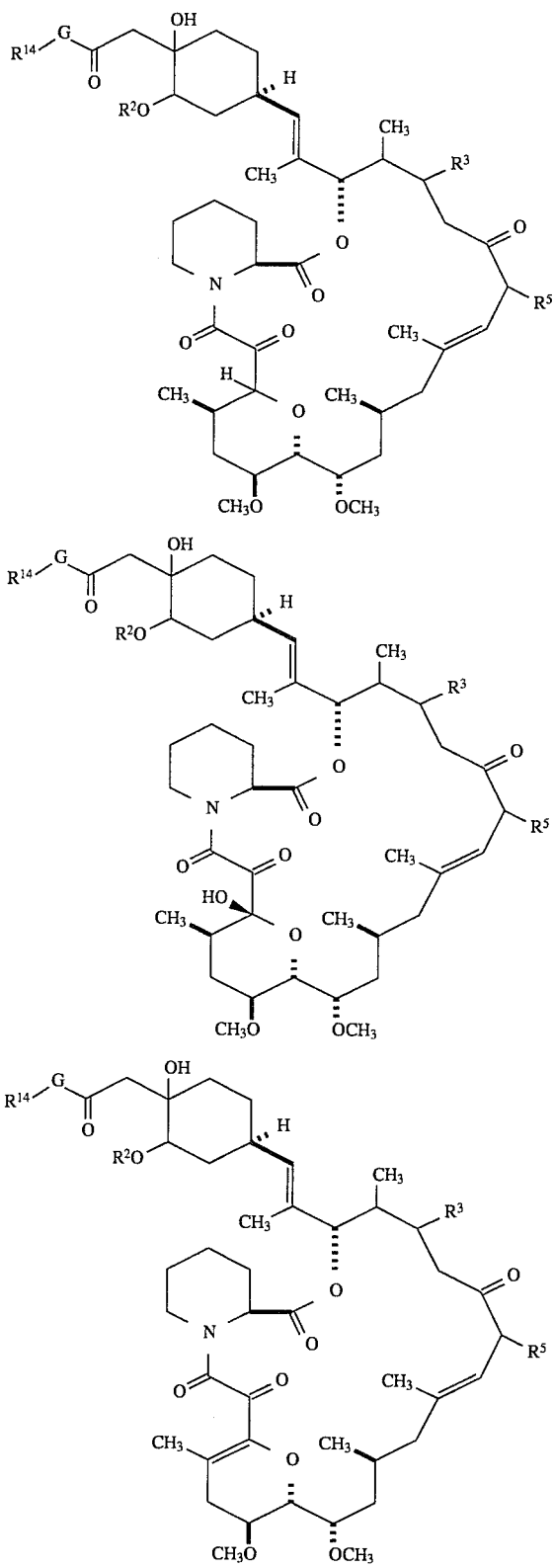

wherein for each of formula 17–19 the definitions of $R^{14}$, G, $R^2$, $R^3$ and $R^5$ are selected from the following groups of substituents:

| $R^{14}$ | G | $R^2$ | $R^3$ | $R^5$ |
| --- | --- | --- | --- | --- |
| 4-HO$_2$C-phenyl | O | CH$_3$ | OH | ethyl |
| 4-H$_2$NCO-phenyl | O | CH$_3$ | OH | ethyl |
| 4-HO-phenyl | O | CH$_3$ | OH | ethyl |
| 4-Cl-phenyl | O | CH$_3$ | OH | ethyl |
| 4-(CH$_3$)$_2$N-phenyl | O | CH$_3$ | OH | ethyl |
| 3-HO$_2$C-phenyl | O | CH$_3$ | OH | ethyl |
| 3-H$_2$NCO-phenyl | O | CH$_3$ | OH | ethyl |
| 3-HO-phenyl | O | CH$_3$ | OH | ethyl |
| 3-Cl-phenyl | O | CH$_3$ | OH | ethyl |
| 3-(CH$_3$)$_2$N-phenyl | O | CH$_3$ | OH | ethyl |
| 2-HO$_2$C-phenyl | O | CH$_3$ | OH | ethyl |
| 2-H$_2$NCO-phenyl | O | CH$_3$ | OH | ethyl |
| 2-HO-phenyl | O | CH$_3$ | OH | ethyl |
| 2-Cl-phenyl | O | CH$_3$ | OH | ethyl |
| 2-(CH$_3$)$_2$N-phenyl | O | CH$_3$ | OH | ethyl |
| 4-pyridylmethyl | O | CH$_3$ | OH | ethyl |
| 3-pyridylmethyl | O | CH$_3$ | OH | ethyl |
| 2-pyridylmethyl | O | CH$_3$ | OH | ethyl |
| 2-O$_2$N-phenyl | O | CH$_3$ | OH | ethyl |
| 3-O$_2$N-phenyl | O | CH$_3$ | OH | ethyl |
| 4-O$_2$N-phenyl | O | CH$_3$ | OH | ethyl |
| 2-F-phenyl | O | CH$_3$ | OH | ethyl |
| 3-F-phenyl | O | CH$_3$ | OH | ethyl |
| 4-F-phenyl | O | CH$_3$ | OH | ethyl |
| 2-F$_3$C-phenyl | O | CH$_3$ | OH | ethyl |
| 3-F$_3$C-phenyl | O | CH$_3$ | OH | ethyl |
| 4-F$_3$C-phenyl | O | CH$_3$ | OH | ethyl |
| 2-Cl-phenyl | O | CH$_3$ | H | ethyl |
| 3-(CH$_3$)$_2$N-phenyl | O | CH$_3$ | H | ethyl |
| 2-HO$_2$C-phenyl | O | CH$_3$ | H | ethyl |
| 2-H$_2$NCO-phenyl | O | CH$_3$ | H | ethyl |
| 2-HO-phenyl | O | CH$_3$ | H | ethyl |
| 2-Cl-phenyl | O | CH$_3$ | H | ethyl |
| 2-(CH$_3$)$_2$N-phenyl | O | CH$_3$ | H | ethyl |
| 4-pyridylmethyl | O | CH$_3$ | H | ethyl |
| 3-pyridylmethyl | O | CH$_3$ | H | ethyl |
| 2-pyridylmethyl | O | CH$_3$ | H | ethyl |
| 2-O$_2$N-phenyl | O | CH$_3$ | H | ethyl |
| 3-O$_2$N-phenyl | O | CH$_3$ | H | ethyl |
| 4-O$_2$N-phenyl | O | CH$_3$ | H | ethyl |
| 2-F-phenyl | O | CH$_3$ | H | ethyl |
| 3-F-phenyl | O | CH$_3$ | H | ethyl |
| 4-F-phenyl | O | CH$_3$ | H | ethyl |
| 2-F$_3$C-phenyl | O | CH$_3$ | H | ethyl |
| 3-F$_3$C-phenyl | O | CH$_3$ | H | ethyl |
| 4-F$_3$C-phenyl | O | CH$_3$ | H | ethyl |
| 3-Cl-phenyl | O | CH$_3$ | OH | allyl |
| 3-(CH$_3$)$_2$N-phenyl | O | CH$_3$ | OH | allyl |
| 2-HO$_2$C-phenyl | O | CH$_3$ | OH | allyl |
| 2-H$_2$NCO-phenyl | O | CH$_3$ | OH | allyl |
| 2-HO-phenyl | O | CH$_3$ | OH | allyl |
| 2-Cl-phenyl | O | CH$_3$ | OH | allyl |
| 2-(CH$_3$)$_2$N-phenyl | O | CH$_3$ | OH | allyl |
| 4-pyridylmethyl | O | CH$_3$ | OH | allyl |
| 3-pyridylmethyl | O | CH$_3$ | OH | allyl |
| 2-pyridylmethyl | O | CH$_3$ | OH | allyl |
| 2-O$_2$N-phenyl | O | CH$_3$ | OH | allyl |
| 3-O$_2$N-phenyl | O | CH$_3$ | OH | allyl |
| 4-O$_2$N-phenyl | O | CH$_3$ | OH | allyl |
| 2-F-phenyl | O | CH$_3$ | OH | allyl |
| 3-F-phenyl | O | CH$_3$ | OH | allyl |
| 4-F-phenyl | O | CH$_3$ | OH | allyl |
| 2-F$_3$C-phenyl | O | CH$_3$ | OH | allyl |
| 3-F$_3$C-phenyl | O | CH$_3$ | OH | allyl |
| 4-F$_3$C-phenyl | O | CH$_3$ | OH | allyl |
| CH$_3$CH$_2$ | O | CH$_3$ | H | ethyl |
| CH$_3$CH$_2$CH$_2$ | O | CH$_3$ | H | ethyl |
| (CH$_3$)$_2$CH | O | CH$_3$ | H | ethyl |
| HO$_2$CCH$_2$CH$_2$ | O | CH$_3$ | H | ethyl |
| H$_2$NCOCH$_2$CH$_2$ | O | CH$_3$ | H | ethyl |
| HOCH$_2$CH$_2$ | O | CH$_3$ | H | ethyl |
| HOCH$_2$CH$_2$CH$_2$ | O | CH$_3$ | H | ethyl |
| CH$_3$ | O | H | OH | ethyl |
| CH$_3$CH$_2$ | O | H | OH | ethyl |
| CH$_3$CH$_2$CH$_2$ | O | H | OH | ethyl |
| (CH$_3$)$_2$CH | O | H | OH | ethyl |

| $R^{14}$ | G | $R^2$ | $R^3$ | $R^5$ |
|---|---|---|---|---|
| HO₂CCH₂CH₂ | O | H | OH | ethyl |
| H₂NCOCH₂CH₂ | O | H | OH | ethyl |
| HOCH₂CH₂ | O | H | OH | ethyl |
| HOCH₂CH₂CH₂ | O | H | OH | ethyl |
| 4-HO₂C-phenyl | NH | CH₃ | OH | ethyl |
| 4-H₂NCO-phenyl | NH | CH₃ | OH | ethyl |
| 4-HO-phenyl | NH | CH₃ | OH | ethyl |
| 4-Cl-phenyl | NH | CH₃ | OH | ethyl |
| 4-(CH₃)₂N-phenyl | NH | CH₃ | OH | ethyl |
| 3-HO₂C-phenyl | NH | CH₃ | OH | ethyl |
| 3-H₂NCO-phenyl | NH | CH₃ | OH | ethyl |
| 3-HO-phenyl | NH | CH₃ | OH | ethyl |
| 3-Cl-phenyl | NH | CH₃ | OH | ethyl |
| 3-(CH₃)₂N-phenyl | NH | CH₃ | OH | ethyl |
| 2-HO₂C-phenyl | NH | CH₃ | OH | ethyl |
| 2-H₂NCO-phenyl | NH | CH₃ | OH | ethyl |
| 2-HO-phenyl | NH | CH₃ | OH | ethyl |
| 2-Cl-phenyl | NH | CH₃ | OH | ethyl |
| 2-(CH₃)₂N-phenyl | NH | CH₃ | OH | ethyl |
| 4-pyridylmethyl | NH | CH₃ | OH | ethyl |
| 3-pyridylmethyl | NH | CH₃ | OH | ethyl |
| 2-pyridylmethyl | NH | CH₃ | OH | ethyl |
| 2-O₂N-phenyl | NH | CH₃ | OH | ethyl |
| 3-O₂N-phenyl | NH | CH₃ | OH | ethyl |
| 4-O₂N-phenyl | NH | CH₃ | OH | ethyl |
| 2-F-phenyl | NH | CH₃ | OH | ethyl |
| 3-F-phenyl | NH | CH₃ | OH | ethyl |
| 4-F-phenyl | NH | CH₃ | OH | ethyl |
| 2-F₃C-phenyl | NH | CH₃ | OH | ethyl |
| 3-F₃C-phenyl | NH | CH₃ | OH | ethyl |
| 4-F₃C-phenyl | NH | CH₃ | OH | ethyl |
| 3-Cl-phenyl | NH | CH₃ | H | ethyl |
| 3-(CH₃)₂N-phenyl | NH | CH₃ | H | ethyl |
| 2-HO₂C-phenyl | NH | CH₃ | H | ethyl |
| 2-H₂NCO-phenyl | NH | CH₃ | H | ethyl |
| 2-HO-phenyl | NH | CH₃ | H | ethyl |
| 2-Cl-phenyl | NH | CH₃ | H | ethyl |
| 2-(CH₃)₂N-phenyl | NH | CH₃ | H | ethyl |
| 4-pyridylmethyl | NH | CH₃ | H | ethyl |
| 3-pyridylmethyl | NH | CH₃ | H | ethyl |
| 2-pyridylmethyl | NH | CH₃ | H | ethyl |
| 2-O₂N-phenyl | NH | CH₃ | H | ethyl |
| 3-O₂N-phenyl | NH | CH₃ | H | ethyl |
| 4-O₂N-phenyl | NH | CH₃ | H | ethyl |
| 2-F-phenyl | NH | CH₃ | H | ethyl |
| 3-F-phenyl | NH | CH₃ | H | ethyl |
| 4-F-phenyl | NH | CH₃ | H | ethyl |
| 2-F₃C-phenyl | NH | CH₃ | H | ethyl |
| 3-F₃C-phenyl | NH | CH₃ | H | ethyl |
| 4-F₃C-phenyl | NH | CH₃ | H | ethyl |
| 3-Cl-phenyl | NH | CH₃ | OH | allyl |
| 3-(CH₃)₂N-phenyl | NH | CH₃ | OH | allyl |
| 2-HO₂C-phenyl | NH | CH₃ | OH | allyl |
| 2-H₂NCO-phenyl | NH | CH₃ | OH | allyl |
| 2-HO-phenyl | NH | CH₃ | OH | allyl |
| 2-Cl-phenyl | NH | CH₃ | OH | allyl |
| 2-(CH₃)₂N-phenyl | NH | CH₃ | OH | allyl |
| 4-pyridylmethyl | NH | CH₃ | OH | allyl |
| 3-pyridylmethyl | NH | CH₃ | OH | allyl |
| 2-pyridylmethyl | NH | CH₃ | OH | allyl |
| CH₃CH₂ | NH | CH₃ | OH | ethyl |
| CH₃CH₂CH₂ | NH | CH₃ | OH | ethyl |
| (CH₃)₂CH | NH | CH₃ | OH | ethyl |
| HO₂CCH₂CH₂ | NH | CH₃ | OH | ethyl |
| H₂NCOCH₂CH₂ | NH | CH₃ | OH | ethyl |
| HOCH₂CH₂ | NH | CH₃ | OH | ethyl |
| HOCH₂CH₂CH₂ | NH | CH₃ | OH | ethyl |
| CH₃ | NH | CH₃ | H | ethyl |
| CH₃CH₂ | NH | CH₃ | H | ethyl |
| CH₃CH₂CH₂ | NH | CH₃ | H | ethyl |
| (CH₃)₂CH | NH | CH₃ | H | ethyl |
| HO₂CCH₂CH₂ | NH | CH₃ | H | ethyl |
| H₂NCOCH₂CH₂ | NH | CH₃ | H | ethyl |
| HOCH₂CH₂ | NH | CH₃ | H | ethyl |
| HOCH₂CH₂CH₂ | NH | CH₃ | H | ethyl |
| CH₃ | NH | H | OH | ethyl |
| CH₃CH₂ | NH | H | OH | ethyl |
| CH₃CH₂CH₂ | NH | H | OH | ethyl |
| (CH₃)₂CH | NH | H | OH | ethyl |
| HO₂CCH₂CH₂ | NH | H | OH | ethyl |
| H₂NCOCH₂CH₂ | NH | H | OH | ethyl |
| HOCH₂CH₂ | NH | H | OH | ethyl |
| HOCH₂CH₂CH₂ | NH | H | OH | ethyl |

Representative compounds of the present invention include the compounds of formula 20–25:

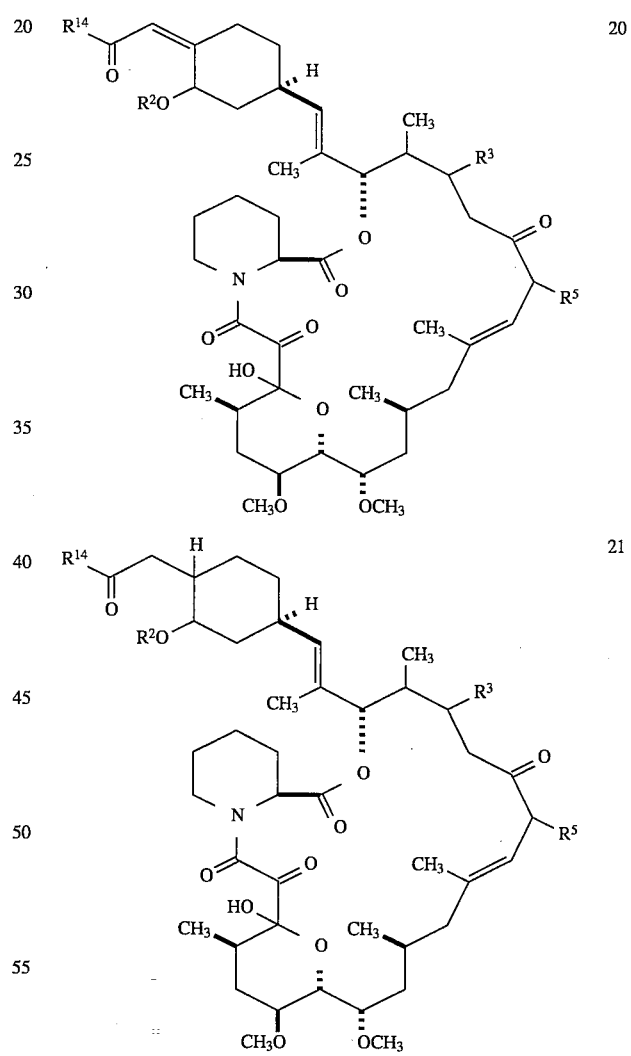

39
-continued

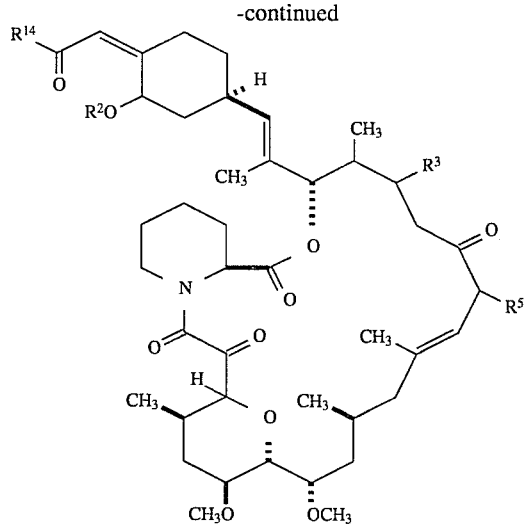

22

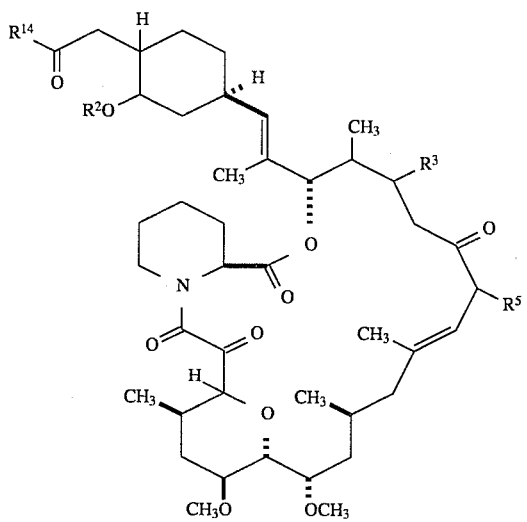

23

24

40
-continued

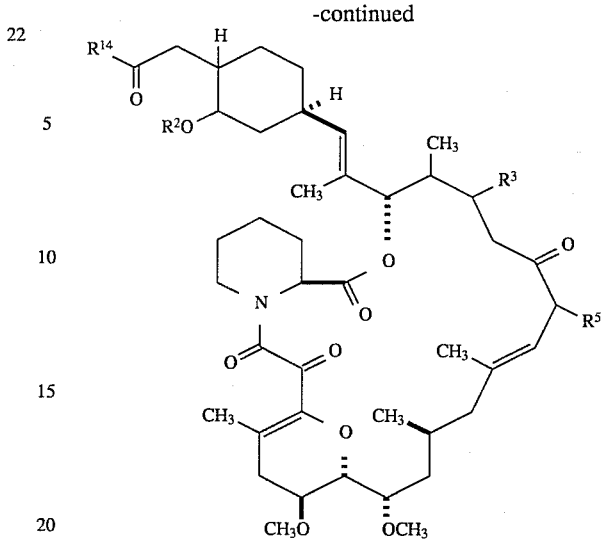

25 wherein for each of formula 20–25 the definitions of $R^2$, $R^3$, $R^5$, and $R^{14}$ are selected from the following groups of substituents:

| $R^{14}$ | $R^2$ | $R^3$ | $R^5$ |
|---|---|---|---|
| $CH_3$ | $CH_3$ | OH | ethyl |
| $CH_3CH_2$ | $CH_3$ | OH | ethyl |
| $CH_2$=$CHCH_2$ | $CH_3$ | OH | ethyl |
| $CH_3CH_2CH_2$ | $CH_3$ | OH | ethyl |
| $(CH_3)_2CH$ | $CH_3$ | OH | ethyl |
| $HO_2CCH_2CH_2$ | $CH_3$ | OH | ethyl |
| $H_2NCOCH_2CH_2$ | $CH_3$ | OH | ethyl |
| $HOCH_2CH_2$ | $CH_3$ | OH | ethyl |
| $HOCH_2CH_2CH_2$ | $CH_3$ | OH | ethyl |
| $(CH_3)_2CH$ | $CH_3$ | OH | ethyl |
| phenyl | $CH_3$ | OH | ethyl |
| 4-pyridyl | $CH_3$ | OH | ethyl |
| 3-pyridyl | $CH_3$ | OH | ethyl |
| 2-pyridyl | $CH_3$ | OH | ethyl |
| 4-pyridylmethyl | $CH_3$ | OH | ethyl |
| 3-pyridylmethyl | $CH_3$ | OH | ethyl |
| 2-pyridylmethyl | $CH_3$ | OH | ethyl |
| benzyl | $CH_3$ | OH | ethyl |
| 4-$HO_2C$-benzyl | $CH_3$ | OH | ethyl |
| 4-$H_2NCO$-benzyl | $CH_3$ | OH | ethyl |
| 4-$CH_3O$-benzyl | $CH_3$ | OH | ethyl |
| 4-HO-benzyl | $CH_3$ | OH | ethyl |
| 4-Cl-benzyl | $CH_3$ | OH | ethyl |
| 4-$(CH_3)_2N$-benzyl | $CH_3$ | OH | ethyl |
| 3-$HO_2C$-benzyl | $CH_3$ | OH | ethyl |
| 3-$H_2NCO$-benzyl | $CH_3$ | OH | ethyl |
| 3-$CH_3O$-benzyl | $CH_3$ | OH | ethyl |
| 3-HO-benzyl | $CH_3$ | OH | ethyl |
| 3-Cl-benzyl | $CH_3$ | OH | ethyl |
| 3-$(CH_3)_2N$-benzyl | $CH_3$ | OH | ethyl |
| 2-$HO_2C$-benzyl | $CH_3$ | OH | ethyl |
| 2-$H_2NCO$-benzyl | $CH_3$ | OH | ethyl |
| 2-$CH_3O$-benzyl | $CH_3$ | OH | ethyl |
| 2-HO-benzyl | $CH_3$ | OH | ethyl |
| 2-Cl-benzyl | $CH_3$ | OH | ethyl |
| 2-$(CH_3)_2N$-benzyl | $CH_3$ | OH | ethyl |
| 2-$O_2N$-benzyl | $CH_3$ | OH | ethyl |
| 3-$O_2N$-benzyl | $CH_3$ | OH | ethyl |
| 4-$O_2N$-benzyl | $CH_3$ | OH | ethyl |
| 2-F-benzyl | $CH_3$ | OH | ethyl |
| 3-F-benzyl | $CH_3$ | OH | ethyl |
| 4-F-benzyl | $CH_3$ | OH | ethyl |
| 2-$F_3C$-benzyl | $CH_3$ | OH | ethyl |
| 3-$F_3C$-benzyl | $CH_3$ | OH | ethyl |
| 4-$F_3C$-benzyl | $CH_3$ | OH | ethyl |
| $CH_3$ | $CH_3$ | H | ethyl |
| $CH_3CH_2$ | $CH_3$ | H | ethyl |
| $CH_2$=$CHCH_2$ | $CH_3$ | H | ethyl |
| $CH_3CH_2CH_2$ | $CH_3$ | H | ethyl |

41
-continued

| R$^{14}$ | R$^2$ | R$^3$ | R$^5$ |
|---|---|---|---|
| (CH$_3$)$_2$CH | CH$_3$ | H | ethyl |
| HO$_2$CCH$_2$CH$_2$ | CH$_3$ | H | ethyl |
| H$_2$NCOCH$_2$CH$_2$ | CH$_3$ | H | ethyl |
| HOCH$_2$CH$_2$ | CH$_3$ | H | ethyl |
| HOCH$_2$CH$_2$CH$_2$ | CH$_3$ | H | ethyl |
| (CH$_3$)$_2$CH$_2$ | CH$_3$ | H | ethyl |
| phenyl | CH$_3$ | H | ethyl |
| 4-pyridyl | CH$_3$ | H | ethyl |
| 3-pyridyl | CH$_3$ | H | ethyl |
| 2-pyridyl | CH$_3$ | H | ethyl |
| 4-pyridylmethyl | CH$_3$ | H | ethyl |
| 3-pyridylmethyl | CH$_3$ | H | ethyl |
| 2-pyridylmethyl | CH$_3$ | H | ethyl |
| benzyl | CH$_3$ | H | ethyl |
| 4-HO$_2$C-benzyl | CH$_3$ | H | ethyl |
| 4-H$_2$NCO-benzyl | CH$_3$ | H | ethyl |
| 4-CH$_3$O-benzyl | CH$_3$ | H | ethyl |
| 4-HO-benzyl | CH$_3$ | H | ethyl |
| 4-Cl-benzyl | CH$_3$ | H | ethyl |
| 4-(CH$_3$)$_2$N-benzyl | CH$_3$ | H | ethyl |
| 3-HO$_2$C-benzyl | CH$_3$ | H | ethyl |
| 3-H$_2$NCO-benzyl | CH$_3$ | H | ethyl |
| 3-CH$_3$O-benzyl | CH$_3$ | H | ethyl |
| 3-HO-benzyl | CH$_3$ | H | ethyl |
| 3-Cl-benzyl | CH$_3$ | H | ethyl |
| 3-(CH$_3$)$_2$N-benzyl | CH$_3$ | H | ethyl |
| 2-HO$_2$C-benzyl | CH$_3$ | H | ethyl |
| 2-H$_2$NCO-benzyl | CH$_3$ | H | ethyl |
| 2-CH$_3$O-benzyl | CH$_3$ | H | ethyl |
| 2-HO-benzyl | CH$_3$ | H | ethyl |
| 2-Cl-benzyl | CH$_3$ | H | ethyl |
| 2-(CH$_3$)$_2$N-benzyl | CH$_3$ | H | ethyl |
| 2-O$_2$N-benzyl | CH$_3$ | H | ethyl |
| 3-O$_2$N-benzyl | CH$_3$ | H | ethyl |
| 4-O$_2$N-benzyl | CH$_3$ | H | ethyl |
| 2-F-benzyl | CH$_3$ | H | ethyl |
| 3-F-benzyl | CH$_3$ | H | ethyl |
| 4-F-benzyl | CH$_3$ | H | ethyl |
| 2-F$_3$C-benzyl | CH$_3$ | H | ethyl |
| 3-F$_3$C-benzyl | CH$_3$ | H | ethyl |
| 4-F$_3$C-benzyl | CH$_3$ | H | ethyl |
| CH$_3$ | CH$_3$ | OH | allyl |
| CH$_3$CH$_2$ | CH$_3$ | OH | allyl |
| CH$_2$=CHCH$_2$ | CH$_3$ | OH | allyl |
| CH$_3$CH$_2$CH$_2$ | CH$_3$ | OH | allyl |
| (CH$_3$)$_2$CH | CH$_3$ | OH | allyl |
| HO$_2$CCH$_2$CH$_2$ | CH$_3$ | OH | allyl |
| H$_2$NCOCH$_2$CH$_2$ | CH$_3$ | OH | allyl |
| HOCH$_2$CH$_2$ | CH$_3$ | OH | allyl |
| HOCH$_2$CH$_2$CH$_2$ | CH$_3$ | OH | allyl |
| (CH$_3$)$_2$CH$_2$ | CH$_3$ | OH | allyl |
| phenyl | CH$_3$ | OH | allyl |
| 4-pyridyl | CH$_3$ | OH | allyl |
| 3-pyridyl | CH$_3$ | OH | allyl |
| 2-pyridyl | CH$_3$ | OH | allyl |
| 4-pyridylmethyl | CH$_3$ | OH | allyl |
| 3-pyridylmethyl | CH$_3$ | OH | allyl |
| 2-pyridylmethyl | CH$_3$ | OH | allyl |
| benzyl | CH$_3$ | OH | allyl |
| 4-HO$_2$C-benzyl | CH$_3$ | OH | allyl |
| 4-H$_2$NCO-benzyl | CH$_3$ | OH | allyl |
| 4-CH$_3$O-benzyl | CH$_3$ | OH | allyl |
| 4-HO-benzyl | CH$_3$ | OH | allyl |
| 4-Cl-benzyl | CH$_3$ | OH | allyl |
| 4-(CH$_3$)$_2$N-benzyl | CH$_3$ | OH | allyl |
| 3-HO$_2$C-benzyl | CH$_3$ | OH | allyl |
| 3-H$_2$NCO-benzyl | CH$_3$ | OH | allyl |
| 3-CH$_3$O-benzyl | CH$_3$ | OH | allyl |
| 3-HO-benzyl | CH$_3$ | OH | allyl |
| 3-Cl-benzyl | CH$_3$ | OH | allyl |
| 3-(CH$_3$)$_2$N-benzyl | CH$_3$ | OH | allyl |
| 2-HO$_2$C-benzyl | CH$_3$ | OH | allyl |
| 2-H$_2$NCO-benzyl | CH$_3$ | OH | allyl |
| 2-CH$_3$O-benzyl | CH$_3$ | OH | allyl |
| 2-HO-benzyl | CH$_3$ | OH | allyl |
| 2-Cl-benzyl | CH$_3$ | OH | allyl |
| 2-(CH$_3$)$_2$N-benzyl | CH$_3$ | OH | allyl. |

Representative compounds of the present invention include the compounds identified as follows:

17-Ethyl-1,14-dihydroxy-12-[2'-(4"-(2-methylcarbonyl methylidene)- 3"-methoxycyclohexyl)-1'-methylvinyl]- 23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-(2-methylcarbonylmethylidene)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-(2-methylcarbonylmethylidene)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-(2-phenylcarbonylmethylidene-3"-methoxycyclohexyl)-1'-methylvinyl]-23, 25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-(2-phenylcarbonylmethylidene)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-(2-phenylcarbonylmethylidene)-3"-methoxycyclohexyl)-1'-methylvinyl]-23, 25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1,14-dihydroxy-12-[2'-(4"-(2-(3-methoxyphenyl)-carbonyl methylidene)-3"-methoxycyclohexyl)-1'-methylvinyl]-23,25-dimethoxy- 13,19,21,27-tetramethyl-11, 28-dioxa-4-azatricyclo-[22.3.1.0$^{4,9}$]octacos- 18-ene-2,3, 10,16-tetraone;

17-Ethyl-1-hydroxy-12-[2'-(4"-hydroxy-4"-(2-(3 -methoxyphenyl)-carbonylmethylidene)- 3"-methoxycyclohexyl)-1'-methylvinyl]-23,25 -dimethoxy-13,19,21,27-tetramethyl-11,28-dioxa-4-azatricyclo-[22.3.1.0$^{4,9}$]octacos-18-ene-2,3,10,16-tetraone;

17-Allyl-1,14-dihydroxy-12-[2'-(4"-hydroxy-4"-(2-(3 -methoxyphenyl)-carbonylmethylidene)- 3"-methoxycyclohexyl)-1'-methylvinyl]-23,25 -dimethoxy-13,19,21, 27-tetramethyl-11,28-dioxa-4-azatricyclo-[22.3.1.0$^{4,9}$] octacos-18-ene-2,3,10,16-tetraone;

17-Ethyl-1,14-dihydroxy-12-[2'-(4"-hydroxy-4"-(2-(4 -methoxyphenyl)-carbonylmethylidene)- 3"-methoxycyclohexyl)-1'-methylvinyl]-23,25 -dimethoxy-13,19,21, 27-tetramethyl-11,28-dioxa-4-azatricyclo-[22.3.1.0$^{4,9}$] octacos-18-ene-2,3,10,16-tetraone;

17-Ethyl-1-hydroxy-12-[2'-(4"-hydroxy-4"-(2-(4 -methoxyphenyl)-carbonylmethylidene)-3"-methoxycyclohexyl)-1'-methylvinyl]-23,25 -dimethoxy-13,19,21,27-tetramethyl-11,28-dioxa-4-azatricyclo-[22.3.1.0$^{4,9}$]octacos-18-ene-2,3,10,16-tetraone;

17-Allyl-1,14-dihydroxy-12-[2'-(4"-hydroxy-4"-(2-(4 -methoxyphenyl)-carbonylmethylidene)-3"-methoxycyclohexyl)-1'-methylvinyl]-23,25 -dimethoxy-13,19,21, 27-tetramethyl-11,28-dioxa-4-azatricyclo-[22.3.1.0$^{4,9}$] octacos-18-ene-2,3,10,16-tetraone;

17-Ethyl-1,14-dihydroxy-12-[2'-(4"-(2-methylcarbonylmethyl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Ethyl-1-hydroxy-12-[2'-(4"-(2-methylcarbonylmethylenyl)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene- 2,3,10,16-tetraone;

17-Allyl-1,14-dihydroxy-12-[2'-(4"-(2-methylcarbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4"-(2-phenylcarbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4"-(2-phenylcarbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Allyl-1,14-dihydroxy-12-[2'-(4"-(2-phenylcarbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4"-(2-(3-methoxyphenyl)-carbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4"-(2-(3-methoxyphenyl)-carbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Allyl-1,14-dihydroxy-12-[2'-(4"-(2-(3-methoxyphenyl)-carbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1,14-dihydroxy-12-[2'-(4"-(2-(4-methoxyphenyl)-carbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Ethyl-1-hydroxy-12-[2'-(4"-(3-methoxyphenyl)carbonyl-methylenyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone;

17-Allyl-1,14-dihydroxy-12-[2'-(4"-hydroxy-4"-(3-methoxyphenyl)-carbonylmethyl)-3"-methoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone; or a pharmaceutically acceptable salt thereof.

Representative compounds of the present invention include the compounds of formula 26-37:

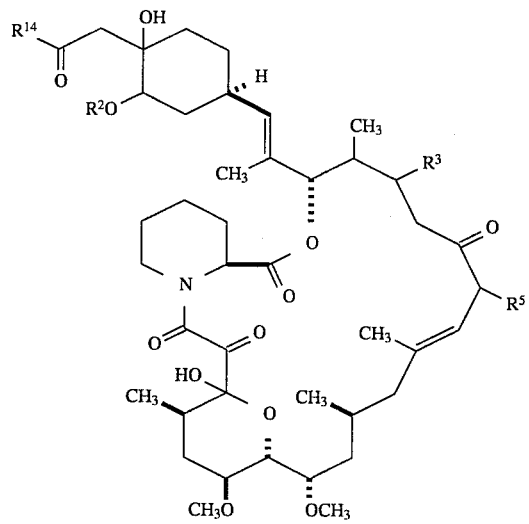

26

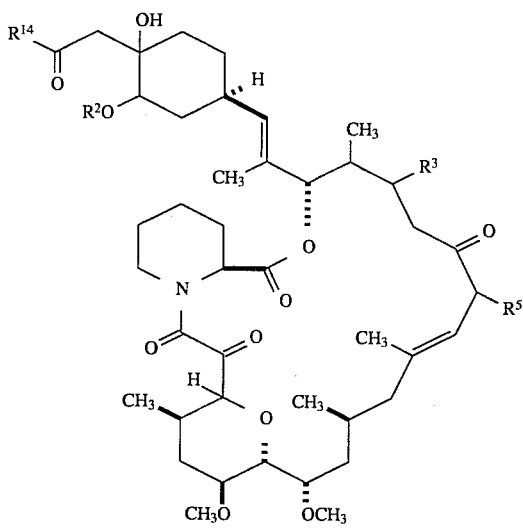

27

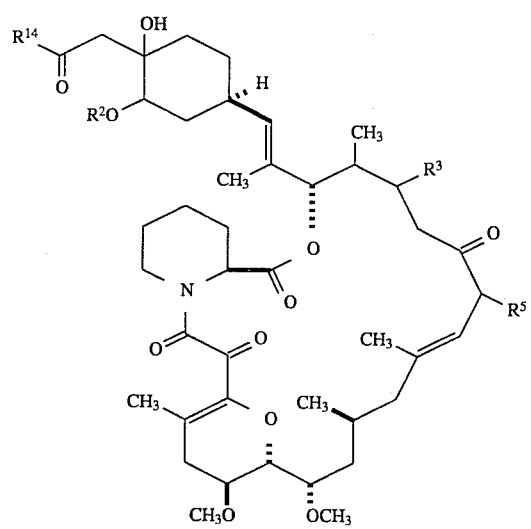

28

45
-continued
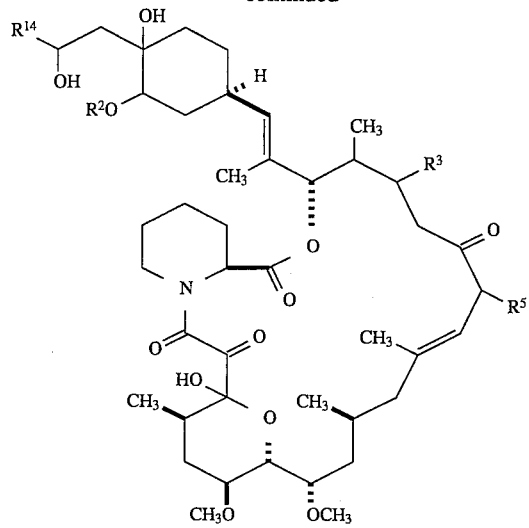
29
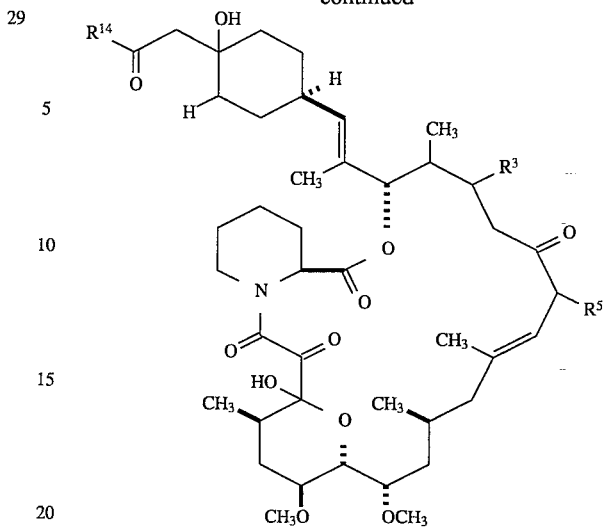
32
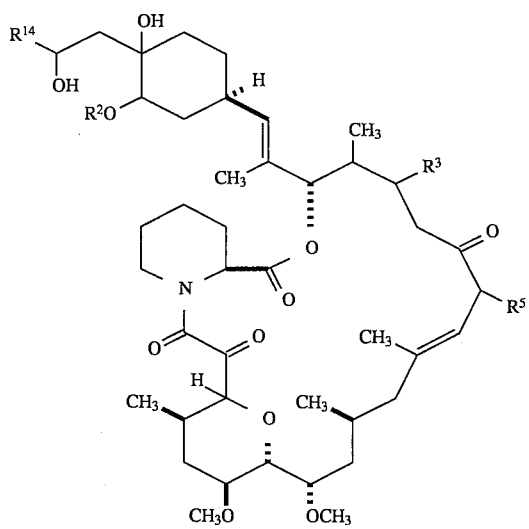
30
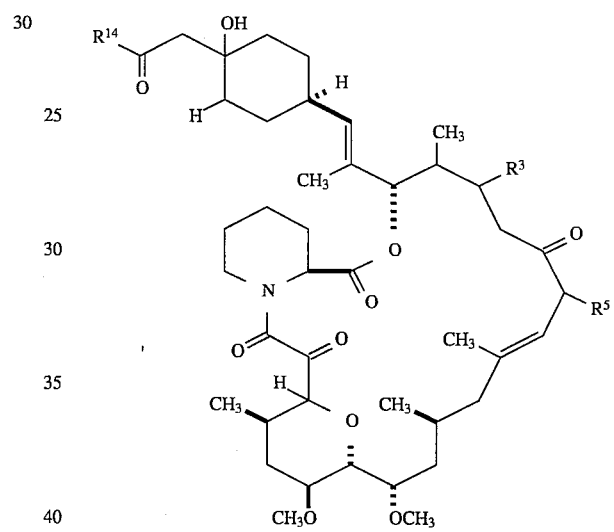
33
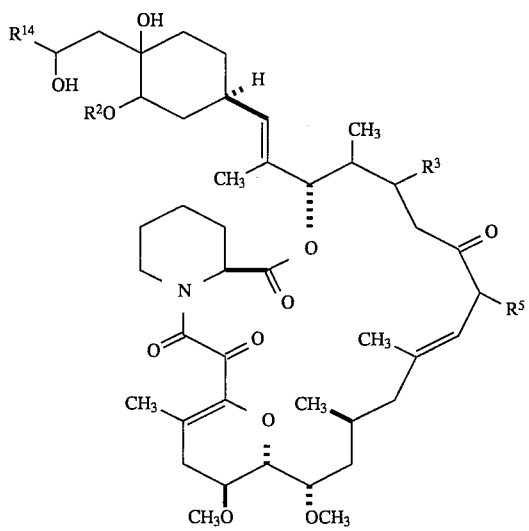
31
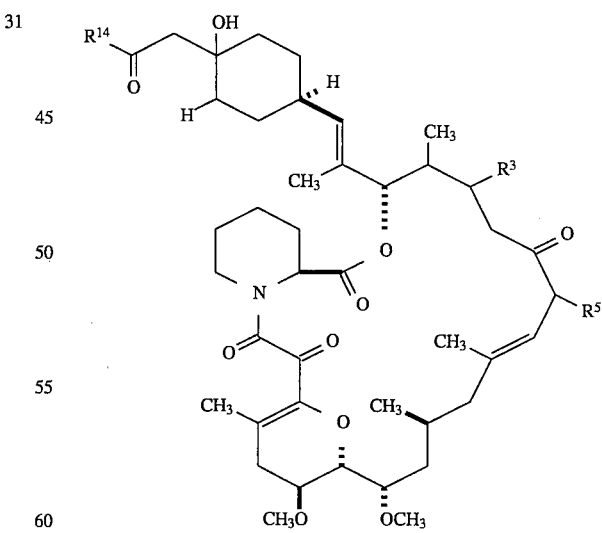
34

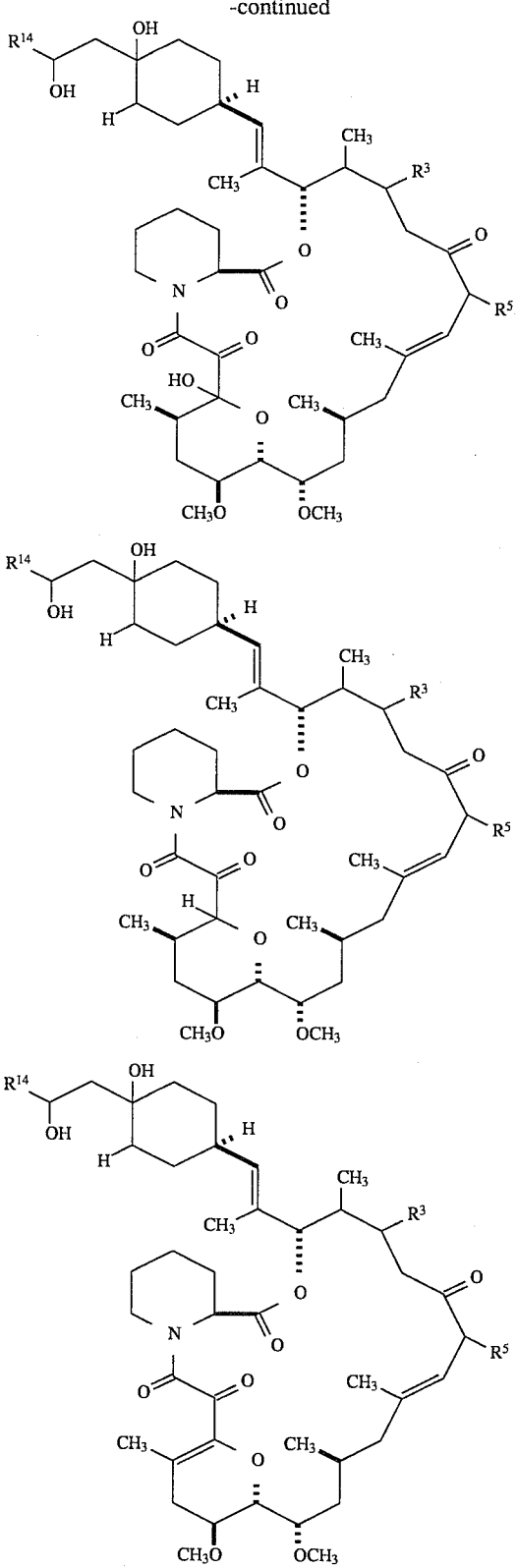

wherein for each of formula 26–37 the definitions of $R^2$, $R^3$, $R^5$, $R^{14}$ are selected from the following groups of substituents:

| $R^{14}$ | $R^2$ | $R^3$ | $R^5$ |
|---|---|---|---|
| $CH_3$ | $CH_3$ | OH | ethyl |
| $CH_3CH_2$ | $CH_3$ | OH | ethyl |
| $CH_2=CHCH_2$ | $CH_3$ | OH | ethyl |
| $CH_3CH_2CH_2$ | $CH_3$ | OH | ethyl |
| $(CH_3)_2CH$ | $CH_3$ | OH | ethyl |
| $HO_2CCH_2CH_2$ | $CH_3$ | OH | ethyl |
| $H_2NCOCH_2CH_2$ | $CH_3$ | OH | ethyl |
| $HOCH_2CH_2$ | $CH_3$ | OH | ethyl |
| $HOCH_2CH_2CH_2$ | $CH_3$ | OH | ethyl |
| $(CH_3)_2CH_2$ | $CH_3$ | OH | ethyl |
| phenyl | $CH_3$ | OH | ethyl |
| 4-pyridyl | $CH_3$ | OH | ethyl |
| 3-pyridyl | $CH_3$ | OH | ethyl |
| 2-pyridyl | $CH_3$ | OH | ethyl |
| 4-pyridylmethyl | $CH_3$ | OH | ethyl |
| 3-pyridylmethyl | $CH_3$ | OH | ethyl |
| 2-pyridylmethyl | $CH_3$ | OH | ethyl |
| benzyl | $CH_3$ | OH | ethyl |
| 4-$HO_2C$-benzyl | $CH_3$ | OH | ethyl |
| 4-$H_2NCO$-benzyl | $CH_3$ | OH | ethyl |
| 4-$CH_3O$-benzyl | $CH_3$ | OH | ethyl |
| 4-HO-benzyl | $CH_3$ | OH | ethyl |
| 4-Cl-benzyl | $CH_3$ | OH | ethyl |
| 4-$(CH_3)_2N$-benzyl | $CH_3$ | OH | ethyl |
| 3-$HO_2C$-benzyl | $CH_3$ | OH | ethyl |
| 3-$H_2NCO$-benzyl | $CH_3$ | OH | ethyl |
| 3-$CH_3O$-benzyl | $CH_3$ | OH | ethyl |
| 3-HO-benzyl | $CH_3$ | OH | ethyl |
| 3-Cl-benzyl | $CH_3$ | OH | ethyl |
| 3-$(CH_3)_2N$-benzyl | $CH_3$ | OH | ethyl |
| 2-$HO_2C$-benzyl | $CH_3$ | OH | ethyl |
| 2-$H_2NCO$-benzyl | $CH_3$ | OH | ethyl |
| 2-$CH_3O$-benzyl | $CH_3$ | OH | ethyl |
| 2-HO-benzyl | $CH_3$ | OH | ethyl |
| 2-Cl-benzyl | $CH_3$ | OH | ethyl |
| 2-$(CH_3)_2N$-benzyl | $CH_3$ | OH | ethyl |
| 2-$O_2N$-benzyl | $CH_3$ | OH | ethyl |
| 3-$O_2N$-benzyl | $CH_3$ | OH | ethyl |
| 4-$O_2N$-benzyl | $CH_3$ | OH | ethyl |
| 2-F-benzyl | $CH_3$ | OH | ethyl |
| 3-F-benzyl | $CH_3$ | OH | ethyl |
| 4-F-benzyl | $CH_3$ | OH | ethyl |
| 2-$F_3C$-benzyl | $CH_3$ | OH | ethyl |
| 3-$F_3C$-benzyl | $CH_3$ | OH | ethyl |
| 4-$F_3C$-benzyl | $CH_3$ | OH | ethyl |
| $CH_3$ | $CH_3$ | H | ethyl |
| $CH_3CH_2$ | $CH_3$ | H | ethyl |
| $CH_2=CHCH_2$ | $CH_3$ | H | ethyl |
| $CH_3CH_2CH_2$ | $CH_3$ | H | ethyl |
| $(CH_3)_2CH$ | $CH_3$ | H | ethyl |
| $HO_2CCH_2CH_2$ | $CH_3$ | H | ethyl |
| $H_2NCOCH_2CH_2$ | $CH_3$ | H | ethyl |
| $HOCH_2CH_2$ | $CH_3$ | H | ethyl |
| $HOCH_2CH_2CH_2$ | $CH_3$ | H | ethyl |
| $(CH_3)_2CH_2$ | $CH_3$ | H | ethyl |
| phenyl | $CH_3$ | H | ethyl |
| 4-pyridyl | $CH_3$ | H | ethyl |
| 3-pyridyl | $CH_3$ | H | ethyl |
| 2-pyridyl | $CH_3$ | H | ethyl |
| 4-pyridylmethyl | $CH_3$ | H | ethyl |
| 3-pyridylmethyl | $CH_3$ | H | ethyl |
| 2-pyridylmethyl | $CH_3$ | H | ethyl |
| benzyl | $CH_3$ | H | ethyl |
| 4-$HO_2C$-benzyl | $CH_3$ | H | ethyl |
| 4-$H_2NCO$-benzyl | $CH_3$ | H | ethyl |
| 4-$CH_3O$-benzyl | $CH_3$ | H | ethyl |
| 4-HO-benzyl | $CH_3$ | H | ethyl |
| 4-Cl-benzyl | $CH_3$ | H | ethyl |
| 4-$(CH_3)_2N$-benzyl | $CH_3$ | H | ethyl |
| 3-$HO_2C$-benzyl | $CH_3$ | H | ethyl |
| 3-$H_2NCO$-benzyl | $CH_3$ | H | ethyl |
| 3-$CH_3O$-benzyl | $CH_3$ | H | ethyl |
| 3-HO-benzyl | $CH_3$ | H | ethyl |
| 3-Cl-benzyl | $CH_3$ | H | ethyl |
| 3-$(CH_3)_2N$-benzyl | $CH_3$ | H | ethyl |
| 2-$HO_2C$-benzyl | $CH_3$ | H | ethyl |
| 2-$H_2NCO$-benzyl | $CH_3$ | H | ethyl |
| 2-$CH_3O$-benzyl | $CH_3$ | H | ethyl |

| R¹⁴ | R² | R³ | R⁵ |
|---|---|---|---|
| 2-HO-benzyl | CH₃ | H | ethyl |
| 2-Cl-benzyl | CH₃ | H | ethyl |
| 2-(CH₃)₂N-benzyl | CH₃ | H | ethyl |
| 2-O₂N-benzyl | CH₃ | H | ethyl |
| 3-O₂N-benzyl | CH₃ | H | ethyl |
| 4-O₂N-benzyl | CH₃ | H | ethyl |
| 2-F-benzyl | CH₃ | H | ethyl |
| 3-F-benzyl | CH₃ | H | ethyl |
| 4-F-benzyl | CH₃ | H | ethyl |
| 2-F₃C-benzyl | CH₃ | H | ethyl |
| 3-F₃C-benzyl | CH₃ | H | ethyl |
| 4-F₃C-benzyl | CH₃ | H | ethyl |
| CH₃ | CH₃ | OH | allyl |
| CH₃CH₂ | CH₃ | OH | allyl |
| CH₂=CHCH₂ | CH₃ | OH | allyl |
| CH₃CH₂CH₂ | CH₃ | OH | allyl |
| (CH₃)2CH | CH₃ | OH | allyl |
| HO₂CCH₂CH₂ | CH₃ | OH | allyl |
| H₂NCOCH₂CH₂ | CH₃ | OH | allyl |
| HOCH₂CH₂ | CH₃ | OH | allyl |
| HOCH₂CH₂CH₂ | CH₃ | OH | allyl |
| (CH₃)₂CH₂ | CH₃ | OH | allyl |
| phenyl | CH₃ | OH | allyl |
| 4-pyridyl | CH₃ | OH | allyl |
| 3-pyridyl | CH₃ | OH | allyl |
| 2-pyridyl | CH₃ | OH | allyl |
| 4-pyridylmethyl | CH₃ | OH | allyl |
| 3-pyridylmethyl | CH₃ | OH | allyl |
| 2-pyridylmethyl | CH₃ | OH | allyl |
| benzyl | CH₃ | OH | allyl |
| 4-HO₂C-benzyl | CH₃ | OH | allyl |
| 4-H₂NCO-benzyl | CH₃ | OH | allyl |
| 4-CH₃O-benzyl | CH₃ | OH | allyl |
| 4-HO-benzyl | CH₃ | OH | allyl |
| 4-Cl-benzyl | CH₃ | OH | allyl |
| 4-(CH₃)₂N-benzyl | CH₃ | OH | allyl |
| 3-HO₂C-benzyl | CH₃ | OH | allyl |
| 3-H₂NCO-benzyl | CH₃ | OH | allyl |
| 3-CH₃O-benzyl | CH₃ | OH | allyl |
| 3-HO-benzyl | CH₃ | OH | allyl |
| 3-Cl-benzyl | CH₃ | OH | allyl |
| 3-(CH₃)₂N-benzyl | CH₃ | OH | allyl |
| 2-HO₂C-benzyl | CH₃ | OH | allyl |
| 2-H₂NCO-benzyl | CH₃ | OH | allyl |
| 2-CH₃O-benzyl | CH₃ | OH | allyl |
| 2-HO-benzyl | CH₃ | OH | allyl |
| 2-Cl-benzyl | CH₃ | OH | allyl |
| 2-(CH₃)₂N-benzyl | CH₃ | OH | allyl |

Representative compounds of the present invention include the compounds of formula 38–43:

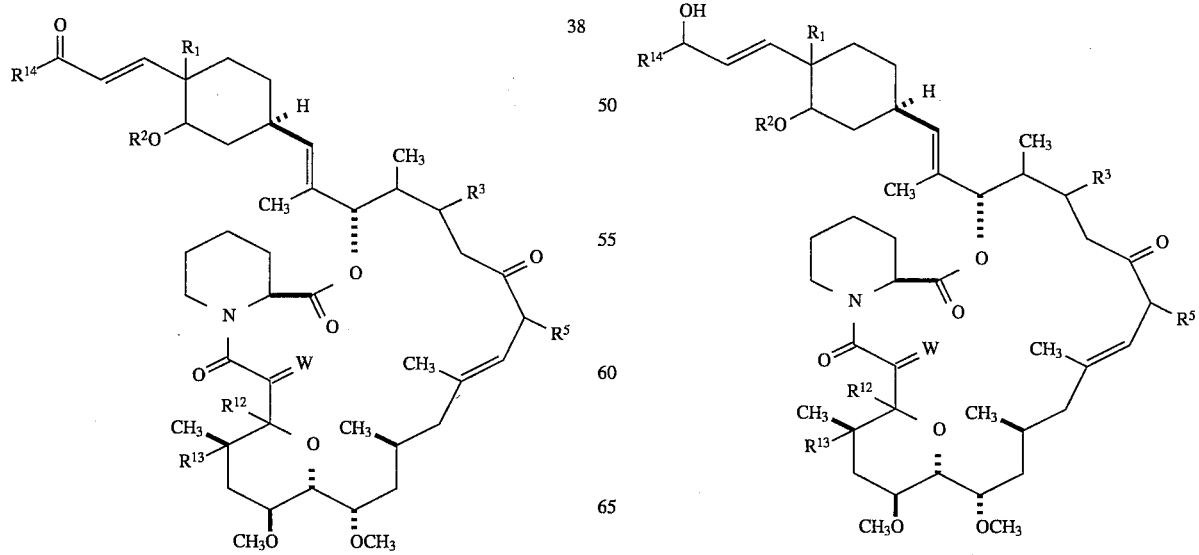

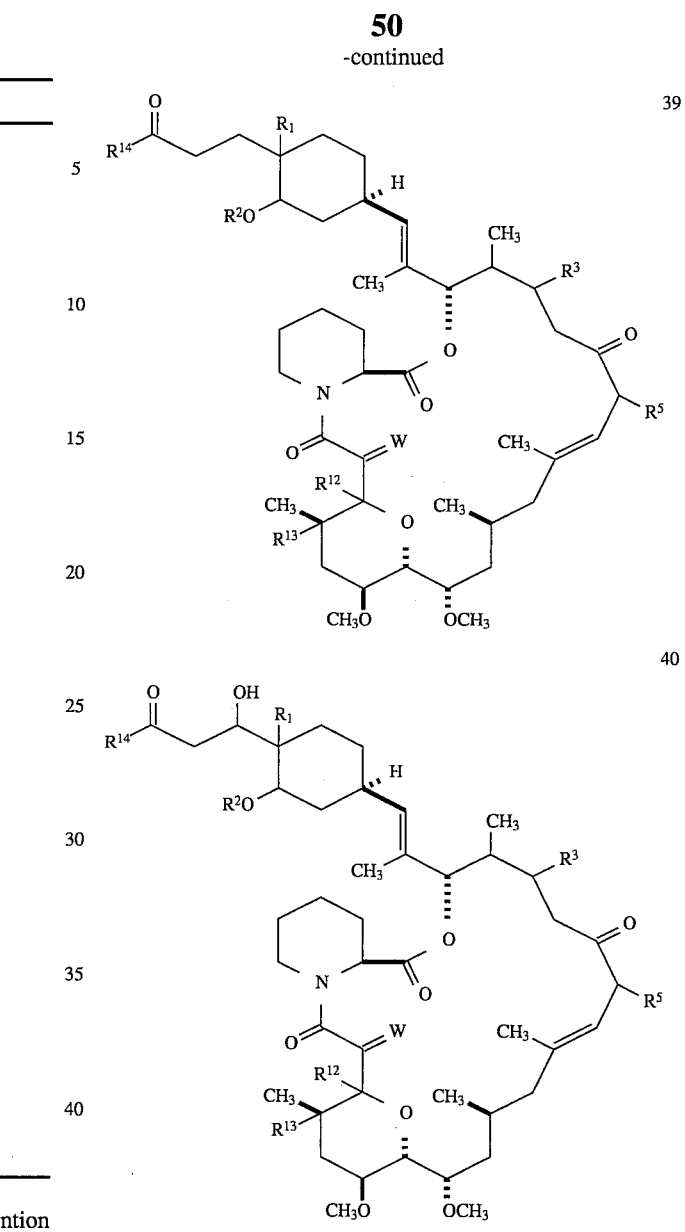

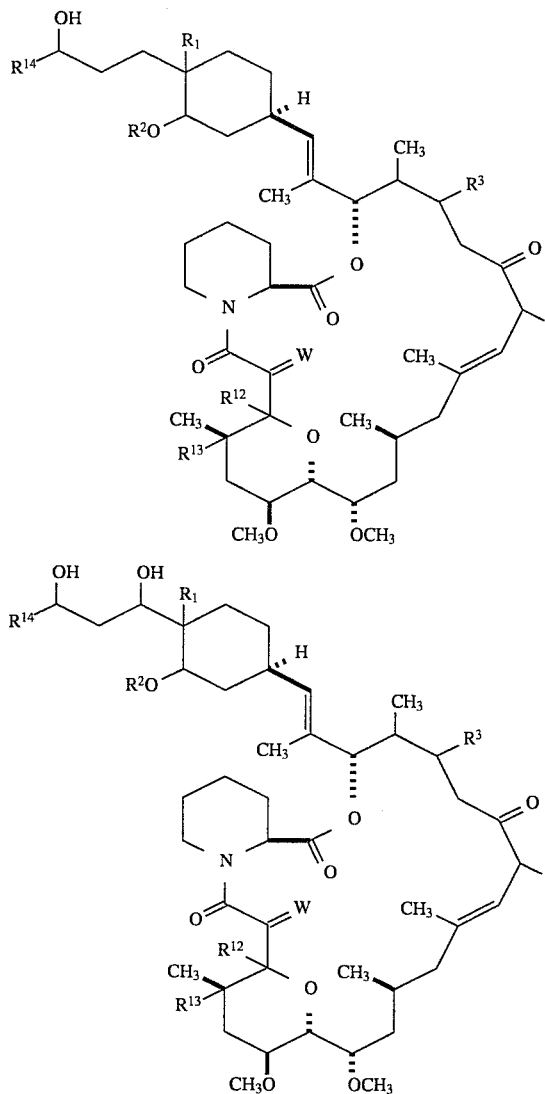

wherein for each of formula 38–43 the definitions of $R^1$, $R^2$, $R^3$ and $R^{14}$ are selected from the following groups of substituents and W, $R^{12}$ and $R^{13}$ have been previously defined:

| $R^{14}$ | $R^1$ | $R^2$ | $R^3$ | $R^5$ |
|---|---|---|---|---|
| 4-HO$_2$C-phenyl | OH | CH$_3$ | OH | ethyl |
| 4-H$_2$NCO-phenyl | OH | CH$_3$ | OH | ethyl |
| 4-HO-phenyl | OH | CH$_3$ | OH | ethyl |
| 4-Cl-phenyl | OH | CH$_3$ | OH | ethyl |
| 4-CH$_3$-phenyl | OH | CH$_3$ | OH | ethyl |
| 4-(CH$_3$)$_2$N-phenyl | OH | CH$_3$ | OH | ethyl |
| 3-HO$_2$C-phenyl | OH | CH$_3$ | OH | ethyl |
| 3-H$_2$NCO-phenyl | OH | CH$_3$ | OH | ethyl |
| 3-HO-phenyl | OH | CH$_3$ | OH | ethyl |
| 3-Cl-phenyl | OH | CH$_3$ | OH | ethyl |
| 3-CH$_3$-phenyl | OH | CH$_3$ | OH | ethyl |
| 3-(CH$_3$)$_2$N-phenyl | OH | CH$_3$ | OH | ethyl |
| 3,5-di(CH$_3$)-phenyl | OH | CH$_3$ | OH | ethyl |
| 2-HO$_2$C-phenyl | OH | CH$_3$ | OH | ethyl |
| 2-H$_2$NCO-phenyl | OH | CH$_3$ | OH | ethyl |
| 2-HO-phenyl | OH | CH$_3$ | OH | ethyl |
| 2-Cl-phenyl | OH | CH$_3$ | OH | ethyl |
| 2-CH$_3$-phenyl | OH | CH$_3$ | OH | ethyl |
| 2-(CH$_3$)$_2$N-phenyl | OH | CH$_3$ | OH | ethyl |
| 4-pyridyl | OH | CH$_3$ | OH | ethyl |
| 3-pyridyl | OH | CH$_3$ | OH | ethyl |
| 2-pyridyl | OH | CH$_3$ | OH | ethyl |
| 1-naphthyl | OH | CH$_3$ | OH | ethyl |
| 2-naphthyl | OH | CH$_3$ | OH | ethyl |
| 5-indolyl | OH | CH$_3$ | OH | ethyl |
| 6-indolyl | OH | CH$_3$ | OH | ethyl |
| 5-(1-(2-hydroxy-ethyl)-indolyl)- | OH | CH$_3$ | OH | ethyl |
| 6-(1-(2-hydroxy-ethyl)-indolyl)- | OH | CH$_3$ | OH | ethyl |
| 2-imidazolyl | OH | CH$_3$ | OH | ethyl |
| 3-imidazolyl | OH | CH$_3$ | OH | ethyl |
| 2-O$_2$N-phenyl | OH | CH$_3$ | OH | ethyl |
| 3-O$_2$N-phenyl | OH | CH$_3$ | OH | ethyl |
| 4-O$_2$N-phenyl | OH | CH$_3$ | OH | ethyl |
| 2-F-phenyl | OH | CH$_3$ | OH | ethyl |
| 3-F-phenyl | OH | CH$_3$ | OH | ethyl |
| 4-F-phenyl | OH | CH$_3$ | OH | ethyl |
| 2-F$_3$C-phenyl | OH | CH$_3$ | OH | ethyl |
| 3-F$_3$C-phenyl | OH | CH$_3$ | OH | ethyl |
| 4-F$_3$C-phenyl | OH | CH$_3$ | OH | ethyl |
| 4-HO$_2$C-phenyl | OH | CH$_3$ | H | ethyl |
| 4-H$_2$NCO-phenyl | OH | CH$_3$ | H | ethyl |
| 4-HO-phenyl | OH | CH$_3$ | H | ethyl |
| 4-Cl-phenyl | OH | CH$_3$ | H | ethyl |
| 4-CH$_3$-phenyl | OH | CH$_3$ | R | ethyl |
| 4-(CH$_3$)$_2$N-phenyl | OH | CH$_3$ | H | ethyl |
| 3-HO$_2$C-phenyl | OH | CH$_3$ | H | ethyl |
| 3-H$_2$NCO-phenyl | OH | CH$_3$ | H | ethyl |
| 3-HO-phenyl | OH | CH$_3$ | H | ethyl |
| 3-Cl-phenyl | OH | CH$_3$ | H | ethyl |
| 3-CH$_3$-phenyl | OH | CH$_3$ | H | ethyl |
| 3-(CH$_3$)$_2$N-phenyl | OH | CH$_3$ | H | ethyl |
| 3,5-di(CH$_3$)-phenyl | OH | CH$_3$ | H | ethyl |
| 2-HO$_2$C-phenyl | OH | CH$_3$ | H | ethyl |
| 2-H$_2$NCO-phenyl | OH | CH$_3$ | H | ethyl |
| 2-HO-phenyl | OH | CH$_3$ | H | ethyl |
| 2-Cl-phenyl | OH | CH$_3$ | H | ethyl |
| 2-CH$_3$-phenyl | OH | CH$_3$ | H | ethyl |
| 2-(CH$_3$)$_2$N-phenyl | OH | CH$_3$ | H | ethyl |
| 4-pyridyl | OH | CH$_3$ | H | ethyl |
| 3-pyridyl | OH | CH$_3$ | H | ethyl |
| 2-pyridyl | OH | CH$_3$ | H | ethyl |
| 1-naphthyl | OH | CH$_3$ | H | ethyl |
| 2-naphthyl | OH | CH$_3$ | H | ethyl |
| 5-indolyl | OH | CH$_3$ | H | ethyl |
| 6-indolyl | OH | CH$_3$ | H | ethyl |
| 5-(1-(2-hydroxy-ethyl)-indolyl)- | OH | CH$_3$ | H | ethyl |
| 6-(1-(2-hydroxy-ethyl)-indolyl)- | OH | CH$_3$ | H | ethyl |
| 2-imidazolyl | OH | CH$_3$ | H | ethyl |
| 3-imidazolyl | OH | CH$_3$ | H | ethyl |
| 2-O$_2$N-phenyl | OH | CH$_3$ | H | ethyl |
| 3-O$_2$N-phenyl | OH | CH$_3$ | H | ethyl |
| 4-O$_2$N-phenyl | OH | CH$_3$ | H | ethyl |
| 2-F-phenyl | OH | CH$_3$ | H | ethyl |
| 3-F-phenyl | OH | CH$_3$ | H | ethyl |
| 4-F-phenyl | OH | CH$_3$ | H | ethyl |
| 4-F$_3$C-phenyl | OH | CH$_3$ | H | ethyl |
| 2-F$_3$C-phenyl | OH | CH$_3$ | H | ethyl |
| 3-F$_3$C-phenyl | OH | CH$_3$ | H | ethyl |
| 4-HO$_2$C-phenyl | OH | CH$_3$ | OH | allyl |
| 4-H$_2$NCO-phenyl | OH | CH$_3$ | OH | allyl |
| 4-HO-phenyl | OH | CH$_3$ | OH | allyl |
| 4-Cl-phenyl | OH | CH$_3$ | OH | allyl |
| 4-CH$_3$-phenyl | OH | CH$_3$ | OH | allyl |
| 4-(CH$_3$)$_2$N-phenyl | OH | CH$_3$ | OH | allyl |
| 4-HO$_2$C-phenyl | OH | CH$_3$ | OH | allyl |
| 3-H$_2$NCO-phenyl | OH | CH$_3$ | OH | allyl |
| 3-HO-phenyl | OH | CH$_3$ | OH | allyl |
| 3-Cl-phenyl | OH | CH$_3$ | OH | allyl |
| 3-CH$_3$-phenyl | OH | CH$_3$ | OH | allyl |
| 3-(CH$_3$)$_2$N-phenyl | OH | CH$_3$ | OH | allyl |
| 3,5-di(CH$_3$)-phenyl | OH | CH$_3$ | OH | allyl |
| 2-HO$_2$C-phenyl | OH | CH$_3$ | OH | allyl |
| 2-H$_2$NCO-phenyl | OH | CH$_3$ | OH | allyl |
| 2-HO-phenyl | OH | CH$_3$ | OH | allyl |

-continued

| $R^{14}$ | $R^1$ | $R^2$ | $R^3$ | $R^5$ |
|---|---|---|---|---|
| 2-Cl-phenyl | OH | $CH_3$ | OH | allyl |
| 2-$CH_3$-phenyl | OH | $CH_3$ | OH | allyl |
| 2-$(CH_3)_2$N-phenyl | OH | $CH_3$ | OH | allyl |
| 4-pyridyl | OH | $CH_3$ | OH | allyl |
| 3-pyridyl | OH | $CH_3$ | OH | allyl |
| 2-pyridyl | OH | $CH_3$ | OH | allyl |
| 1-naphthyl | OH | $CH_3$ | OH | allyl |
| 2-naphthyl | OH | $CH_3$ | OH | allyl |
| 5-indolyl | OH | $CH_3$ | OH | allyl |
| 6-indolyl | OH | $CH_3$ | OH | allyl |
| 5-(1-(2-hydroxy-ethyl)-indolyl)- | OH | $CH_3$ | OH | allyl |
| 6-(1-(2-hydroxy-ethyl)-indolyl)- | OH | $CH_3$ | OH | allyl |
| 2-imidazolyl | OH | $CH_3$ | OH | allyl |
| 3-imidazolyl | OH | $CH_3$ | OH | allyl |
| 2-$O_2$N-phenyl | OH | $CH_3$ | OH | allyl |
| 3-$O_2$N-phenyl | OH | $CH_3$ | OH | allyl |
| 4-$O_2$N-phenyl | OH | $CH_3$ | OH | allyl |
| 2-F-phenyl | OH | $CH_3$ | OH | allyl |
| 3-F-phenyl | OH | $CH_3$ | OH | allyl |
| 4-F-phenyl | OH | $CH_3$ | OH | allyl |
| 2-$F_3$C-phenyl | OH | $CH_3$ | OH | allyl |
| 3-$F_3$C-phenyl | OH | $CH_3$ | OH | allyl |
| 4-$F_3$C-phenyl | OH | $CH_3$ | OH | allyl |
| $CH_3$ | H | $CH_3$ | OH | ethyl |
| $CH_3CH_2$ | H | $CH_3$ | OH | ethyl |
| $CH_3CH_2CH_2$ | H | $CH_3$ | OH | ethyl |
| $(CH_3)_2CH$ | H | $CH_3$ | OH | ethyl |
| $HO_2CCH_2CH_2$ | H | $CH_3$ | OH | ethyl |
| $H_2NCOCH_2CH_2$ | H | $CH_3$ | OH | ethyl |
| $HOCH_2CH_2$ | H | $CH_3$ | OH | ethyl |
| $HOCH_2CH_2CH_2$ | H | $CH_3$ | OH | ethyl |
| $CH_3$ | H | $CH_3$ | H | ethyl |
| $CH_3CH_2$ | H | $CH_3$ | H | ethyl |
| $H_2NCOCH_2CH_2$ | H | $CH_3$ | H | ethyl |
| $(CH_3)_2CH$ | H | $CH_3$ | H | ethyl |
| $HO_2CCH_2CH_2$ | H | $CH_3$ | H | ethyl |
| $H_2NCOCH_2CH_2$ | H | $CH_3$ | H | ethyl |
| $HOCH_2CH_2$ | H | $CH_3$ | H | ethyl |
| $HOCH_2CH_2CH_2$ | H | $CH_3$ | H | ethyl |
| $CH_3$ | H | H | H | ethyl |
| $CH_3CH_2$ | H | H | OH | ethyl |
| $CH_3CH_2CH_2$ | H | H | H | ethyl |
| $(CH_3)_2CH$ | H | H | OH | ethyl |
| $HO_2CCH_2CH_2$ | H | H | OH | ethyl |
| $H_2NCOCH_2CH_2$ | H | H | OH | ethyl |
| $HOCH_2CH_2$ | H | H | OH | ethyl |
| $HOCH_2CH_2CH_2$ | H | H | OH | ethyl. |

B. Preparation of Compounds Within the Scope of the Present Invention

The starting materials for the preparation of the compounds of this invention are represented by Formula II:

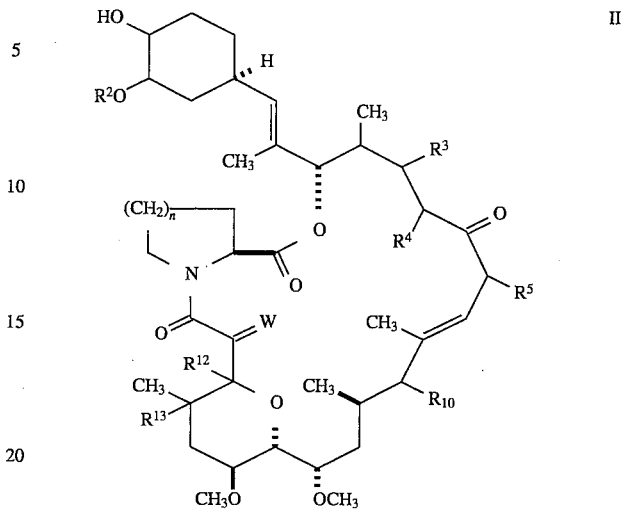

wherein:

$R^2$ is hydrogen or methyl;

$R^3$ is hydrogen, hydroxy, or $C_{1-6}$ alkoxy;

$R^4$ is hydrogen, or $R^3$ and $R^4$ taken together form a double bond;

$R^5$ is methyl, ethyl, propyl or allyl;

$R^{10}$ is hydrogen, hydroxy or fluoro;

$R^{12}$ is hydrogen, hydroxy, $R^{12}$ is hydrogen or $R^{12}$ and $R^{13}$ taken together form a double bond;

W is O, (H, OH) or (H,H); and n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No, 3,244,592 issued Apr. 15, 1966; EPO Publication No. 0,323,042; EPO Publication No. 0,356,399; PBJ Disclosure 63-17884; *J. Am. Chem. Soc.*, 1987, 109, 5031; *J. Antibiotics*, 1987, 40, 1249, *J. Antibiotics*, 1988, 41(11), 1592; and *J. Antibiotics*, 1992, 45(1), 118). Both biological fermentation and synthetic processes may be found. A synthetic route to compounds of Formula II can involve modifications of a route described in J. Am. Chem. Soc., 1989, 111, 1157.

Biological fermentation followed by synthetic modification is presently favored in the an as the method to produce compounds of Formula II. Organisms belonging to the genus Streptomyces such as *Streptomyces tsukubaensis*, No. 9993 and *Streptomyces hygroscopicus*, var. *ascomycetis*, No. 14891 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where $R^2$ is methyl, W is O, $R^3$ is hydroxyl, $R^4$ is hydrogen, $R^5$ is allyl and n is 2; (B) where $R^2$ is methyl, W is O, $R^3$ is hydroxyl, $R^4$ is hydrogen, $R^5$ is ethyl and n is 2; (C) where $R^2$ is methyl, W is O, $R^3$ is hydroxyl, $R^4$ is hydrogen, $R^5$ is methyl and n is 2; and (D) where $R^2$ is methyl, W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1–3, Higashi 1-chome, Yatabemachi Tsukuba-gun, Ibaraki Prefecture, Japan) under the deposit number of FERM P-7886 (deposit date: October 5th, 1984), and then convened to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxyl at C-4" may also be protected. In addition, the hydroxy of $R^3$ may be reduced to a hydrogen or eliminated to form a double bond with $R^4$ (by methods disclosed in U.S. Pat. No. 4,894,366, EPO Publication No. 0,323,042 or EPO Publication No. 0,413,532). The carbonyl of W may be reduced to the alcohol by methods disclosed in EPO Publication No. 0,323,042 or by methods disclosed in EPO Publication No. 0,445,975.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at E above by using the microorganism Actinomycetales ATCC No. 53771 (described in U.S. Pat. No. 4,981,792) or by using the microorganism *Streptomyces tsukubaensis*, No. 9993 (described in EPO. Publication No. 0,353,678). Similarly, compound B named under Formula II above may be demethylated at E above by using the microorganism *Actinoplanacete sp.* ATCC No. 53771 (described in EPO Publication No. 0,349,061). In addition the compound of Formula II wherein E is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication No. 0,388,152). Similarly, the compound of Formula II wherein E is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (EPO Publication No. 0,388,153). The hydroxy of C-3" may be protected by methods similar to those known for the protection of the hydroxyl groups of $R^3$ and/or C-4", for example as disclosed in U.S. Pat. No. 4,894,366.

Suitable protecting groups for hydroxyl include those groups well known in the an such as: methylthiomethyl, ethylthiomethyl; trisubstituted silyl such as trimethylsilyl, triethylsilyl, tributylsilyl, tri-i-propylsilyl, t-butyldimethylsilyl, tri-t-butylsilyl, methyl-diphenylsilyl, ethyldiphenylsilyl, t-butyldiphenylsilyl, and the like; acyl such as acetyl, pivaloyl benzoyl, 4-methoxybenzoyl, 4-nitrobenzoyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, dated Jan. 16, 1990, U.S. Pat. No. 4,929,611, issued May 29, 1990 and U.S. Pat. No. 5,110,811, issued May 5, 1992.

The novel processes for preparing the novel compounds of the present invention are illustrated as follows, wherein R, $R^1$, $R^2$, $R^3$, $R^5$, $R^6$, $R^7$, $R^8$, $R^9$, $R^{10}$, $R^{11}$, $R^{12}$, $R^{13}$, W and n are as defined above unless otherwise indicated. It will be readily apparent to one of ordinary skill in the an reviewing the synthetic route depicted below that other compounds within Formula I can be synthesized by substitution of appropriate reactants and agents in the synthesis shown below.

REACTION SCHEME A

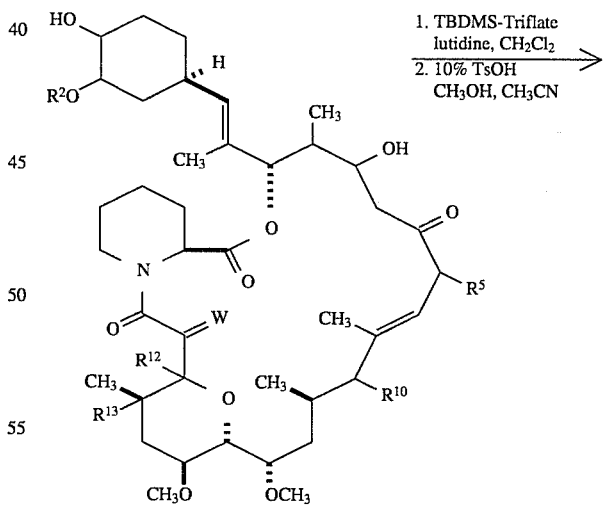

1

-continued
REACTION SCHEME A
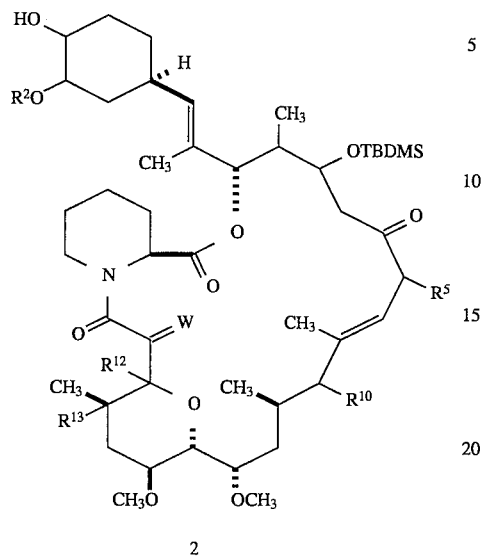
2
-continued
REACTION SCHEME B
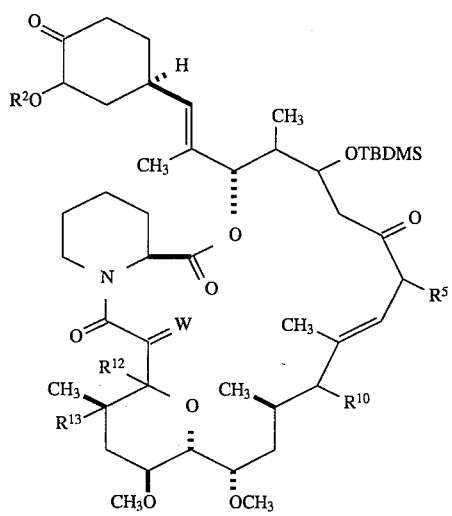
3
REACTION SCHEME B
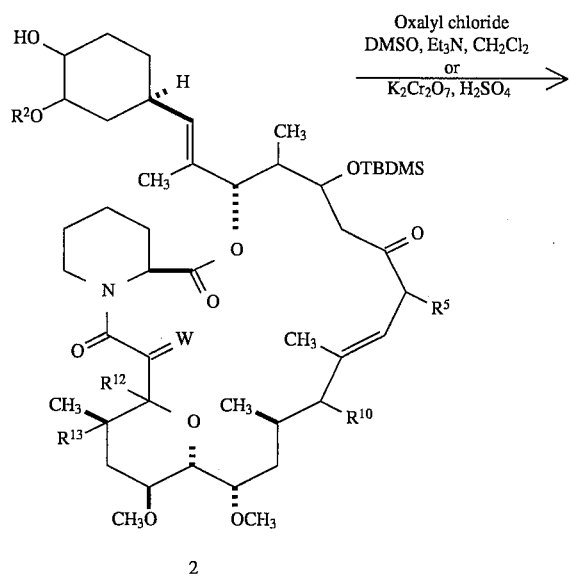
2
$$\xrightarrow[\text{K}_2\text{Cr}_2\text{O}_7, \text{H}_2\text{SO}_4]{\substack{\text{Oxalyl chloride} \\ \text{DMSO, Et}_3\text{N, CH}_2\text{Cl}_2 \\ \text{or}}}$$
REACTION SCHEME C
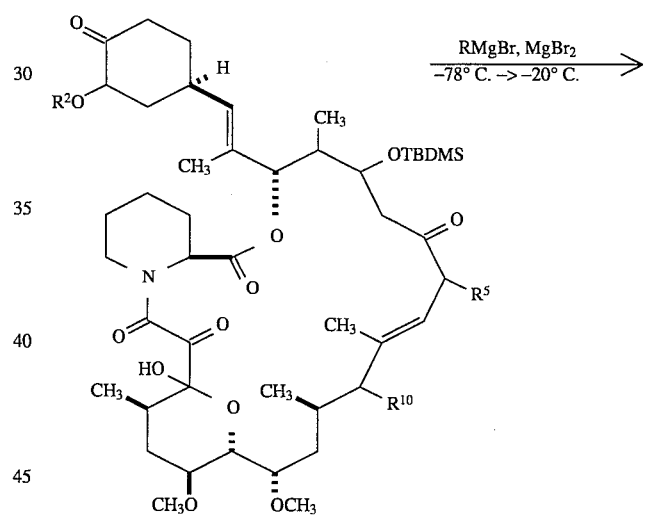
3
$$\xrightarrow[-78°\text{C.} \rightarrow -20°\text{C.}]{\text{RMgBr, MgBr}_2}$$

-continued
REACTION SCHEME C
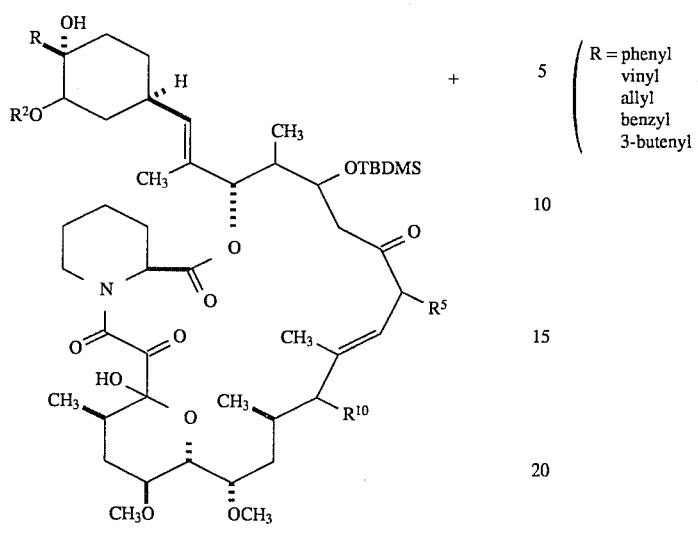
4a
+    R = phenyl
     vinyl
     allyl
     benzyl
     3-butenyl
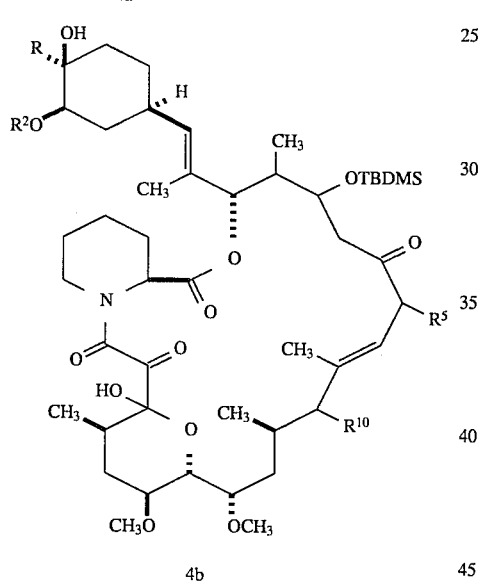
4b REACTION SCHEME D
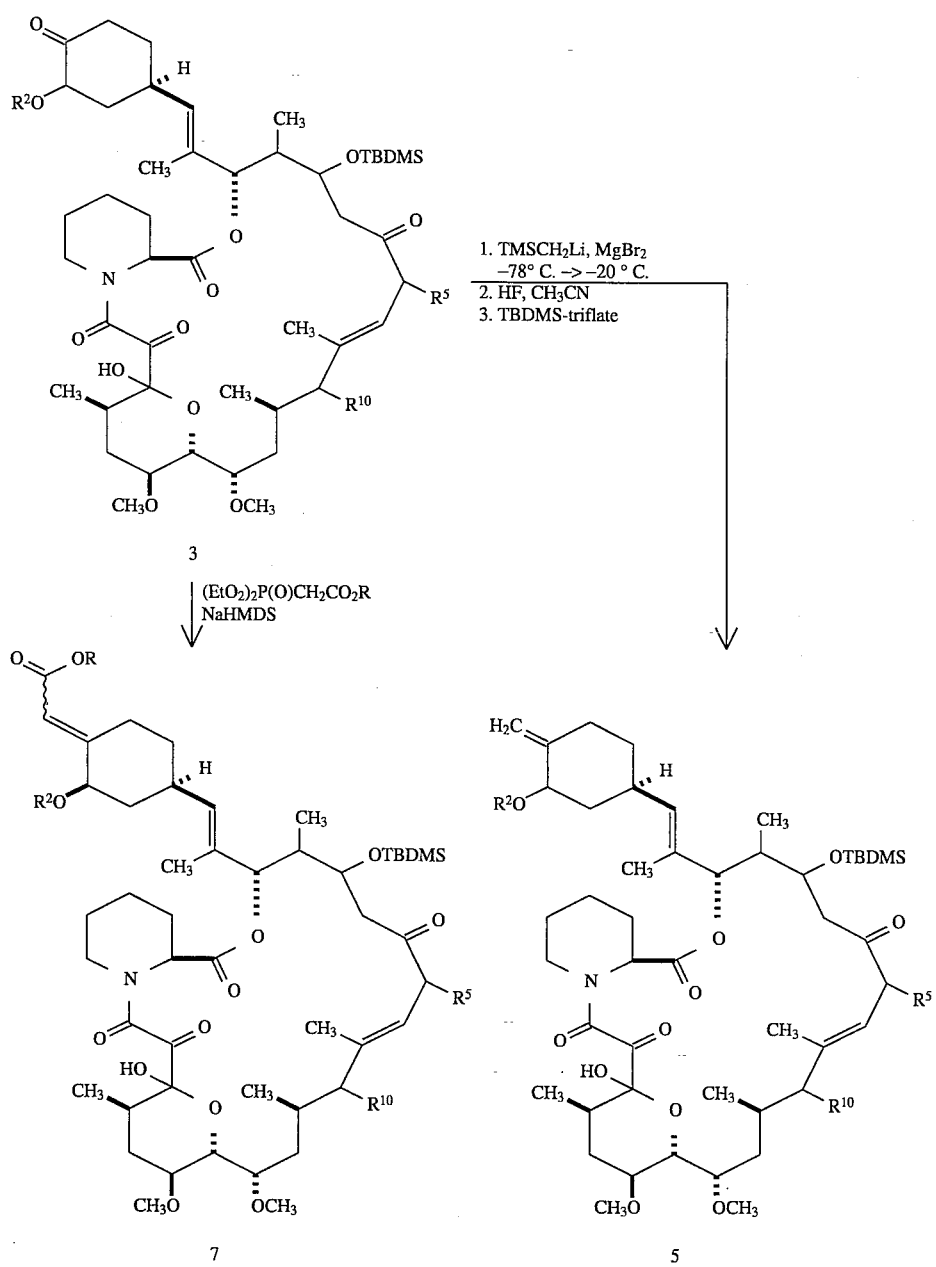

REACTION SCHEME F(1)
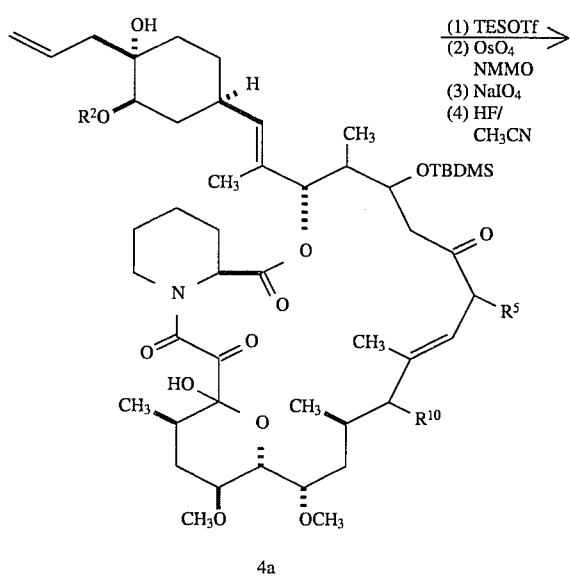
4a
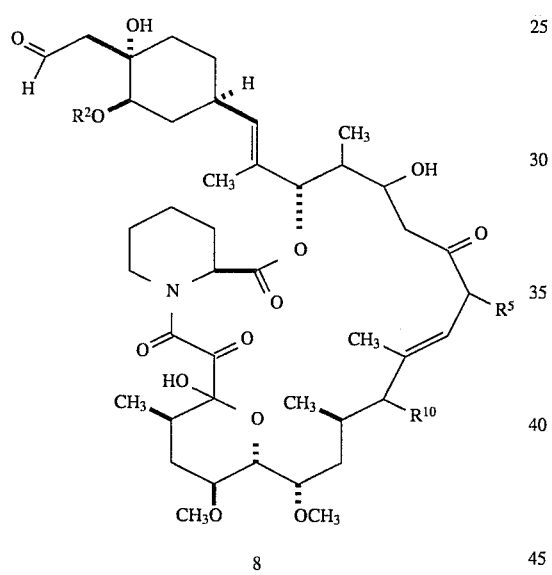
8
REACTION SCHEME F(2)
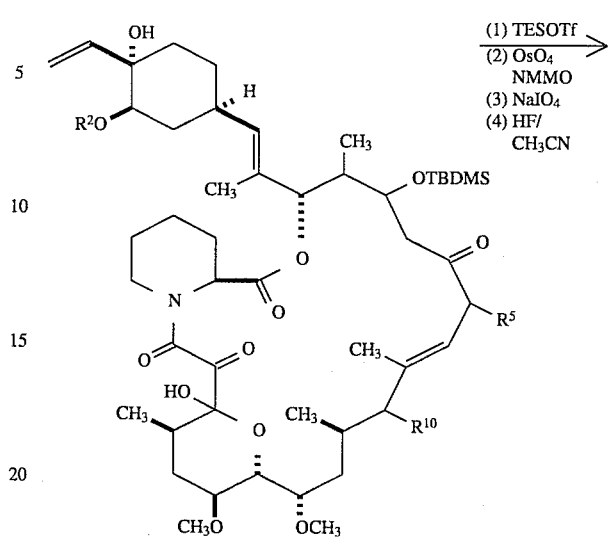
4b
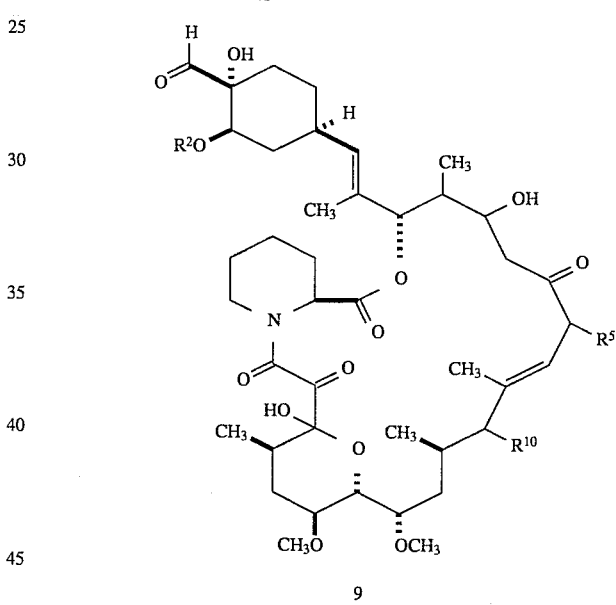
9

REACTION SCHEME F(3)
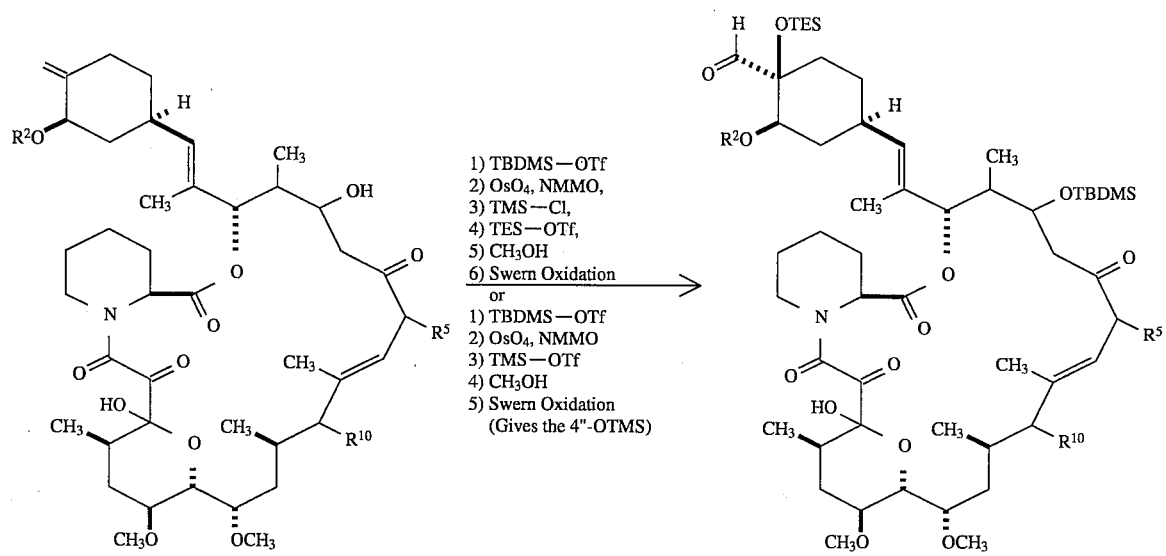
1) TBDMS—OTf
2) OsO$_4$, NMMO,
3) TMS—Cl,
4) TES—OTf,
5) CH$_3$OH
6) Swern Oxidation
or
1) TBDMS—OTf
2) OsO$_4$, NMMO
3) TMS—OTf
4) CH$_3$OH
5) Swern Oxidation
(Gives the 4"-OTMS)
REACTION SCHEME G(1)
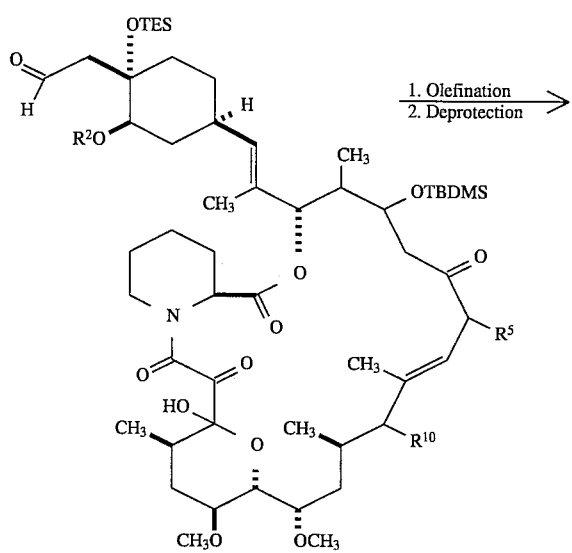
1. Olefination
2. Deprotection
-continued
REACTION SCHEME G(1)
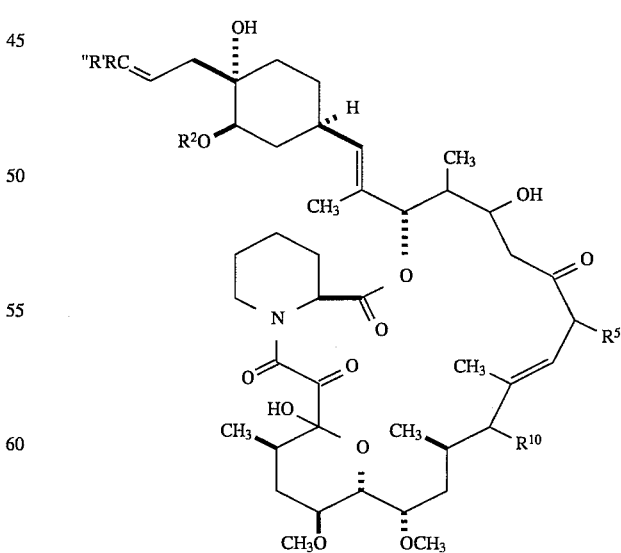

REACTION SCHEME G(2)
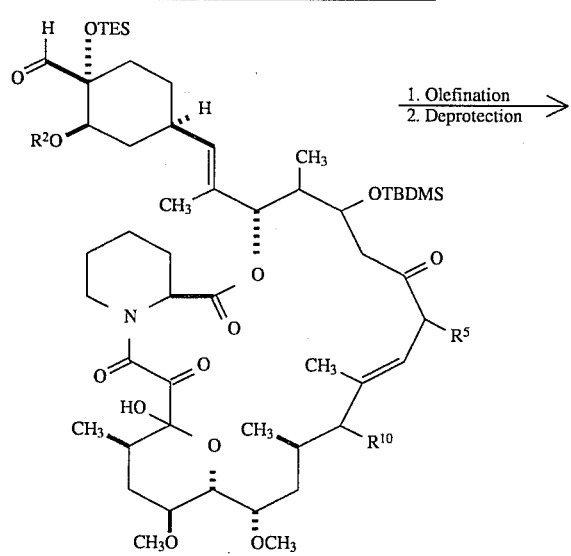
9
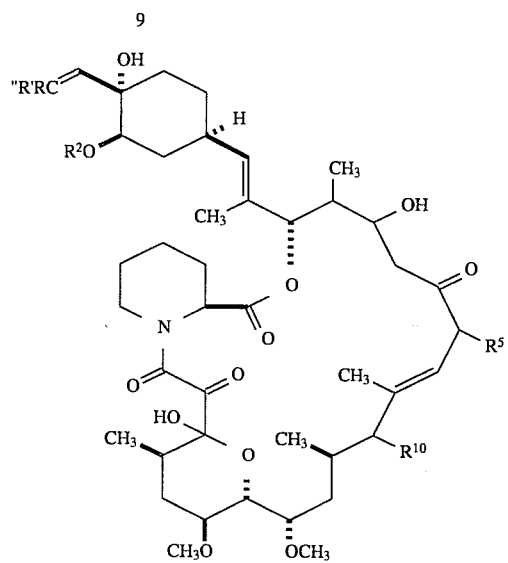
12
REACTION SCHEME G(3)
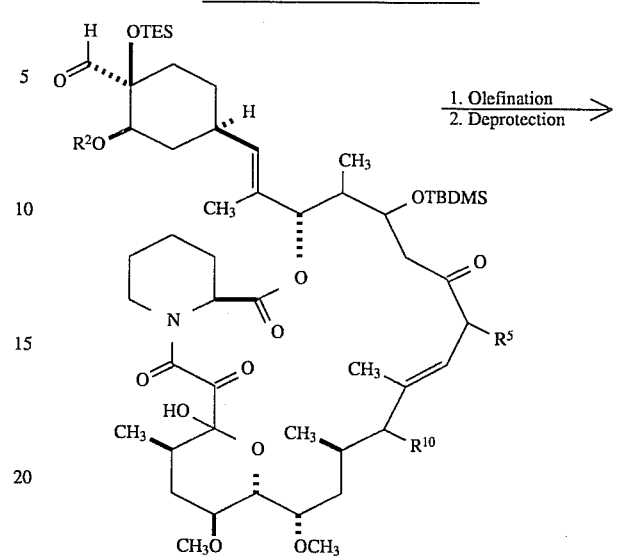
10
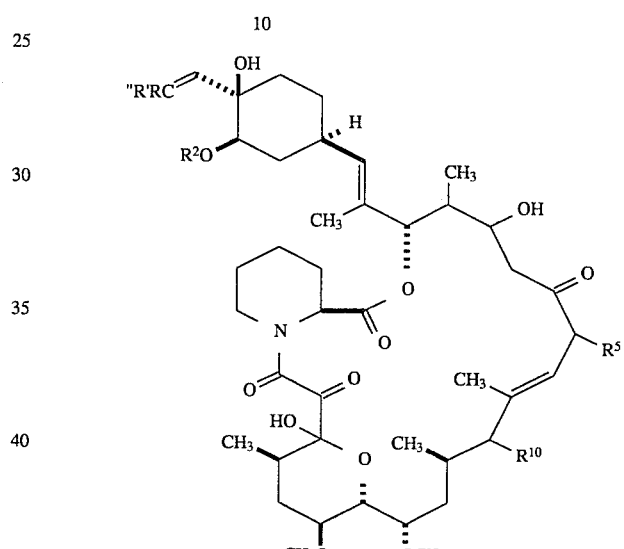
13

REACTION SCHEME H(1)
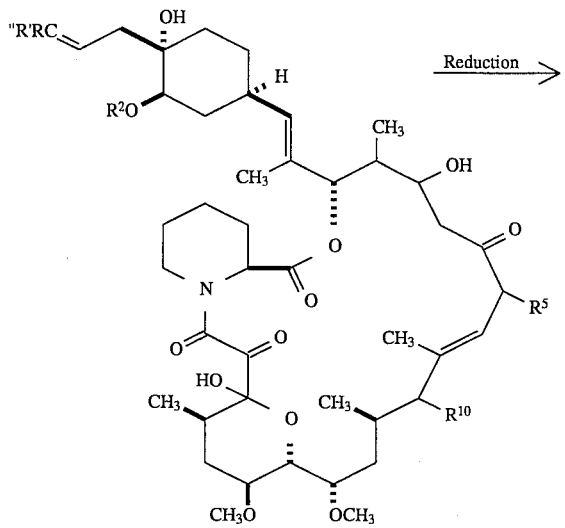
11
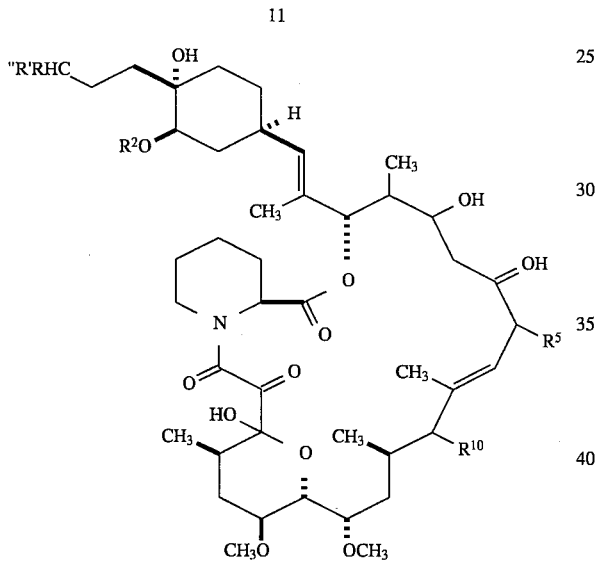
14
REACTION SCHEME H(2)
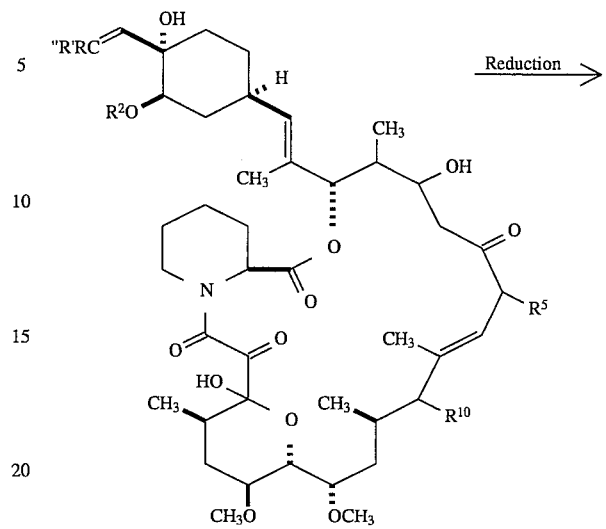
12
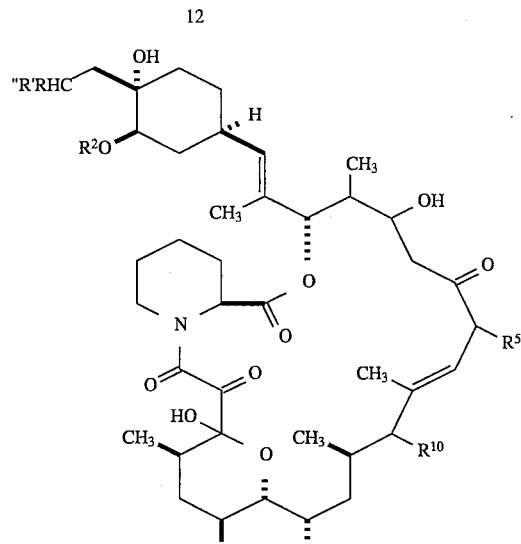
15

71
REACTION SCHEME H(3)
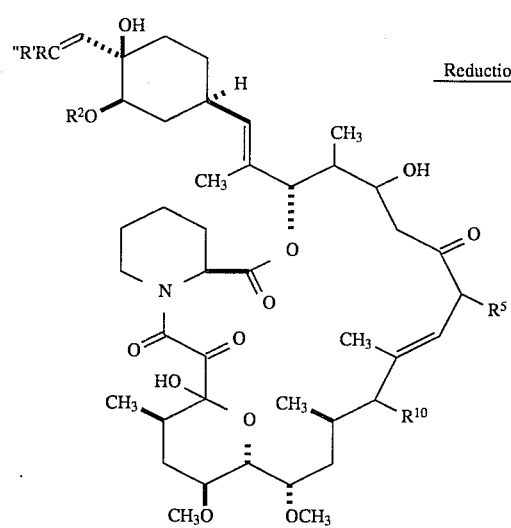
13
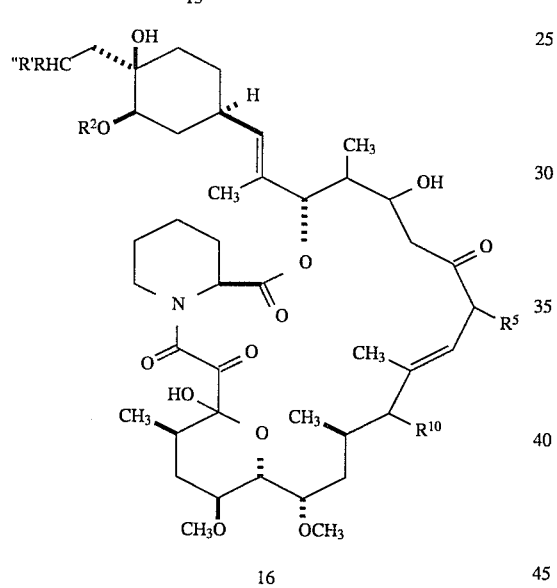
16
72
REACTION SCHEME I(1)
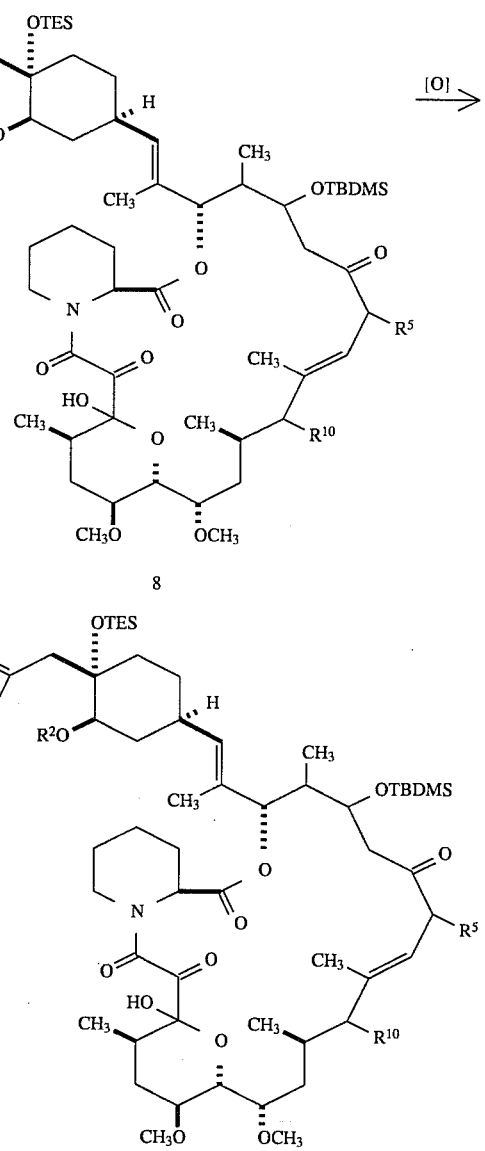
8
17

REACTION SCHEME I(2)
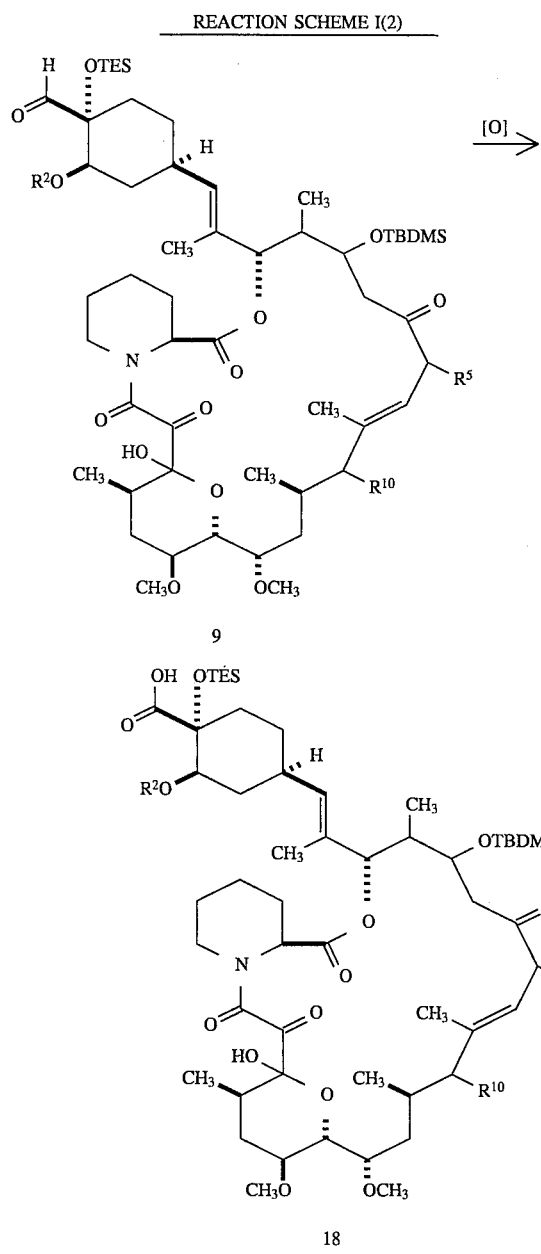
REACTION SCHEME I(3)
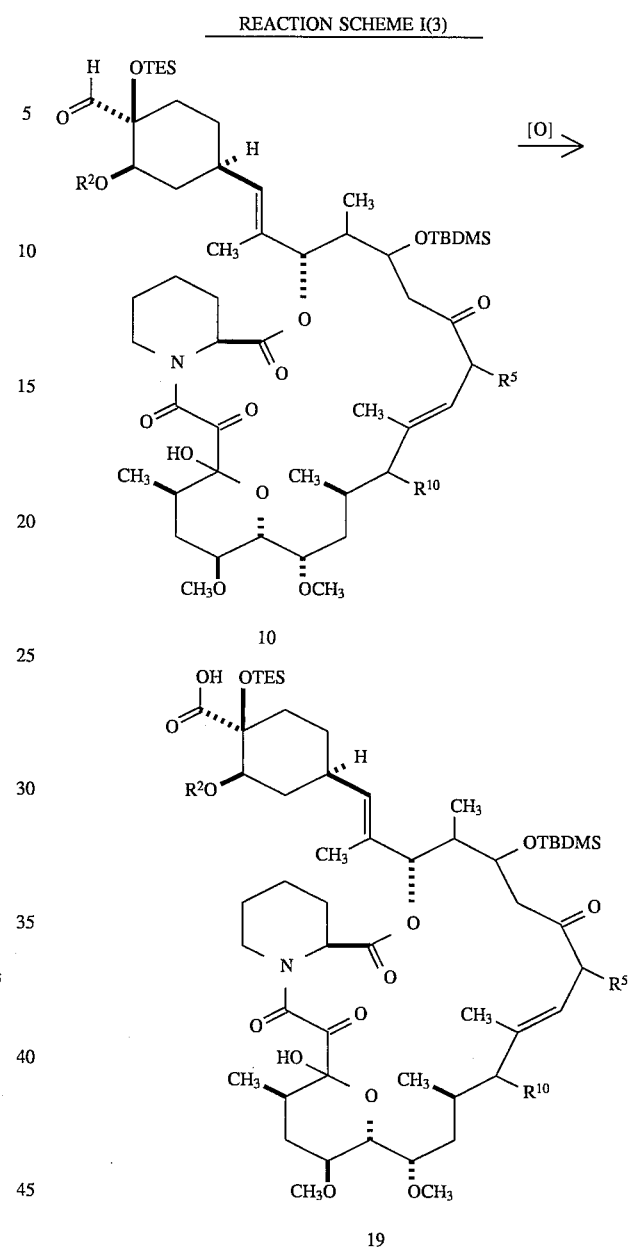

REACTION SCHEME J
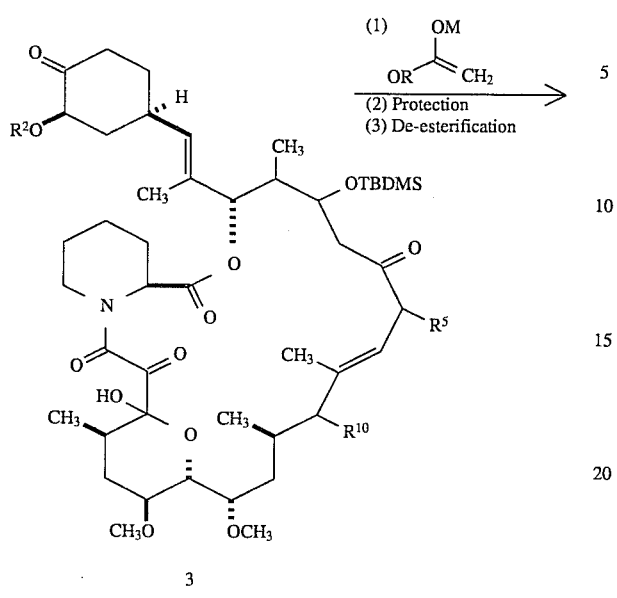
3
(1) OM / OR / CH2
(2) Protection
(3) De-esterification
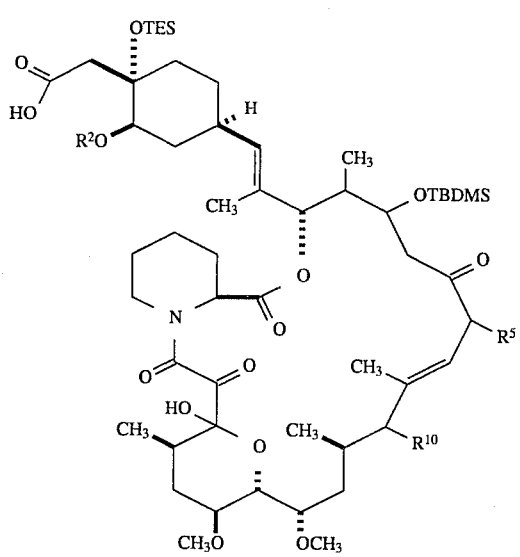
17
REACTION SCHEME K
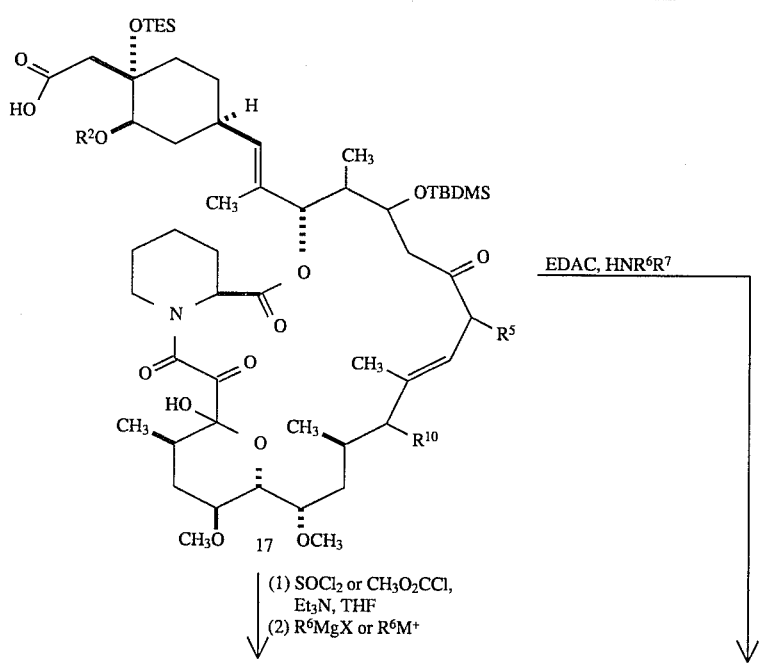
(1) SOCl₂ or CH₃O₂CCl, Et₃N, THF
(2) R⁶MgX or R⁶M⁺
EDAC, HNR⁶R⁷

5,550,233
-continued
REACTION SCHEME K
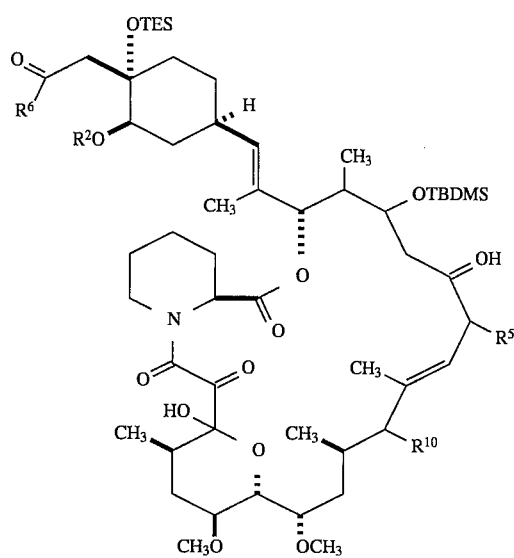
21
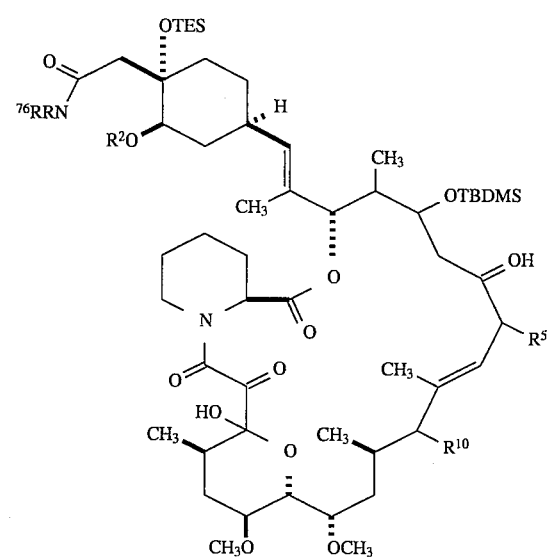
20
REACTION SCHEME L
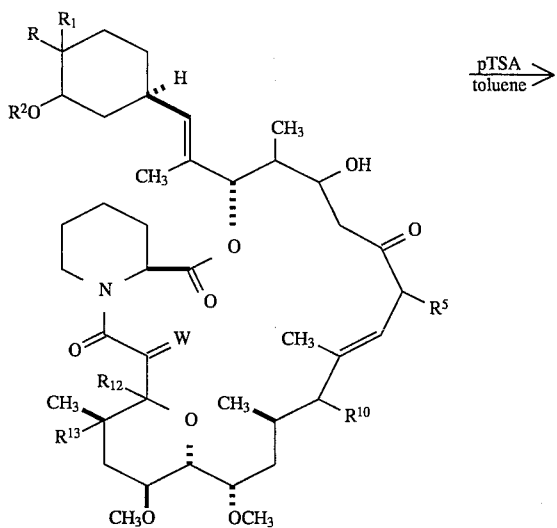
22
$\xrightarrow[\text{toluene}]{\text{pTSA}}$
-continued
REACTION SCHEME L
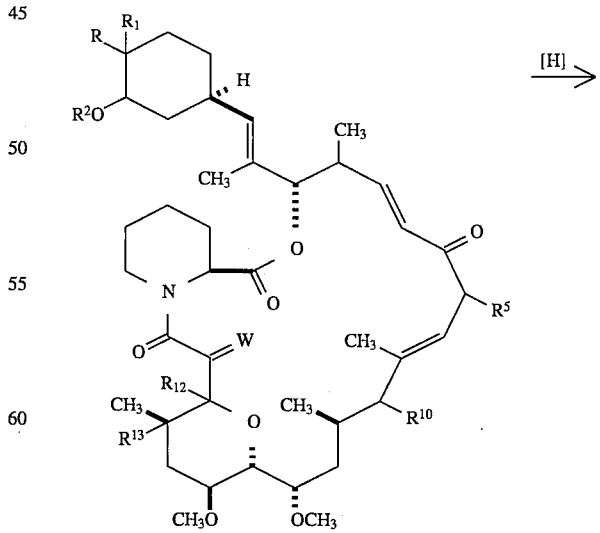
23
$\xrightarrow{[H]}$ -continued
REACTION SCHEME L
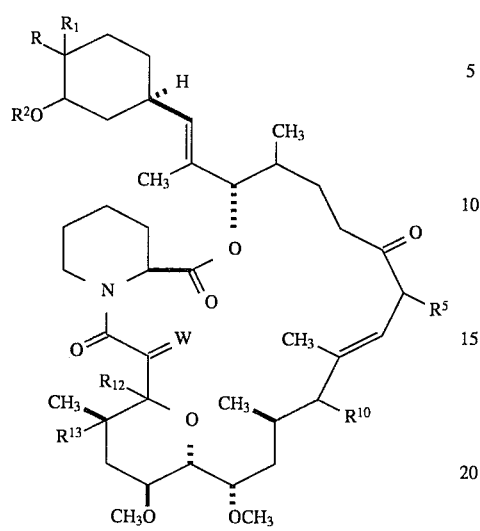
24
REACTION SCHEME M
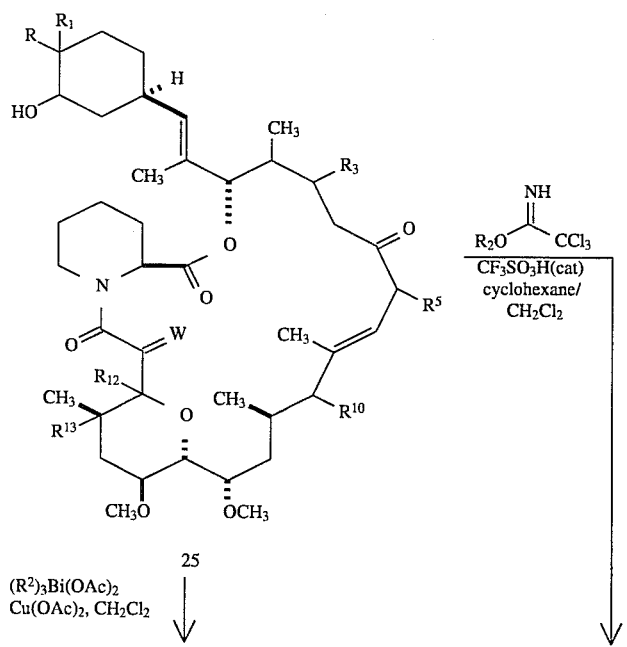
25
$(R^2)_3Bi(OAc)_2$
$Cu(OAc)_2, CH_2Cl_2$ -continued
REACTION SCHEME M
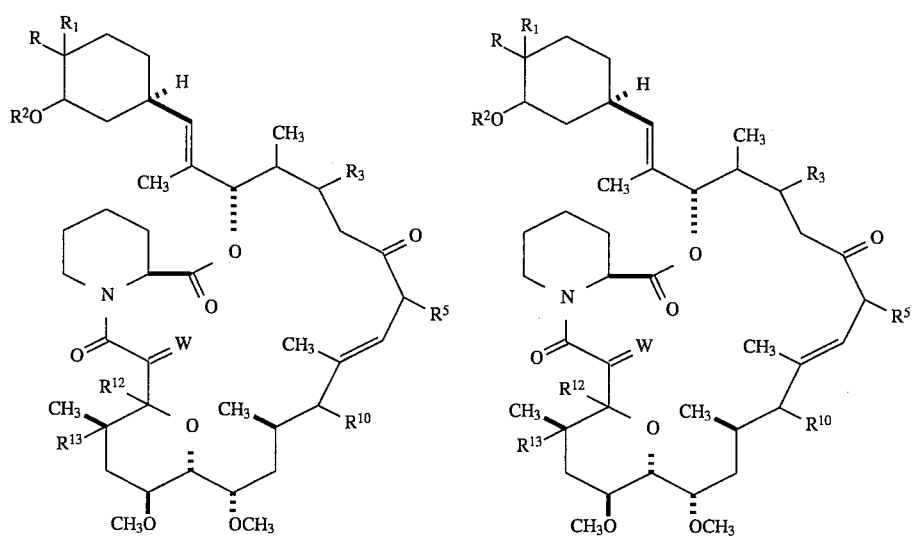
REACTION SCHEME N
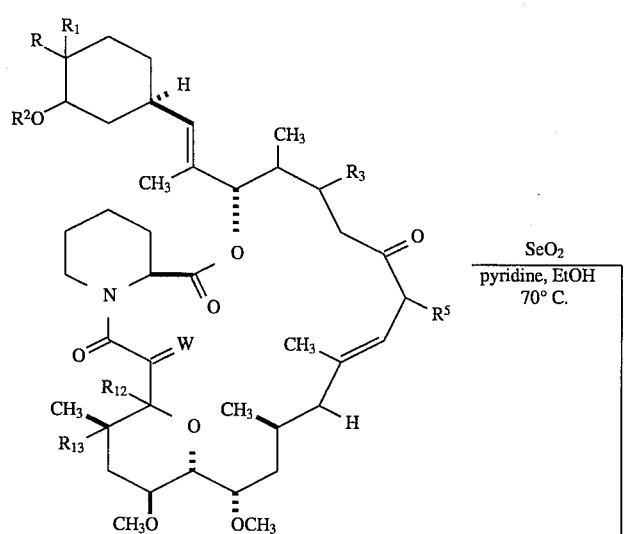

-continued
REACTION SCHEME N
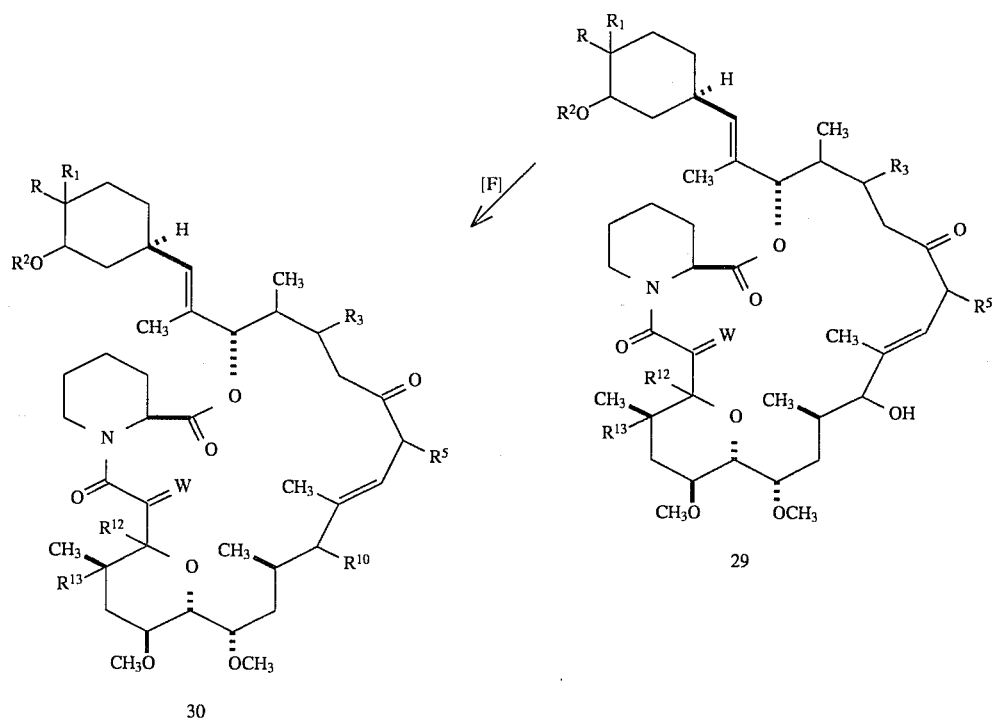
REACTION SCHEME O
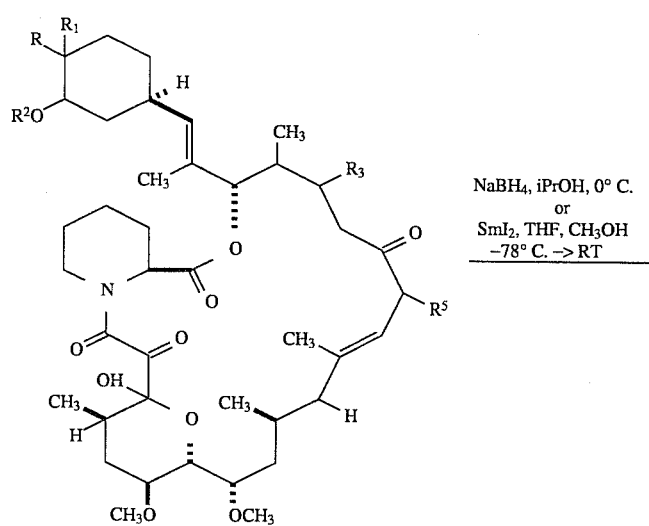

-continued
REACTION SCHEME O
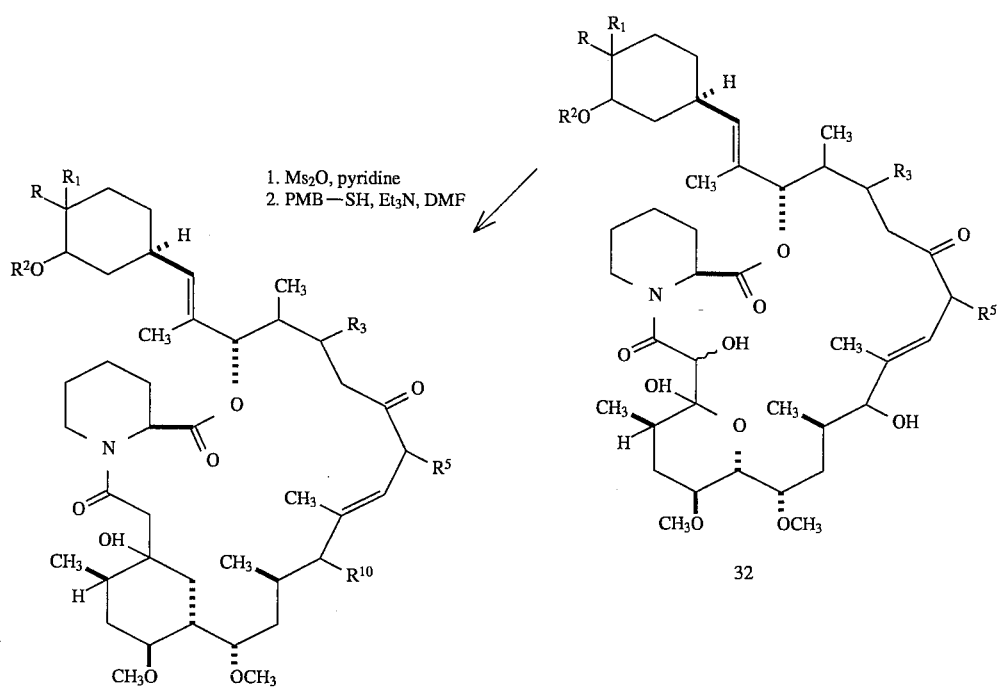
33     1. Ms₂O, pyridine     2. PMB—SH, Et₃N, DMF     32
REACTION SCHEME P
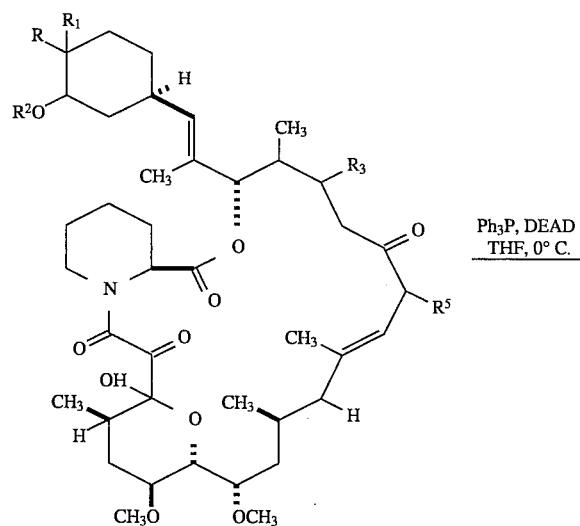
34     Ph₃P, DEAD THF, 0° C.

-continued
REACTION SCHEME P
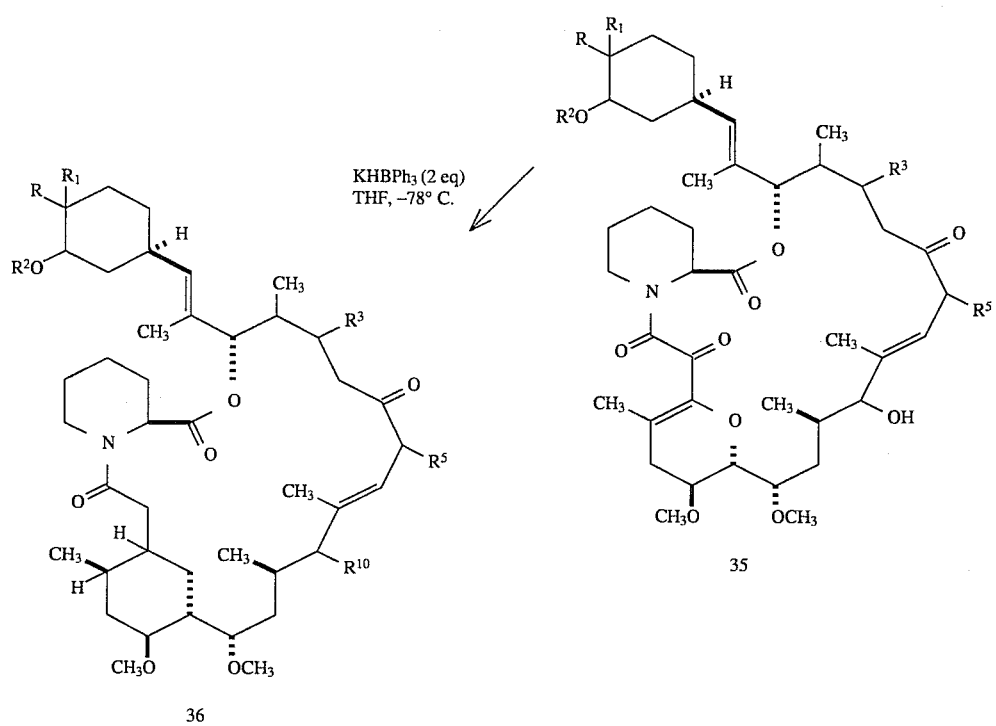
REACTION SCHEME Q
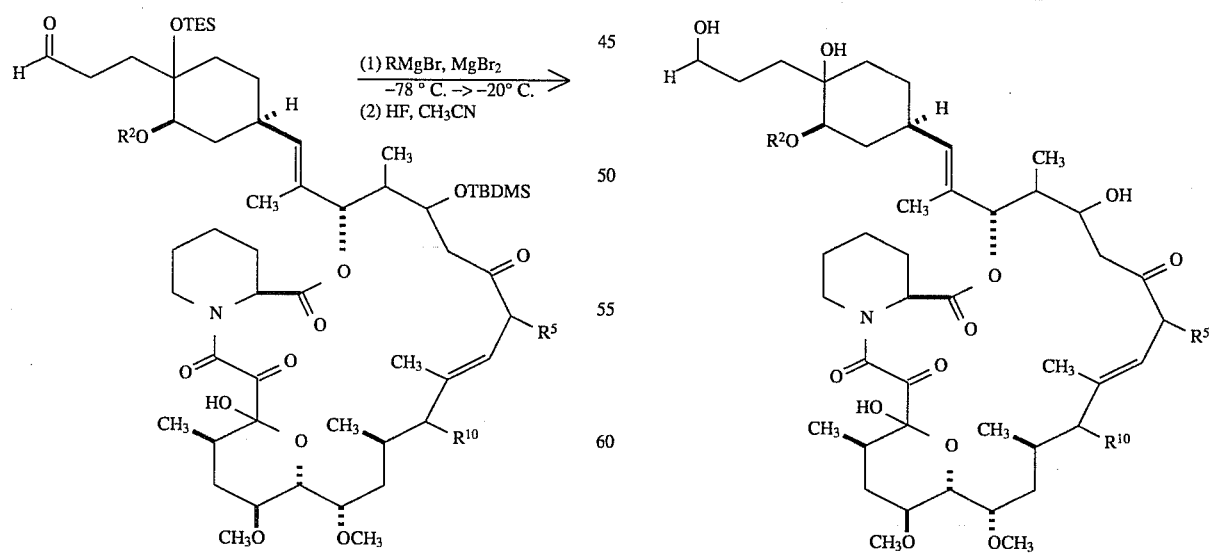

REACTION SCHEME R
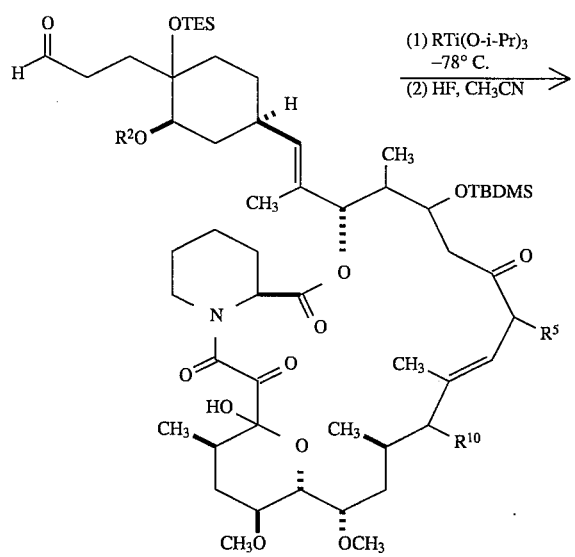
REACTION SCHEME S
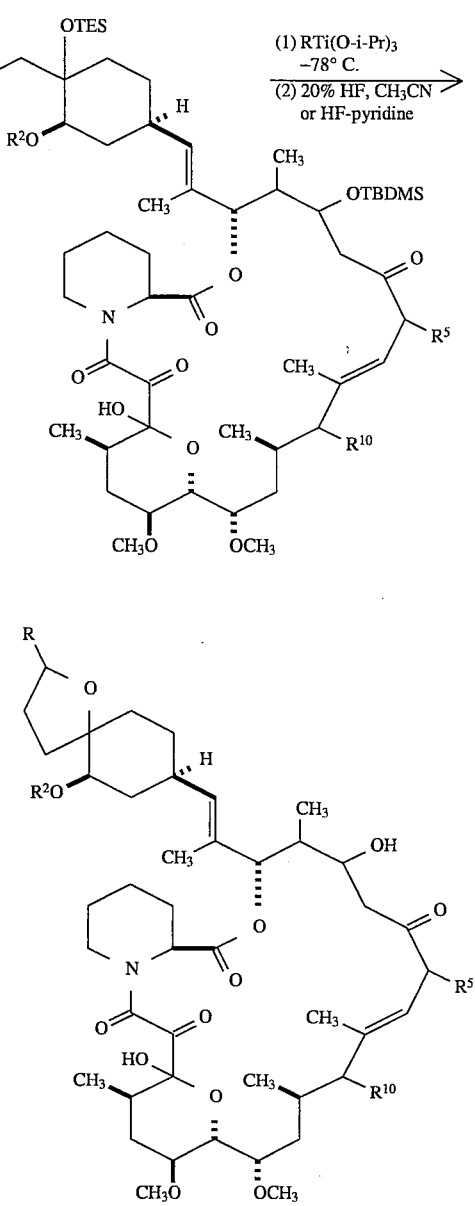

Reaction Scheme A:

Protection of the C-3", C-4" and/or the C-14 hydroxyl group(s) may be accomplished by methods known in the art for compounds of Formula II such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of dichloromethane; pyridine and p-nitrobenzoyl chloride in a solution of dichloromethane; imidazole and t-butyldiphenylsilyl chloride in a solution of methylene chloride; and the like. For example, as shown in Reaction Scheme A, the C-4",14-dihydroxy-C-3"-methoxy macrolide 2 may be protected at C-14 as the t-butyldimethylsilyl ether by treatment with t-butyldimethylsilyl trifluoromethanesulfonate in methylene chloride to give the C-4", 14-di-O-TBDMS macrolide. Treatment with toluenesulfonic acid in methanol results in selective removal of the C-4" silyl ether to give the C-14-O-TBDMS macrolide 3. An alternative method employs 2.5% HF in acetonitrile at 0° C.

Reaction Scheme B:

A key intermediate for the compounds claimed herein is ketone 3 which is easily prepared by oxidation of alcohol 2. A variety of methods may be successfully employed to achieve ketone 3. They include use of the Swern reaction (oxalyl chloride, DMSO and triethylamine ($Et_3N$) in methylene chloride). Another reagent that works very well is commonly called the Jones reagent. This is a solution of chromic acid and sulfuric acid in $H_2O$.

Reaction Scheme C:

Analogs of 4 may be produced by the use of Grignard reagents (RMgX). A convenient procedure employs a suitable Grignard reagent that is either prepared according to standard procedures or is purchased in the presence of 1 to 2 equivalents of $MgBr_2$ in ether at low temperatures (−78° C.). When using the $MgBr_2$ reagent, the configuration of R is the same as $R^2O$—. By this method may be prepared analogs of 4 wherein R can be aryl, heteroaryl, benzyl, allyl, vinyl etc.

Reaction Scheme D:

Olefinations may be achieved at the 4"-ketone group by employing a variety of commonly used methods. The simple methylene analog 5 may be prepared by using trimethylsilyllithium with $MgBr_2$ etherate. Elimination of the trimethylsilyl group may be achieved by treating the compound with HF in acetonitrile. This also removes the C14-TBDMS group which may be reattached by procedures outlined in Reaction Scheme A. Analogs of 7 may be prepared with phosphorous ylide reagents. In particular, the "Homer-Emmons" or "Wadsworth-Emmons" reagents [$(RO)_2P(O)$—$CH_2CCOR'$] are particularly effective (for a review, see *Organic Reactions* 25, 75–253, (1977)).

Reaction Scheme F:

When $R^5$ is not allyl, olefinic analogs of 4 such as 4a and 4b, may be selectively converted to aldehydes 8 and 9. For convenience, the 4"-hydroxy group is first protected, in this case as the triethylsilyl (TES) ether by utilizing triethylsilyltriflate (TESOTf) by procedures described in Reaction Scheme A. The olefin is then cleaved by the 2-step oxidative sequence using catalytic amounts of osmium tetroxide ($OsO_4$) using N-methyl morpholine N-oxide (NMMO) for regeneration. The resulting glycol is readily cleaved to aldehydes 8 and 9 by standard procedures.

Aldehyde 10 wherein the configuration of the aldehyde group is opposite to that for 9 may be prepared from methylene analog 5 by a multistep approach. Compound 5 is first oxidized to its diol intermediate with osmium tetroxide. The two hydroxy groups are then differentially protected. The primary alcohol may be protected as its trimethylsilyl (TMS) ether using trimethylsilyl chloride (TMS-Cl) and an amine base such as triethylamine. The secondary alcohol may be protected as its TES ether as described above. Next, the primary siloxy group is selectively deprotected with methanol and oxidized to the corresponding aldehyde. For this procedure, the "Swern" procedure may be employed (oxalyl chloride, DMSO, $Et_3N$, $CH_2Cl_2$). Alternatively, the diol is protected as the bis-TMS ether with trimethylsilyl trifluoromethanesulfonate. Then the primary silyloxy group is selectively deprotected with methanol and oxidized to the aldehyde as shown above.

Reaction Scheme G:

Aldehydes 8, 9 and 10 may be converted to olefins 11, 12 and 13 by any number of well known olefination procedures. Several of these procedures utilize phosphorous ylides including the Wittig reagent ($Ph_3P$-CHR'R") which is discussed and referenced in *Advanced Organic Chemistry; Reactions, mechanisms and structure*, Third edition (author: Jerry March). Another variant of the Wittig reagent (also referenced in the March text) include the Horner-Emmons (also called the Wadsworth-Emmons) reagent ($(RO)_2POCHR'R"$ (also reviewed in *Acc. Chem. Research* 16, 411–417 (1983)). A third reagent of choice is the Peterson reagent (($CH_3)_2SiR'Li$ (reviewed in *Accounts of Chemical Research* 10, 442–448, (1977)). Following olefination, the protecting groups may be removed by the standard deprotection procedures discussed previously. They include the use of HF in pyridine at reduced temperature.

Reaction Scheme H:

In cases when there are no other competing olefins such as when $R^5$=allyl, compounds 11, 12 and 13 (protected or unprotected) may be reduced to their saturated analogs 14, 15 and 16 by utilizing any of the many methods of catalytic hydrogenation.

Reaction Schemes I & J:

Aldehydes 8–10 may be oxidized to carboxylic acids 17–19 by any number of methods including use of the Jones reagent as outlined in Reaction Scheme B. Ketone design 17 is also prepared via a condensation reaction between ketone 3 and an enolate anion of an appropriate acetate ester such as the sodium enolate of 2-phenylthioethyl acetate or benzyl acetate (Reaction Scheme J). The resultant esters may be converted to 17 via reaction of HF-pyridine for the phenylthioethyl ester or by hydrogenolysis of the benzyl ester. Other acetate esters are also used as long as the ester may be removed under mild conditions.

Reaction Scheme K:

Carboxylic acids 17–19 are convened to amides and ketones by standard reaction practices. For example, acid 17 is converted to amide 20 by reaction with an appropriate amine and a suitable activating reagent such as dicyclohexylcarbodiimide (DCC) or the water soluble ethyldimethylamino-propylcarbodiimide hydrochloride (EDC, EDAC) in a solvent such as dichloromethane.

Ketone 21 is prepared from 17 via activation of the carboxyl group to an acid chloride (with thionyl chloride) or a mixed anhydride (with an alkylchloroformate such as methylchloroformate in THF with $Et_3N$) followed by treatment with a Grignard or other related organometallic reagent.

Reaction Scheme L:

As shown in Reaction Scheme L the 14-hydroxy group of a macrolide (wherein $R_1$, $R_2$, $R_5$, $R_{10}$, W and n are as defined above) may be eliminated by treatment with p-toluenesulfonic acid, benzenesulfonic acid or methanesulfonic acid in an inert organic solvent such as benzene, or toluene at from 40° C. to 60° C., for about 0.5 to 6 hours, or a sufficient period of time to eliminate the 14-hydroxy group. Neutralization with an aqueous solution of a weak base such as aqueous saturated sodium bicarbonate gives the 14,15-dehydro macrolides 23. The 14-hydroxy group may also be eliminated by activation followed by basic elimination, as described in U.S. Pat. No. 4,894,366.

In cases when there are no other competing olefins present, compound 23 may be reduced to the saturated analog 24 by utilizing any of the many methods of catalytic hydrogenation.

By suitable selection of protecting groups and the sequence of synthetic steps, all possible variations of substitution may be achieved.

Reaction Scheme M:

As shown in Reaction Scheme M, $R_2$ may be modified in any number of ways utilizing benzyl or alkenyl trichloroacetimidate reagents. When $R_2=$ H either as a starting material or after R and $R_1$ have been prepared and a protecting group $R^2$ has been removed, the hydroxy group of 25 may be reacted in an inert organic solvent such as methylene chloride, chloroform, pentane, hexane, cyclohexane, heptane or mixtures thereof with a heteroarylalkyl, heteroarylalkenyl or heteroarylalkynyl trichloroacetimidate reagent (prepared by the reaction of an appropriate sodium alkoxide with trichloroacetonitrile, such as described by Wessel, H. P., Iversen, T., Bundle, D. R.; *J. Chem, Soc., Perkin Trans. I*, 1985, 2247) in the presence of a mild acid catalyst such as trifluoro-methanesulfonic acid, p-toluenesulfonic acid, methanesulfonic acid, or mixtures thereof at a temperature of 20°–50° C. for a period of from one hour to seven days to give the 4"-O-heteroarylalkyl-, 4"-O-heteroarylalkenyl- or 4"-O-heteroarylalkynyl-3"-methoxy macrolide 26.

Alternatively, aryl or heteroaryl ether derivatives of $R^2$ may be prepared. A solution of 25 in an inert organic solvent such as methylene chloride, benzene, toluene, chloroform, or the like or mixtures thereof is treated with a triaryl- or triheteroarylbismuth diacetate reagent (prepared immediately prior to use by the addition of acetic acid to a suspension of a triaryl- or triheteroarylbismuth carbonate in an inert organic solvent such as methylene chloride, choroform or the like or mixture thereof) in the presence of a catalytic amount of copper(II) acetate at a temperature of 20°–50° C., preferably room temperature, for a period of one hour to seven days, preferably one day, to give 27. Alternatively, the triaryl- or triheteroarylbismuth(V) reagent may be prepared by treatment of a triaryl- or triheteroarylbismuthine with a suitable oxidant such as peracetic acid, iodobenzene diacetate, bis(trifluoroacetoxy) iodobenzene and the like in an inert solvent such as methylene chloride, chloroform, benzene, toluene and the like. The triaryl- or triheteroarylbismuth(V) reagent may be used without purification or may be purified by silica gel chromatography. Triaryl- or triheteroarylbismuthines may be prepared by the reaction of an appropriate aryl or heteroaryl grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triheteroaryl bismuth reagents may be found in Barton, D.H.E., et al., *J., Chem. Soc. Chem. Commun.*, 65, 1986 and references cited therein.

Reaction Scheme N:

A hydroxyl or fluoro group may be introduced at C-20 essentially by the procedures of Reaction Scheme N. The suitably protected macrolide 28 is oxidized at C-20 by treatment with selenium dioxide in an alcoholic solvent such as ethanol in the presence of pyridine at solvent reflux temperature to give the 20-hydroxy macrolide (29). The 20-hydroxy macrolide may be further derivatized at C-20 by alkylation, acylation or phosphorylation to give ether, ester or phosphate derivatives by procedures well known to the practitioner of the art. As further illustrated, treatment of the 20-hydroxy macrolide 29 with diethylaminosulfur trifluoride in an inert organic solvent such as methylene chloride, chloroform or the like at a temperature of about 0° C. to –90° C., preferably about –78° C., gives the 20-fluoro 4", 14-di-OTBS macrolide (30). The procedures of Reaction Scheme J may be conducted prior to, concurrent with, or subsequent to the procedures of Reaction Schemes A–M.

Reaction Scheme O:

Suitably modified and protected compound 31 may be modified in the tricarbonyl region. Keto group at the 2-position may be selectively reduced using several procedures. Reaction of compound 31 with sodium borohydride ($NaBH_4$) in isopropanol at reduced temperatures may provide compound 32. Alternatively, Samarium iodide ($SmI_2$) in THF and methanol at –78° C. with slow warming to rt is also effective.

$C_2$-hydroxy analog 32 may be converted to methylene derivative 33 a two-step sequence. The first step requires activation by use of methanesulfonyl anhydride, for example, to give the methanesulfonate ester. This may be carried out in pyridine. The second step requires reaction with a mercaptan reagent such as paramethoxybenzylmercaptan (PMB-SH) in a solvent such as DMF with $Et_3N$ in an oxygenated atmosphere. This reaction sequence may be accomplished in good yield.

The procedures of Reaction Scheme O may be conducted prior to, concurrent with, or subsequent to the procedures of Reaction Schemes A–N.

Reaction Scheme P:

The C-1 hydroxy group of compound 34 may be removed by dehydration using triphenylphosphine ($Ph_3P$) and diethylazodicarboxylate (DEAD) in THF at reduced temperatures to provide dehydro derivative 35.

Compound 35 may be selectively reduced to saturated analog 36 by conjugate reduction. One reagent that is particularly effective is potassium triphenylborohydride ($KHBPh_3$) in THF at –78° C.

The procedures of Reaction Scheme P may be conducted prior to, concurrent with, or subsequent to the procedures of Reaction Schemes A–N.

Reaction Scheme O

Carbanions may be added to the aldehyde to afford the corresponding alcohol. A convenient procedure employs a suitable Grignard reagent that is either prepared according to standard procedures or is purchased in the presence of 1 to 2 equivalents of MgBr2 in ether or tetrahydrofuran at low temperatures (–78° C. to –20° C.). Under these conditions, both diastereomers at the new center are obtained. Following addition, the silyl groups may be removed by treatment with 5–10% HF in acetonitrile as described above.

Reaction Scheme R

Titanium reagents may be added to the aldehyde to afford the corresponding alcohol. A convenient procedure employs a suitable titanium reagent that is prepared via transmetallation of an alkyllithium or Grignard reagent with chlorotitanium triisopropoxide. The titanium reagent is added to the aldehyde in ether or tetrahydrofuran at low temperatures (–78° C. to –20° C.). Under these conditions, both diastereomers at the new center are obtained. Following addition, the silyl groups may be removed by treatment with 5–10% HF in acetonitrile as described above.

Reaction Scheme S

The tetrahydrofuran analog may be obtained via cyclization of the hydroxypropyl analog under strong Lewis acid condition, such as 20% HF in acetonitrile or HF-pyridine over several days. This step also deprotects the 24-silyl group.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*J. Am. Chem. Soc.* 1989, 111, 1157; *J. Am. Chem. Soc*, 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J,. Org. Chem.* 1989, 54, 9; *J. Org. Chem.* 1989, 54, 11; *J. Org. Chem.* 1989, 54, 12; *J, Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts (which are negative counterions defined herein as M−) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as M+) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne Alopecia arcata, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of the invention are also indicated in certain eye diseases such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' ophthalmopathy, severe intraocular inflammation, and the like.

The compounds of Formula I are also useful for treating multidrug resistance of tumor cells, (i.e. enhancing the activity and/or sensitivity of chemotherapeutic agents), preventing or treating inflammation of mucosa or blood vessels (such as leukotriene $B_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis), or intestinal lesions associated with thermal burns, cytomegalovirus infection, particularly HCMV infection.

Further, the compounds of Formula I are also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compounds of the invention are indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compounds of the invention are also indicated for use as antimicrobial agents, and thus may be used in the treatment of diseases caused by pathogenic microorganisms and the like.

The compounds of Formula I may also be useful in the prevention or treatment of immunodepression (such as trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428, 169. Oral dosage forms may be prepared essentially as described by T. Hondo, et al., *Transplantation Proceedings,* 1987, XIX, Supp. 6, 17–22. Dosage forms for external application may be prepared essentially as described in EPO Publication 0,423,7 14. The active object compound is included in the pharmaceutical composition in an amount sufficient to produce the desired effect upon the process or condition of diseases.

For the treatment of these conditions and diseases caused by immmunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

For modifying the activity and/or toxicity of FK-506-type immunosuppressants, a compound of Formula I may be administered prior to, in conjuction with or subsequent to the administration of an FK-506-type of a compound.

The compounds of Formula I may optionally be employed in co-therapy with anti-proliferative agents. Particularly preferred is co-therapy with an antiproliferative agent selected from the group consisting of azathioprine (AZA), brequinar sodium, deoxyspergualin (DSG), mizaribine, mycophenolic acid morpholino ester (RS-61443), cyclosporin and rapamycin.

The compounds of Formula I may also be employed in conjunction with (or in a pharmaceutical composition additionally comprising):

(1) a 5α-reductase inhibitor, (2) a cyclosporin, (3) a potassium channel opener (such as minoxidil), or (4) a phospholipid.

Such co-therapy is particularly useful in hair revitalizing, such as in the treatment of male pattern alopecia, female pattern alopecia, alopecia senilis or alopecia areata, by providing epilation prevention, hair germination, and/or a promotion of hair generation and hair growth.

Such co-therapy is further useful in treating the hyperandrogenic conditions of androgenic alopecia, acne vulgaris, seborrhea, and female hirsutism.

For co-therapy of these conditions and diseases a compound of Formula I may be administered in combination with prior to, concurrent to, or subsequent to the administration of other agent(s).

For hair revitalizing the compound of Formula I may be administered topically or orally. Cyclosporin may be administered topically or orally. Although the 5α-reductase inhibitor or the potassium channel opener may be administered topically or orally, it is preferable that it be administered topically to the scalp. For unitary formulation, however, the preferred mode of administration is topically. It is especially preferred that the hair revitalizing composition of the present invention is administered by a percutaneous administration or by spraying onto the skin.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at daily, semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

PREPARATION OF STARTING INTERMEDIATES

EXAMPLE 1

17-Ethyl-1-hydroxy-12-[2'-( 4"-hydroxy-3"-methoxycy-clo-hexyl)-1'-methylvinyl]-23,25-dimethoxy-13,19,21,27-tetramethyl- 11,28-dioxa-4-azatricyclo[22.3.1.0$^{3,9}$]octacos-18-end- 2,3,10,16-tetraone A solution of 500 mg of 17-ethyl-1,14-di-hydroxy- 12-[2'-( 4"-hydroxy-3"-methoxycyclohexyl)-1'-methylvinyl]-23,25-dimethoxy- 13,19,21,27-tetramethyl-11,28-dioxa-4-azatricyclo[22.3.1.0$^{4,91}$ octacos- 18-ene-2,3,10,16-tetraone in 7 ml of benzene was treated with 10 mg of p-toluene-sulfonic acid and the solution was heated at 60° C. for two hours. The reaction mixture was quenched into saturated sodium bicarbonate solution and extracted with ethyl acetate. The combined organic layers were washed with water and saturated sodium chloride solution, dried with anhydrous magnesium sulfate and concentrated. The residue was chromatographed on silica gel (66% ethyl acetate: 33% hexane: 1% methanol) to give 350 mg of product. This material was dissolved in 10 ml of ethyl acetate and treated with 15 mg of 5% Rh/C. A balloon containing hydrogen was placed over the reaction mixture and the mixture stirred until the reaction was complete. The mixture was filtered through diatomaceous earth, concentrated and the residue subjected to chromatography (75% $CH_2Cl_2$: 5% MeOH: 20% Hexane) to give 294 mg of product.

EXAMPLE 2

17-Ethyl-1-hydroxy-12-[2'-( 4",3"-dihydroxyoxycyclo-hexyl)-1'-methylvinyl]-23,25-dimethoxy-13,19,21,27-tetramethyl-11,28-dioxa- 4-azatricyclo[22.3.1.0$^{4,9}$]octacos-18-ene-2,3,10,16-tetraone A solution of 17-ethyl-1,14-dihydroxy-12-[2'-(4"-hydroxy- 3"-hydroxycyclohexyl)-1'-methylvinyl]-23,25-dimethoxy- 13,19,21,27-tetramethyl-11,28-dioxa-4-azatricyclo-[22.3.1.0$^{4,9}$]octacos-18-ene- 2,3,10,16-tetraone (210 mg) and a catalytic amount of p-toluenesulfonic acid in 40 ml of benzene was refluxed for 4 hours under a nitrogen atmosphere. The solvent was removed under reduced pressure and the dark residue was purified by chromatography (silica gel, 7% i-propanol/$CH_2Cl_2$) to give 17-ethyl-1-hydroxy-12-[2'-( 4",3"-dihydroxycyclohexyl)-1'-methylvinyl]-23,25-dimethoxy-13,19,21,- 27-tetramethyl-11,28-dioxa-4-azatricyclo-[22.3.1.0$^{4,9}$]octacos- 14,18-diene-2,3,10, 16-tetraone (180mg) as a white solid. This material was dissolved in ethanol (20 ml) and treated with 5% Rh/C (40 mg). Hydrogen was introduced via balloon for 30 min. and the mixture was filtered through celite. Removal of solvent followed by chromatography (silica gel) gave 172 mg of the title compound. Mass, $^1H$ and 13C NMR data were consistent with the title structure.

EXAMPLE 3

17-Ethyl-1-hydroxy-12-[2'-(4"-hydroxy- 3"-methoxycyclo-hexyl)-1'-methylvinyl]-14-triisopropyl-silyloxy-23,25-dimethoxy- 13,19,21,27-tetramethyl-11,-28-dioxa-4-azatricyclo[22.3.1.0$^{4,9}$]octacos-18-ene- 2,3,10,16-tetraone Step 3A:

17-Ethyl-1-hydroxy-12-[2'-(4"-triisopropylsilyloxy-3"-methoxycyclohexyl)-1'-methylvinyl]-14-triisopropylsi-lyloxy- 23,25-dimethoxy-13,19,21,27-tetramethyl-11,28-dioxa-4-azatricyclo-[22.3.1.0$^{4,9}$]octacos-18-ene-2,3,10,16-tetraone To a cooled solution (0° C.) of 17-ethyl-1,14-dihydroxy-12-[2'-(4"-hydroxy-3"-methoxycyclohexyl)- 1'-methylvinyl]- 23,25-dimethoxy-13,19,21,27-tetramethyl-11,28-dioxa- 4-azatricyclo-[22.3.1.0$^{4,9}$]octacos-18-ene- 2,3,10,16-tetraone (120 mg) in dry methylene chloride (15 ml) was added 2,6-lutidine (64.3 mg) followed by triisopropylsilyl-trifluoromethane sulfonate (184 mg). Reaction temperature was raised to rt and stirred overnight under nitrogen atmosphere. The reaction was quenched with 10 ml of water and extracted with ethyl acetate. Organic layer was washed (water, sat'd $NaHCO_3$, sat'd NaCl) and dried (anhydrous $MgSO_4$). Removal of solvent followed by chromatography on silica gel (70% hexane/ethyl acetate) gave 150 mg of product. MASS: (FAB) 1110 (M+ + Li).

Step 3B:

17-Ethyl-1-hydroxy-12-[2'-(4"-hydroxy- 3"-methoxycyclo-hexyl)-1'-methylvinyl]- 14-triisopropylsilyloxy-23,25-dimethoxy- 13,19,21,27-tetramethyl-11,28-dioxa-4-azatri-cyclo[22.3.1.0$^{4,9}$]octacos-18-ene- 2,3,10,16-tetraone The title compound from the previous preparation (680 mg) was dissolved in methylene chloride (45 ml) and 10% solution of p-toluenesulfonic acid in methanol (45 ml) was added with stirring. The mixture was stirred at room temperature and the progress was followed by tlc analysis. After 4 hr, reaction was quenched with sat'd sodium bicarbonate and extracted with ethyl acetate three times. Normal workup and removal of solvent followed by purification on silica gel column (80% ethyl acetate/hexane) gave 560 mg of the title compound as a white solid. MASS: (FAB) 954 (M+ + Li).

EXAMPLE 4

17-Ethyl-1-hydroxy-12-[2'-(4"-hydroxy- 3"-methoxycyclohexyl)-1'-methylvinyl]-14-t-butyldimethylsilyloxy-23,25-dimethoxy-13,19,21, 27-tetramethyl-11,28-dioxa-4-azatricyclo[22.3.1.0$^{4,9}$]octacos-18-ene- 2,3,10,16-tetraone Step 4A:
17-Ethyl-1-hydroxy-12-[2'-(4"-t-butyldimethylsilyloxy-3"-methoxycyclohexyl)-1'-methylvinyl]-14-t-butyldimethylsilyloxy- 23,25-dimethoxy-13,19,21,27-tetramethyl-11,28-dioxa-4-azatricyclo[22.3.1.0$^{4,9}$]octacos-18-ene-2,3,10, 16-tetraone To a cooled solution (0° C.) of 17-ethyl-1,14-dihydroxy-12-[2'-(4"-hydroxy-3"-methoxycyclohexyl)-1'-methylvinyl]- 23,25-dimethoxy-13,19,21,27-tetramethyl-11,28-dioxa-4-azatricyclo-[22.3.1.0$^{4,9}$]octacos-18-ene-2,3,10,16-tetraone (395 mg) in dry methylene chloride (15 ml) was added 2,6-lutidine (160 mg) followed by t-butyldimethylsilyl trifluoromethanesulfonate (250 mg). The reaction was stirred under nitrogen atmosphere and then the temperature was raised to rt. After 6 hr, the reaction was quenched with 10 ml of water and extracted with ethyl acetate. The organic layer was washed (water, saturated NaHCO$_3$, saturated NaCl) and dried (anhydrous MgSO$_4$). Removal of solvent under reduced pressure gave 500 mg of crude product. MASS: (FAB) 1023 (M$^+$ + Li).

Step 4B:
17-Ethyl-1-hydroxy-12-[2'-(4"-hydroxy-3"-methoxycyclohexyl)- 1'-methylvinyl]-14-t-butyl-dimethylsilyloxy-23,25-dimethoxy- 13,19,21,27-tetramethyl-11,28-dioxa-4-azatricyclo[22.3.1.0$^{4,9}$]octacos-18-ene-2,3,10,16-tetraone The product from Step 4A (500 mg) was dissolved in acetonitrile (20 ml) and 100 ml of hydrogen fluoride (48%) was added. The reaction was stirred for 20 minutes at room temperature, quenched with saturated sodium bicarbonate, then extracted with ethyl acetate. Removal of solvent in vacuo followed by chromatography on silica gel (80% ethyl acetate/hexane) gave 300 mg of product (Mass, 1 H and 13C NMR data consistent with the title compound.

EXAMPLE 5

17-Ethyl-1-hydroxy-12-[2'-( 4"-(tert-butyldimethylsiloxy)-3"-hydroxycyclohexyl) 1'-methylvinyl]-23,25-dimethoxy-13,19, 21,27-tetramethyl-11,28-dioxa-4-azatricyclo [22.3.1.0$^{4,9}$]octacos-18-ene-2,3,10,16-tetraone To a solution of 17-ethyl-1-hydroxy-12-[2'-(3", 4"-dihydroxycyclohexyl)- 1'-methylvinyl]-23,25-dimethoxy- 13,19, 21,27-tetramethyl- 11,28-dioxa-4-azatricyclo[22.3.1.0$^{4,9}$] octacos- 18-ene- 2,3,10,16-tetraone (Example 2, 3.01 g) in dry methylene chloride (70 ml) was added an excess of imidazole (809 mg) followed by tertbutyldimethylsilyl chloride (716 mg). After 3 days of stirring at room temperature, the mixture was diluted with ethyl acetate which in turn was washed with $^1$N HCl, saturated sodium bicarbonate and brine, dried over magnesium sulfate and purified by flash chromatography (ethyl acetate:hexane (1:3)) to give the title compound (941 mg). $^1$H NMR consistent with the desired structure.

EXAMPLE 6

17-Ethyl-20-fluoro-1-hydroxy-12-[2'-( 4"-(hydroxy-3"-methoxycyclohexyl)- 1'-methylvinyl]-23,25-dimethoxy- 13,19,21,27-tetramethyl-11,28-dioxa-4-azatricyclo [22.3.1.0$^{4,9}$]octacos- 18-ene-2,3,10,16-tetraone Step 6A:
17-Ethyl-1-hydroxy-12-[2'-(4"-(tert-butyldimethylsilyloxy)- 3"-methoxycyclohexyl)-1'-methylvinyl]-23,25-dimethoxy-13,19, 21,27-tetramethyl-11,28-dioxa-4-azatricyclo[22.3.1.0$^{4,9}$]octacos 18-ene-2,3,10,16-tetraone.

To a solution of 17-ethyl-1-hydroxy-12-[2'-(4"-hydroxy-3"-methoxycyclohexyl)-1'-methylvinyl]-23,25-dimethoxy-13,19,21,-27-tetramethyl-11,28-dioxa-4-azatricyclo [22.3.1.0$^{4,9}$]octacos-18-ene- 2,3,10,16-tetraone (200 mg) in dry methylene chloride (3 ml) was added an excess of 2,6-lutidine (45 ml) and the mixture was stirred at room temperature. After 10 minutes, tert-butyldimethylsilyl trifluoromethanesulfonate (64 ml) was added by syringe. After 15 minutes the reaction mixture was diluted with ethyl acetate, extracted from saturated bicarbonate, washed with brine and the organic phase dried over magnesium sulfate. Removal of solvent in vacuo and flash chromatography on silica gel (ethyl acetate:hexane (1:2)+1% methanol) gave the title compound (235 mg). (1H NMR consistent with the desired structure).

Step 6B:
17-Ethyl-1,20-dihydroxy-12-[2'-(4"-tert-butyldimethylsilyloxy)- 3"-methoxycyclohexyl)-4'1'-methylvinyl]-23,25-dimethoxy-13,19, 21,27-tetramethyl-11,28-dioxa-4-azatricyclo[22.3.1.0$^{4,9}$]octacos- 18-ene-2,3,10,16-tetraone To a stirred solution of 17-ethyl-1-hydroxy-12-[2'-( 4"-(tert-butyldimethylsilyloxy)-3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3, 10,16-tetraone (235 mg) in 95% ethanol (2.2 ml) was added 53 ml of pyridine followed by selenium dioxide (58 mg). The flask was fitted with a water condenser and heated to 70° C. on a mantle. After 20 hours the mixture was cooled to room temperature filtered through diatomaceous earth and the filtrate poured into a saturated sodium bicarbonate solution. This was extracted with ethyl acetate, washed with brine and dried over magnesium sulfate. The solution was concentrated and purified by flash chromatography on silica gel (ethyl acetate:hexane (1:2)+ 1% methanol) to give the title compound (89 mg).( 1H NMR consistent with the desired structure).

Step 6C:
17-Ethyl-20-fluoro-1-hydroxy-12-[2'-( 4"-(tert-butyldimethylsiloxy)-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone A solution of 17-ethyl-20-dihydroxy-12-[2'-(4"-(tert-butyldimethylsiloxy)-3"-methoxycyclohexyl)-1'-methylvinyl]- 23,25-dimethoxy-13,19,21,27-tetramethyl-11,28-dioxa-4-azatricyclo-[22.3.1.0$^{4,9}$ octacos-18-ene-2,3,10,16-tetraone (30.5 mg) in methylene chloride (0.5 ml) was cooled to −78° C. in a dry ice/isopropanol bath. To this stirred solution, diethylaminosulfur trifluoride (4.5 ml) was added. After 3 minutes, saturated sodium bicarbonate (500 ml) was added followed by ethyl acetate (2 ml) and the mixture was warmed to room temperature. Extraction from ethyl acetate, drying over magnesium sulfate and purification by flash chromatography on silica gel (ethyl acetate:hexane (1:2)+ 1% MeOH) gave the title compound (22 mg). ($^1$H NMR consistent with the desired structure).

Step 6D:
17-Ethyl-20-fluoro-1-hydroxy-12-[2'-(4"-(hydroxy-3"-methoxycyclo-hexyl)-1'-methylvinyl]-23,25-dimethoxy-13,19,21,27-tetramethyl-11,28-dioxa-4-azatricyclo [22.3.1.0$^{4,9}$]octacos- 18-ene-2,3,10,16-tetraone To a solution of 17-ethyl-20-fluoro-1-hydroxy-12-[2'-( 4"-(tert-butyldimethylsiloxy)-3"-methoxycyclohexyl)-1"- methylvinyl]- 23,25-dimethoxy-13,19,21,27-tetramethyl-11,28-dioxa-4-azatricyclo-[22.3.1.0$^{4,9}$]octacos-18-ene-2,3, 10,16-tetraone (7 mg) in acetonitrile (0.3 ml) was added a solution of 2% hydrogen fluoride in aqueous acetonitrile (100 ml), and the mixture stirred at room temperature. After 2 hours the solution was diluted with ethyl acetate, extracted with saturated sodium bicarbonate and the organic phase dried by passage through a magnesium sulfate column. Purification of the concentrate by flash chromatography on silica gel (ethyl acetate:hexane (1:1)+ 1% methanol) gave the title compound. MASS:(FAB) 816 (M+Na). Partial $^{13}$C NMR δ: 211.5 (C-16); 196.1 (2) 169.3(10); 165.0 (3); 138.1 (C- 19); 135.8 (C-1); 121.0 (C-18' major); 84.1 (C-3"); 43.1 (C-15); 26.0 (C-21).

EXAMPLE 7

17-Ethyl-1,20-dihydroxy-12-[2'-(4"-(hydroxy- 3"-methoxycyclohexyl)-1'-methylvinyl]-23,25-dimethoxy- 13,19,21, 27-tetramethyl- 11,28-dioxa-4-azatricyclo[22.3.1.0$^{4,9}$]octacos-18-ene- 2,3,10,16-tetraone To a solution of 17-ethyl:1,20-dihydroxy-12-[2'-( 4"-(tert-butyldimethylsiloxy)-3"-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone (7 mg) (Step 6B) in acetonitrile (0.3 ml) was added a solution of 2% hydrogen fluoride in aqueous acetonitrile (100 ml), and the mixture stirred at room temperature. After 28 hours the solution was diluted with ethyl acetate, extracted with saturated sodium bicarbonate and the organic phase dried by passage through a magnesium sulfate column. Purification of the concentrate by flash chromatography on silica gel (ethyl acetate:hexane (2:1)+ 1% methanol) gave the title compound.

EXAMPLE 8

17-Ethyl-1,14,20-trihydroxy-12-[2'-(4"-hydroxy-3"-ethoxycyclohexyl)-1'-methylvinyl]-23,25-dimethoxy-13,19,21,27-tetramethyl- 11,28-dioxa-4-azatricyclo [22.3.1.0$^{4,9}$]octacos-18-ene-2,3,10,16-tetraone To a solution of 17-ethyl-1,14-dihydroxy-12-[2'-( 4"-hydroxy-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone (5.15 gm, 0.065 mol) in glacial acetic acid (500 ml) at room temperature, was added a solution of selenium dioxide (9.27 gm, 0.083 mol) in H$_2$O (90 ml). The reaction mixture was stirred at room temperature for 41 hours whereupon, it was poured into a stirred mixture of H$_2$O (3 L) and celite. After stirring for 15 minutes, the mixture was filtered through a pad of celite and extracted with diethyl ether (1×2L, 2X1L). The organic fractions were washed with saturated sodium bicarbonate and brine, dried over magnesium sulfate, filtrated and evaporated in vacuo. The product was purified by chromatography (silica, acetone:hexanes 2:5) to give the title compound MASS and $^1$H NMR were consistent with the structure.

EXAMPLE 9

17-Ethyl-1-hydroxy-12-[2'-(4"-oxo- 3"-methoxycyclohexyl)-1'-methylvinyl]-14-t-butyldimethylsilyloxy-23,25-dimethoxy-13,19, 21,27-tetramethyl-11,28-dioxa-4-azatricyclo[22.3.1.0$^{4,9}$]octacos 18-ene-2,3,10,16-tetraone A solution of 17-Ethyl-1-hydroxy-12-[2'-( 4"-hydroxy-3"methoxycyclohexyl)-1'-methylvinyl]- 14-t-butyl-dimethylsilyloxy- 23,25-dimethoxy-13,19,21,27-tetramethyl-11, 28-dioxa- 4-azatricyclo-[22.3.1.0$^{4,9}$]octacos-18-ene-2,3,10, 16-tetraone (Example 4) (30 gm, 0.0331 mol) in acetone (200 ml) was cooled to 0° C. To the solution was added 16.5 mL of Jones reagent (prepared by dissolving 26.72 g CrO$_3$ in 23 mL of concentrated H$_2$SO$_4$, then diluting the solution to 100 mL with H$_2$O) (The reaction was monitored by TLC 20% acetone/hexanes). After 60 minutes, the reaction was complete and excess oxidant was destroyed by slow addition of 10 mL of 2-propanol. After 10 min., the mixture had become bright green, and the reaction mixture was diluted with 800 mL of water and 1 L of ether. The layers were separated and the aqueous layer was washed with four equal portions of ether. Each ether layer was sequentially washed with two equal portions of water, then twice with 1 M KHCO$_3$ solution, then with brine (Virtually all of the green color was removed following the KHCO$_3$ washes). MS: 796 (M+7). The ether layers were combined, dried over MgSO4, and concentrated to a pale yellow gum that was lyophilized from benzene to afford 26.8 g (89%) of the title compound as a white solid. MS 796 (M+7).

PREPARATION OF INSTANT COMPOUNDS

EXAMPLE 10

17-Ethyl-1,14-dihydroxy-12-[2'-(4"-methylidenyl-3"-methoxycyclo-hexyl)-1'-methylvinyl]-23,25-dimethoxy-13,19,21,27-tetramethyl-11,28-dioxa-4-azatricyclo [22.3.1.0$^{4,9}$]octacos 18-ene-2,3,10,16-tetraone To a solution of MgBr$_2$-etherate (2.58 gm, 10 mmol) in pentane (10 mL) in an N$_2$ atmosphere was added a solution of trimethylsilylmethyllithium (TMSCH$_2$-Li) (10 mL of 1 M solution in diethylether). To a solution of 17-Ethyl-1-hydroxy-12-[2'-(4"-oxo- 3"-methoxycyclohexyl)-1'-methylvinyl]-14-t-butyl-dimethylsilyloxy- 23,25-dimethoxy-13,19, 21,27-tetramethyl-11,28-dioxa-4-azatricyclo-[22.3.1.0$^{4,9}$] octacos-18-ene-2,3,10,16-tetraone (Example 9) (0.2 gm, 0.22 mmol) in THF (5 mL in an N$_2$ atmosphere was added the TMSCH$_2$Li-MgBr$_2$ solution (2 ml) and the temperature was warmed to −20° C. (reaction was monitored by TLC, 3:10, ethyl acetate:hexanes). When the reaction was complete, the mixture was quenched with acetic acid (0.1 mL) and partitioned between diethyl ether and KHCO$_3$ solution. The organic fraction was washed successively with KHCO$_3$ solution and brine and concentrated in vacuo. The residue was dissolved in a solution of 10% HF in acetonitrile and the reaction mixture was stirred at room temperature for 2 hours. The reaction was subsequently concentrated in vacuo and purified by chromatography (silica, 2:10 ethyl acetate:hexanes) to give 0.092 gm (53%) of the title compound. MS=794 (M+Li)

EXAMPLE 11

17-Ethyl-1,14-dihydroxy-12-[2'-( 4"-methoxycarbonylmethylidenyl-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone Step 11A:

17-Ethyl-1-hydroxy-12-[2'-(4"-methoxycarbonylmethylidenyl- 3"-methoxycyclohexyl)-14-t-butyl-dimethylsilyloxy-1"-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone To a solution of (EtO)$_2$P(O)CH$_2$CO$_2$CH$_3$ (0.212 gm, 1.0 mmol) in THF (2 ml) at −40° C. was added sodium hexamethyldisilazane (NaHMDS) (1 ml of a 1 M solution in THF). After stirring for 20 min., a solution of 17-Ethyl-1-hydroxy-12-[2'-(4"-oxo- 3"-methoxycyclohexyl)-1'-methylvinyl]-14-t-butyl-dimethylsilyloxy- 23,25-dimethoxy-13,19,21,27-tetramethyl-11,28-dioxa-4-azatricyclo-[22.3.1.0$^{4,9}$]octacos-18-ene-2,3,10,16-tetraone (200 mg, 0.022 mmol) in 2 mL of THF was added dropwise. The reaction progress was monitored by TLC (silica, 35% ethyl acetate:hexanes). After 4 hours, the reaction was quenched with 0.1 ml HOAc and partitioned between diethyl ether and H$_2$O. The organic fraction was washed with KHCO$_3$ solution, brine, dried over MgSO$_4$, filtered and concentrated in vacuo. The residue was purified by chromatography (silica, 30% ethyl acetate: hexanes) to give two separated isomers of the title compound: Isomer A (0.014 gm) MS (FAB) 959 (M+Li). Isomer B (0.004 gm) MS (FAB) 959(M+Li).

Step 11B:
17-Ethyl-1,14-hydroxy-12-[2'-(4"-methoxycarbonylmethylidenyl- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone A solution of 17-Ethyl-1-hydroxy-12-[2'-(4"-methoxycarbonyl methylidenyl-3"-methoxycyclohexyl)- 14-t-butyl-dimethylsilyloxy-1'-methylvinyl]-23,25-dimethoxy-13,19, 21,27-tetramethyl- 11,28-dioxa-4-azatricyclo[22.3.1.0$^{4,9}$] octacos-18-ene-2,3,10,16-tetraone (0.04 gm, 0.041 mmol) in 10% HF in acetonitrile (2 ml) was stirred at room temperature for 2 hours. The reaction was then diluted with trimethylsilylethyl ether and concentrated in vacuo to give 0.028 gm of the title compound. TLC (silica, 3:10, ethyl acetate:hexanes); MS (FAB) 845 (M+Li).

EXAMPLE 12

17-Ethyl-1,14-hydroxy-12-[2'-(4"-t-butoxycarbonylmethylidenyl- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone The title compound was prepared by the procedures of Example 11. MS (FAB) 894 (M+Li).

EXAMPLE 13

17-Ethyl-1,14-hydroxy-12-[2'-(4"-carbonylmethylidenyl-3"methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene- 2,3,10,16-tetraone The title compound was prepared by the procedures of Example 11. MS (FAB) 822 (M+Li).

EXAMPLE 14

17-Ethyl-1,14-hydroxy-12-[2'-(4"-hydroxy- 4"(β)-vinyl-3"-methoxycyclohexyl)-1'-methylvinyl]- 23,25-dimethoxy-13,19,21,27-tetramethyl-11,28-dioxa-4-azatricyclo[22.3.1.0$^{4,9}$] octacos-18-ene- 2,3,10,16-tetraone Step 14A:
17-Ethyl-1-hydroxy-12-[2'-(4"-hydroxy-4"-(β)-vinyl-3"-methoxycyclohexyl)-1'-methylvinyl]-14-t-butyl-dimethylsilyloxy- 23,25-dimethoxy-13,19,21,27-tetramethyl-11,28-dioxa-4-azatricyclo [22.3.1.0$^{4,9}$]octacos-18-ene-2,3,10,16-tetraone.

To a solution of 17-Ethyl-1-hydroxy-12-[2'-(4"-oxo-3"-methoxy-cyclohexyl)-1'-methylvinyl]-14-t-butyl-dimethylsilyloxy- 23,25-dimethoxy-13,19,21,27-tetramethyl-11,28-dioxa-4-azatricyclo-[22.3.1.0$^{4,9}$]-octacos-18-ene-2,3, 10,16-tetraone (0.2 gm, 0.22 mmol) in THF (1 ml) at 0° C. in an N$_2$ atmosphere was added dropwise a solution of vinyl magnesium bromide in ether (0.5 ml of a 1 M solution). The reaction mixture was then warmed to −25° C. After 2 h, the reaction was quenched with 0.1 ml of acetic acid and the reaction mixture was partitioned between diethyl ether and KHCO$_3$ solution. The ether layer was washed with KHCO$_3$ solution, saturated NaCl solution, dried over MgSO$_4$, filtered and concentrated in vacuo. The residue was purified by chromatography (silica, 30% ethyl acetate:hexanes) to give 0.118 gm of the title compound. MS (FAB) 939 (M+Li).

Step 14B:
17-Ethyl-1,14-hydroxy-12-[ 2'-(4"-hydroxy- 4"-(β)-vinyl-3"-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene- 2,3,10,16-tetraone A solution of the product from Step 14A in 1 mL of 10% HF in CH$_3$CN at 0° C. was stirred for 2 hours at which time the reaction was quenched with trimethylsilylethyl ether and concentrated in vacuo. The residue was purified (silica, 20% acetone:hexanes) to give 0.063 gm of the title compound. MS (FAB) 825 (M+Li).

EXAMPLE 15

17-Ethyl-1,14-dihydroxy-12-[2'-(4"-hydroxy-4"-(β)-benzyl- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone To a solution of 17-Ethyl-1-hydroxy-12-[2'-(4"-oxo-3"-methoxy-cyclohexyl)-1'-methylvinyl]-14-t-butyl-dimethylsilyloxy- 23,25-dimethoxy-13,19,21,27-tetramethyl-11,28-dioxa-4-azatricyclo-[22.3.1.0$^{4,9}$]-octacos-18-ene-2,3, 10,16-tetraone (0.1 gm, 0.1 mmol) in THF (5 mL at room temperature was added MgBr$_2$.Et$_2$O (258 mg). The reaction was cooled to −78° C. and to it was added benzylmagnesiumbromide (120 uL, 2 M solution, 0.24 mmol). The reaction was stirred for 30 minutes and then warmed to −20° C. After 45 min., the reaction mixture was quenched with HOAc and partitioned between NH$_4$Cl and diethyl ether. The ether layer was dried over MgSO$_4$, filtered, and evaporated in vacuo. The residue was deprotected with 10% HF in acetonitrile by procedures previously described to give the title compound (25 mg). $^1$H and $^{13}$C NMR consistent with the desired structure), MS (FAB 888 (M+Li), TLC (silica, 20% acetone:hexanes) Rf=0.30

EXAMPLE 16

17- Ethyl-1,14-dihydroxy-12-[2'-(4"-hydroxy-4"-(β)-phenyl- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone The title compound was prepared according to procedures described in Example 15. $^1$H and $^{13}$C NMR consistent with the desired structure), MS (FAB) 874 (M+Li), TLC (silica, 20% acetone:hexanes) Rf=0.25

EXAMPLE 17

17-Ethyl-1,14-dihydroxy-12-[2'-(4"-hydroxy-4"-(β)-allyl-3"-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene- 2,3,10,16-tetraone The title compound was prepared according to procedures described in Example 15. MS (FAB) 838 (M+Li), TLC (silica, 30% acetone:hexanes) Rf=0.35

EXAMPLE 18

17-Ethyl-1,14-dihydroxy-12-[2'-(4"-hydroxy- 4"-(β)-but-3-en-1-yl- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone The title compound was prepared according to procedures described in Example 15. MS (FAB) 852 (M+Li).

EXAMPLE 19

17-Ethyl-1,14-dihydroxy-12-[2'-(4"-hydroxy- 4"-(α)-hydroxymethyl- 3"-methoxycyclohexyl)-1'-methylvinyl]-23, 25-dimethoxy- 13,19,21,27-tetramethyl-11,28-dioxa-4-azatricyclo[22.3.1.0$^{4,9}$]octacos-18-ene- 2,3,10,16-tetraone Step 19A:

17-Ethyl-1-hydroxy-12-[2'-(4"-hydroxy-4"-(α)-hydroxymethyl- 3"-methoxycyclohexyl)-14-t-butyl-dimethylsilyloxy-1'-methylvinyl]-23, 25-dimethoxy-13,19,21,27-tetramethyl-11,28-dioxa-4-azatricyclo-[22.3.1.0$^{4,9}$]octacos-18-ene-2,3, 10,16-tetraone To a solution of 17-Ethyl-1-hydroxy-12-[2'-( 4"-methylidenyl-3"-methoxycyclohexyl)-14-t-butyl-dimethylsilyloxy-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Example 10, 0.065 gm, 0.076 mmol), 0.065 of N-methylmorpholine-N-oxide in THF (1 ml) at room temperature was added 0.05 ml of a 0.1 M solution of osmium tetroxide in THF and the reaction mixture was stirred until TLC showed that reaction was complete (silica, 30% ethyl acetate: hexanes). After 1 hour, 1 M NaHSO$_3$ solution was added to the reaction mixture and it was partitioned between diethyl ether and H$_2$O. The organic fraction was washed with 1 M NaHSO$_3$ solution, saturated NaCl solution, dried over MgSO$_4$, filtered and concentrated in vacuo. The residue was purified (silica, 20% acetone:hexanes) to give 0.061 gm of the title compound. MS (FAB) 935 (M+Li).

Step 19B:

17-Ethyl-1,14-dihydroxy-12-[2'-(4"-hydroxy-4"-(α)-hydroxymethyl- 3"-methoxycyclohexyl)-1'-methylvinyl]-23, 25-dimethoxy- 13,19,21,27-tetramethyl-11,28-dioxa-4-azatricyclo[22.3.1.0$^{4,9}$]octacos-18-ene- 2,3,10,16-tetraone The title compound from Step 19A (0.30 gm, 0.03 mmol) in 1 ml of 5% HF solution in acetonitrile was stirred for 1 hour at room temperature. The reaction was quenched with TMSOEt, concentrated in vacuo and purified (silica, 30% acetone:hexanes) to give 0.02 gm of the title compound. MS (FAB) 821 (M+Li).

EXAMPLE 20

17-Ethyl-1,14-dihydroxy-12-[2'-(4"-hydroxy-4"-(β)-( 1,2-dihydroxyethyl)-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-8-ene- 2,3,10,16-tetraone Step 20A:

17-Ethyl-1-hydroxy-12-[2'-(4"-hydroxy- 4"(β)-(1,2-dihydroxyethyl)- 3"-methoxycyclohexyl)-1'-methylvinyl]-14-t-butyl-dimethylsilyloxy- 23,25-dimethoxy-13,19,21,27-tetramethyl-11,28-dioxa-4-azatricyclo-[22.3.1.0$^{4,9}$]octacos-18-ene-2,3,10,16-tetraone A solution of 17-Ethyl-1-hydroxy-12-[2'-( 4"-hydroxy-4"-(β)-vinyl- 3"-methoxycyclohexyl)-1'-methylvinyl]- 14-t-butyldimethylsilyloxy-23,25-dimethoxy- 13,19,21,27-tetramethyl-11,28-dioxa-4-azatricyclo[22.3.1.0$^{4,9}$]octacos-18-ene-2,3,10,16-tetraone (Example 14, 0.05 gm, 0.06 mmol), 50 mg N-methylmorpholino-N-oxide, and OsO$_4$ (5 mg) in THF (2 ml) was stirred at room temperature until reaction was complete (TLC, silica, 30% ethyl acetate:hexane). The reaction mixture was then quenched with NaHSO$_3$ and extracted with diethyl ether. The ether fraction was washed with KHCO$_3$ solution and brine, dried over MgSO$_4$, filtered and concentrated in vacuo. The residue was purified (silica, 30% ethyl acetate:hexane) to give 0.046 gm of the title compound. MS (FAB) 972 (M+Li).

Step 20B:

17-Ethyl-1,14-dihydroxy-12-[2'-(4"-hydroxy- 4"-(β)-( 1,2-dihydroxyethyl)-3"-methoxycyclohexyl)-1'-methylvinyl]- 23,25-dimethoxy- 13,19,21,27-tetramethyl-11,28-dioxa-4-azatricyclo[22.3.1.0$^{4,9}$] octacos- 18-ene-2,3,10,16-tetraone A 15 mg sample of the product of Step 20A (0.155 mmole) was deprotected with 10% HF in acetonitrile by procedures previously discussed to give the title compound (8.5 mg). MS (FAB) 858).

EXAMPLE 21

17-Ethyl-1-hydroxy-12-[2'-(4"-triethylsilyloxy- 4"-(β)-oxomethyl)- 3"-methoxycyclohexyl)-1'-methylvinyl]-14-t-butyl-dimethylsilyloxy- 23,25-dimethoxy-13,19,21,27-tetramethyl-11,28-dioxa-4-azatricyclo-[22.3.1.0$^{4,9}$]octacos-18-ene-2,3,10,16-tetraone Step 21A:

17-Ethyl-1-hydroxy-12-[2'-(4"-triethylsilyloxy- 4"-(β)-(1,2-dihydroxyethyl)-3"-methoxycyclohexyl)-1'-methylvinyl]- 14-t-butyl-dimethylsilyloxy-23,25-dimethoxy-13,19,21,27-tetramethyl-11,28-dioxa- 4-azatricyclo[22.3.1.0$^{4,9}$]octacos-118-ene-2,3,10,16-tetraone A solution of 0.300 g (0.322 mmole) of 17-ethyl-1-hydroxy-12-[2'-(4"-hydroxy-4"-(β)-( 1,2-dihydroxyethyl)- 3"-methoxy-cyclohexyl)- 1'-methylvinyl]-14-t-butyl-dimethylsilyloxy- 23,25-dimethoxy-13,19,21,27-tetramethyl-11,28-dioxa-4-azatricyclo-[22.3.1.0$^{4,9}$]octacos-18-ene-2,3, 10,16-tetraone and 0.5 mL 2,6-lutidine in 5 mL of dichloromethane was cooled to 0° C. under nitrogen. Then 0.25 mL (1mmole) of triethylsilyl trifluoromethanesulfonate was added and the solution was allowed to warm to room temperature. After 30 min., the reaction was partitioned between ether and water and the aqueous layer was washed with ether. The ether layers were sequentially washed with 2 M H$_2$SO$_4$, brine, KHCO$_3$, and brine. The two layers were combined, dried over MgSO$_4$, and concentrated. The oily residue was purified by silica gel chromatography with 10% ether:hexane to afford 0.313 g (93%) of the title compound. MS (FAB) 1086 (M+Li).

Step 21B:

17-Ethyl-1-hydroxy-12-[2'-(4"-triethylsilyloxy- 4"-(β)-oxomethyl)-3"-methoxycyclohexyl)- 1'-methylvinyl]-14-t-butyl-dimethylsilyloxy- 23,25-dimethoxy-13,19,21,27-tetramethyl-11,28-dioxa- 4-azatricyclo-[22.3.1.0$^{4,9}$]-octacos-18-ene- 2,3,10,16-tetraone To a solution of 17-Ethyl-1-hydroxy-12-[2'-( 4"-t-butyl-dimethylsilyloxy-4"-(b)-(1,2-dihydroxyethyl)- 3"-methoxycyclo-hexyl) 1'-methylvinyl]-14-t-butyl-dimethylsilyloxy- 23,25-dimethoxy- 13,19,21,27-tetramethyl-11,28-dioxa-4-azatricyclo[22.3.1.0$^{4,9}$]octacos- 18-ene-2,3,10,16-tetraone (0.2 gm, 0.185 mmol) in methanol (2 ml) was added a solution of NaIO$_4$ (0.08 gm, 0.38 mmol) in H$_2$O (2 ml) and the reaction mixture was stirred until reaction was complete (approximately 2 hours, reaction was monitored by TLC, silica, 30% acetone: hexanes). The reaction mixture was partitioned between diethyl ether and H$_2$O. The organic fraction was washed with NaHSO$_3$ solution and brine solution. The organic fraction was dried over MgSO$_4$, filtered and the filtrate was evaporated in vacuo. The residue was purified by chromatography silica, 20% acetone:hexanes) to give the title compound (0.173 gm). MS (FAB) 1054 (M+Li).

EXAMPLE 22

17-Ethyl-1-hydroxy-12-[ 2'-( 4"-trimethylsilyloxy-4"-(α)-oxomethyl)- 3"-methoxycyclohexyl)-1'-methylvinyl]-14-t- butyl-dimethylsilyloxy- 23,25-dimethoxy-13,19,21,27-tetramethyl-11,28-dioxa-4azatricyclo[22.3.1.0$^{4,9}$]octacos-18-ene-2,3,10,16-tetraone.

To a solution of 17-Ethyl-1-hydroxy-12-[2'-( 4"-hydroxy-4"-(α)-hydroxymethyl-3"-methoxycyclohexyl)-1'-methylvinyl]- 14-triethylsilyloxy-23,25-dimethoxy-13,19,21,27-tetramethyl- 11,28-dioxa-4-azatricyclo[22.3.1.0$^{4,9}$]octacos-18-ene- 2,3,10,16-tetraone (Example 19) (0.622 gm, 0.665 mmol) in THF (2 ml) and lutidine (0.5 ml) at 0° C. was added TMSOTf (0.35 ml, 1.75 mmol). The reaction was monitored by TLC (silica, 30% acetone:hexanes). After stirring for 2 hours, the reaction mixture was diluted with diethyl ether and washed with KHCO$_3$ and brine solutions. The organic fraction was dried over MgSO$_4$, filtered and concentrated in vacuo. The residue was dissolved in methanol and stirred for 6 hours and concentrated in vacuo. To a solution of 0.1 gm of this material (approximately 0.099 mmol) in CH$_2$Cl$_2$ was added a solution of oxalyl chloride (1 ml of a 2 M solution) and the reaction mixture was cooled to −78° C. To the cooled solution was added DMSO (1 ml of a 4 M solution in CH$_2$Cl$_2$). The reaction progress was monitored by tlc (silica, 20% acetone: hexanes). After 4 hours, triethylamine (2 ml) was added. After 30 min. the reaction mixture was diluted with diethyl ether and washed with KHCO$_3$ and brine solutions, dried over MgSO$_4$, filtered and concentrated in vacuo. The residue was purified by chromatography (silica, 20% acetone:hexanes) to give 0.063 gm of the title compound. MS (FAB) 826 (M+Li).

EXAMPLE 23

17-Ethyl-1,14-dihydroxy-12-[2'-(4"-triethylsilyloxy-4"-(β)-2-oxoethyl- 3"-methoxycyclohexyl)-1'-methylvinyl]-23,25-dimethoxy- 13,19,21,27-tetramethyl-11,28-dioxa-4-azatricyclo-[22.3.1.0$^{4,9}$]octacos-18-ene- 2,3,10,16-tetraone Step 23A:

17-Ethyl-1-hydroxy-12-[2'-(4"-triethylsilyloxy- 4"-(β)-allyl-3"-methoxycyclohexyl)- 1'-methylvinyl]-triethylsilyloxy-23,25-dimethoxy-13,19,21,27-tetramethyl- 11,28-dioxa-4-azatricyclo[22.3.1.0$^{4,9}$]octacos-18-ene-2,3,10,16-tetraone To a solution of 17-ethyl-1,14-dihydroxy-12-[2'-( 4"-hydroxy-4"-(β)-allyl- 3"-methoxycyclohexyl)-1'-methylvinyl]- 23,25-dimethoxy-13,19,21,27-tetramethyl- 11,28-dioxa-4-azatricyclo-[22.3.1.0$^{4,9}$] octacos-18-ene-2,3,10,16-tetraone (Example 17, 0.33 gm, 0.4 mmole) in CH$_2$Cl$_2$ (15 ml) and 2,6-lutidine (0.17 ml, 1.5 mmole) was added triethylsilyltriflate (0.27 ml, 1.2 mmole) and the reaction mixture was stirred for 2 hr at rt at which time TLC (30% EtOAc:hexanes) indicated that the reaction was complete. To the reaction mixture was added CH$_3$OH and it was partitioned between Et$_2$O and H$_2$O. The organic fraction was washed successively with 1N H$_2$SO$_4$, sat. NaHCO$_3$, and sat NaCl, dried over MgSO$_4$, filtered and the filtrate concentrated in vacuo to give 0.41 gm of the title compound. NMR was consistent with structure.

Step 23B:

17-Ethyl-1-hydroxy-12-[2'-(4"-triethylsilyloxy- 4"-(β)-(2,3-dihydroxypropyl)-3"-methoxycyclohexyl)- 1'-methylvinyl]-14-triethylsilyloxy-23,25-dimethoxy- 13,19,21,27-tetramethyl-11,28-dioxa-4-azatricyclo[22.3.1.0$^{4,9}$]octacos-18-ene-2,3,10,16-tetraone To a solution of 17-Ethyl-1-hydroxy-12-[2'-( 4"-triethylsilyloxy-4"-(β)-allyl-3"-methoxycyclohexyl)- 1'-methylvinyl]- 14-triethylsilyloxy-23,25-dimethoxy-13,19,21,27-tetramethyl- 11,28-dioxa-4-azatricyclo[22.3.1.0$^{4,9}$]octacos-18-ene- 2,3,10,16-tetraone (0.4 gm, 0.37 mmol) in THF (25 ml) at room temperature was added a THF solution of OsO$_4$ (0.266 ml, 0.15 M, 0.04 mmol) and NMMO (86 mg, 0.74 mmol) and the reaction was stirred. The reaction progress was monitored by TLC (25% acetone:hexanes) and added OsO$_4$ solution was added as needed. When the reaction was complete, it was quenched with 1 ml of saturated NaHSO$_3$ solution. The organic fraction was washed with H$_2$O, saturated NaHSO$_3$ solution, brine, dried over Na$_2$SO$_4$, filtered and concentrated in vacuo to a foam.

Step 23C: 17-Ethyl-1-hydroxy-12-[2'-(4-triethylsilyloxy-4"-(β)-2-oxoethyl- 3"-methoxycyclohexyl)-1'-methylvinyl]-14-triethylsilyloxy- 23,25-dimethoxy-13,19,21,27-tetramethyl-11,28-dioxa-4-azatricyclo-[22.3.1.0$^{4,9}$]octacos-18-ene-2,3,10,16-tetraone To a solution of the product of Step 23B (approx 0.3 mmol) in methanol (7 ml) at room temperature was added NaIO$_4$ (0.07 gm, 0.33 mmol) in H$_2$O (2 ml). The reaction mixture was stirred for 2 hours at room temperature. The reaction was quenched with methanol and partitioned between H$_2$O and diethyl ether. The organic fraction was dried over MgSO$_4$, filtered and concentrated in vacuo. Silica gel chromatography with 15% Ethyl acetate:hexane gave 210 mg of title compound. MASS: (FAB) 1068 (M$^+$ + Li).

EXAMPLE 24

17-Ethyl-1,14-dihydroxy-12-[2'-( 4"-hydroxy-4"(β)[(4-methoxyphenylvinyl]- 3"-methoxycyclohexyl)-1'-methylvinyl]- 23,25-dimethoxy-13,19,21,27-tetramethyl- 11,28-dioxa-4-azatricyclo-[22.3.1.0$^{4,9}$]octacos-18-ene-2,3,10,16-tetraone Step 24A:

2-(4-Methoxyphenyl)vinyl bromide

To a solution of bromomethyltriphenylphosphonium bromide (5.23 gm, 12 mmol) in THF (40 ml) at −78° C. was added NaHMDS (1 M, 11 mL). After stirring for 30 min., 4-methoxyphenylcarboxaldehyde (1.36 gm, 10 mmol) was added and the reaction mixture was stirred for 2 hours at which time reaction was complete (TLC, silica, 2:10 ethyl acetate:hexanes). To the reaction mixture was added NH$_4$C;, and it was extracted with Et$_2$O. The organic fractions were washed with KHCO$_3$ solution and brine, dried over MgSO$_4$, filtered and the filtrate was concentrated in vacuo. The residue was purified by chromatography (silica, 20% EtOAc in hexanes) to give the title compound.

Step 24B:

17-Ethyl-1-hydroxy-12-[2'-(4"-hydroxy- 4"(β)[(4-methoxyphenylvinyl]- 3"-methoxycyclohexyl)-1'-methylvinyl]-14-t-butyl-dimethylsilyloxy- 23,25-dimethoxy-13,19,21,27-tetramethyl-11,28-dioxa- 4azatricyclo[22.3.10$^{4,9}$]octacos-18-ene-2,3,10,16-tetraone To a solution of 2-(4-methoxyphenyl)vinyl bromide (0.213 gm, 1 mmol) in 4 ml of a 4:1:1 THF:Et$_2$O: pentane) solution was at −120° C. under argon, was added nBuLi (1.7 M, 1.2 mL) and the reaction was stirred for 1 hr. At this point, 17-ethyl-1-hydroxy-12-[2'-( 4"-oxo-3"-methoxycyclohexyl)-1'-methylvinyl]- 14-t-butyl-dimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone (0.2 gm, 0.22 mmol) was added to the reaction mixture and stirring was continued at −78° C. After 1 hour, TLC (silica, 30% EtOAc:hexanes) indicated that the reaction was complete. To the reaction mixture was added HOAc (0.1 mL) and the mixture was partitioned between Et$_2$O and H$_2$O. The organic fractions were washed with KHCO$_3$ solution and brine, dried over MgSO$_4$, filtered and the filtrate was concentrated in vacuo. The residue was purified by chromatography (silica, 20% EtOAc in hexanes) to give the title compound.

Step 24C:
17-Ethyl-1,14-Dihydroxy-12-[2'-(4"-hydroxy- 4" (β)[(4-methoxyphenyl-vinyl]-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene-2,3,10,16-tetraone The product from Step 24C (40 mg, 0.039 mmol) was stirred in a 10% HF-pyridine solution at rt for 3 hours. The reaction mixture was quenched with TMSOEt, concentrated in vacuo and purified by chromatography (silica, 20% acetone:hexanes) to give the title compound. MS, NMR.

EXAMPLE 25

17-Ethyl-1,14-dihydroxy-12-[2'-(4"-hydroxy-4 "-[3-( 3-nitro-phenyl)-prop-2-en-1-yl]-3"-methoxycyclohexyl)-1 '-methylvinyl]- 23,25-dimethoxy-13,19,21,27-tetramethyl-11,28-dioxa-4-azatricyclo-[22.3.1.0$^{4,9}$]octacos-18-ene-2,3,10,16-tetraone Step 25A:
3-Nitrobenzyltriphenylphosphonium bromide A solution of 3-nitrobenzylbromide (5 gm, 23 mmol) and triphenylphosphine (6.1 gm, 23 mmol) were stirred in toluene at 75° C. for 6 hr. After cooling to rt, the crystalline product was isolated by filtration. The product was washed with toluene and dried in vacuo.

Step 25B:
17-Ethyl-1-hydroxy-12-[2'-(4"-hydroxy- 4"-[3-(3-nitrophenyl)-prop- 2-en-1-yl]-3"-methoxycyclohexyl)-1'-methylvinyl]1-4-triethylsilyloxy- 23,25-dimethoxy-13,19,21,27-tetramethyl-11,28-dioxa-4-azatricyclo-[22.3.1.0$^{4,9}$]octacos-18-ene-2,3,10,16-tetraone.

To a solution of 3-nitrobenzyltriphenylphosphonium bromide (0.07 1 gm, 0.015 mmol) in THF at –78° C. was added NaHMDS (1 M, 0.14 ml, 0.14 mmol) and the reaction was stirred for 1 hr at –78° C. To the reaction mixture was then added 17-Ethyl- 1,14-dihydroxy-12-[2'-(4"-triethylsilyloxy-4"-(β)-2-oxoethyl- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone (Example 22, 0.053 gm, 0.05 mmol). The reaction mixture was stirred for 2 hr at –78° C. and then permitted to warm to 0° C. and reaction was monitored by TLC (silica, 25% EtOAc:hexanes). When the reaction was complete, it was quenched with HOAc, and partitioned between Et$_2$O and H$_2$O. The organic fractions were washed with NaHCO$_3$, H$_2$O and brine, were dried over MgSO$_4$ and filtered. The filtrate was concentrated in vacuo and purified by chromatography (silica, 25% EtOAc:hexanes) to give the title compound as a 3:2 trans:cis mixture of isomers. MASS: (FAB) 1187 (M$^+$ + Li). $^1$H and $^{13}$C NMR consistent with the desired structure.

Step 25C:
17-Ethyl-1,14-dihydroxy-12-[ 2'-(4"-hydroxy- 4"-[3-(3-nitrophenyl)-prop- 2-en-1-yl]-3"-methoxycyclohexyl)-1'-methylvinyl]- 23,25-dimethoxy- 13,19,21,27-tetramethyl-11,28-dioxa-4-azatricyclo-[22.3.1.0$^{4,9}$]octacos-18-ene-2,3,10,16-tetraone The product of Step 25B was deprotected according to conditions previously described to give after purification (silica, 25% EtOAc:hexanes) the title compound. MASS: (FAB) 959 (M$^+$ + Li). $^1$H and $^{13}$C NMR consistent with the desired structure.

EXAMPLE 26

17-Ethyl-1,14-dihydroxy-12-[2'-(4"-hydroxy-4"-[3-(4-methoxyphenyl)-prop-2-en-1-yl]- 3"-methoxycyclohexyl)-1'-methylvinyl]- 23,25-dimethoxy-13,19,21,27-tetramethyl-11,28-dioxa-4-azatricyclo-[22.3.1.0$^{4,9}$]octacos-18-ene-2,3,10,16-tetraone The title compound was prepared by the procedures of Example 25. MASS: (FAB) 944 (M$^+$ + Li). $^1$H and $^{13}$C NMR consistent with the desired structure.

EXAMPLE 27

17-Ethyl-1,14-dihydroxy-12-[2'-(4"-hydroxy-4"-[3-(3,5-dimethoxyphenyl)-prop-2-en-1-yl]-3"-methoxycyclohexyl)-1'-methylvinyl]- 23,25-dimethoxy-13,19,21,27-tetramethyl-11,28-dioxa-4-azatricyclo-[22.3.1.0$^{4,9}$]octacos-18-ene-2,3,10,16-tetraone The title compound was prepared by the procedures of Example 25. (NMR) MASS: (FAB) 974 (M$^+$ + Li) 1128 (M+Li+matrix).

EXAMPLE 28

17-Ethyl-1,14-dihydroxy-12-[2'-(4"-hydroxy-4"-[3-(4-benzyloxyphenyl)-prop-2-en-1-yl]-3"-methoxycyclohexyl)-1'-methylvinyl]- 23,25-dimethoxy-13,19,21,27-tetramethyl-11,28-dioxa-4-azatricyclo-[22.3.1.0$^{4,9}$]octacos-18-ene-2,3,10,16-tetraone The title compound was prepared by the procedures of Example 25. (NMR) MASS: (FAB) 1020(M$^+$ + Li).

EXAMPLE 29

17-Ethyl-1,14-dihydroxy-12-[2'-(4"-hydroxy-4"-[3-(4-hydroxyphenyl)-prop-2-en-1-yl]- 3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the procedures of Example 25. MASS: (FAB) 930 (M$^+$ + Li).

EXAMPLE 30

17-Ethyl-1,14-dihydroxy-12-[2'-(4"-hydroxy-4"-[3-(2-thienyl)-prop-2-en-1-yl]- 3"-methoxycyclohexyl)-1'-methylvinyl]- 23,25-dimethoxy-13,19,21,27-tetramethyl-11,28-dioxa- 4-azatricyclo-[22.3.1.0$^{4,9}$]octacos-18-ene-2,3,10,16-tetraone The title compound was prepared by the procedures of Example 25. MASS (FAB) 920 (M$^+$ + Li).

EXAMPLE 31

17-Ethyl-1,14-dihydroxy-12-[2'-(4"-hydroxy-4"-[3-phenyl-3-hydroxy-propyl]-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene-2,3,10,16-tetraone Step 31A:
17-Ethyl-1-hydroxy-12-[2'-(4"-hydroxy-4"-[but- 3-en-1-yl]-3"-methoxycyclohexyl)-1'-methylvinyl]- 14-t-butyl-dimethylsilyloxy- 23,25-dimethoxy-13,19,21,27-tetramethyl-11,28-dioxa- 4-azatricyclo-[22.3.1.0$^{4,9}$]octacos-18-ene-2,3,10,16-tetraone The title compound (0.9 gm) was prepared according to procedures described in Example 15. MASS:(FAB) 966 (M$^+$ + Li).

Step 31B:
17-Ethyl-1,14-dihydroxy-12-[2'-(4"-triethylsilyloxy- 4"-[but-3-en-1-yl]-3"-methoxycyclohexyl)-1'-methylvinyl]-14-t-butyl-dimethylsilyloxy- 23,25-dimethoxy-13,19,21,27-tetramethyl-11,28-dioxa- 4-azatricyclo[22.3.1.0$^{4,9}$]octacos-18-ene-2,3,10,16-tetraone To a solution of 17-ethyl-1-hydroxy-12-[2'-(4"-hydroxy-4"-[but-3-en-1-yl]-3"-methoxycyclohexyl)-1'-methylvinyl]-14-t-butyl-dimethylsilyloxy-23,25-dimethoxy- 13,19,21,27-tetramethyl-11,28-dioxa-4-azatricyclo[22.3.1.0$^{4,9}$]octacos-18-ene-2,3,10,16-tetraone (0.9 gm, 0.94 mmol) in $CH_2Cl_2$ (25 ml) at room temperature was added 2,6-lutidine (0.33 mL) followed by triethylsilyltriflate (0.52 mL, 2.3 mmole) and the reaction mixture was stirred at room temperature. The reaction progress was monitored by TLC (silica, 20% acetone:hexanes). After 1 hr, the reaction was diluted with $CH_3OH$ and partitioned between diethyl ether and $H_2O$. The organic layer was washed successively with 1N $H_2SO_4$, $H_2O$, $NaHSO_3$ and brine solutions. The organic fraction was then dried over $MgSO_4$, filtered and concentrated in vacuo to give the title compound (1.47 gm). MASS: (FAB) 1080 ($M^+ + Li$).

Step 31C:
17-Ethyl-1-hydroxy-12-[2'-(4"-triethylsilyloxy-4"-[3-oxoprop-1-yl]-3"-methoxycyclohexyl)-1'-methylvinyl]- 14-t-butyl-dimethylsilyloxy-23,25-dimethoxy- 13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-( 4"-triethylsilyloxy-4"-[but-3-en-1-yl]- 3"-methoxycyclohexyl)-1'-methylvinyl]- 14-t-butyl-dimethylsilyloxy-23,25-dimethoxy-13,19,21,27-tetramethyl- 11,28-dioxa-4-azatricyclo[22.3.1.0$^{4,9}$]octacos-18-ene-2,3,10,16-tetraone (1gm, 0.9 mmole) in THF (50 mL) was added $OsO_4$ (0.15 M in THF, 0.6 mL, 0.09 mmole) and N-methylmorpholine-N-oxide (0.21 gm, 1.8 mmole). The reaction mixture was stirred for 6 hr at room temperature while monitoring the reaction progress by TLC (1:4, acetone:hexanes). The reaction mixture was diluted with saturated $NaHSO_4$ and partitioned between diethyl ether, $CH_2Cl_2$ and $H_2O$. The aqueous layer was extracted once with diethyl ether and the combined organic fractions were washed with brine, dried over $Na_2SO_4$, filtered and evaporated in vacuo. The crude diol product was dissolved in $CH_3OH$ (15 mL) and to it was added a solution $NaIO_4$ (0.255 gm, 1.2 mmole) in $H_2O$ (5 mL). The reaction mixture was stirred at room temperature for 4 hours and the reaction progress was monitored by TLC (20% acetone:hexanes). The reaction was then partitioned between diethyl ether and $H_2O$. Washed aqueous layer twice with ether and combined. The organic layer was washed with brine, dried over $MgSO_4$, filtered and concentrated in vacuo. The crude product was purified by chromatography (20% acetone:hexanes) to give the title compound (0.6 gm) MASS:(FAB) 1075 ($M^+ + Li$).

Step 31D:
17-Ethyl-1 -hydroxy-12-[2'-(4"-triethylsilyloxy-4'-[3-phenyl-3-hydroxypropyl]-3"-methoxycyclohexyl)-1'-methylvinyl]- 14-t-butyl-dimethylsilyloxy-23,25-dimethoxy- 13,19,21,27-tetramethyl- 11,28-dioxa-4-azatricyclo[22.3.1.0$^{4,9}$]octacos- 18-ene-2,3,10,16-tetraone To a solution of 17-ethyl-1-hydroxy-12-[2'-(4"-triethylsilyloxy-4"-[ 3-oxoprop- 1-yl]-3"-methoxycyclohexyl)-1'methylvinyl]-14-t-butyl-dimethylsilyloxy- 23,25-dimethoxy- 13,19,21,27-tetramethyl-11,28-dioxa-4-azatricyclo[22.3.1.0$^{4,9}$]octacos-18-ene- 2,3,10,16-tetraone (0.1 gm, 0.093 mmole) in THF was added $MgBr_2$ (0.093 mmole). After stirring for 5 min. at room temperature, the reaction mixture was cooled to −78° C. and to it was added phenylmagnesium bromide (1 M in THF, 0.2 mL, 0.2 mmole). The reaction was warmed to −40° C. and stirring was continued. When the reaction was complete (TLC, 15:4: 1, hexanes:t-Butylmethylether:$CH_3CN$) the reaction was quenched with HOAc and partitioned between $NH_4C_1$ solution and diethyl ether. The organic fraction was washed with $H_2O$ and brine solution, dried over $MgSO_4$, filtered and evaporated in vacuo. The crude product was purified by chromatography (silica, 20:4: 1, hexanes:t-Butylmethylether:$CH_3CN$) to give the title compound (25 rag). MASS:(FAB) 1160($M^+ + Li$).

Step 31E:
17-Ethyl-1,14-dihydroxy-12-[ 2'-( 4"-hydroxy-4"-[3-phenyl- 3-hydroxypropyl]-3"-methoxycyclohexyl)- 1'-methylvinyl]-23,25-dimethoxy- 13,19,21,27-tetramethyl-11,28-dioxa-4-azatricyclo[22.3.1.0$^{4,9}$]octacos-18-ene,2,3,10,16-tetraone The title compound (18 mg) was obtained upon deprotection of the product of Step 31D via procedures (HF, $CH_3CN$) disclosed in previous examples. MASS:(FAB) 932 ($M^+ + Li$).

EXAMPLE 32

17-Ethyl-1,14-dihydroxy-12-[2'-(4"-hydroxy-4"-[3-phenyl-3-oxopropyl]-3"-methoxycyclohexyl)-1'-methylvinyl]-23, 25-dimethoxy- 13,19,21,27-tetramethyl-11,28-dioxa-4-azatricyclo[22.3.1.0$^{4,9}$]octacos- 18-ene-2,3,10,16-tetraone Step 32A:
17-Ethyl-1-hydroxy-12-[2'-(4"-triethylsilyloxy- 4"-[3-phenyl-3oxopropyl]- 3"-methoxycyclohexyl)-1'-methylvinyl]-14-t-butyldimethylsilyloxy-23,25-dimethoxy-13,19,21,27-tetramethyl- 11,28-dioxa-4-azatricyclo[22.3.1.0$^{4,9}$]octacos-18-ene-2,3,10,16-tetraone To a solution of 17-ethyl-1-hydroxy-12-[2'-( 4"-triethylsilyloxy-4"-[3-phenyl-3-hydroxypropyl]-3"-methoxycyclohexyl)- 1'-methylvinyl]-14-t-butyl-dimethylsilyloxy-23,25-dimethoxy- 13,19,21,27-tetramethyl-11,28-dioxa-4-azatricyclo[22.3.1.0$^{4,9}$]octacos- 18-ene-2,3,10,16-tetraone (10 mg, 0.009 mmole) in $CH_2Cl_2$ (2 mL) was added NaOAc (1.6 mg, 0.020 mmole) and PCC (3 mg, 0.014 mmole). The reaction mixture was then stirred 1 hour at room temperature when reaction was complete (TLC, silica, 1:4 acetone: hexane). Celite was added and the reaction was diluted with diethyl ether. After 20 min. the reaction mixture was filtered and concentrated in vacuo to give 6 mg of the title compound. MASS:(FAB) 1158($M^+ + Li$).

Step 32B:
17-Ethyl-1,14-dihydroxy-12-[ 2'-(4"-hydroxy-4 "-[3-phenyl-3-oxopropyl]- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone The product of Step 32A was deprotected (HF, $CH_3CN$) according to standard procedures to give the title compound. MASS:(FAB) 930 ($M^+ + Li$).

EXAMPLE 33

17-Ethyl-1,14-dihydroxy-12-[2'-(4"-hydroxy-4"-[3-(3-methylphenyl)-3-oxopropyl]- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone The title compound was prepared by the procedures of Example 31 and 32. MASS:' (FAB) 944 ($M^+ + Li$).

EXAMPLE 34

17-Ethyl-1,14-dihydroxy-12-[2'-( 4"-hydroxy-4"-[3-(3-methylphenyl)- 3-hydroxypropyl]-3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3, 10,16-tetraone The title compound was prepared by the procedures of Example 31 and 32. MASS: (FAB) 946 (M$^+$ + Li).

EXAMPLE 35

17-Ethyl-1,14-dihydroxy-12-[2'-( 4"-[benzyloxycarbonylmethylidenyl]- 3"-methoxycyclohexyl)-1'-methylvinyl]-23, 25-dimethoxy- 13,19,21,27-tetramethyl-11,28-dioxa- 4-azatricyclo[22.3.1.0$^{4,9}$]octacos-18-ene- 2,3,10,16-tetraone Step 35A:

17-Ethyl-1-hydroxy-12-[2'-( 4"-[benzyloxycarbonylmethylidenyl]- 3"-methoxycyclohexyl)-1'-methylvinyl]-14-tert-butyldimethylsilyloxy- 23,25-dimethoxy-13,19,21,27-tetramethyl-11,28-dioxa-4-azatricyclo[22.3.1.0$^{4,9}$]octacos-18-ene-2,3,10,16-tetraone A solution of 20 mL of a 1.0 M solution of sodium hexamethyldisilamide in THF was cooled to 0° C. in an ice bath under nitrogen. Then a solution of 5.85 g (20 mmole) of benzyl diethylphosphonoacetate in 10 mL of dry THF was added and the solution was stirred at 0° C. under nitrogen. After 15 min., the solution was cooled to –40° C. (dry ice-acetonitrile bath) under nitrogen, and 4.5 g (5 mmole) of 17-ethyl-1-hydroxy-12-[2'-( 4"-oxo-3"-methoxycyclohexyl)-1'-methylvinyl]- 14-t-butyl-dimethylsilyloxy- 23,25-dimethoxy-13,19,21,27-tetramethyl- 11,28-dioxa-4-azatricyclo[22.3.1.0$^{4,9}$]octacos-18-ene-2,3,10,16-tetraone (Example 9) in 10 mL of dry tetrahydrofuran was added dropwise over 5 minutes and the solution was stirred at –40° C. under nitrogen. After 3 hr, the reaction was quenched by addition of 2 mL of glacial acetic acid in 10 mL of dry THF. Et$_2$O was added and the mixture was partitioned between Et$_2$O and water and the aqueous layer was washed with Et$_2$O. The organic extracts were sequentially washed with saturated KHCO$_3$ solution and brine, then the combined extract was dried over MgSO$_4$, filtered and the filtrate was concentrated in vacuo. The oily residue was purified by flash chromatography (silica gel, 6 cm×20 cm) using ethyl acetate-hexane to afford 3.28 g (63%) of the title compound as a colorless foam; NMR (CDCl$_3$) indicated about a 9:1 mixture of E::Z olefin isomers; MS (FAB) 1042 (M+Li).

Step 35B

17-Ethyl-1,14-dihydroxy-12-[2'-( 4"-[benzyloxycarbonylmethylidenyl]- 3"-methoxycyclohexyl)-1'-methylvinyl]-23, 25-dimethoxy- 13,19,21,27-tetramethyl-11,28-dioxa-4-azatricyclo[22.3.1.0$^{4,9}$]octacos-18-ene- 2,3,10,16-tetraone A solution of 0.200 g (0.193 mmole) of 17-ethyl- 1-hydroxy-12-[2'-(4"-[benzyloxycarbonylmethylidenyl]-3"-methoxycyclohexyl)-1'-methylvinyl]-14-tert-butyldimethylsilyloxy- 23,25-dimethoxy-13,19,21,27-tetramethyl-11,28-dioxa-4-azatricyclo[22.3.1.0$^{4,9}$]octacos-18-ene-2,3, 10,16-tetraone in 5 mL of 10% (48% aqueous HF)-acetonitrile was stirred at room temperature for 8 hr. The reaction was quenched by addition of 5 mL of trimethylethoxy-silane and the solution was concentrated under vacuum. The residue was purified by flash chromatography (silica gel, 1.5 cm×10 cm) using 20% acetoneohexane and the product lyophilized from benzene to afford 0.152 g (85%) of the title compound as a colorless solid; NMR (CDCl$_3$) indicated a 9:1 mixture of olefin isomers; MS (FAB) 921 (M+Li).

Step 35C

Separation of the olefin isomers of 17-Ethyl-1,14-dihydroxy-12-[2'-(4"-[benzyloxycarbonylmethylidenyl]-3"-methoxycyclohexyl)- 1'-methylvinyl]-3,25-dimethoxy-13, 19,21,27-tetramethyl- 11,28-dioxa-4-azatricyclo[22.3.1.0$^{4,9}$]octacos- 18-ene-2,3,10,16-tetraone A sample of 100 mg of the product from Example 35B was applied to 6 preparatory TLC plates (Analtech, 20×20 cm, 500 micron). The plates were eluted two times with 1:3:6 acetonitrile: methyl-tert-butylether:hexanes. The faster band from the six plates was collected and eluted with 40% acetone-hexane to afford 15 mg of the faster isomer. The slower band from the six plates was collected and eluted with 40% acetone:hexanes to afford 80 mg of the slower isomer.

EXAMPLE 36

17-Ethyl-1,14-dihydroxy-12-[2'-(4"[phenylthioethoxycarbonyl methylidenyl]-3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the procedures of Example 35A-C. NMR (CDCl$_3$) indicated 9:1 mixture of olefin isomers; MS (FAB) 974 (M+Li).

EXAMPLE 37

17-Ethyl-1,14-dihydroxy-12-[2'-(4"-[2-[N-methyl-N-methoxyaminocarbonylmethylidenyl]- 3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18ene-2,3, 10,16-tetraone The title compound was prepared by the procedures of Example 35A-C. NMR (CDCl$_3$) indicated 9:1 mixture of olefin isomers; MS (FAB) 881 (M+Li).

EXAMPLE 38

17-Ethyl-1,14-dihydroxy-12-[2'-(4"-[5-oxa- 4-oxo]-2-heptenylidene]- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone.

The title compound was prepared by the procedures of Example 35A-C. NMR (CDCl$_3$) indicated a mixture of olefin isomers; MS (FAB) 892 (M+Li).

EXAMPLE 39

17-Ethyl-1,14-dihydroxy-12-[2'-(4"-[5-oxa-4-oxo-6-phenyl]-2-hexenylidene]- 3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the procedures of Example 35A-C. NMR (CDCl$_3$) indicated a mixture of olefin isomers; MS (FAB) 954 (M+Li).

EXAMPLE 40

17-Ethyl-1,14-dihydroxy-12-[2'-(4"-[ 2-carboxymethylidene]-3"-methoxycyclohexyl)-1'-methylvinyl]- 23,25-dimethoxy-13,19,21,27-tetramethyl- 11,28-dioxa-4-azatricyclo[22.3.1.0$^{4,9}$]octacos-18-ene- 2,3,10,16-tetraone Step 40A 17-Ethyl-1-hydroxy-12-[2'-(4"-[2-carboxymethylidene]-3"-methoxycyclohexyl)-1'-methylvinyl]-14-tert-butyldimethylsilyloxy- 23,25-dimethoxy-13,19,21,27-tetramethyl-11,28-dioxa-4-azatricyclo[22.3.1.0$^{4,9}$]octacos-18-ene-2,3, 10,16-tetraone A solution of 0.520 g (0.5 mmole) of 17-Ethyl- 1-dihydroxy-12-[2'-(4"[phenylthioethoxycarbonyl methylidenyl]-3"methoxycyclohexyl)- 1'-methylvinyl]-14-tert-butyldimethylsilyloxy- 23,25-dimethoxy-13,19,21,27-tetramethyl-11,28-dioxa-4-azatricyclo[22.3.1.0$^{4,9}$]octacos-18-ene-2,3, 10,16-tetraone (Example 36), 0.200 g of 10% palladium on charcoal, and 0.5 mL of 1-methylcyclohexa-1,4-diene in 10 mL of methanol was stirred at room temperature. After 30 min., the solution was filtered through Celite and concentrated. The residue was purified by flash chromatography (1 cm×10 cm) using 10% isopropanol-dichloromethane and the product lyophilized from benzene to afford 0.460 g (98%) of the title compound as a white solid; s MS (FAB) 959 (M+2Li), 957 (M+Li).

Step 40B

17-Ethyl-1,14-dihydroxy-12-[ 2'-(4"-[2-carboxymethylidene]- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone A solution of 0.050 g (0.053 mmole) of 17-ethyl- 1-hydroxy-12-[2'-(4"-[2-carboxymethylidene]- 3"-methoxycyclohexyl)-1'methylvinyl]- 14-tert-butyldimethylsilyloxy-23, 25-dimethoxy- 13,19,21,27-tetramethyl-11,28-dioxa-4-azatricyclo[22.3.1.0$^{4,9}$]octacos- 18-ene-2,3,10,16-tetraone in 2 mL of 10% (48% aqueous HF)-CH$_3$CN was stirred at room temperature for 16 h. The reaction was quenched by addition of 2 mL of trimethylethoxysilane and the solution was concentrated. The residue was purified by flash chromatography (1 cm×10 cm) using 10% isopropanol-dichloromethane and lyophilized from benzene to afford 0.038 g (86%) of the title compound as a white solid; MS (FAB) 845 (M+2Li), 838 (M+Li).

EXAMPLE 41

17-Ethyl-1,14-dihydroxy-12-[2'-(4"-[4-carboxy-2-butylidene]- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone The title compound was prepared by the procedures of Example 40 A and B. NMR indicated a mixture of olefin isomers; MS (FAB) 871 (M+2Li), 864 (M+Li).

EXAMPLE 42

17-Ethyl-1,14-dihydroxy-12-[2'-( 4"-[phenylaminocarbonylmethylidene]- 3"-methoxycyclohexyl)-1'-methylvinyl]- 23,25-dimethoxy- 13,19,21,27-tetramethyl-11,28-dioxa-4-azatricyclo[22.3.1.0$^{4,9}$]octacos- 18-ene-2,3,10,16-tetraone Step 42A 17-Ethyl-1-hydroxy-12-[2'-( 4"-[phenylaminocarbonylmethylidene]- 3"-methoxycyclohexyl)-1'-methylvinyl]-14-tert-butyldimethylsilyloxy- 23,25-dimethoxy-13,19,21,27-tetramethyl-11,28-dioxa-4-azatricyclo[22.3.1.0$^{4,9}$]octacos-18-ene-2,3,10,16-tetraone A solution of 0.050 g (0.053 mmole) of 17-ethyl- 1-hydroxy-12-[2'-(4"-[2-carboxymethylidene]- 3"-methoxycyclohexyl)- 1'-methylvinyl]-14-tert-butyldimethylsilyloxy-23,25-dimethoxy- 13,19,21,27-tetramethyl-11,28-dioxa-4-azatricyclo[22.3.1.0$^{4,9}$]octacos- 18-ene-2,3,10,16-tetraone, 0.050 g (0.536 mmole) of aniline, and 0.050 g (0.253 mmole) of 1-ethyl-3,3-dimethylaminopropyl carbodiimide hydrochloride in 1 mL of dichloromethane was stirred at room temperature. After 2 h, the solution was partitioned between diethylether and water and the aqueous layer was washed with ether. The two ether extracts were Sequentially washed with 2 M H$_2$SO$_4$, brine, saturated KHCO$_3$, and brine, then combined, dried over MgSO$_4$, and concentrated. The residue was dissolved in dichloromethane and applied to two preparatory TLC plates (Analtech, 20 cm×20 cm, 500 micron). The plates were eluted two times using 1:3:6 acetonitrile: methyl-tert-butyl ether:hexanes and the major band collected and eluted with 20% acetone:hexanes to afford to afford 0.043 g (79%) of the title compound as a white foam; NMR (CDCl$_3$) indicated a 1:2 ratio of olefin isomers; MS (FAB) 1027 (M+Li).

Step 42B

17-Ethyl-1,14-dihydroxy-12-[2'-( 4"-[phenylaminocarbonylmethylidene]- 3"-methoxycyclohexyl)-1'-methylvinyl]- 23,25-dimethoxy- 13,19,21,27-tetramethyl-11,28-dioxa-4-azatricyclo[22.3.1.0$^{4,9}$]octacos-18-ene-2,3,10,16.-tetraone A solution of 0.040 g (0.039 mmole) of 17-ethyl- 1-hydroxy-12-[2'-(4"-[phenylaminocarbonylmethylidene]- 3"-methoxycyclohexyl)-1'-methylvinyl]-14-tert-butyldimethylsilyloxy 23,25-dimethoxy-13,19,21,27-tetramethyl-11,28-dioxa- 4-azatricyclo 22.3.1.0$^{4,9}$]octacos-18-ene-2,3, 10,16-tetraone in 2 mL of 10% (48% aqueous HF)-acetonitrile was stirred at room temperature. After 16 h, the reaction was quenched by addition of 2 mL of trimethylethoxysilane and the solution was concentrated. The oily residue was dissolved in dichloromethane and applied to two preparatory TLC plates. The plates were eluted twice with 1:3:6 acetonitrile:methyl-tert-butylether:hexanes and the two separated bands from each were collected like bands were combined. The two products were each eluted using 1:3:6 acetonitrile: methyl-tert-butylether:hexanes and the residues were lyophilized to afford 0.013 g (36%) of the faster isomer of the title compound and 0.020 g (56%) of the slower isomer of the title compound; NMR (CDCl$_3$) of the faster isomer was consistent with the Z-olefin; MS (FAB) 913 (M+Li); NMR (CDCl$_3$) of the slower isomer was consistent with the E-olefin; MS (FAB) 913 (M+Li).

EXAMPLE 43

17-Ethyl-1,14-dihydroxy-12-[2'-(4"-[N-benzylaminocabonylmethylidene-]- 3"-methoxycyclohexyl)-1'-methylvinyl]- 23,25-dimethoxy- 13,19,21,27-tetramethyl-11,28-dioxa-4-azatricyclo[22.3.1.0$^{4,9}$]octacos-18-ene-2,3,10,16-tetraone The title compound was prepared by the procedures of Example 42A and B. NMR (CDCl$_3$) indicated a 9:1 mixture of geometrical isomers; MS (FAB) 927 (M+Li).

EXAMPLE 44

17-Ethyl-1,14-dihydroxy-12-[2'-(4"-[indol- 3-ylethyl)aminocarbonylmethylidene]- 3"-methoxycyclohexyl)-1'-methylvinyl]- 23,25-dimethoxy-13,19,21,27-tetramethyl-11,28-dioxa- 4-azatricyclo[22.3.1.0$^{4,9}$]octacos-18-ene-2,3,10,16-tetraone The title compound was prepared by the procedures of Example 42A and B. NMR (CDCl$_3$) indicated a 9:1 mixture of geometrical isomers; MS (FAB) 980 (M+Li).

EXAMPLE 45

17-Ethyl-1,14-dihydroxy-12-[2'-( 4"-[(2-pyridylmethyl)aminocarbonylmethylidene]- 3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18ene-2,3, 10,16-tetraone The title compound was prepared by the procedures of Example 42A and B. NMR (CDCl$_3$) indicated a 9:1 mixture of geometrical isomers; MS (FAB) 928 (M+Li).

EXAMPLE 46

17-Ethyl-1,14-dihydroxy-12-[2'-(4"-[indol- 5-yl)aminocarbonylmethyl-idene]-3"-methoxycyclohexyl)-1'-methylvinyl]- 23,25-dimethoxy-13,19,21,27-tetramethyl-11,28-dioxa-4-azatricyclo] 22.3.1.0$^{4,9}$]octacos-18-ene-2,3,10,16-tetraone The title compound was prepared by the procedures of Example 42A and B. NMR (CDCl$_3$) of the faster isomer was consistent with the Z-olefin; MS (FAB) 952 (M+Li); NMR (CDCl$_3$) of the slower isomer was consistent with the E-olefin; MS (FAB) 952 (M+Li).

EXAMPLE 47

17-Ethyl-1,14-dihydroxy-12-[ 2'-(4"-hydroxy- 4"-[benzyloxycarbonylmethyl]-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3.10,16-tetraone

Step 47A

7-Ethyl-1-hydroxy-12-[2'-(4"-hydroxy- 4"-[benzyloxycarbonylmethyl]- 3"-methoxycyclohexyl)-1'-methylvinyl]-14-tert-butyldimethylsilyloxy- 23,25-dimethoxy-13,19,21,27-tetramethyl-11,28-dioxa-4-azatricyclo[22.3.1.0$^{4,9}$]octacos-18-ene-2,3,10,16-tetraone A solution of 20 mL of a 1.0 M solution of sodium hexamethyldisilamide in tetrahydrofuran was cooled to −78° C. in an ice bath under nitrogen. Then a solution of 3.00 g (20 mmole) of benzyl acetate in 10 mL of dry THF was added and the solution was stirred at 0° C. under nitrogen. After 15 min., 4.5 g (5 mmole) of 17-ethyl-1-hydroxy-12-[2'-(4"-oxo-3"-methoxycyclohexyl)- 1'-methylvinyl]- 14-t-butyldimethylsilyloxy-23,25-dimethoxy-13,19,21,27-tetramethyl- 11,28-dioxa-4-azatricyclo[22.3.1.0$^{4,9}$]octacos-18-ene-2,3,10, 16-tetraone (Example 9) in 10 mL of dry tetrahydrofuran was added dropwise over 5 minutes and the solution was stirred at −78° C. under nitrogen. After 3 h, the reaction was quenched by addition of 2 mL of glacial acetic acid in 10 mL of dry tetrahydrofuran. Diethylether was added and the mixture was partitioned between ether and water and the aqueous layer was washed with ether. The organic fraction was sequentially washed with saturated KHCO$_3$ solution and brine, dried over MgSO$_4$, filtered and concentrated. The oily residue was purified by flash chromatography (silica gel, 6 cm×20 cm) using ethyl acetate-hexane to afford 2.58 g (49%) of the title compound as a colorless foam; MS (FAB) 1060 (M+Li).

Step 47B

17-Ethyl-1,14-dihydroxy-12-[2'-(4"-hydroxy- 4"-[benzyloxycarbonylmethyl]- 3"-methoxycyclohexyl)-1'-methylvinyl]-23,25-dimethoxy= 13,19,21,27-tetramethyl-11,28-dioxa-4-azatricyclo[22.3.1.0$^{4,9}$]octacos-18-ene-2,3,10,16-tetraone A solution of 0.200 g ( 0.191 mmole) of 17-ethyl-1-hydroxy-12-[ 2'-(4"-hydroxy-4"-[benzyloxycarbonylmethyl]- 3"-methoxycyclohexyl)-1'-methylvinyl]-14-tert-butyldimethylsilyloxy- 23,25-dimethoxy-13,19,21,27-tetramethyl-11,28-dioxa- 4-azatricyclo[22.3.1.0$^{4,9}$]octacos-18-ene-2,3,10,16-tetraone in 5 mL of 10% (48% aqueous HF)-acetonitrile was stirred at room temperature for 16 h. The reaction was quenched by addition of 5 mL of trimethyl-ethoxy-silane and the solution was concentrated under vacuum. The residue was purified by flash chromatography (silica gel, 1.5 cm×10 cm) using acetone-hexane and the product lyophilized from benzene to afford 0.148 g (82%) of the title compound as a colorless solid; MS (FAB) 946 (M+Li).

EXAMPLE 48

17-Ethyl-1,14-dihydroxy-12-[2'-( 4"-hydroxy-4"-[phenylthioethoxycarbonylmethyl]- 3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the procedures of Example 47A and B. MS (FAB) 990 (M+Li).

EXAMPLE 49

17-Ethyl-1,14-dihydroxy-12-[2'-( 4"-hydroxy-4"-[2-carboxymethyl]- 3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene- 2,3,10,16-tetraone

Step 49A

17-Ethyl-1-hydroxy-12-[ 2'-(4"-hydroxy- 4"-[2-carboxymethyl]- 3"-methoxycyclohexyl)-1'-methylvinyl]- 14-tert-butyldimethylsilyloxy- 23,25-dimethoxy-13,19,21,27-tetramethyl-11,28-dioxa- 4-azatricyclo[2.2.3.1.0$^{4,9}$]octacos-18-ene-2,3,10,16-tetraone A solution of 0.526 g (0.5 mmole) of 17-ethyl-1-hydroxy-12-[2'-(4"-hydroxy-4"-[phenylthioethoxycarbonylmethyl]- 3"-methoxycyclohexyl)-1'-methylvinyl]-14-tert-butyldimethylsilyloxy- 23,25-dimethoxy-13,19,21,27-tetramethyl-11,28-dioxa- 4-azatricyclo[22.3.1.0$^{4,9}$]octacos-18-ene-2,3, 10,16-tetraone, 0.200 g of 10% palladium on charcoal, and 0.5 mL of 1-methylcyclohexa-1,4-diene in 10 mL of methanol was stirred at room temperature. After 30 min., the solution was filtered through Celite and concentrated. The residue was purified by flash chromatography (1 cm×10 cm) using 10% isopropanol-dichloromethane and the product lyophilized from benzene to afford 0.470 g (99%) of the title compound as a whim solid; MS (FAB) 977 (M+2Li), 970 (M+Li).

Step 49B

17-Ethyl-1,14-dihydroxy-12-[2'-( 4"-[2-carboxymethyl]-3"-methoxycyclohexyl)-1'-methylvinyl]- 23,25-dimethoxy-13,19,21,27-tetramethyl-11,28-dioxa- 4-azatricyclo [22.3.1.0$^{4,9}$]octacos-18-ene- 2,3,10,16-tetraone A solution of 0.050 g (0.053 mmole) of 17-ethyl- 1-hydroxy-12-[2'-(4"-hydroxy-4"-[2-carboxymethyl]- 3"-methoxycyclohexyl)-1'-methylvinyl]- 14-tert-butyldimethylsilyloxy- 23,25-dimethoxy-13,19,21,27-tetramethyl- 11,28-dioxa-4-azatricyclo[22.3.1.0$^{4,9}$]octacos-18-ene-2,3,10,16-tetraone in 2 mL of 10% (48% aqueous HF)-CH$_3$CN was stirred at room temperature for 16 h. The reaction was quenched by addition of 2 mL of trimethylethoxysilane and the solution was concentrated. The residue was purified by flash chromatography (1 cm×10 cm) using 10% isopropanoldichloromethane and lyophilized from benzene to afford 0.040 g (88%) of the title compound as a white solid; MS (FAB) 863 (M+2Li), 856 (M+Li).

EXAMPLE 50

17-Ethyl-1,14-dihydroxy-12-[2'-( 4"-hydroxy-[phenylaminocarbonylmethyl]- 3"-methoxycyclohexyl)-1'-methylvinyl]- 23,25-dimethoxy- 13,19,21,27-tetramethyl-11,28-dioxa-4-azatricyclo[22.3.1.0$^{4,9}$]octacos-18-ene-2,3,10,16-tetraone

Step 50A

17-Ethyl-1-hydroxy-12-[2'-( 4"-hydroxy-4"-[phenylaminocarbonylmethyl]-3"-methoxycyclohexyl)-1'-methylvinyl]- 14-tert-butyl-dimethylsiloyloxy-23,25-dimethoxy-13,19,21,27-tetramethyl- 11,28-dioxa-4azatricyclo [22.3.1.0$^{4,9}$]octacos- 18-ene-2,3,10,16-tetraone A solution of 0.050 g (0.05 1 mmole) of 17-ethyl-1-hydroxy-12-[2'-(4"-hydroxy-4"-[carboxymethyl]-3"-methoxycyclohexyl)- 1'-methylvinyl]-14-tert-butyldimethylsilyloxy- 23,25-dimethoxy-13,19,21,27-tetramethyl-11,28-dioxa- 4-azatricyclo[22.3.1.0$^{4,9}$]octacos-18-ene-2,3, 10,16-tetraone, 0.050 g (0.536 mmole) of aniline, and 0.050 g (0.253 mmole) of 1-ethyl-3,3-dimethylaminopropyl carbodiimide hydrochloride in 1 mL of dichloromethane was stirred at room temperature. After 2 h, the solution was partitioned between ether and water and the aqueous layer was washed with ether. The two ether extracts were sequentially washed with 2 M $H_2SO_4$, brine, saturated $KHCO_3$, and brine, then combined, dried over $MgSO_4$, and concentrated. The residue was dissolved in dichloromethane and applied to two preparatory TLC plates (Analtech, 20 cm×20 cm, 500 micron). The plates were eluted two times using 1:3:6 acetonitrile-methyl-tert-butyl ether-hexane and the major band collected and eluted with 1:3:6 acetonitrile:methyl-tert-butylether: hexanes to afford 0.043 g (79%) of the title compound as a white foam; NMR ($CDCl_3$) consistent with the assigned structure; MS (FAB) 1027 (M+Li).

Step 50B

17-Ethyl-1,14-dihydroxy-12-[2'-( 4"-hydroxy-4"-[phenylaminocarbonyl methyl]-3"-methoxycyclohexyl)-1'-methylvinyl]- 23,25-dimethoxy-13,19,21,27-tetramethyl-11,28- dioxa- 4-azatricyclo[22.3.1.0$^{4,9}$]octacos-18-ene-2,3,10,16-tetraone A solution of 0.040 g (0.039 mmole) of 17-ethyl- 1-hydroxy-12-[2'-(4"-hydroxy- 4"-[phenylaminocarbonylmethyl]- 3"-methoxycyclohexyl)-1'-methylvinyl]- 14-tert-butyldimethylsilyloxy- 23,25-dimethoxy-13,19,21,27-tetramethyl- 11,28-dioxa-4-azatricyclo[ [22.3.1.0$^{4,9}$] octacos-18-ene-2,3,10,16-tetraone in 2 mL of 10% (48% aqueous HF)-acetonitrile was stirred at room temperature. After 16 h, the reaction was quenched by addition of 2 mL of trimethylethoxysilane and the solution was concentrated. The oily residue was dissolved in dichloromethane and applied to two preparatory TLC plates. The plates were eluted twice with 1:3:6 acetonitrile:methyl-tert-butylether:hexanes and the two separated bands from each were collected like bands were combined. The product was eluted using 1:3:6 acetonitrile:methyl-tert-butylether:hexanes and the residue was lyophilized from benzene to afford 0.030 g (84%) of the title compound as a colorless solid; NMR ($CDCl_3$) consistent with the assigned structure; MS (FAB) 931 (M+Li).

EXAMPLE 51

17-Ethyl-1,14-dihydroxy-12-[2'-(4"-hydroxy-4"-[indol-5-ylaminocarbonylmethyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the procedures of Example 50A and B. NMR ($CDCl_3$) consistent with the assigned structure; MS (FAB) 970 (M+Li).

EXAMPLE 52

17-Ethyl-1,14-dihydroxy-12-[2'-(4"-hydroxy-4"-[thienylaminocarbonylmethyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared by the procedures of Example 50A and B. NMR ($CDCl_3$) consistent with the assigned structure; MS (FAB) 937(M+Li).

EXAMPLE 53

17-Ethyl-1,14-dihydroxy-12-[2'-(4"-[benzylaminocarbonylmethyl]-3"-methoxycyclohexyl)-1'-methylvinyl]-23,25-dimethoxy-13,19,21,27 -tetramethyl-11,28-dioxa-4-azatricyclo [22.3.1.0$^{4,9}$]octacos-18-ene- 2,3,10,16-tetraone Step 53A 17-Ethyl-1-hydroxy-12-[2'-(4"-[benzylaminocarbonylmethyl]-3"-methoxycyclohexyl)-1'-methylvinyl]-14-tert-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone A solution of 0.250 g (0.241 mmole) of 17-ethyl-1-hydroxy- 12-[benzyloxycarbonylmethylidene]-3"-methoxycyclohexyl)- 1'-methylvinyl]-14-tert-butyldimethylsilyloxy-23,25-dimethoxy- 13,19,21,27-tetramethyl-11,28-dioxa-4-azatricyclo[22.3.1.0$^{4,9}$]octacos- 18-ene-2,3,10,16-tetraone, 0.050 g (0.536 mmole) of tetrakistriphenylphosphine-palladium and 0.100 g (1.67 mmole) of glacial acetic acid in 10 mL of benzene was stirred at room temperature. After 10 min., a solution of 1 mL of tributyltin hydride in 2 mL of benzene was added and the solution was stirred at room temperature. A second aliquot of 1 mL of tributyltin hydride was added after 1 h and the solution was left at room temperature overnight. The next day, the solution was applied to a 15 mL pad of silica gel packed with hexane. The pad was washed with 50 mL of hexane, until all of the tin residues had been eluted. Then the product was eluted with 1:3:6 acetonitrile:methyl-tert-butylether:hexanes and concentrated. The residue was purified by flash chromatography (1 cm×10 cm, silica gel) with 20% ethyl acetate:hexane to afford 0.102 g (45%) of the title compound as a colorless foam. $^1$H NMR and $^{13}$C NMR ($CDCl_3$) indicated a 1:1 mixture of isomers; MS (FAB) 1044 (M+Li).

Step 53B

17-Ethyl-1,14-dihydroxy-12-[2'-(4"-[benzyloxycarbonylmethyl]-3"-methoxycyclohexyl)-1'-methylvinyl]-23,25-dimethoxy-13,19,21,27-tetramethyl- 11,28-dioxa-4-azatricyclo[22.3.1.0$^{4,9}$] octacos-18-ene-2,3,10,16-tetraone A solution of 0.040 g (0.039 mmole) of 17-ethyl-1-hydroxy- 12-[benzyloxycarbonylmethyl]-3"-methoxycyclohexyl)-1'-methylvinyl]-14-tert-butyldimethylsiloyloxy-23, 25-dimethoxy- 13,19,21,27-tetramethyl-11,28-dioxa-4-azatricyclo[22.3.1.0$^{4,9}$]octacos-18-ene-2,3,10,16-tetraone in 2 mL of 10% (48% aqueous HF)-acetonitrile was stirred at room temperature. After 16 h, the reaction was quenched by addition of 2 mL of trimethylethoxysilane and the solution was concentrated. The oily residue was dissolved in dichloromethane and applied to two preparatory TLC plates. The plates were eluted twice with 1:3:6 acetonitrile:methyl-tert-butyl ether:hexanes and the major band was collected and eluted with 1:3:6 acetonitrile:methyl-tert-butylether:hexanes. The residue was lyophilized from benzene to afford 0.031 g (88%) of the title compound; $^1$H NMR and $^{13}$C NMR ($CDCl_3$) indicated a 1:1 mixture of 4" isomers; MS (FAB) 930 (M+Li).

EXAMPLE 54

17-Ethyl-1,14-dihydroxy-12-[2'-(4"-hydroxy-4"-
[3-phenyl-2-oxopropyl]-3"-methoxycyclohexyl)-
1'-methylvinyl]-23,25-dimethoxy-
13,19,21,27-tetramethyl-11,28-dioxa-4-azatricyclo
[22.3.1.0$^{4,9}$]octacos- 18-ene-2,3,10,16-tetraone Step 54A 17-Ethyl-1-hydroxy-12-[2'-(4"-hydroxy-4"-
[3-phenyl-2-oxopropyl]-
3"-methoxycyclohexyl)-1'-methylvinyl]-14-
tert-butyldimethylsilyloxy-23,25-dimethoxy-13,
19,21,27-tetramethyl-11,28-dioxa-4-azatricyclo
[22.3.1.0$^{4,9}$]octacos-18-ene-2,3,10,16-tetraone A solution of 20 mL of a 1.0M solution of sodium hexamethyldisilamide in tetrahydrofuran was cooled to −78° C. in an ice bath under nitrogen. Then a solution of 3.0 g (20 mmole) of benzyl methyl ketone in 10 mL of dry THF was cooled to −78° C. and added dropwise by canula to the first solution. After 5 min., a pre-cooled (−78° C.) solution of 4.5 g (5 mmole) of 17-ethyl-1-hydroxy-12-[2'-(4"-oxo-3"-methoxycyclohexyl)-1'-methylvinyl]-14-t-butyldimethylsilyloxy- 23,25-dimethoxy-13,19,21,27-tetramethyl-11,28-dioxa-4-azatricyclo[22.3.1.0$^{4,9}$]octacos-18-ene-2,3,10,16-tetraone (Example 9) in 10 mL of dry tetrahydrofuran was added dropwise over 5 minutes and the solution was stirred at −78° C. under nitrogen. After 1 h, the reaction was quenched by addition of 2 mL of glacial acetic acid in 10 mL of dry tetrahydrofuran. Ether was added and the mixture was partitioned between ether and water and the aqueous layer was washed with ether. The two ether extracts were sequentially washed with saturated KHCO$_3$ solution and brine, then the combined extract was dried over MgSO$_4$, filtered and concentrated. The oily residue was purified by HPLC (silica gel, Waters RCM) using 1:3:6 acetonitrile: methyl-tert-butylether:hexanes to afford 2.36 g (46%) of the title compound as a colorless foam; NMR (CDCl$_3$) shows distinct AB pattern at 2.6 ppm; MS (FAB) 1044 (M+Li).

Step 54B

17-Ethyl-1,14-dihydroxy-12-[2'-(4"-hydroxy-4"-
[3-phenyl-2-oxopropyl]-3"-methoxycyclohexyl)-
1'-methylvinyl]-23,25-dimethoxy-
13,19,21,27-tetramethyl-11,28-dioxa-4-
azatricyclo[22.3.1.0$^{4,9}$]octacos-18-ene-2,3,10,16-tetraone A solution of 0.040 g (0.039 mmole) of 17-ethyl-1-hydroxy- 12-[2'-(4"-[3-phenyl-2-oxopropyl]-3"-methoxycyclohexyl)-1'-methylvinyl]-14-tert-butyldimethylsiloyloxy-23,25-dimethoxy- 13,19,21,27-tetramethyl-11,28-dioxa-4-azatricyclo[22.3.1.0$^{4,9}$]octacos- 18-ene-2,3,10,16-tetraone in 2 mL of 10% (48% aqueous HF)-acetonitrile was stirred at room temperature. After 16 h, the reaction was quenched by addition of 2 mL of trimethylethoxysilane and the solution was concentrated. The oily residue was dissolved in dichloromethane and applied to two preparatory TLC plates. The plates were eluted twice with 1:3:6 acetonitrile-methyl-tert-butyl ether-hexane and the major band was collected and eluted with 1:3:6 acetonitrile:methyl-tert-butylether:hexanes. The residue was lyophilized from benzene to afford 0.029 g (80%) of the title compound; NMR shows a distinct AB pattern at 2.6 ppm; MS (FAB) 930 (M+Li).

EXAMPLE 55

17-Ethyl-1,14-dihydroxy-12-[2'-(4"-hydroxy-4"-
[3-(2-methoxyphenyl)-
2-oxopropyl]-3"-methoxycyclohexyl)-1'-
methylvinyl]-23,25-dimethoxy-
13,19,21,27-tetramethyl-11,28-dioxa-4-
azatricyclo[22.3.1.0$^{4,9}$]octacos-
18-ene-2,3,10,16-tetraone The title compound was prepared by the procedures of Example 54A and B. NMR shows a distinct AB pattern at 2.6 ppm; MS (FAB) 960 (M+Li).

EXAMPLE 56

17-Ethyl-1,14-dihydroxy-12-[2'-(4"-hydroxy-4"-
[1-phenyl-2-oxopropyl]-3"-methoxycyclohexyl)-1'-
methylvinyl]-23,25-dimethoxy-
13,19,21,27-tetramethyl-11,28-dioxa-4-
azatricyclo[22.3.1.0$^{4,9}$]octacos-18-ene-
2,3,10,16-tetraone Step 56A 17-Ethyl-1-hydroxy-12-[2'-(4"-hydroxy-4"-
[1-phenyl-2-oxopropyl]-
3"-methoxycyclohexyl)-1'-methylvinyl]-
14-tert-butyldimethylsilyloxy-
23,25-dimethoxy-13,19,21,27-tetramethyl-
11,28-dioxa-4-azatricyclo[22.3.1.0$^{4,9}$]octacos-
18-ene-2,3,10,16-tetraone A solution of 20 mL of a 1.0M solution of sodium hexamethyldisilamide in tetrahydrofuran was cooled to −78° C. in an ice bath under nitrogen. Then a solution of 3.0 g (20 mmole) of benzyl methyl ketone in 10 mL of dry THF was cooled to −78° C. and added dropwise by canula to the first solution. After 5 min., 20 mL of a 1M solution of triisopropoxytitanium chloride in dichloromethane was added and the solution grew deep orange. After 10 min., a pre-cooled (−78° C.) solution of 4.5 g (5 mmole) of 17-ethyl-1-hydroxy-12-[2'-(4"-oxo- 3"-methoxycyclohexyl)-1'-methylvinyl]-14-t-butyl-dimethylsilyloxy- 23,25-dimethoxy-13,19,21,27-tetramethyl-11,28-dioxa-4-azatricyclo[22.3.1.0$^{4,9}$] octacos-18-ene-2,3,10,16-tetraone (Example 9) in 10 mL of dry tetrahydrofuran was added dropwise over 5 minutes and the solution was stirred at −78° C. under nitrogen. After 1 h, the reaction was quenched by addition of 2 mL of glacial acetic acid in 10 mL of dry tetrahydrofuran. Ether was added and the mixture was partitioned between ether and water. The cloudy mixture was filtered through Celite and the aqueous layer was washed with ether. The two ether extracts were sequentially washed with saturated KHCO$_3$ solution and brine, then the combined extract was dried over MgSO$_4$, filtered and concentrated. The oily residue was purified by HPLC (silica gel, Waters RCM) using 1:3:6 acetonitrile:methyl-tert-butylether:hexane to afford 3.15 g (61%) of the title compound as a colorless foam; NMR (CDCl$_3$) shows singlet at 2.1 ppm; MS (FAB) 1044 (M+Li).

Step 56B

17-Ethyl-1,14-dihydroxy-12-[2'-(4"-hydroxy-4"-
[1-phenyl-2-oxopropyl]-3"-methoxycyclohexyl)-1'-
methylvinyl]-23,25-dimethoxy-
13,19,21,27-tetramethyl-11,28-dioxa-4-azatricyclo
[22.3.1.0$^{4,9}$]octacos-18-ene-2,3,10,16-tetraone A solution of 0.050 g (0.048 mmole) of 17-ethyl-1-hydroxy- 12-[2'-(4"-[1-phenyl-2-oxopropyl]-3"-methoxycyclohexyl)-1'-methylvinyl]-14-tert-butyldimethylsilyloxy- 23,25-dimethoxy- 13,19,21,27-tetramethyl-11,28-dioxa-4-azatricyclo[22.3.1.0$^{4,9}$]octacos- 18-ene-2,3,10,16-tetraone in 2 mL of 10% (48% aqueous HF)-acetonitrile was stirred at room temperature. After 16 h, the reaction was quenched by addition of 2 mL of trimethylethoxysilane and the solution was concentrated. The oily residue was dissolved in dichloromethane and applied to two preparatory TLC plates. The plates were eluted twice with 1:3:6 acetonitrile-methyl-tert-butyl ether-hexane and the major band was collected and eluted with 1:3:6 acetonitrile:methyl-tert-butylether:hexanes. The residue was lyophilized from benzene to afford 0.036 g (81%) of the title compound; NMR shows a singlet at 2.1 ppm; MS (FAB) 930 (M+Li).

EXAMPLE 57

17-Ethyl-1,14-dihydroxy-12-[2'-(4"-hydroxy-4"-[1-(3-methoxyphenyl)-
2-oxopropyl]-3"-methoxycyclohexyl)-1'-methylvinyl]-
23,25-dimethoxy-
13,19,21,27-tetramethyl-11,28-dioxa-4-azatricyclo
[22.3.1.0$^{4,9}$]octacos- 18-ene-2,3,10,16-tetraone The title compound was prepared by the procedures of Example 56. NMR shows a singlet at 2.1 ppm; MS (FAB) 960 (M+Li).

EXAMPLE 58

7-Ethyl-1,14-dihydroxy-12-[2'-(4"-hydroxy-4"-
[3-(3,5-dimethylphenyl)-
3-hydroxypropyl]-3"-methoxycyclohexyl)-1'-
methylvinyl]-
23,25-dimethoxy-13,19,21,27-tetramethyl-11,28-
dioxa-4-azatricyclo[22.3.1.0$^{4,9}$]octacos-18-ene-
2,3,10,16-tetraone Part A: (3,5-dimethylphenyl)titanium triisopropoxide A solution of 10 mmoles of 3,5-dimethylphenylmagnesium bromide in 10 mL of ether was cooled to −78° C. under nitrogen and to this was added 10 mL of a 1M solution of chlorotitanium triisopropoxide. The solution was stirred at −78° C. for 30 minutes and used in the next step.

Part B:
7-Ethyl-1-hydroxy-12-[2'-(4"-triethylsilyloxy-4"-[3-(3,5
-dimethylphenyl)-3-hydroxypropyl]-3"-
methoxycyclohexyl)-1'-methylvinyl]-14-
t-butyldimethylsilyloxy-23,25-dimethoxy-
13,19,21,27-tetramethyl-11,28-dioxa-4-azatricyclo
[22.3.1.0$^{4,9}$]octacos-18-ene-2,3,10,16-tetraone A solution of 0.322 g (0.30 mmole) of ethyl-1-hydroxy-12-[2'-(4"-triethylsilyloxy-4"-[3-oxopropyl]-3"-methoxycyclohexyl)-1'-methylvinyl]-14-t-butyldimethylsilyloxy-23, 25-dimethoxy-13,19,21,27-tetramethyl- 11,28-dioxa-4-azatricyclo[22.3.1.0$^{4,9}$]octacos-18-ene- 2,3,10,16-tetraone in 5 mL of dry tetrahydrofuran was degassed under nitrogen and cooled to −78° C. To this solution was added 3 mL of the 0.4M solution of (3,5-dimethylphenyl)titanium triisopropoxide from Part A and the solution was stirred at −78° C. After 1 h the reaction was quenched with 0.1 mL of glacial acetic acid and the solution was diluted with 20 mL of saturated NH$_4$Cl and 20 mL of ether. The whole mixture was filtered through Celite and the residue was washed with ether. The layers of the filtrate were separated and then the ether layer was first washed with saturated NaHCO$_3$ solution and brine and then dried over MgSO$_4$. The solution was concentrated to an oil that was purified by chromatography on silica gel using 20% acetone-hexane to afford 0.220 g (67%) of the title compound as a colorless foam. MASS 1188 (M+Li).

Part C:
7-Ethyl-1,14-dihydroxy-12-[2'-(4"-hydroxy-4"-[3-(3,5
-dimethylphenyl)-3-hydroxypropyl]-3"-
methoxycyclohexyl)-1'-methylvinyl]-23,25-
dimethoxy-13,19,21,27-tetramethyl-11,28-dioxa-4-
azatricyclo[22.3.1.0$^{4,9}$]octacos-18-ene-2,3,10,16-
tetraone (Isomer 1)

A solution of 220 mg (0.186 mmole) of 7-ethyl-1-hydroxy-12-[2'-(4"-triethylsilyloxy-4"-[3-(3,5-dimethylphenyl)-3-hydroxypropyl]-3"-methoxycyclohexyl)-1'-methylvinyl]-14-t-butyldimethylsilyloxy-23,25-dimethoxy-13, 19,21,27-tetramethyl-11,28-dioxa-4-azatricyclo[22.3.1.0$^{4,9}$] octacos-18-ene-2,3,10,16-tetraone in 10 mL of a 10% HF-acetonitrile solution was stirred at room temperature. After 18 h, the reaction was quenched with 5 mL of ethoxytrimethylsilane and the solution was concentrated. The oily residue was purified by HPLC (Waters RCM silica gel, 25×100 mm) using hexane-methyl t-butyl ether-acetonitrile (6:3:1) to afford 45 mg of the faster diastereomer as a white solid. MASS: 960 (M+Li)

Part D:
7-Ethyl-1,14-dihydroxy-12-[2'-(4"-hydroxy-4"-[3-(3,5
-dimethylphenyl)-3-hydroxypropyl]-3"-
methoxycyclohexyl)-1'-methylvinyl]-23,25-
dimethoxy-13,19,21,27-tetramethyl-11,28-dioxa-4-
azatricyclo[22.3.1.0$^{4,9}$]octacos-18-ene-2,3,10,16-
tetraone (Isomer 2)

Further elution of the above column afforded 55 mg of the slower diastereomer as a white solid. MASS: 960 (M+Li).

EXAMPLE 59

7-Ethyl-1,14-dihydroxy-12-[2'-(4"-hydroxy-4"-
[3-(3-fluorophenyl)-3
-hydroxypropyl]-3"-methoxycyclohexyl)-1'-
methylvinyl]-23,25-dimethoxy-13,19,21,27-
tetramethyl-11,28-dioxa-4-azatricyclo[22.3.1.0$^{4,9}$]
octacos-18-ene-2,3,10,16-tetraone The title compound was prepared according to the procedures described in Example 58. MASS: 950.

EXAMPLE 60

7-Ethyl-1,14-dihydroxy-12-[2'-(4"-hydroxy-4"-[3-
(2-benzo[b]thienyl)-3-hydroxypropyl]-3"-
methoxycyclohexyl)-1'-methylvinyl]-23,25-
dimethoxy-13,19,21,27-tetramethyl-11,28-dioxa-4-
azatricyclo[22.3.1.0$^{4,9}$]octacos-18-ene-2,3,10,
16-tetraone The title compound was prepared according to the procedures described in Example 58. MASS: 988 (M+Li).

EXAMPLE 61

7-Ethyl-1,14-dihydroxy-12-[2'-(4"-hydroxy-4"-[3-(2-naphthyl)-3-hydroxypropyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared according to the procedures described in Example 58. MASS: 982 (M+Li).

EXAMPLE 62

7-Ethyl-1,14-dihydroxy-12-[2'-(4"-hydroxy-4"-[3-(3-methylphenyl)-3-hydroxypropyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared according to the procedures described in Example 58. MASS: 946 (M+Li).

EXAMPLE 63

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 150 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at 2.5×10$^5$ cells/ml in complete culture medium composed of RPMI 1640 medium with 10% heat-inactivated fetal calf serum, 100 mM glutamine, 1 mM sodium pyruvate, 2×10$^{-5}$M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The various dilutions of the compound to be tested were then added in triplicate wells at 20 µl/well. The compound 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone was used as a standard. The culture plates were then incubated at 37° C. in a humidified atmosphere of 5% CO$_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay:

11, 12, 13, 14, 15, 16, 17, 18, 19, 20, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, and 62.

The results of this assay are representative of the intrinsic immunosuppressive activity of the compounds of the present invention.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

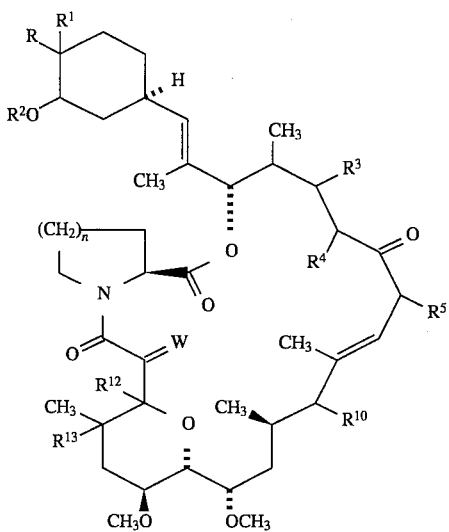

or a pharmaceutically acceptable salt thereof, wherein:
R is selected from:
(1) $C_{1-10}$alkyl
(2) substituted $C_{1-10}$alkyl wherein the alkyl is substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl
(o) —NR$^6$R$^7$, wherein R$^6$ and R$^7$ are independently selected from:
(i) hydrogen,
(ii) $C_{1-10}$alkyl unsubstituted or substituted with one or more of the substituent(s) selected from:
(a') aryl, which is unsubstituted or substituted with X, Y and Z,
(b') heteroaryl, which is unsubstituted or substituted with X, Y and Z,
(c') —OH,
(d') $C_{1-6}$alkoxy,
(e') —CO$_2$H,
(f') —CO$_2$—$C_{1-6}$alkyl,
(g') —$C_{3-7}$cycloalkyl, and
(h') —OR$^{11}$,
(iii) $C_{3-10}$alkenyl unsubstituted or substituted with one or more of the substituent(s) selected from:
(a') aryl, which is unsubstituted or substituted with X, Y and Z,
(b') heteroaryl, which is unsubstituted or substituted with X, Y and Z,
(c') —OH,
(d') $C_{1-6}$alkoxy,
(e') —CO$_2$H,
(f') —CO$_2$—$C_{1-6}$alkyl,
(g') —$C_{3-7}$cycloalkyl, and
(h') —OR$^{11}$,
(iv) or where R$^6$ and R$^7$ and the N to which they are attached may form an unsubstituted or substituted 3–7-membered heterocyclic ring which may include one or two additional heteroatoms independently selected from the group consisting of O, S(O)$_p$, NR$^{14}$, wherein R$^{14}$ is hydrogen or $C_{1-6}$ alkyl unsubstituted or substituted by phenyl, and p is 0, 1 or 2, such as morpholine, thiomorpholine, piperidine, or piperizine,
(p) —NR$^6$CO—$C_{1-6}$alkyl-R$^7$,
(q) —NR$^6$CO$_2$—$C_{1-6}$alkyl-R$^7$,
(r) —NR$^6$CONR$^6$R$^7$,
(s) —OCONR$^6$R$^7$,
(t) —COOR$^6$,
(u) —CHO,
(v) —OR$^{11}$, and
(w) —S(O)$_p$—$C_{1-6}$alkyl;
(3) substituted or unsubstituted $C_{1-10}$alkyl wherein one or more of the alkyl carbons is replaced by a group selected from: —NR$^6$—, —O—, —S(O)$_p$—, —CO$_2$—, —O$_2$C—, —CONR$^6$—, —NR$^6$CO—, and —NR$^6$CONR$^7$—, and the alkyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl,
(o) —NR$^6$R$^7$, wherein R$^6$ and R$^7$ are defined above,
(p) —NR$^6$CO—$C_{1-6}$alkyl-R$^7$,
(q) —NR$^6$CO$_2$—$C_{1-6}$alkyl-R$^7$,
(r) —NR$^6$CONR$^6$R$^7$,
(s) —OCONR$^6$R$^7$,
(t) —COOR$^6$,
(u) —CHO,
(v) —OR$^{11}$, and
(w) —S(O)$_p$—$C_{1-6}$alkyl;
(4) $C_{1-10}$alkenyl wherein alkenyl contains one to four double bonds;
(5) substiuted $C_{1-10}$alkenyl wherein the alkenyl contains one to four double bonds and the alkyl or alkenyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z, (e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl
(o) —NR$^6$R$^7$, wherein R$^6$ and R$^7$ are as defined above,
(p) —NR$^6$CO—$C_{1-6}$alkyl-R$^7$,
(q) —NR$^6$CO$_2$—$C_{1-6}$alkyl-R$^7$,
(r) —NR$^6$CONR$^6$R$^7$,
(s) —OCONR$^6$R$^7$,
(t) —COOR$^6$,
(u) —CHO,
(v) —OR$^{11}$, and
(w) —S(O)$_p$—$C_{1-6}$alkyl;

(6) $C_{2-10}$alkenyl wherein alkenyl contains one to four double bonds and wherein one or more of the alkyl carbons is replaced by a group selected from: —NR$^6$—, —O—, —S(O)$_p$—, —CO$_2$—, —O$_2$C—, —CONR$^6$—, —NR$^6$CO—, and —NR$^6$CONR$^7$—;

(7) substituted $C_{2-10}$alkenyl wherein alkenyl contains one to four double bonds and wherein one or more of the alkyl carbons may be replaced by a group selected from: —NR$^6$—, —O—, —S(O)$_p$—, —CO$_2$—, —O$_2$C—, —CONR$^6$—, —NR$^6$CO—, and —NR$^6$CONR$^7$, and the alkyl or alkenyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl,
(o) —NR$^6$R$^7$, wherein R$^6$ and R$^7$ are as defined above,
(p) —NR$^6$CO—$C_{1-6}$alkyl-R$^7$,
(q) —NR$^6$CO$_2$—$C_{1-6}$alkyl-R$^7$,
(r) —NR$^6$CONR$^6$R$^7$,
(s) —OCONR$^6$R$^7$,
(t) —COOR$^6$,
(u) —CHO,
(v) —OR$^{11}$, and
(w) —S(O)$_p$—$C_{1-6}$alkyl;

(8) $C_{2-10}$alkynyl wherein the alkynyl contains one to four double bonds;

(9) subsituted $C_{2-10}$alkynyl wherein the alkynyl contains one to four double bonds and the alkyl or alkynyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl,
(o) —NR$^6$R$^7$, wherein R$^6$ and R$^7$ are as defined above,
(p) —NR$^6$CO—$C_{1-6}$alkyl-R$^7$,
(q) —NR$^6$CO$_2$—$C_{1-6}$alkyl-R$^7$,
(r) —NR$^6$CONR$^6$R$^7$,
(s) —OCONR$^6$R$^7$,
(t) —COOR$^6$,
(u) —CHO,
(v) —OR$^{11}$, and
(w) —S(O)$_p$—$C_{1-6}$alkyl;

(10) $C_{2-10}$alkynyl wherein alkynyl contains one to four double bonds and wherein one or more of the alkyl carbons is replaced by a group selected from: —NR$^6$—, —O—, —S(O)$_p$—, —CO$_2$—, —O$_2$C—, —CONR$^6$—, —NR$^6$CO—, and —NR$^6$CONR$^7$—;

(11) substituted $C_{2-10}$alkynyl wherein alkynyl contains one to four double bonds and wherein one or more of the alkyl carbons may be replaced by a group selected from: —NR$^6$—, —O—, —S(O)$_p$—, —CO$_2$—, —O$_2$C—, —CONR$^6$—, —NR$^6$CO—, and —NR$^6$CONR$^7$, and the alkyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl
(o) —NR$^6$R$^7$, wherein R$^6$ and R$^7$ are as defined above,
(p) —NR$^6$CO—$C_{1-6}$alkyl-R$^7$,
(q) —NR$^6$CO$_2$—$C_{1-6}$alkyl-R$^7$,
(r) —NR$^6$CONR$^6$R$^7$,
(s) —OCONR$^6$R$^7$,
(t) —COOR$^6$, (u) —CHO,
(v) —OR$^{11}$, and
(w) —S(O)$_p$—C$_{1-6}$alkyl;
(12) aryl
(13) heteroaryl;
(14) substituted aryl in which the substituents are X, Y and Z;
(15) substituted heteroaryl in which the substituents are X, Y and Z;

R$^1$ is selected from:
(1) hydrogen,
(2) hydroxy,
(3) C$_{1-6}$alkoxy,
(4) aryl-C$_{1-3}$alkoxy,
(5) substituted aryl-C$_{1-3}$alkoxy, in which the substituents on aryl are X, Y and Z,
(6) unsubstituted or substituted aryloxy, in which the substituents on aryl are X, Y and Z,
(7) heteroaryl-C$_{1-3}$alkoxy,
(8) substituted heteroaryl-C$_{1-3}$alkoxy, in which the substituents on heteroaryl are X, Y and Z,
(9) unsubstituted or substituted heteroaryloxy, in which the substituents on aryl are X, Y and Z,
(10) —OCO—C$_{1-6}$alkyl,
(11) —OCONR$^6$R$^7$, and
(12) —OR$^{11}$, and R$^2$ is selected from:
(1) hydrogen;
(2) C$_{1-10}$alkyl;
(3) substituted-C$_{1-10}$alkyl in which one or more substituent(s) is (are) selected from:
(a) hydroxy,
(b) oxo,
(c) C$_{1-6}$alkoxy,
(d) aryl-C$_{1-3}$alkoxy,
(e) substituted aryl-C$_{1-3}$alkoxy, in which the substituents on aryl are X, Y and Z,
(f) unsubstituted or substituted aryloxy, in which the substituents on aryl are X, Y and Z,
(g) —OCO—C$_{1-6}$alkyl,
(h) —NR$^6$R$^7$, wherein R$^6$ and R$^7$ are as defined above
(i) —NR$^6$CO—C$_{1-6}$alkyl-R$^7$, wherein R$^6$ and R$^7$ are as defined above,
(j) —COOR$^6$, wherein R$^6$ is as defined above,
(k) —CHO,
(l) —OR$^{11}$,
(m) —S(O)$_p$—C$_{1-6}$alkyl;
(4) C$_{3-10}$alkenyl;
(5) substituted C$_{3-10}$alkenyl in which one or more substituent(s) is(are) selected from:
(a) hydroxy,
(b) oxo,
(c) C$_{1-6}$alkoxy,
(d) aryl-C$_{1-3}$alkoxy,
(e) substituted aryl-C$_{1-3}$alkoxy, in which the substituents on aryl are X, Y and Z,
(f) unsubstituted or substituted aryloxy, in which the substituents on aryl are X, Y and Z,
(g) —OCO—C$_{1-6}$alkyl,
(h) —NR$^6$R$^7$, wherein R$^6$ and R$^7$ are as defined above
(i) —NR$^6$CO—C$_{1-6}$alkyl-R$^7$, wherein R$^6$ and R$^7$ are as defined above,
(j) —COOR$^6$, wherein R$^6$ is as defined above,
(k) —CHO,
(l) —OR$^{11}$,
(m) —S(O)$_p$—C$_{1-6}$alkyl;
(6) C$_{3-10}$alkynyl;
(7) substituted C$_{3-10}$alkynyl in which one or more substituent(s) is(are) selected from:
(a) hydroxy,
(b) oxo,
(c) C$_{1-6}$alkoxy,
(d) aryl-C$_{1-3}$alkoxy,
(e) substituted aryl-C$_{1-3}$alkoxy, in which the substituents on aryl are X, Y and Z,
(f) unsubstituted or substituted aryloxy, in which the substituents on aryl are X, Y and Z,
(g) —OCO—C$_{1-6}$alkyl,
(h) —NR$^6$R$^7$, wherein R$^6$ and R$^7$ are as defined above
(i) —NR$^6$CO—C$_{1-6}$alkyl-R$^7$, wherein R$^6$ and R$^7$ are as defined above,
(j) —COOR$^6$, wherein R$^6$ is as defined above,
(k) —CHO,
(l) —OR$^{11}$,
(m) —S(O)$_p$—C$_{1-6}$alkyl;

R$^3$ is hydrogen, hydroxy, —OR$^{11}$, or C$_{1-6}$alkoxy;
R$^4$ is hydrogen, or R$^3$ and R$^4$ taken together form a double bond;
R$^5$ is methyl, ethyl, propyl or allyl;
R$^{10}$ is hydrogen, hydroxy, —OR$^{11}$ or fluoro;
R$^{11}$ is selected from:
(a) —PO(OH)O—M$^+$, wherein M$^+$ is a positively charged inorganic or organic counterion,
(b) —SO$_3$—M$^+$,
(c) —CO(CH$_2$)$_q$CO$_2$—M$^+$, wherein q is 1–3, and
(d) —CO—C$_{1-6}$alkyl-NR$^6$R$^7$, wherein R$^6$ and R$^7$ are as defined above and the alkyl is unsubstituted or substituted with one or more substituents selected from:
(i) hydroxy,
(ii) C$_{1-6}$alkoxy,
(iii) —NR$^{16}$R$^{17}$, wherein R$^{16}$ and R$^{17}$ are independently selected from:
(a') hydrogen, and
(b') C$_{1-6}$alkyl,
(iv) —COOR$^6$, wherein R$^6$ is as defined above,
(v) phenyl,
(iv) substituted phenyl in which the substituents are X, Y and Z,
(vii) heteroaryl,
(viii) —SH, and
(ix) —S—C$_{1-6}$alkyl;
R$^{12}$ is OH, H, or R$^{12}$ and R$^{13}$ taken together form a double bond;
W is O, (H, OH) or (H, H);
X, Y and Z independently are selected from:
(a) hydrogen,
(b) C$_{1-10}$alkyl, unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) —OR$^6$,
(vii) —OR$^{11}$,
(viii) —OCOR$^6$, (ix) —OCO$_2$R$^6$,
(x) —NR$^6$R$^7$,
(xi) —CHO,
(xii) —NR$^6$COC$_{1-6}$alkyl-R$^7$,
(xiii) —NR$^6$CO$_2$C$_{1-6}$alkyl-R$^7$,
(xiv) —NR$^6$CONR$^6$R$^7$,
(xv) —OCONR$^6$R$^7$,
(xvi) —CONR$^6$R$^7$, (c) C$_{1-10}$alkyl wherein one or more of the alkyl carbons is replaced by a group selected from —NR$^6$—, —O—, —S(O)$_p$—, —CO$_2$—, —O$_2$C—, —CONR$^6$—, —NR$^6$CO—, —NR$^6$CONR$^7$—, —CO—, —CH(OH)—, alkenyl or alkynyl and the alkyl may be unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y', and Z',
(vi) —OR$^6$,
(vii) —OR$^{11}$,
(viii) —OCOR$^6$,
(ix) —OCO$_2$R$^6$,
(x) —NR$^6$R$^7$,
(xi) —CHO
(xii) —NR$^6$COC$_{1-6}$alkyl-R$^7$,
(xiii) —NR$^6$CO$_2$C$_{1-6}$alkyl-R$^7$,
(xiv) —NR$^6$CONR$^6$R$^7$,
(xv) —OCONR$^6$R$^7$,
(xvi) —CONR$^6$R$^7$, (d) aryl,
(e) substituted aryl wherein the substituents are X', Y' or Z',
(f) heteroaryl,
(g) substituted heteroaryl wherein the substituents are X', Y' or Z',
(h) substituted and unsubstituted aryloxy wherein the substitutents are X', Y', or Z',
(i) substituted and unsubstituted heteroaryloxy wherein the substitutents are X', Y', or Z',
(j) —NO$_2$,
(k) halogen,
(l) —NR$^6$R$^7$,
(m) —CN,
(n) —CHO,
(o) —CF$_3$,
(p) —SR$^8$, wherein R$^8$ is hydrogen, C$_{1-6}$alkyl, trifluoromethyl, or phenyl,
(q) —SOR$^8$,
(r) —SO$_2$R$^8$,
(s) —CONR$^6$R$^7$,
(t) R$^9$O(CH$_2$)$_m$— wherein R$^9$ is hydrogen, C$_{1-6}$alkyl, hydroxy-C$_{2-3}$alkyl, —CF$_3$, phenyl, R$^{11}$ or naphthyl and m is 0, 1, 2, or 3,
(u) —CH(OR$^{12}$)(OR$^{13}$), wherein R$^{12}$ and R$^{13}$ are C$_{1-3}$alkyl or taken together form an ethyl or propyl bridge,
(v) R$^9$CO(CH$_2$)$_m$— wherein R$^9$ and m are as defined above,
(w) R$^9$O$_2$C(CH$_2$)$_m$— wherein R$^9$ and m are as defined above, and
(x) —R$^{11}$; or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;

X', Y' and Z' independently are selected from:
(a) hydrogen,
(b) C$_{1-7}$alkyl,
(c) C$_{2-6}$alkenyl,
(d) halogen,
(e) —NO$_2$,
(f) —NR$^6$R$^7$, wherein R$^6$, and R$^7$ are as defined above,
(g) —CN,
(h) —CHO,
(i) —CF$_3$,
(j) —SR$^8$, wherein R$^8$ is hydrogen, C$_{1-6}$alkyl, trifluoromethyl, or phenyl,
(k) —SOR$^8$, wherein R$^8$ is as defined above,
(l) —SO$_2$R$^8$, wherein R$^8$ is as defined above,
(m) —CONR$^6$R$^7$, wherein R$^6$ and R$^7$ are as defined above,
(n) R$^9$O(CH$_2$)$_m$— wherein R$^9$ and m are as defined above,
(o) —CH(OR$^{12}$)(OR$^{13}$), wherein R$^{12}$ and R$^{13}$ are as defined above,
(p) R$^9$CO(CH$_2$)$_m$— wherein R$^9$ and m are as defined above,
(q) R$^9$O$_2$C(CH$_2$)$_m$— wherein R$^9$ and m are as defined above, and
(r) —R$^{11}$;

n is 1 or 2; heteroaryl, as used herein in the claim is: acridine, carbazole, cinnoline, dibenzofuran, dibenzothiophene, quinoxaline, pyrrazole, benzoxazole, indole, imidazole, thiazole, benzothiazole, benzotriazole, furan, benzofuran, benzimidazole, quinoline, isoquinoline, oxazole, pyrazine, pyridazine, pyridine, pyrimidine and pyrrole.

2. The compound of claim 1 wherein the absolute configuration is as defined in formula III:

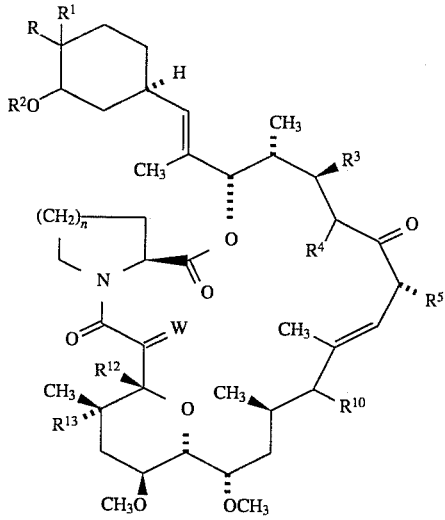

3. The compound of claim 1 wherein R is selected from:
(1) substituted C$_{2-6}$alkyl wherein the alkyl is substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z, (e) $C_{1-6}$alkoxy,
(f) hydroxy,
(g) oxo, and
(h) —$OR^{11}$;

(2) substituted or unsubstituted $C_{2-6}$alkyl wherein one or more of the alkyl carbons is replaced by a group selected from: —$NR^6$—, —O—, —$S(O)_p$—, —$CO_2$—, —$O_2C$—, —$CONR^6$—, —$NR^6CO$—, and —$NR^6CONR^7$—, and the alkyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) hydroxy,
(g) oxo, and
(h) —$OR^{11}$;

(3) subsituted $C_{3-6}$alkenyl wherein the alkenyl contains one to two double bonds and the alkyl or alkenyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) hydroxy,
(g) oxo, and
(h) —$OR^{11}$.

4. The compound of claim 1 wherein $R^1$ is selected from:
(1) hydrogen,
(2) hydroxy,
(3) $C_{1-6}$alkoxy, and
(4) —$OR^{11}$.

5. The compound of claim 1 wherein $R^2$ is selected from:
(1) hydrogen,
(2) methyl,
(3) ethyl,
(4) propyl,
(5) allyl,
(6) $R^{11}$,
(7) —$C_{2-3}$alkyl-OH; and
(8) —$C_{2-3}$alkyl-$OR^{11}$;

$R^3$ is selected from:
(1) hydrogen,
(2) hydroxy,
(3) —$OR^{11}$, or $R^3$ and $R^4$ taken together form a double bond;

$R^{10}$ is hydrogen, hydroxy, fluoro, or —$OR^{11}$;
$R^{12}$ is hydroxy, hydrogen or with $R^{13}$ forms a double bond;
W is O or (H,H); and
n is 2.

6. The compound of claim 1 which is selected from a compound of formula 1–4:

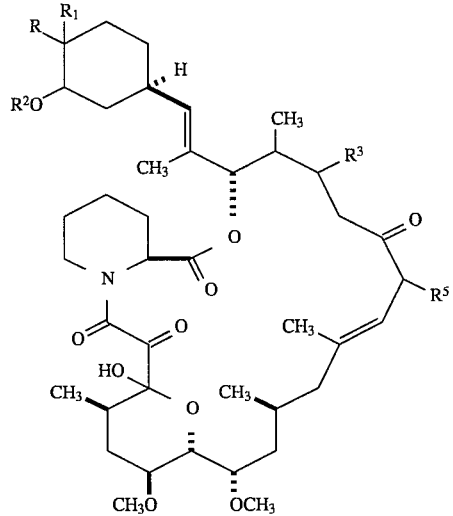

1

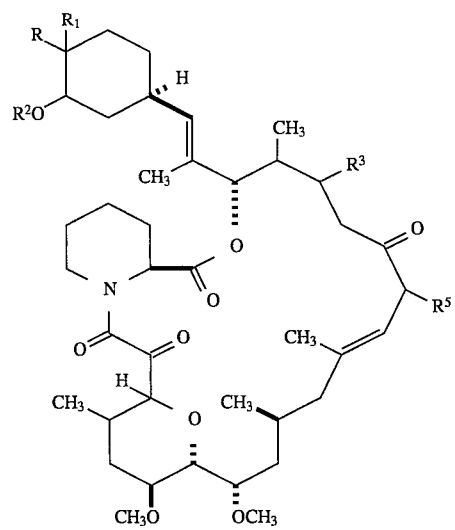

2

3

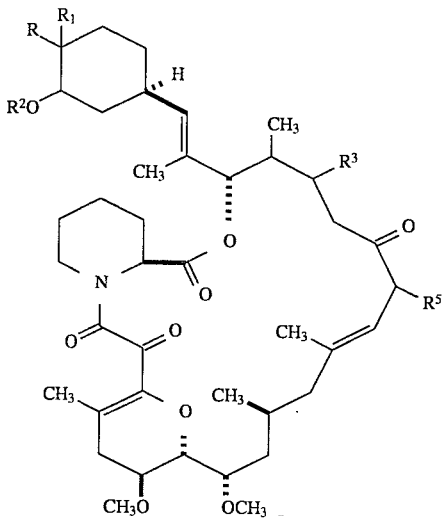

4

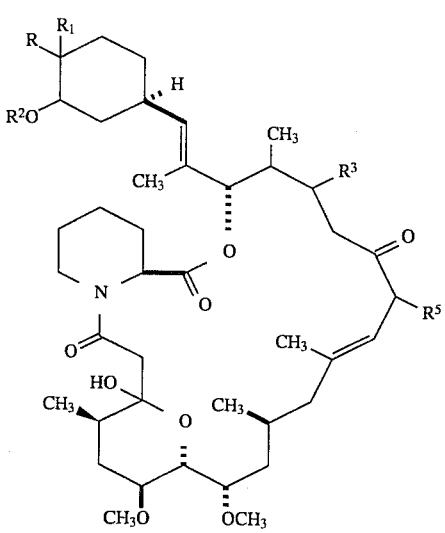

wherein for each of formula 1–4 the definitions of R, $R^1$, $R^3$ and $R^5$ are selected from the following groups of substituents:

| R | $R^1$ | $R^2$ | $R^3$ | $R^5$ |
|---|---|---|---|---|
| 4-HO₂C-phenyl | OH | CH₃ | OH | ethyl |
| 4-H₂NCO-phenyl | OH | CH₃ | OH | ethyl |
| 4-HO-phenyl | OH | CH₃ | OH | ethyl |
| 4-Cl-phenyl | OH | CH₃ | OH | ethyl |
| 4-(CH₃)₂N-phenyl | OH | CH₃ | OH | ethyl |
| 3-HO₂C-phenyl | OH | CH₃ | OH | ethyl |
| 3-H₂NCO-phenyl | OH | CH₃ | OH | ethyl |
| 3-HO-phenyl | OH | CH₃ | OH | ethyl |
| 3-Cl-phenyl | OH | CH₃ | OH | ethyl |
| 3-(CH₃)₂N-phenyl | OH | CH₃ | OH | ethyl |
| 2-HO₂C-phenyl | OH | CH₃ | OH | ethyl |
| 2-H₂NCO-phenyl | OH | CH₃ | OH | ethyl |
| 2-HO-phenyl | OH | CH₃ | OH | ethyl |
| 2-Cl-phenyl | OH | CH₃ | OH | ethyl |
| 2-(CH₃)₂N-phenyl | OH | CH₃ | OH | ethyl |
| 4-pyridyl | OH | CH₃ | OH | ethyl |
| 3-pyridyl | OH | CH₃ | OH | ethyl |
| 2-pyridyl | OH | CH₃ | OH | ethyl |
| 2-O₂N-phenyl | OH | CH₃ | OH | ethyl |
| 3-O₂N-phenyl | OH | CH₃ | OH | ethyl |
| 4-O₂N-phenyl | OH | CH₃ | OH | ethyl |
| 2-F-phenyl | OH | CH₃ | OH | ethyl |
| 3-F-phenyl | OH | CH₃ | OH | ethyl |
| 4-F-phenyl | OH | CH₃ | OH | ethyl |
| 2-F₃C-phenyl | OH | CH₃ | OH | ethyl |
| 3-F₃C-phenyl | OH | CH₃ | OH | ethyl |
| 4-F₃C-phenyl | OH | CH₃ | OH | ethyl |
| 4-HO₂C-phenyl | OH | CH₃ | H | ethyl |
| 4-H₂NCO-phenyl | OH | CH₃ | H | ethyl |
| 4-HO-phenyl | OH | CH₃ | H | ethyl |
| 4-Cl-phenyl | OH | CH₃ | H | ethyl |
| 4-(CH₃)₂N-phenyl | OH | CH₃ | H | ethyl |
| 3-HO₂C-phenyl | OH | CH₃ | H | ethyl |
| 3-H₂NCO-phenyl | OH | CH₃ | H | ethyl |
| 3-HO-phenyl | OH | CH₃ | H | ethyl |
| 3-Cl-phenyl | OH | CH₃ | H | ethyl |
| 3-(CH₃)₂N-phenyl | OH | CH₃ | H | ethyl |
| 2-HO₂C-phenyl | OH | CH₃ | H | ethyl |
| 2-H₂NCO-phenyl | OH | CH₃ | H | ethyl |
| 2-HO-phenyl | OH | CH₃ | H | ethyl |
| 2-Cl-phenyl | OH | CH₃ | H | ethyl |
| 2-(CH₃)₂N-phenyl | OH | CH₃ | H | ethyl |
| 4-pyridyl | OH | CH₃ | H | ethyl |
| 3-pyridyl | OH | CH₃ | H | ethyl |
| 2-pyridyl | OH | CH₃ | H | ethyl |
| 2-O₂N-phenyl | OH | CH₃ | H | ethyl |
| 3-O₂N-phenyl | OH | CH₃ | H | ethyl |
| 4-O₂N-phenyl | OH | CH₃ | H | ethyl |
| 2-F-phenyl | OH | CH₃ | H | ethyl |
| 3-F-phenyl | OH | CH₃ | H | ethyy |
| 4-F-phenyl | OH | CH₃ | H | ethyl |
| 2-F₃C-phenyl | OH | CH₃ | H | ethyl |
| 3-F₃C-phenyl | OH | CH₃ | H | ethyl |
| 4-F₃C-phenyl | OH | CH₃ | H | ethyl |
| 3-(CH₃)₂N-phenyl | OH | CH₃ | OH | allyl |
| 2-HO₂C-phenyl | OH | CH₃ | OH | allyl |
| 2-H₂NCO-phenyl | OH | CH₃ | OH | allyl |
| 2-HO-phenyl | OH | CH₃ | OH | allyl |
| 2-Cl-phenyl | OH | CH₃ | OH | allyl |
| 2-(CH₃)₂N-phenyl | OH | CH₃ | OH | allyl |
| 4-pyridyl | OH | CH₃ | OH | allyl |
| 3-pyridyl | OH | CH₃ | OH | allyl |
| 2-pyridyl | OH | CH₃ | OH | allyl |
| 2-O₂N-phenyl | OH | CH₃ | OH | allyl |
| 3-O₂N-phenyl | OH | CH₃ | OH | allyl |
| 4-O₂N-phenyl | OH | CH₃ | OH | allyl |
| 2-F-phenyl | OH | CH₃ | OH | allyl |
| 3-F-phenyl | OH | CH₃ | OH | allyl |
| 4-F-phenyl | OH | CH₃ | OH | allyl |
| 2-F₃C-phenyl | OH | CH₃ | OH | allyl |
| 3-F₃C-phenyl | OH | CH₃ | OH | allyl |
| 4-F₃C-phenyl | OH | CH₃ | OH | allyl |
| CH₃ | OH | CH₃ | H | ethyl |
| CH₃CH₂ | OH | CH₃ | H | ethyl |
| H₂NCOCH₂CH₂ | OH | CH₃ | H | ethyl |
| (CH₃)₂CH | OH | CH₃ | H | ethyl |
| HO₂CCH₂CH₂ | OH | CH₃ | H | ethyl |
| H₂NCOCH₂CH₂ | OH | CH₃ | H | ethyl |
| HOCH₂CH₂ | OH | CH₃ | H | ethyl |
| HOCH₂CH₂CH₂ | OH | CH₃ | H | ethyl |
| CH₃ | OH | H | OH | ethyl |
| CH₃CH₂ | OH | H | OH | ethyl |
| H₂NCOCH₂CH₂ | OH | H | OH | ethyl |
| (CH₃)₂CH | OH | H | OH | ethyl |
| HO₂CCH₂CH₂ | OH | H | OH | ethyl |
| H₂NCOCH₂CH₂ | OH | H | OH | ethyl |
| HOCH₂CH₂ | OH | H | OH | ethyl |
| HOCH₂CH₂CH₂ | OH | H | OH | ethyl |
| 4-HO₂C-phenyl | H | CH₃ | OH | ethyl |
| 4-H₂NCO-phenyl | H | CH₃ | OH | ethyl |
| 4-HO-phenyl | H | CH₃ | OH | ethyl |
| 4-Cl-phenyl | H | CH₃ | OH | ethyl |
| 4-(CH₃)₂N-phenyl | H | CH₃ | OH | ethyl |
| 3-HO₂C-phenyl | H | CH₃ | OH | ethyl |
| 3-H₂NCO-phenyl | H | CH₃ | OH | ethyl |
| 3-HO-phenyl | H | CH₃ | OH | ethyl |

-continued

| R | R¹ | R² | R³ | R⁵ |
|---|----|----|----|----|
| 3-Cl-phenyl | H | CH₃ | OH | ethyl |
| 3-(CH₃)₂N-phenyl | H | CH₃ | OH | ethyl |
| 2-HO₂C-phenyl | H | CH₃ | OH | ethyl |
| 2-H₂NCO-phenyl | H | CH₃ | OH | ethyl |
| 2-HO-phenyl | H | CH₃ | OH | ethyl |
| 2-Cl-phenyl | H | CH₃ | OH | ethyl |
| 2-(CH₃)₂N-phenyl | H | CH₃ | OH | ethyl |
| 4-pyridyl | H | CH₃ | OH | ethyl |
| 3-pyridyl | H | CH₃ | OH | ethyl |
| 2-pyridyl | H | CH₃ | OH | ethyl |
| 2-O₂N-phenyl | H | CH₃ | OH | ethyl |
| 3-O₂N-phenyl | H | CH₃ | OH | ethyl |
| 4-O₂N-phenyl | H | CH₃ | OH | ethyl |
| 2-F-phenyl | H | CH₃ | OH | ethyl |
| 3-F-phenyl | H | CH₃ | OH | ethyl |
| 4-F-phenyl | H | CH₃ | OH | ethyl |
| 2-F₃C-phenyl | H | CH₃ | OH | ethyl |
| 3-F₃C-phenyl | H | CH₃ | OH | ethyl |
| 4-F₃C-phenyl | H | CH₃ | OH | ethyl |
| 3-Cl-phenyl | H | CH₃ | H | ethyl |
| 3-(CH₃)₂N-phenyl | H | CH₃ | H | ethyl |
| 2-HO₂C-phenyl | H | CH₃ | H | ethyl |
| 2-H₂NCO-phenyl | H | CH₃ | H | ethyl |
| 2-HO-phenyl | H | CH₃ | H | ethyl |
| 2-Cl-phenyl | H | CH₃ | H | ethyl |
| 2-(CH₃)₂N-phenyl | H | CH₃ | H | ethyl |
| 4-pyridyl | H | CH₃ | H | ethyl |
| 3-pyridyl | H | CH₃ | H | ethyl |
| 2-pyridyl | H | CH₃ | H | ethyl |
| 2-O₂N-phenyl | H | CH₃ | H | ethyl |
| 3-O₂N-phenyl | H | CH₃ | H | ethyl |
| 4-O₂N-phenyl | H | CH₃ | H | ethyl |
| 2-F-phenyl | H | CH₃ | H | ethyl |
| 3-F-phenyl | H | CH₃ | H | ethyl |
| 4-F-phenyl | H | CH₃ | H | ethyl |
| 2-F₃C-phenyl | H | CH₃ | H | ethyl |
| 4-F₃C-phenyl | H | CH₃ | H | ethyl |
| 3-F₃C-phenyl | H | CH₃ | H | ethyl |
| 3-Cl-phenyl | H | CH₃ | OH | allyl |
| 3-(CH₃)₂N-phenyl | H | CH₃ | OH | allyl |
| 2-HO₂C-phenyl | H | CH₃ | OH | allyl |
| 2-H₂NCO-phenyl | H | CH₃ | OH | allyl |
| 2-HO-phenyl | H | CH₃ | OH | allyl |
| 2-Cl-phenyl | H | CH₃ | OH | allyl |
| 2-(CH₃)₂N-phenyl | H | CH₃ | OH | allyl |
| 4-pyridyl | H | CH₃ | OH | allyl |
| 3-pyridyl | H | CH₃ | OH | allyl |
| 2-pyridyl | H | CH₃ | OH | allyl |
| 2-O₂N-phenyl | H | CH₃ | OH | allyl |
| 3-O₂N-phenyl | H | CH₃ | OH | allyl |
| 4-O₂N-phenyl | H | CH₃ | OH | allyl |
| 2-F-phenyl | H | CH₃ | OH | allyl |
| 3-F-phenyl | H | CH₃ | OH | allyl |
| 4-F-phenyl | H | CH₃ | OH | allyl |
| 2-F₃C-phenyl | H | CH₃ | OH | allyl |
| 3-F₃C-phenyl | H | CH₃ | OH | allyl |
| 4-F₃C-phenyl | H | CH₃ | OH | allyl |
| CH₃ | H | CH₃ | H | ethyl |
| CH₃CH₂ | H | CH₃ | H | ethyl |
| CH₃CH₂CH₂ | H | CH₃ | H | ethyl |
| (CH₃)₂CH | H | CH₃ | H | ethyl |
| HO₂CCH₂CH₂ | H | CH₃ | H | ethyl |
| H₂NCOCH₂CH₂ | H | CH₃ | H | ethyl |
| HOCH₂CH₂ | H | CH₃ | H | ethyl |
| HOCH₂CH₂CH₂ | H | CH₃ | H | ethyl |
| CH₃ | H | H | OH | ethyl |
| CH₃CH₂ | H | H | OH | ethyl |
| H₂NCOCH₂CH₂ | H | H | OH | ethyl |
| (CH₃)₂CH | H | H | OH | ethyl |
| HO₂CCH₂CH₂ | H | H | OH | ethyl |
| H₂NCOCH₂CH₂ | H | H | OH | ethyl |
| HOCH₂CH₂ | H | H | OH | ethyl |
| HOCH₂CH₂CH₂ | H | H | OH | ethyl. |

7. The compound of claim 1 which is selected from a compound of formula 5–12:

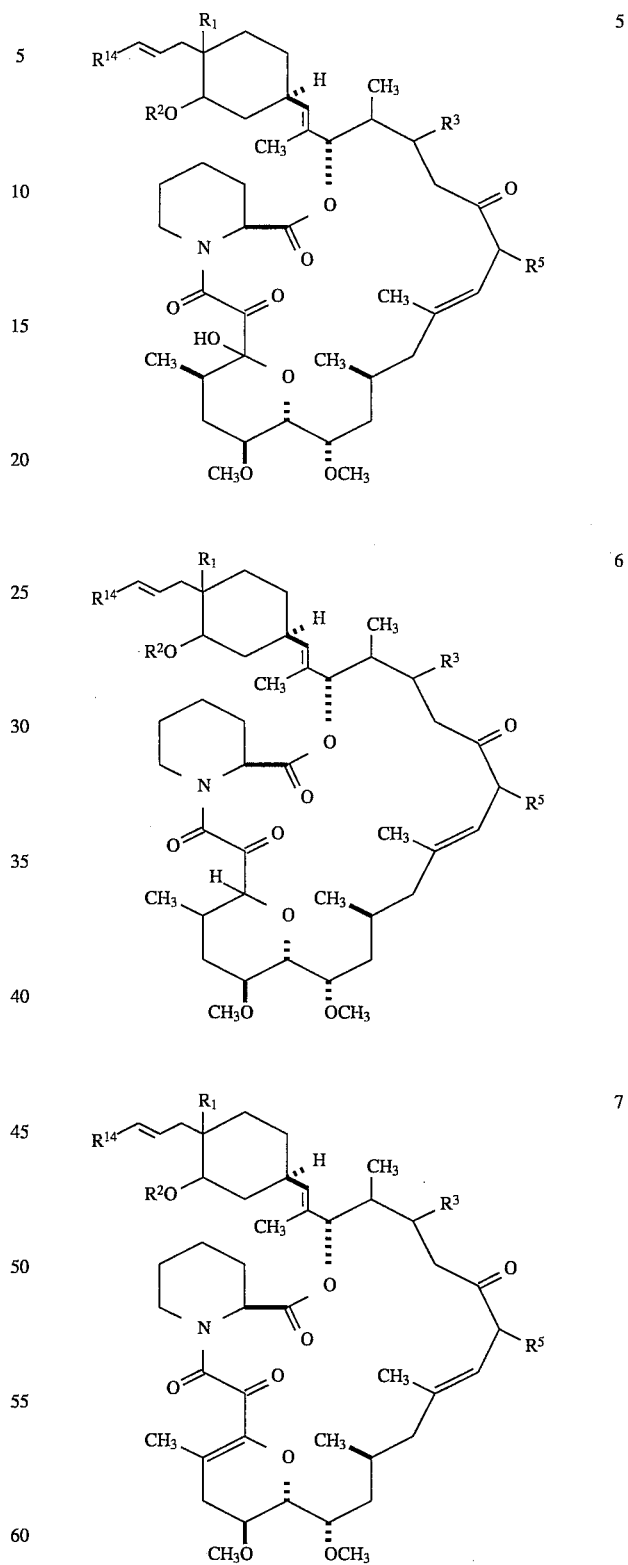

143
-continued

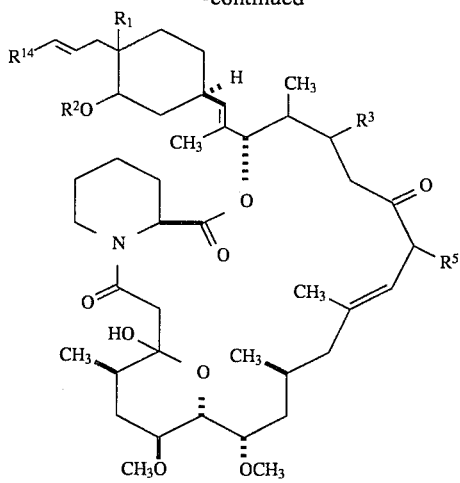

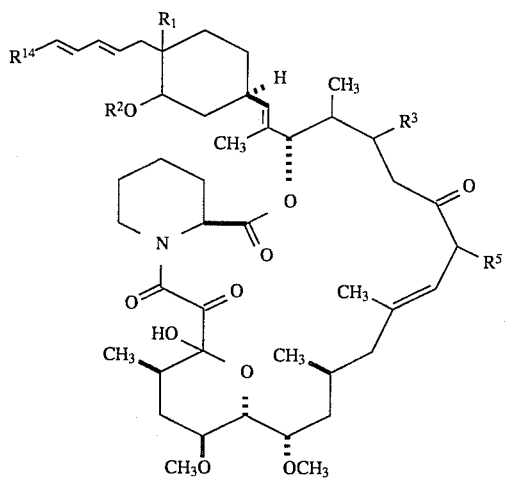

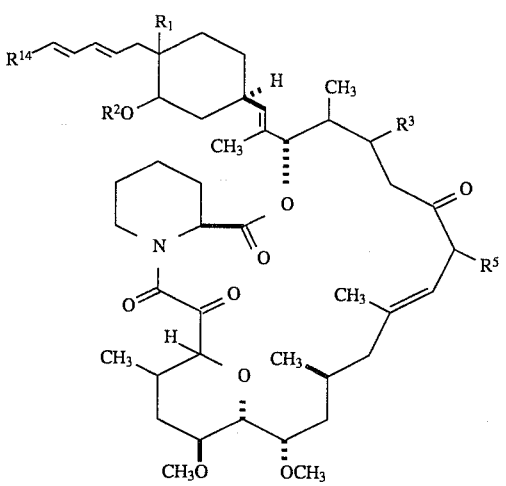

144
-continued

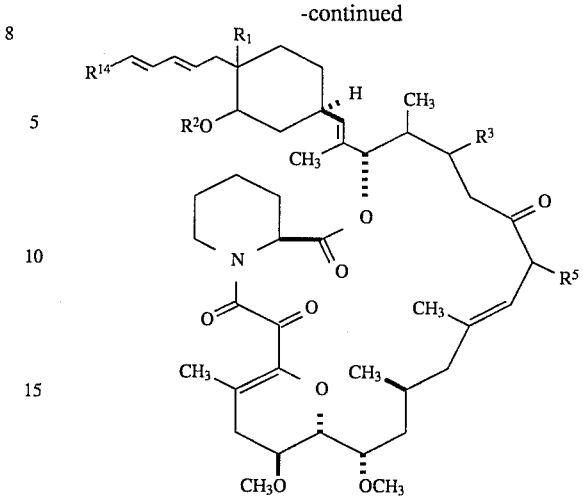

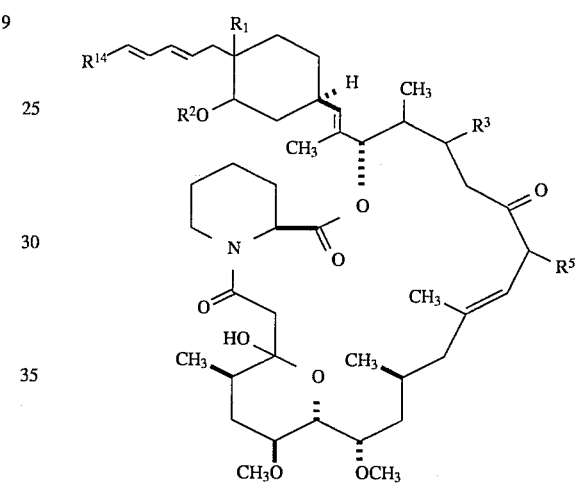

wherein for each of formula 5–12 the definitions of $R^1$, $R^3$, $R^5$, and $R^{14}$ are selected from the following groups of substituents:

| $R^{14}$ | $R^1$ | $R^2$ | $R^3$ | $R^5$ |
|---|---|---|---|---|
| 4-HO$_2$C-phenyl | OH | CH$_3$ | OH | ethyl |
| 4-H$_2$NCO-phenyl | OH | CH$_3$ | OH | ethyl |
| 4-HO-phenyl | OH | CH$_3$ | OH | ethyl |
| 4-Cl-phenyl | OH | CH$_3$ | OH | ethyl |
| 4-(CH$_3$)$_2$N-phenyl | OH | CH$_3$ | OH | ethyl |
| 3-HO$_2$C-phenyl | OH | CH$_3$ | OH | ethyl |
| 3-H$_2$NCO-phenyl | OH | CH$_3$ | OH | ethyl |
| 3-HO-phenyl | OH | CH$_3$ | OH | ethyl |
| 3-Cl-phenyl | OH | CH$_3$ | OH | ethyl |
| 3-(CH$_3$)$_2$N-phenyl | OH | CH$_3$ | OH | ethyl |
| 2-HO$_2$C-phenyl | OH | CH$_3$ | OH | ethyl |
| 2-H$_2$NCO-phenyl | OH | CH$_3$ | OH | ethyl |
| 2-HO-phenyl | OH | CH$_3$ | OH | ethyl |
| 2-Cl-phenyl | OH | CH$_3$ | OH | ethyl |
| 2-(CH$_3$)$_2$N-phenyl | OH | CH$_3$ | OH | ethyl |
| 4-pyridyl | OH | CH$_3$ | OH | ethyl |
| 3-pyridyl | OH | CH$_3$ | OH | ethyl |
| 2-pyridyl | OH | CH$_3$ | OH | ethyl |
| 2-O$_2$N-phenyl | OH | CH$_3$ | OH | ethyl |
| 3-O$_2$N-phenyl | OH | CH$_3$ | OH | ethyl |
| 4-O$_2$N-phenyl | OH | CH$_3$ | OH | ethyl |
| 2-F-phenyl | OH | CH$_3$ | OH | ethyl |
| 3-F-phenyl | OH | CH$_3$ | OH | ethyl |
| 4-F-phenyl | OH | CH$_3$ | OH | ethyl |

| $R^{14}$ | $R^1$ | $R^2$ | $R^3$ | $R^5$ |
|---|---|---|---|---|
| 2-F$_3$C-phenyl | OH | CH$_3$ | OH | ethyl |
| 3-F$_3$C-phenyl | OH | CH$_3$ | OH | ethyl |
| 4-F$_3$C-phenyl | OH | CH$_3$ | OH | ethyl |
| 4-HO$_2$C-phenyl | OH | CH$_3$ | H | ethyl |
| 4-H$_2$NCO-phenyl | OH | CH$_3$ | H | ethyl |
| 4-HO-phenyl | OH | CH$_3$ | H | ethyl |
| 4-Cl-phenyl | OH | CH$_3$ | H | ethyl |
| 4-(CH$_3$)$_2$N-phenyl | OH | CH$_3$ | H | ethyl |
| 3-HO$_2$C-phenyl | OH | CH$_3$ | H | ethyl |
| 3-H$_2$NCO-phenyl | OH | CH$_3$ | H | ethyl |
| 3-HO-phenyl | OH | CH$_3$ | H | ethyl |
| 3-Cl-phenyl | OH | CH$_3$ | H | ethyl |
| 3-(CH$_3$)$_2$N-phenyl | OH | CH$_3$ | H | ethyl |
| 2-HO$_2$C-phenyl | OH | CH$_3$ | H | ethyl |
| 2-H$_2$NCO-phenyl | OH | CH$_3$ | H | ethyl |
| 2-HO-phenyl | OH | CH$_3$ | H | ethyl |
| 2-Cl-phenyl | OH | CH$_3$ | H | ethyl |
| 2-(CH$_3$)$_2$N-phenyl | OH | CH$_3$ | H | ethyl |
| 4-pyridyl | OH | CH$_3$ | H | ethyl |
| 3-pyridyl | OH | CH$_3$ | H | ethyl |
| 2-pyridyl | OH | CH$_3$ | H | ethyl |
| 2-O$_2$N-phenyl | OH | CH$_3$ | H | ethyl |
| 3-O$_2$N-phenyl | OH | CH$_3$ | H | ethyl |
| 4-O$_2$N-phenyl | OH | CH$_3$ | H | ethyl |
| 2-F-phenyl | OH | CH$_3$ | H | ethyl |
| 3-F-phenyl | OH | CH$_3$ | H | ethyl |
| 4-F-phenyl | OH | CH$_3$ | H | ethyl |
| 2-F$_3$C-phenyl | OH | CH$_3$ | H | ethyl |
| 3-F$_3$C-phenyl | OH | CH$_3$ | H | ethyl |
| 4-F$_3$C-phenyl | OH | CH$_3$ | H | ethyl |
| 3-(CH$_3$)$_2$N-phenyl | OH | CH$_3$ | OH | allyl |
| 2-HO$_2$C-phenyl | OH | CH$_3$ | OH | allyl |
| 2-H$_2$NCO-phenyl | OH | CH$_3$ | OH | allyl |
| 2-HO-phenyl | OH | CH$_3$ | OH | allyl |
| 2-Cl-phenyl | OH | CH$_3$ | OH | allyl |
| 2-(CH$_3$)$_2$N-phenyl | OH | CH$_3$ | OH | allyl |
| 4-pyridyl | OH | CH$_3$ | OH | allyl |
| 3-pyridyl | OH | CH$_3$ | OH | allyl |
| 2-pyridyl | OH | CH$_3$ | OH | allyl |
| 2-O$_2$N-phenyl | OH | CH$_3$ | OH | allyl |
| 3-O$_2$N-phenyl | OH | CH$_3$ | OH | allyl |
| 4-O$_2$N-phenyl | OH | CH$_3$ | OH | allyl |
| 2-F-phenyl | OH | CH$_3$ | OH | allyl |
| 3-F-phenyl | OH | CH$_3$ | OH | allyl |
| 4-F-phenyl | OH | CH$_3$ | OH | allyl |
| 2-F$_3$C-phenyl | OH | CH$_3$ | OH | allyl |
| 3-F$_3$C-phenyl | OH | CH$_3$ | OH | allyl |
| 4-F$_3$C-phenyl | OH | CH$_3$ | OH | allyl |
| CH$_3$ | OH | CH$_3$ | H | ethyl |
| CH$_3$CH$_2$ | OH | CH$_3$ | H | ethyl |
| CH$_3$CH$_2$CH$_2$ | OH | CH$_3$ | H | ethyl |
| (CH$_3$)$_2$CH | OH | CH$_3$ | H | ethyl |
| HO$_2$CCH$_2$CH$_2$ | OH | CH$_3$ | H | ethyl |
| H$_2$NCOCH$_2$CH$_2$ | OH | CH$_3$ | H | ethyl |
| HOCH$_2$CH$_2$ | OH | CH$_3$ | H | ethyl |
| HOCH$_2$CH$_2$CH$_2$ | OH | CH$_3$ | H | ethyl |
| CH$_3$ | OH | H | OH | ethyl |
| CH$_3$CH$_2$ | OH | H | OH | ethyl |
| H$_2$NCOCH$_2$CH$_2$ | OH | H | OH | ethyl |
| (CH$_3$)$_2$CH | OH | H | OH | ethyl |
| HO$_2$CCH$_2$CH$_2$ | OH | H | OH | ethyl |
| H$_2$NCOCH$_2$CH$_2$ | OH | H | OH | ethyl |
| HOCH$_2$CH$_2$ | OH | H | OH | ethyl |
| HOCH$_2$CH$_2$CH$_2$ | OH | H | OH | ethyl |
| 4-HO$_2$C-phenyl | H | CH$_3$ | OH | ethyl |
| 4-H$_2$NCO-phenyl | H | CH$_3$ | OH | ethyl |
| 4-HO-phenyl | H | CH$_3$ | OH | ethyl |
| 4-Cl-phenyl | H | CH$_3$ | OH | ethyl |
| 4-(CH$_3$)$_2$N-phenyl | H | CH$_3$ | OH | ethyl |
| 3-HO$_2$C-phenyl | H | CH$_3$ | OH | ethyl |
| 3-H$_2$NCO-phenyl | H | CH$_3$ | OH | ethyl |
| 3-HO-phenyl | H | CH$_3$ | OH | ethyl |
| 3-Cl-phenyl | H | CH$_3$ | OH | ethyl |
| 3-(CH$_3$)$_2$N-phenyl | H | CH$_3$ | OH | ethyl |
| 2-HO$_2$C-phenyl | H | CH$_3$ | OH | ethyl |
| 2-H$_2$NCO-phenyl | H | CH$_3$ | OH | ethyl |
| 2-HO-phenyl | H | CH$_3$ | OH | ethyl |
| 2-Cl-phenyl | H | CH$_3$ | OH | ethyl |
| 2-(CH$_3$)$_2$N-phenyl | H | CH$_3$ | OH | ethyl |
| 4-pyridyl | H | CH$_3$ | OH | ethyl |
| 3-pyridyl | H | CH$_3$ | OH | ethyl |
| 2-pyridyl | H | CH$_3$ | OH | ethyl |
| 2-O$_2$N-phenyl | H | CH$_3$ | OH | ethyl |
| 3-O$_2$N-phenyl | H | CH$_3$ | OH | ethyl |
| 4-O$_2$N-phenyl | H | CH$_3$ | OH | ethyl |
| 2-F-phenyl | H | CH$_3$ | OH | ethyl |
| 3-F-phenyl | H | CH$_3$ | OH | ethyl |
| 4-F-phenyl | H | CH$_3$ | OH | ethyl |
| 2-F$_3$C-phenyl | H | CH$_3$ | OH | ethyl |
| 3-F$_3$C-phenyl | H | CH$_3$ | OH | ethyl |
| 4-F$_3$C-phenyl | H | CH$_3$ | OH | ethyl |
| 3-Cl-phenyl | H | CH$_3$ | H | ethyl |
| 3-(CH$_3$)$_2$N-phenyl | H | CH$_3$ | H | ethyl |
| 2-HO$_2$C-phenyl | H | CH$_3$ | H | ethyl |
| 2-H$_2$NCO-phenyl | H | CH$_3$ | H | ethyl |
| 2-HO-phenyl | H | CH$_3$ | H | ethyl |
| 2-Cl-phenyl | H | CH$_3$ | H | ethyl |
| 2-(CH$_3$)$_2$N-phenyl | H | CH$_3$ | H | ethyl |
| 4-pyridyl | H | CH$_3$ | H | ethyl |
| 3-pyridyl | H | CH$_3$ | H | ethyl |
| 2-pyridyl | H | CH$_3$ | H | ethyl |
| 2-O$_2$N-phenyl | H | CH$_3$ | H | ethyl |
| 3-O$_2$N-phenyl | H | CH$_3$ | H | ethyl |
| 4-O$_2$N-phenyl | H | CH$_3$ | H | ethyl |
| 2-F-phenyl | H | CH$_3$ | H | ethyl |
| 3-F-phenyl | H | CH$_3$ | H | ethyl |
| 4-F-phenyl | H | CH$_3$ | H | ethyl |
| 2-F$_3$C-phenyl | H | CH$_3$ | H | ethyl |
| 3-F$_3$C-phenyl | H | CH$_3$ | H | ethyl |
| 4-F$_3$C-phenyl | H | CH$_3$ | H | ethyl |
| 3-Cl-phenyl | H | CH$_3$ | OH | allyl |
| 3-(CH$_3$)$_2$N-phenyl | H | CH$_3$ | OH | allyl |
| 2-HO$_2$C-phenyl | H | CH$_3$ | OH | allyl |
| 2-H$_2$NCO-phenyl | H | CH$_3$ | OH | allyl |
| 2-HO-phenyl | H | CH$_3$ | OH | allyl |
| 2-Cl-phenyl | H | CH$_3$ | OH | allyl |
| 2-(CH$_3$)$_2$N-phenyl | H | CH$_3$ | OH | allyl |
| 4-pyridyl | H | CH$_3$ | OH | allyl |
| 3-pyridyl | H | CH$_3$ | OH | allyl |
| 2-pyridyl | H | CH$_3$ | OH | allyl |
| 2-O$_2$N-phenyl | H | CH$_3$ | OH | allyl |
| 3-O$_2$N-phenyl | H | CH$_3$ | OH | allyl |
| 4-O$_2$N-phenyl | H | CH$_3$ | OH | allyl |
| 2-F-phenyl | H | CH$_3$ | OH | allyl |
| 3-F-phenyl | H | CH$_3$ | OH | allyl |
| 4-F-phenyl | H | CH$_3$ | OH | allyl |
| 2-F$_3$C-phenyl | H | CH$_3$ | OH | allyl |
| 3-F$_3$C-phenyl | H | CH$_3$ | OH | allyl |
| 4-F$_3$C-phenyl | H | CH$_3$ | OH | allyl |
| CH$_3$ | H | CH$_3$ | H | ethyl |
| CH$_3$CH$_2$ | H | CH$_3$ | H | ethyl |
| CH$_3$CH$_2$CH$_2$ | H | ai3 | H | ethyl |
| (CH$_3$)$_2$CH | H | CH$_3$ | H | ethyl |
| HO$_2$CCH$_2$CH$_2$ | H | CH$_3$ | H | ethyl |
| H$_2$NCOCH$_2$CH$_2$ | H | CH$_3$ | H | ethyl |
| HOCH$_2$CH$_2$ | H | CH$_3$ | H | ethyl |
| HOCH$_2$CH$_2$CH$_2$ | H | CH$_3$ | H | ethyl |
| CH$_3$ | H | H | OH | ethyl |
| CH$_3$CH$_2$ | H | H | OH | ethyl |
| H$_2$NCOCH$_2$CH$_2$ | H | H | OH | ethyl |
| (CH$_3$)$_2$CH | H | H | OH | ethyl |
| HO$_2$CCH$_2$CH$_2$ | H | H | OH | ethyl |
| H$_2$NCOCH$_2$CH$_2$ | H | H | OH | ethyl |
| HOCH$_2$CH$_2$ | H | H | OH | ethyl |
| HOCH$_2$CH$_2$CH$_2$ | H | H | OH | ethyl. |

8. The compound of claim 1 which is selected from a compound of formula 13-16:

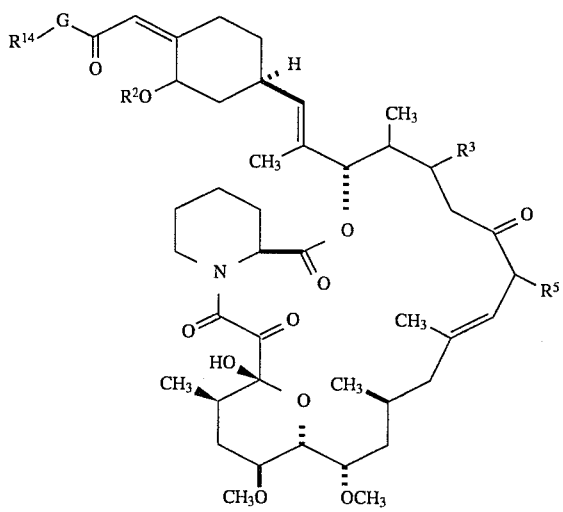

13

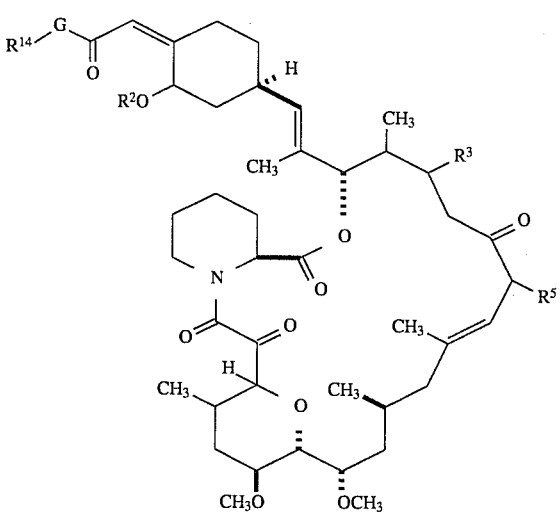

14

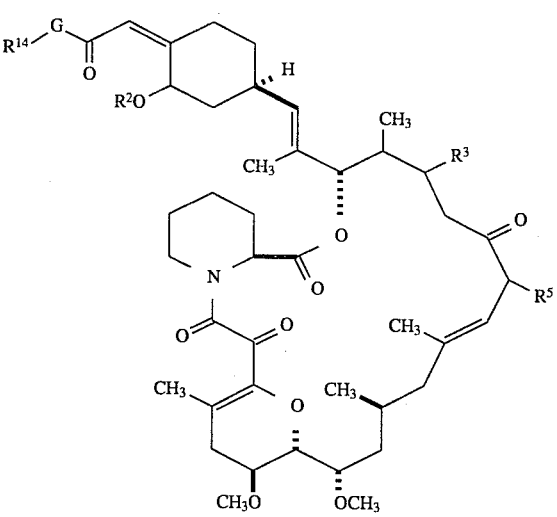

15

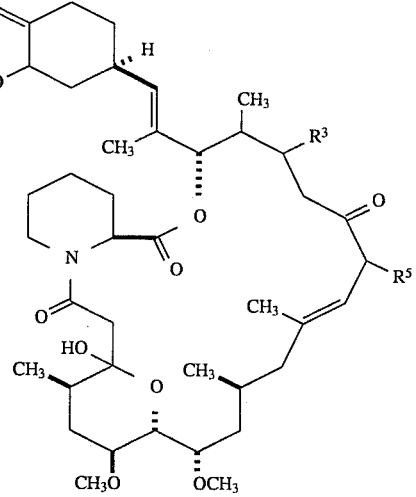

16 wherein for each of formula 13-16 the definitions of $R^{14}$, G, $R^2$, $R^3$ and $R^5$ are selected from the following groups of substituents:

| $R^{14}$ | G | $R^2$ | $R^3$ | $R^5$ |
|---|---|---|---|---|
| 4-HO$_2$C-phenyl | O | CH$_3$ | OH | ethyl |
| 4-H$_2$NCO-phenyl | O | CH$_3$ | OH | ethyl |
| 4-HO-phenyl | O | CH$_3$ | OH | ethyl |
| 4-Cl-phenyl | O | CH$_3$ | OH | ethyl |
| 4-(CH$_3$)$_2$N-phenyl | O | CH$_3$ | OH | ethyl |
| 3-HO$_2$C-phenyl | O | CH$_3$ | OH | ethyl |
| 3-H$_2$NCO-phenyl | O | CH$_3$ | OH | ethyl |
| 3-HO-phenyl | O | CH$_3$ | OH | ethyl |
| 3-Cl-phenyl | o | CH$_3$ | OH | ethyl |
| 3-(CH$_3$)$_2$N-phenyl | O | CH$_3$ | OH | ethyl |
| 2-HO$_2$C-phenyl | O | CH$_3$ | OH | ethyl |
| 2-H$_2$NCO-phenyl | O | CH$_3$ | OH | ethyl |
| 2-HO-phenyl | O | CH$_3$ | OH | ethyl |
| 2-Cl-phenyl | O | CH$_3$ | OH | ethyl |
| 2-(CH$_3$)$_2$N-phenyl | O | CH$_3$ | OH | ethyl |
| 4-pyridylmethyl | O | CH$_3$ | OH | ethyl |
| 3-pyridylmethyl | O | CH$_3$ | OH | ethyl |
| 2-pyridylmethyl | O | CH$_3$ | OH | ethyl |
| 2-O$_2$N-phenyl | O | CH$_3$ | OH | ethyl |
| 3-O$_2$N-phenyl | O | CH$_3$ | OH | ethyl |
| 4-O$_2$N-phenyl | O | CH$_3$ | OH | ethyl |
| 2-F-phenyl | O | CH$_3$ | OH | ethyl |
| 3-F-phenyl | O | CH$_3$ | OH | ethyl |
| 4-F-phenyl | O | CH$_3$ | OH | ethyl |
| 2-F$_3$C-phenyl | O | CH$_3$ | OH | ethyl |
| 3-F$_3$C-phenyl | O | CH$_3$ | OH | ethyl |
| 4-F$_3$C-phenyl | O | CH$_3$ | OH | ethyl |
| 3-Cl-phenyl | O | CH$_3$ | H | ethyl |
| 3-(CH$_3$)$_2$N-phenyl | O | CH$_3$ | H | ethyl |
| 2-HO$_2$C-phenyl | O | CH$_3$ | H | ethyl |
| 2-H$_2$NCO-phenyl | O | CH$_3$ | H | ethyl |
| 2-HO-phenyl | O | CH$_3$ | H | ethyl |
| 2-Cl-phenyl | O | CH$_3$ | H | ethyl |
| 2-(CH$_3$)$_2$N-phenyl | O | CH$_3$ | H | ethyl |
| 4-pyridylmethyl | O | CH$_3$ | H | ethyl |
| 3-pyridylmethyl | O | CH$_3$ | H | ethyl |
| 2-pyridylmethyl | O | CH$_3$ | H | ethyl |
| 2-O$_2$N-phenyl | O | CH$_3$ | H | ethyl |
| 3-O$_2$N-phenyl | O | CH$_3$ | H | ethyl |
| 4-O$_2$N-phenyl | O | CH$_3$ | H | ethyl |
| 2-F-phenyl | O | CH$_3$ | H | ethyl |
| 3-F-phenyl | O | CH$_3$ | H | ethyl |
| 4-F-phenyl | O | CH$_3$ | H | ethyl |
| 2-F$_3$C-phenyl | O | CH$_3$ | H | ethyl |
| 3-F$_3$C-phenyl | O | CH$_3$ | H | ethyl |
| 4-F$_3$C-phenyl | O | CH$_3$ | H | ethyl |

149
-continued

| R¹⁴ | G | R² | R³ | R⁵ |
|---|---|---|---|---|
| 3-Cl-phenyl | O | CH₃ | OH | allyl |
| 3-(CH₃)₂N-phenyl | O | CH₃ | OH | allyl |
| 2-HO₂C-phenyl | O | CH₃ | OH | allyl |
| 2-H₂NCO-phenyl | O | CH₃ | OH | allyl |
| 2-HO-phenyl | O | CH₃ | OH | allyl |
| 2-Cl-phenyl | O | CH₃ | OH | allyl |
| 2-(CH₃)₂N-phenyl | O | CH₃ | OH | allyl |
| 4-pyridylmethyl | O | CH₃ | OH | allyl |
| 3-pyridylmethyl | O | CH₃ | OH | allyl |
| 2-pyridylmethyl | O | CH₃ | OH | allyl |
| 2-O₂N-phenyl | O | CH₃ | OH | allyl |
| 3-O₂N-phenyl | O | CH₃ | OH | allyl |
| 4-O₂N-phenyl | O | CH₃ | OH | allyl |
| 2-F-phenyl | O | CH₃ | OH | allyl |
| 3-F-phenyl | O | CH₃ | OH | allyl |
| 4-F-phenyl | O | CH₃ | OH | allyl |
| 2-F₃C-phenyl | O | CH₃ | OH | allyl |
| 3-F₃C-phenyl | O | CH₃ | OH | allyl |
| 4-F₃C-phenyl | O | CH₃ | OH | allyl |
| CH₃CH₂ | O | CH₃ | H | ethyl |
| CH₃CH₂CH₂ | O | CH₃ | H | ethyl |
| (CH₃)₂CH | O | CH₃ | H | ethyl |
| HO₂CCH₂CH₂ | O | CH₃ | H | ethyl |
| H₂NCOCH₂CH₂ | O | CH₃ | H | ethyl |
| HOCH₂CH₂ | O | CH₃ | H | ethyl |
| HOCH₂CH₂CH₂ | O | CH₃ | H | ethyl |
| CH₃ | O | H | OH | ethyl |
| CH₃CH₂ | O | H | OH | ethyl |
| CH₃CH₂CH₂ | O | H | OH | ethyl |
| (CH₃)₂CH | O | H | OH | ethyl |
| HO₂CCH₂CH₂ | O | H | OH | ethyl |
| H₂NCOCH₂CH₂ | O | H | OH | ethyl |
| HOCH₂CH₂ | O | H | OH | ethyl |
| HOCH₂CH₂CH₂ | O | H | OH | ethyl |
| 4-HO₂C-phenyl | NH | CH₃ | OH | ethyl |
| 4-H₂NCO-phenyl | NH | CH₃ | OH | ethyl |
| 4-HO-phenyl | NH | CH₃ | OH | ethyl |
| 4-Cl-phenyl | NH | CH₃ | OH | ethyl |
| 4-(CH₃)₂N-phenyl | NH | CH₃ | OH | ethyl |
| 3-HO₂C-phenyl | NH | CH₃ | OH | ethyl |
| 3-H₂NCO-phenyl | NH | CH₃ | OH | ethyl |
| 3-HO-phenyl | NH | CH₃ | OH | ethyl |
| 3-Cl-phenyl | NH | CH₃ | OH | ethyl |
| 3-(CH₃)₂N-phenyl | NH | CH₃ | OH | ethyl |
| 2-HO₂C-phenyl | NH | CH₃ | OH | ethyl |
| 2-H₂NCO-phenyl | NH | CH₃ | OH | ethyl |
| 2-HO-phenyl | NH | CH₃ | OH | ethyl |
| 2-Cl-phenyl | NH | CH₃ | OH | ethyl |
| 2-(CH₃)₂N-phenyl | NH | CH₃ | OH | ethyl |
| 4-pyridylmethyl | NH | CH₃ | OH | ethyl |
| 3-pyridylmethyl | NH | CH₃ | OH | ethyl |
| 2-pyridylmethyl | NH | CH₃ | OH | ethyl |
| 2-O₂N-phenyl | NH | CH₃ | OH | ethyl |
| 3-O₂N-phenyl | NH | CH₃ | OH | ethyl |
| 4-O₂N-phenyl | NH | CH₃ | OH | ethyl |
| 2-F-phenyl | NH | CH₃ | OH | ethyl |
| 3-F-phenyl | NH | CH₃ | OH | ethyl |
| 4-F-phenyl | NH | CH₃ | OH | ethyl |
| 2-F₃C-phenyl | NH | CH₃ | OH | ethyl |
| 3-F₃C-phenyl | NH | CH₃ | OH | ethyl |
| 4-F₃C-phenyl | NH | CH₃ | OH | ethyl |
| 3-Cl-phenyl | NH | CH₃ | H | ethyl |
| 3-(CH₃)₂N-phenyl | NH | CH₃ | H | ethyl |
| 2-HO₂C-phenyl | NH | CH₃ | H | ethyl |
| 2-H₂NCO-phenyl | NH | CH₃ | H | ethyl |
| 2-HO-phenyl | NH | CH₃ | H | ethyl |
| 2-Cl-phenyl | NH | CH₃ | H | ethyl |
| 2-(CH₃)₂N-phenyl | NH | CH₃ | H | ethyl |
| 4-pyridylmethyl | NH | CH₃ | H | ethyl |
| 3-pyridylmethyl | NH | CH₃ | H | ethyl |
| 2-pyridylmethyl | NH | CH₃ | H | ethyl |
| 2-O₂N-phenyl | NH | CH₃ | H | ethyl |
| 3-O₂N-phenyl | NH | CH₃ | H | ethyl |

150
-continued

| R¹⁴ | G | R² | R³ | R⁵ |
|---|---|---|---|---|
| 4-O₂N-phenyl | NH | CH₃ | H | ethyl |
| 2-F-phenyl | NH | CH₃ | H | ethyl |
| 3-F-phenyl | NH | CH₃ | H | ethyl |
| 4-F-phenyl | NH | CH₃ | H | ethyl |
| 2-F₃C-phenyl | NH | CH₃ | H | ethyl |
| 3-F₃C-phenyl | NH | CH₃ | H | ethyl |
| 4-F₃C-phenyl | NH | CH₃ | H | ethyl |
| 3-Cl-phenyl | NH | CH₃ | H | allyl |
| 3-(CH₃)₂N-phenyl | NH | CH₃ | OH | allyl |
| 2-HO₂C-phenyl | NH | CH₃ | OH | allyl |
| 2-H₂NCO-phenyl | NH | CH₃ | OH | allyl |
| 2-HO-phenyl | NH | CH₃ | OH | allyl |
| 2-Cl-phenyl | NH | CH₃ | OH | allyl |
| 2-(CH₃)₂N-phenyl | NH | CH₃ | OH | allyl |
| 4-pyridylmethyl | NH | CH₃ | OH | allyl |
| 3-pyridylmethyl | NH | CH₃ | OH | allyl |
| 2-pyridylmethyl | NH | CH₃ | OH | allyl |
| CH₃CH₂ | NH | CH₃ | OH | ethyl |
| CH₃CH₂CH₂ | NH | CH₃ | OH | ethyl |
| (CH₃)₂CH | NH | CH₃ | OH | ethyl |
| HO₂CCH₂CH₂ | NH | CH₃ | OH | ethyl |
| H₂NCOCH₂CH₂ | NH | CH₃ | OH | ethyl |
| HOCH₂CH₂ | NH | CH₃ | OH | ethyl |
| HOCH₂CH₂CH₂ | NH | CH₃ | OH | ethyl |
| CH₃ | NH | CH₃ | H | ethyl |
| CH₃CH₂ | NH | CH₃ | H | ethyl |
| CH₃CH₂CH₂ | NH | CH₃ | H | ethyl |
| (CH₃)₂CH | NH | CH₃ | H | ethyl |
| HO₂CCH₂CH₂ | NH | CH₃ | H | ethyl |
| H₂NCOCH₂CH₂ | NH | CH₃ | H | ethyl |
| HOCH₂CH₂ | NH | CH₃ | H | ethyl |
| HOCH₂CH₂CH₂ | NH | CH₃ | H | ethyl |
| CH₃ | NH | H | OH | ethyl |
| CH₃CH₂ | NH | H | OH | ethyl |
| CH₃CH₂CH₂ | NH | H | OH | ethyl |
| (CH₃)₂CH | NH | H | OH | ethyl |
| HO₂CCH₂CH₂ | NH | H | OH | ethyl |
| H₂NCOCH₂CH₂ | NH | H | OH | ethyl |
| HOCH₂CH₂ | NH | H | OH | ethyl |
| HOCH₂CH₂CH₂ | NH | H | OH | ethyl. |

9. The compound of claim 1 which is selected from a compound of formula 17–19:

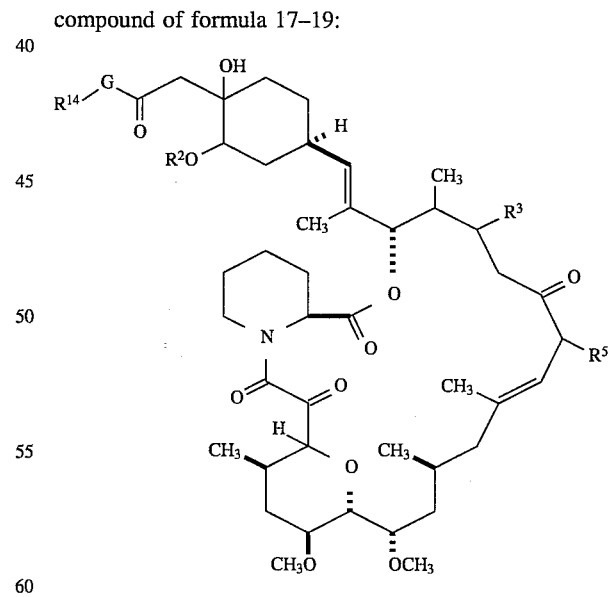

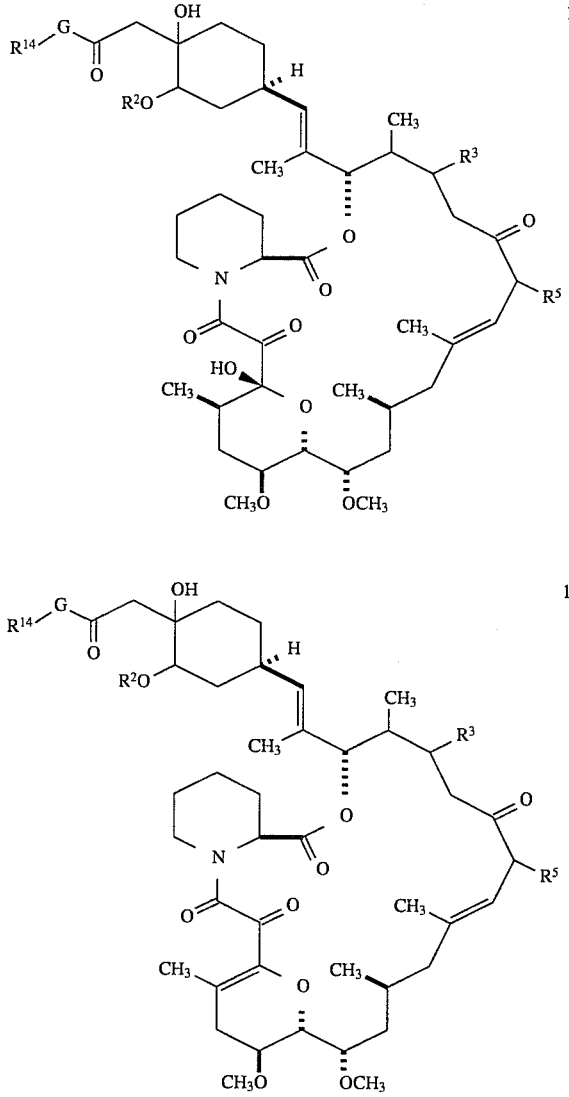

wherein for each of formula 17–19 the definitions of $R^{14}$, G, $R^2$, $R^3$ and $R^5$ are selected from the following groups of substituents:

| $R^{14}$ | G | $R^2$ | $R^3$ | $R^5$ |
|---|---|---|---|---|
| 4-HO$_2$C-phenyl | O | CH$_3$ | OH | ethyl |
| 4-H$_2$NCO-phenyl | O | CH$_3$ | OH | ethyl |
| 4-HO-phenyl | O | CH$_3$ | OH | ethyl |
| 4-Cl-phenyl | O | CH$_3$ | OH | ethyl |
| 4-(CH$_3$)$_2$N-phenyl | O | CH$_3$ | OH | ethyl |
| 3-HO$_2$C-phenyl | O | CH$_3$ | OH | ethyl |
| 3-H$_2$NCO-phenyl | O | CH$_3$ | OH | ethyl |
| 3-HO-phenyl | O | CH$_3$ | OH | ethyl |
| 3-Cl-phenyl | O | CH$_3$ | OH | ethyl |
| 3-(CH$_3$)$_2$N-phenyl | O | CH$_3$ | OH | ethyl |
| 2-HO$_2$C-phenyl | O | CH$_3$ | OH | ethyl |
| 2-H$_2$NCO-phenyl | O | CH$_3$ | OH | ethyl |
| 2-HO-phenyl | O | CH$_3$ | OH | ethyl |
| 2-Cl-phenyl | O | CH$_3$ | OH | ethyl |
| 2-(CH$_3$)$_2$N-phenyl | O | CH$_3$ | OH | ethyl |
| 4-pyridylmethyl | O | CH$_3$ | OH | ethyl |
| 3-pyridylmethyl | O | CH$_3$ | OH | ethyl |
| 2-pyridylmethyl | O | CH$_3$ | OH | ethyl |
| 2-O$_2$N-phenyl | O | CH$_3$ | OH | ethyl |
| 3-O$_2$N-phenyl | O | CH$_3$ | OH | ethyl |
| 4-O$_2$N-phenyl | O | CH$_3$ | OH | ethyl |
| 2-F-phenyl | O | CH$_3$ | OH | ethyl |
| 3-F-phenyl | O | CH$_3$ | OH | ethyl |
| 4-F-phenyl | O | CH$_3$ | OH | ethyl |
| 2-F$_3$C-phenyl | O | CH$_3$ | OH | ethyl |
| 3-F$_3$C-phenyl | O | CH$_3$ | OH | ethyl |
| 4-F$_3$C-phenyl | O | CH$_3$ | OH | ethyl |
| 3-Cl-phenyl | O | CH$_3$ | H | ethyl |
| 3-(CH$_3$)$_2$N-phenyl | O | CH$_3$ | H | ethyl |
| 2-HO$_2$C-phenyl | O | CH$_3$ | H | ethyl |
| 2-H$_2$NCO-phenyl | O | CH$_3$ | H | ethyl |
| 2-HO-phenyl | O | CH$_3$ | H | ethyl |
| 2-Cl-phenyl | O | CH$_3$ | H | ethyl |
| 2-(CH$_3$)$_2$N-phenyl | O | CH$_3$ | H | ethyl |
| 4-pyridylmethyl | O | CH$_3$ | H | ethyl |
| 3-pyridylmethyl | O | CH$_3$ | H | ethyl |
| 2-pyridylmethyl | O | CH$_3$ | H | ethyl |
| 2-O$_2$N-phenyl | O | CH$_3$ | H | ethyl |
| 3-O$_2$N-phenyl | O | CH$_3$ | H | ethyl |
| 4-O$_2$N-phenyl | O | CH$_3$ | H | ethyl |
| 2-F-phenyl | O | CH$_3$ | H | ethyl |
| 3-F-phenyl | O | CH$_3$ | H | ethyl |
| 4-F-phenyl | O | CH$_3$ | H | ethyl |
| 2-F$_3$C-phenyl | O | CH$_3$ | H | ethyl |
| 3-F$_3$C-phenyl | O | CH$_3$ | H | ethyl |
| 4-F$_3$C-phenyl | O | CH$_3$ | H | ethyl |
| 3-Cl-phenyl | O | CH$_3$ | OH | allyl |
| 3-(CH$_3$)$_2$N-phenyl | O | CH$_3$ | OH | allyl |
| 2-HO$_2$C-phenyl | O | CH$_3$ | OH | allyl |
| 2-H$_2$NCO-phenyl | O | CH$_3$ | OH | allyl |
| 2-HO-phenyl | O | CH$_3$ | OH | allyl |
| 2-Cl-phenyl | O | CH$_3$ | OH | allyl |
| 2-(CH$_3$)$_2$N-phenyl | O | CH$_3$ | OH | allyl |
| 4-pyridylmethyl | O | CH$_3$ | OH | allyl |
| 3-pyridylmethyl | O | CH$_3$ | OH | allyl |
| 2-pyridylmethyl | O | CH$_3$ | OH | allyl |
| 2-O$_2$N-phenyl | O | CH$_3$ | OH | allyl |
| 3-O$_2$N-phenyl | O | CH$_3$ | OH | allyl |
| 4-O$_2$N-phenyl | O | CH$_3$ | OH | allyl |
| 2-F-phenyl | O | CH$_3$ | OH | allyl |
| 3-F-phenyl | O | CH$_3$ | OH | allyl |
| 4-F-phenyl | O | CH$_3$ | OH | allyl |
| 2-F$_3$C-phenyl | O | CH$_3$ | OH | allyl |
| 3-F$_3$C-phenyl | O | CH$_3$ | OH | allyl |
| 4-F$_3$C-phenyl | O | CH$_3$ | OH | allyl |
| CH$_3$CH$_2$ | O | CH$_3$ | H | ethyl |
| CH$_3$CH$_2$CH$_2$ | O | CH$_3$ | H | ethyl |
| (CH$_3$)$_2$CH | O | CH$_3$ | H | ethyl |
| HO$_2$CCH$_2$CH$_2$ | O | CH$_3$ | H | ethyl |
| H$_2$NCOCH$_2$CH$_2$ | O | CH$_3$ | H | ethyl |
| HOCH$_2$CH$_2$ | O | CH$_3$ | H | ethyl |
| HOCH$_2$CH$_2$CH$_2$ | O | CH$_3$ | H | ethyl |
| CH$_3$ | O | H | OH | ethyl |
| CH$_3$CH$_2$ | O | H | OH | ethyl |
| CH$_3$CH$_2$CH$_2$ | O | H | OH | ethyl |
| (CH$_3$)$_2$CH | O | H | OH | ethyl |
| HO$_2$CCH$_2$CH$_2$ | O | H | OH | ethyl |
| H$_2$NCOCH$_2$CH$_2$ | O | H | OH | ethyl |
| HOCH$_2$CH$_2$ | O | H | OH | ethyl |
| HOCH$_2$CH$_2$CH$_2$ | O | H | OH | ethyl |
| 4-HO$_2$C-phenyl | NH | CH$_3$ | OH | ethyl |
| 4-H$_2$NCO-phenyl | NH | CH$_3$ | OH | ethyl |
| 4-HO-phenyl | NH | CH$_3$ | OH | ethyl |
| 4-Cl-phenyl | NH | CH$_3$ | OH | ethyl |
| 4-(CH$_3$)$_2$N-phenyl | NH | CH$_3$ | OH | ethyl |
| 3-HO$_2$C-phenyl | NH | CH$_3$ | OH | ethyl |
| 3-H$_2$NCO-phenyl | NH | CH$_3$ | OH | ethyl |
| 3-HO-phenyl | NH | CH$_3$ | OH | ethyl |
| 3-Cl-phenyl | NH | CH$_3$ | OH | ethyl |
| 3-(CH$_3$)$_2$N-phenyl | NH | CH$_3$ | OH | ethyl |
| 2-HO$_2$C-phenyl | NH | CH$_3$ | OH | ethyl |
| 2-H$_2$NCO-phenyl | NH | CH$_3$ | OH | ethyl |
| 2-HO-phenyl | NH | CH$_3$ | OH | ethyl |
| 2-Cl-phenyl | NH | CH$_3$ | OH | ethyl |
| 2-(CH$_3$)$_2$N-phenyl | NH | CH$_3$ | OH | ethyl |
| 4-pyridylmethyl | NH | CH$_3$ | OH | ethyl |
| 3-pyridylmethyl | NH | CH$_3$ | OH | ethyl |

-continued

| R¹⁴ | G | R² | R³ | R⁵ |
|---|---|---|---|---|
| 2-pyridylmethyl | NH | CH₃ | OH | ethyl |
| 2-O₂N-phenyl | NH | CH₃ | OH | ethyl |
| 3-O₂N-phenyl | NH | CH₃ | OH | ethyl |
| 4-O₂N-phenyl | NH | CH₃ | OH | ethyl |
| 2-F-phenyl | NH | CH₃ | OH | ethyl |
| 3-F-phenyl | NH | CH₃ | OH | ethyl |
| 4-F-phenyl | NH | CH₃ | OH | ethyl |
| 2-F₃C-phenyl | NH | CH₃ | OH | ethyl |
| 3-F₃C-phenyl | NH | CH₃ | OH | ethyl |
| 4-F₃C-phenyl | NH | CH₃ | OH | ethyl |
| 3-Cl-phenyl | NH | CH₃ | H | ethyl |
| 3-(CH₃)₂N-phenyl | NH | CH₃ | H | ethyl |
| 2-HO₂C-phenyl | NH | CH₃ | H | ethyl |
| 2-H₂NCO-phenyl | NH | CH₃ | H | ethyl |
| 2-HO-phenyl | NH | CH₃ | H | ethyl |
| 2-Cl-phenyl | NH | CH₃ | H | ethyl |
| 2-(CH₃)₂N-phenyl | NH | CH₃ | H | ethyl |
| 4-pyridylmethyl | NH | CH₃ | H | ethyl |
| 3-pyridylmethyl | NH | CH₃ | H | ethyl |
| 2-pyridylmethyl | NH | CH₃ | H | ethyl |
| 2-O₂N-phenyl | NH | CH₃ | H | ethyl |
| 3-O₂N-phenyl | NH | CH₃ | H | ethyl |
| 4-O₂N-phenyl | NH | CH₃ | H | ethyl |
| 2-F-phenyl | NH | CH₃ | H | ethyl |
| 3-F-phenyl | NH | CH₃ | H | ethyl |
| 4-F-phenyl | NH | CH₃ | H | ethyl |
| 2-F₃C-phenyl | NH | CH₃ | H | ethyl |
| 3-F₃C-phenyl | NH | CH₃ | H | ethyl |
| 4-F₃C-phenyl | NH | CH₃ | H | ethyl |
| 3-Cl-phenyl | NH | CH₃ | H | allyl |
| 3-(CH₃)₂N-phenyl | NH | CH₃ | OH | allyl |
| 2-HO₂C-phenyl | NH | CH₃ | OH | allyl |
| 2-H₂NCO-phenyl | NH | CH₃ | OH | allyl |
| 2-HO-phenyl | NH | CH₃ | OH | allyl |
| 2-Cl-phenyl | NH | CH₃ | OH | allyl |
| 2-(CH₃)₂N-phenyl | NH | CH₃ | OH | allyl |
| 4-pyridylmethyl | NH | CH₃ | OH | allyl |
| 3-pyridylmethyl | NH | CH₃ | OH | allyl |
| 2-pyridylmethyl | NH | CH₃ | OH | allyl |
| CH₃CH₂ | NH | CH₃ | OH | ethyl |
| CH₃CH₂CH₂ | NH | CH₃ | OH | ethyl |
| (CH₃)₂CH | NH | CH₃ | OH | ethyl |
| HO₂CCH₂CH₂ | NH | CH₃ | OH | ethyl |
| H₂NCOCH₂CH₂ | NH | CH₃ | OH | ethyl |
| HOCH₂CH₂ | NH | CH₃ | OH | ethyl |
| HOCH₂CH₂CH₂ | NH | CH₃ | OH | ethyl |
| CH₃ | NH | CH₃ | H | ethyl |
| CH₃CH₂ | NH | CH₃ | H | ethyl |
| CH₃CH₂CH₂ | NH | CH₃ | H | ethyl |
| (CH₃)₂CH | NH | CH₃ | H | ethyl |
| HO₂CCH₂CH₂ | NH | CH₃ | H | ethyl |
| H₂NCOCH₂CH₂ | NH | CH₃ | H | ethyl |
| HOCH₂CH₂ | NH | CH₃ | H | ethyl |
| HOCH₂CH₂CH₂ | NH | CH₃ | H | ethyl |
| CH₃ | NH | H | OH | ethyl |
| CH₃CH₂ | NH | H | OH | ethyl |
| CH₃CH₂CH₂ | NH | H | OH | ethyl |
| (CH₃)₂CH | NH | H | OH | ethyl |
| HO₂CCH₂CH₂ | NH | H | OH | ethyl |
| H₂NCOCH₂CH₂ | NH | H | OH | ethyl |
| HOCH₂CH₂ | NH | H | OH | ethyl |
| HOCH₂CH₂CH₂ | NH | H | OH | ethyl. |

10. The compound of claim 1 which is selected from a compound of formula 20–25:

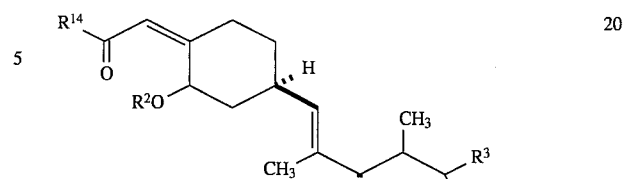

20

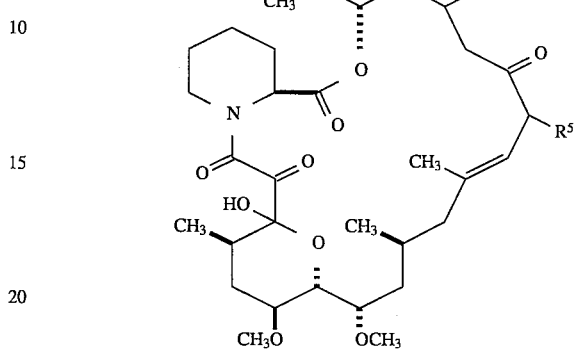

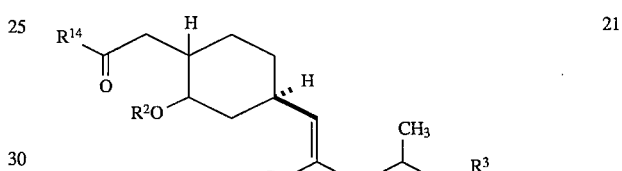

21

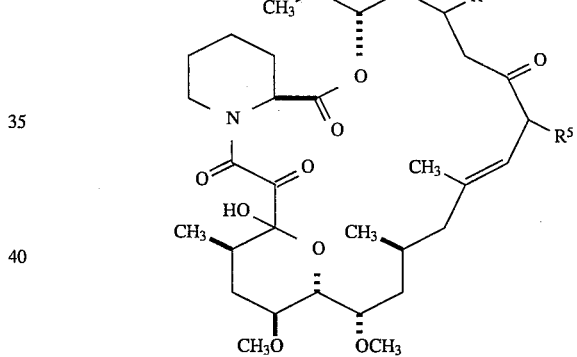

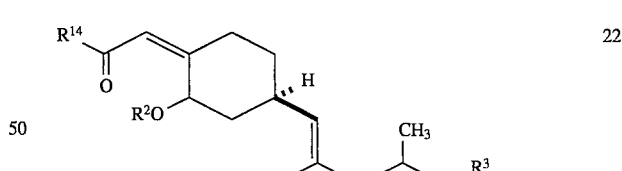

22

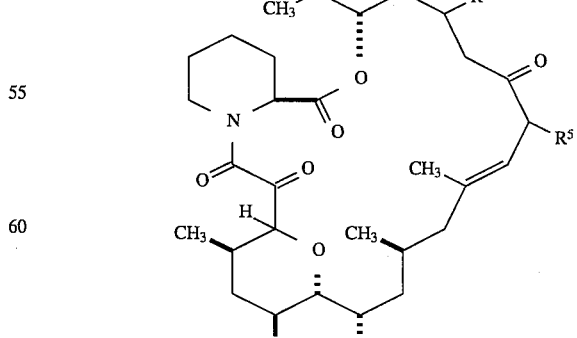

-continued

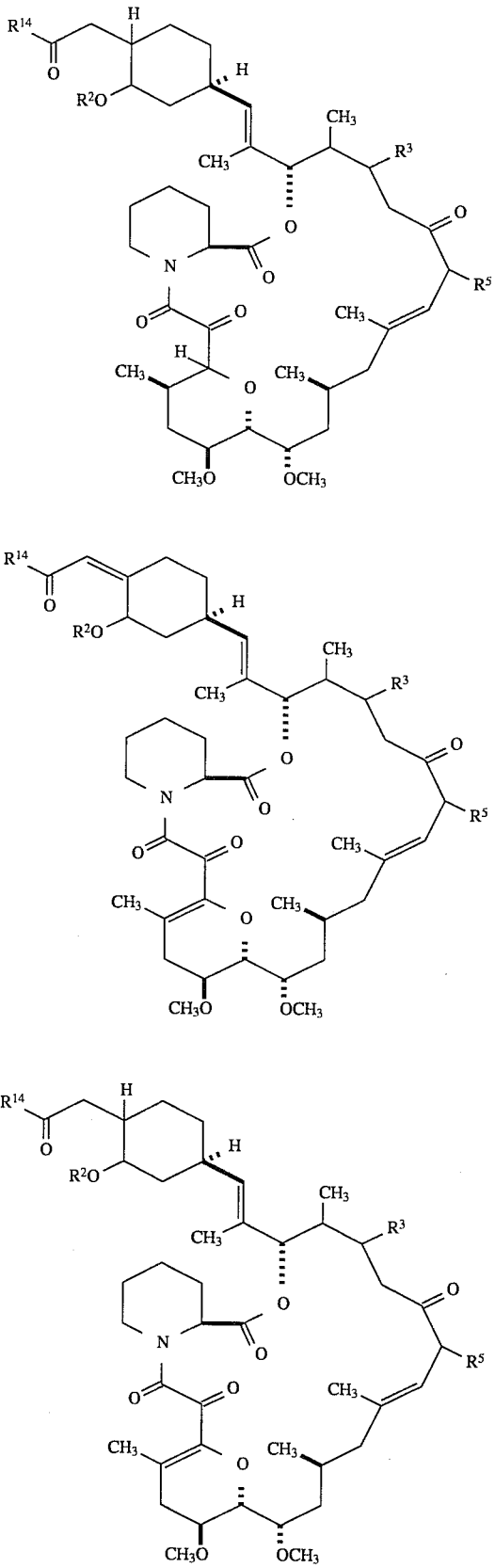

wherein for each of formula 20–25 the definitions of $R^2$, $R^3$, $R^5$, and $R^{14}$ are selected from the following groups of substituents:

| $R^{14}$ | $R^2$ | $R^3$ | $R^5$ |
|---|---|---|---|
| $CH_3$ | $CH_3$ | OH | ethyl |
| $CH_3CH_2$ | $CH_3$ | OH | ethyl |
| $CH_2=CHCH_2$ | $CH_3$ | OH | ethyl |
| $CH_3CH_2CH_2$ | $CH_3$ | OH | ethyl |
| $(CH_3)_2CH$ | $CH_3$ | OH | ethyl |
| $HO_2CCH_2CH_2$ | $CH_3$ | OH | ethyl |
| $H_2NCOCH_2CH_2$ | $CH_3$ | OH | ethyl |
| $HOCH_2CH_2$ | $CH_3$ | OH | ethyl |
| $HOCH_2CH_2CH_2$ | $CH_3$ | OH | ethyl |
| $(CH_3)_2CH_2$ | $CH_3$ | OH | ethyl |
| phenyl | $CH_3$ | OH | ethyl |
| 4-pyridyl | $CH_3$ | OH | ethyl |
| 3-pyridyl | $CH_3$ | OH | ethyl |
| 2-pyridyl | $CH_3$ | OH | ethyl |
| 4-pyridylmethyl | $CH_3$ | OH | ethyl |
| 3-pyridylmethyl | $CH_3$ | OH | ethyl |
| 2-pyridylmethyl | $CH_3$ | OH | ethyl |
| benzyl | $CH_3$ | OH | ethyl |
| 4-$HO_2C$-benzyl | $CH_3$ | OH | ethyl |
| 4-$H_2NCO$-benzyl | $CH_3$ | OH | ethyl |
| 4-$CH_3O$-benzyl | $CH_3$ | OH | ethyl |
| 4-HO-benzyl | $CH_3$ | OH | ethyl |
| 4-Cl-benzyl | $CH_3$ | OH | ethyl |
| 4-$(CH_3)_2N$-benzyl | $CH_3$ | OH | ethyl |
| 3-$HO_2C$-benzyl | $CH_3$ | OH | ethyl |
| 3-$H_2NCO$-benzyl | $CH_3$ | OH | ethyl |
| 3-$CH_3O$-benzyl | $CH_3$ | OH | ethyl |
| 3-HO-benzyl | $CH_3$ | OH | ethyl |
| 3-Cl-benzyl | $CH_3$ | OH | ethyl |
| 3-$(CH_3)_2N$-benzyl | $CH_3$ | OH | ethyl |
| 2-$HO_2C$-benzyl | $CH_3$ | OH | ethyl |
| 2-$H_2NCO$-benzyl | $CH_3$ | OH | ethyl |
| 2-$CH_3O$-benzyl | $CH_3$ | OH | ethyl |
| 2-HO-benzyl | $CH_3$ | OH | ethyl |
| 2-Cl-benzyl | $CH_3$ | OH | ethyl |
| 2-$(CH_3)_2N$-benzyl | $CH_3$ | OH | ethyl |
| 2-$O_2N$-benzyl | $CH_3$ | OH | ethyl |
| 3-$O_2N$-benzyl | $CH_3$ | OH | ethyl |
| 4-$O_2N$-benzyl | $CH_3$ | OH | ethyl |
| 2-F-benzyl | $CH_3$ | OH | ethyl |
| 3-F-benzyl | $CH_3$ | OH | ethyl |
| 4-F-benzyl | $CH_3$ | OH | ethyl |
| 2-$F_3C$-benzyl | $CH_3$ | OH | ethyl |
| 3-$F_3C$-benzyl | $CH_3$ | OH | ethyl |
| 4-$F_3C$-benzyl | $CH_3$ | OH | ethyl |
| $CH_3$ | $CH_3$ | H | ethyl |
| $CH_3CH_2$ | $CH_3$ | H | ethyl |
| $CH_2=CHCH_2$ | $CH_3$ | H | ethyl |
| $CH_3CH_2CH_2$ | $CH_3$ | H | ethyl |
| $(CH_3)_2CH$ | $CH_3$ | H | ethyl |
| $HO_2CCH_2CH_2$ | $CH_3$ | H | ethyl |
| $H_2NCOCH_2CH_2$ | $CH_3$ | H | ethyl |
| $HOCH_2CH_2$ | $CH_3$ | H | ethyl |
| $HOCH_2CH_2CH_2$ | $CH_3$ | H | ethyl |
| $(CH_3)_2CH_2$ | $CH_3$ | H | ethyl |
| phenyl | $CH_3$ | H | ethyl |
| 4-pyridyl | $CH_3$ | H | ethyl |
| 3-pyridyl | $CH_3$ | H | ethyl |
| 2-pyridyl | $CH_3$ | H | ethyl |
| 4-pyridylmethyl | $CH_3$ | H | ethyl |
| 3-pyridylmethyl | $CH_3$ | H | ethyl |
| 2-pyridylmethyl | $CH_3$ | H | ethyl |
| benzyl | $CH_3$ | H | ethyl |
| 4-$HO_2C$-benzyl | $CH_3$ | H | ethyl |
| 4-$H_2NCO$-benzyl | $CH_3$ | H | ethyl |
| 4-$CH_3O$-benzyl | $CH_3$ | H | ethyl |
| 4-HO-benzyl | $CH_3$ | H | ethyl |
| 4-Cl-benzyl | $CH_3$ | H | ethyl |
| 4-$(CH_3)_2N$-benzyl | $CH_3$ | H | ethyl |
| 3-$HO_2C$-benzyl | $CH_3$ | H | ethyl |
| 3-$H_2NCO$-benzyl | $CH_3$ | H | ethyl |
| 3-$CH_3O$-benzyl | $CH_3$ | H | ethyl |
| 3-HO-benzyl | $CH_3$ | H | ethyl |
| 3-Cl-benzyl | $CH_3$ | H | ethyl |

-continued

| $R^{14}$ | $R^2$ | $R^3$ | $R^5$ |
|---|---|---|---|
| 3-$(CH_3)_2$N-benzyl | $CH_3$ | H | ethyl |
| 2-$HO_2$C-benzyl | $CH_3$ | H | ethyl |
| 2-$H_2$NCO-benzyl | $CH_3$ | H | ethyl |
| 2-$CH_3$O-benzyl | $CH_3$ | H | ethyl |
| 2-HO-benzyl | $CH_3$ | H | ethyl |
| 2-Cl-benzyl | $CH_3$ | H | ethyl |
| 2-$(CH_3)_2$N-benzyl | $CH_3$ | H | ethyl |
| 2-$O_2$N-benzyl | $CH_3$ | H | ethyl |
| 3-$O_2$N-benzyl | $CH_3$ | H | ethyl |
| 4-$O_2$N-benzyl | $CH_3$ | H | ethyl |
| 2-F-benzyl | $CH_3$ | H | ethyl |
| 3-F-benzyl | $CH_3$ | H | ethyl |
| 4-F-benzyl | $CH_3$ | H | ethyl |
| 2-$F_3$C-benzyl | $CH_3$ | H | ethyl |
| 3-$F_3$C-benzyl | $CH_3$ | H | ethyl |
| 4-$F_3$C-benzyl | $CH_3$ | H | ethyl |
| $CH_3$ | $CH_3$ | OH | allyl |
| $CH_3CH_2$ | $CH_3$ | OH | allyl |
| $CH_2$=$CHCH_2$ | $CH_3$ | OH | allyl |
| $CH_3CH_2CH_2$ | $CH_3$ | OH | allyl |
| $(CH_3)_2$CH | $CH_3$ | OH | allyl |
| $HO_2CCH_2CH_2$ | $CH_3$ | OH | allyl |
| $H_2NCOCH_2CH_2$ | $CH_3$ | OH | allyl |
| $HOCH_2CH_2$ | $CH_3$ | OH | allyl |
| $HOCH_2CH_2CH_2$ | $CH_3$ | OH | allyl |
| $(CH_3)_2CH_2$ | $CH_3$ | OH | allyl |
| phenyl | $CH_3$ | OH | allyl |
| 4-pyridyl | $CH_3$ | OH | allyl |
| 3-pyridyl | $CH_3$ | OH | allyl |
| 2-pyridyl | $CH_3$ | OH | allyl |
| 4-pyridylmethyl | $CH_3$ | OH | allyl |
| 3-pyridylmethyl | $CH_3$ | OH | allyl |
| 2-pyridylmethyl | $CH_3$ | OH | allyl |
| benzyl | $CH_3$ | OH | allyl |
| 4-$HO_2$C-benzyl | $CH_3$ | OH | allyl |
| 4-$H_2$NCO-benzyl | $CH_3$ | OH | allyl |
| 4-$CH_3$O-benzyl | $CH_3$ | OH | allyl |
| 4-HO-benzyl | $CH_3$ | OH | allyl |
| 4-Cl-benzyl | $CH_3$ | OH | allyl |
| 4-$(CH_3)_2$N-benzyl | $CH_3$ | OH | allyl |
| 3-$HO_2$C-benzyl | $CH_3$ | OH | allyl |
| 3-$H_2$NCO-benzyl | $CH_3$ | OH | allyl |
| 3-$CH_3$O-benzyl | $CH_3$ | OH | allyl |
| 3-HO-benzyl | $CH_3$ | OH | allyl |
| 3-Cl-benzyl | $CH_3$ | OH | allyl |
| 3-$(CH_3)_2$N-benzyl | $CH_3$ | OH | allyl |
| 2-$HO_2$C-benzyl | $CH_3$ | OH | allyl |
| 2-$H_2$NCO-benzyl | $CH_3$ | OH | allyl |
| 2-$CH_3$O-benzyl | $CH_3$ | OH | allyl |
| 2-HO-benzyl | $CH_3$ | OH | allyl |
| 2-Cl-benzyl | $CH_3$ | OH | allyl |
| 2-$(CH_3)_2$N-benzyl | $CH_3$ | OH | allyl. |

11. The compound of claim 1 which is selected from a compound of formula 26–37:

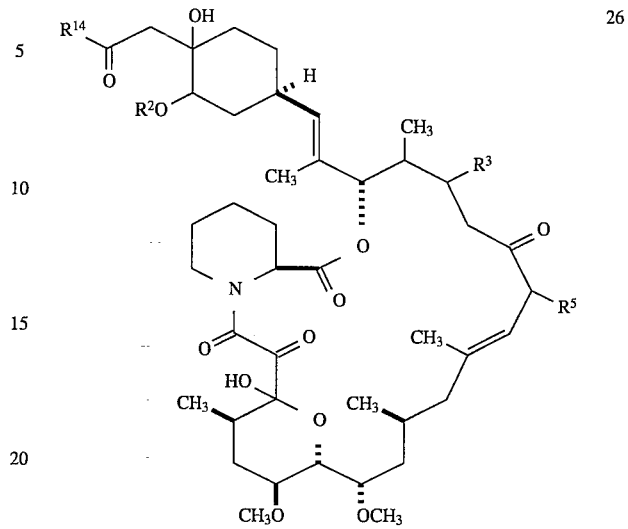

26

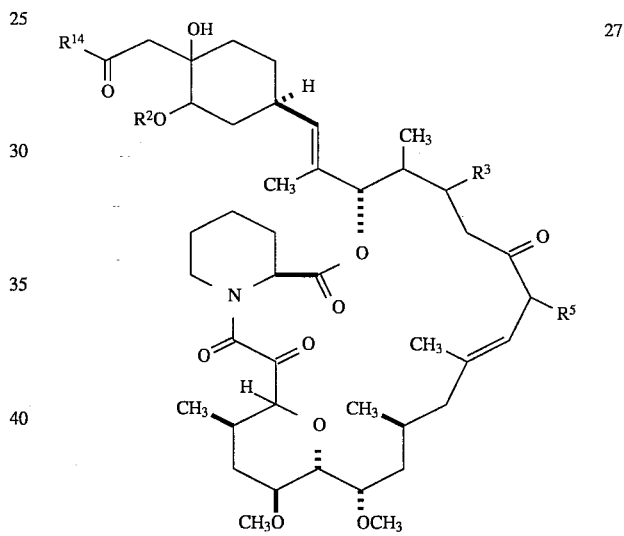

27

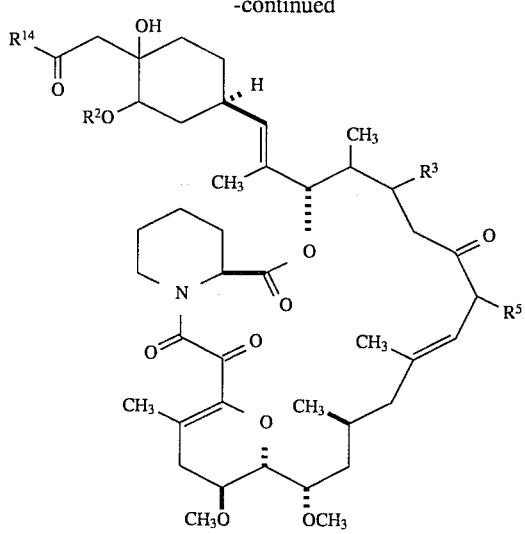
28
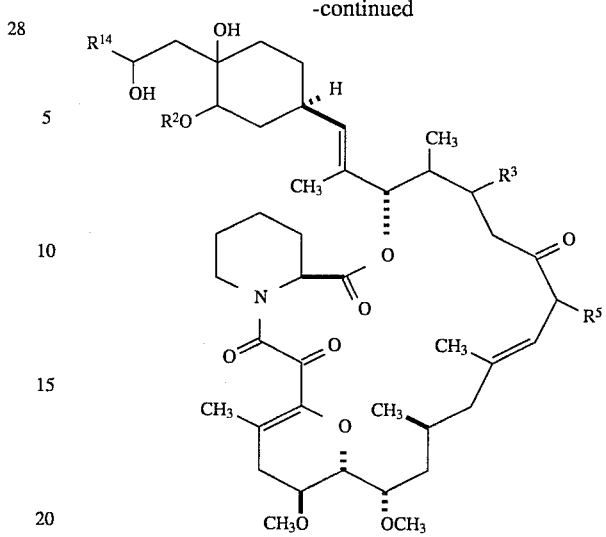
31
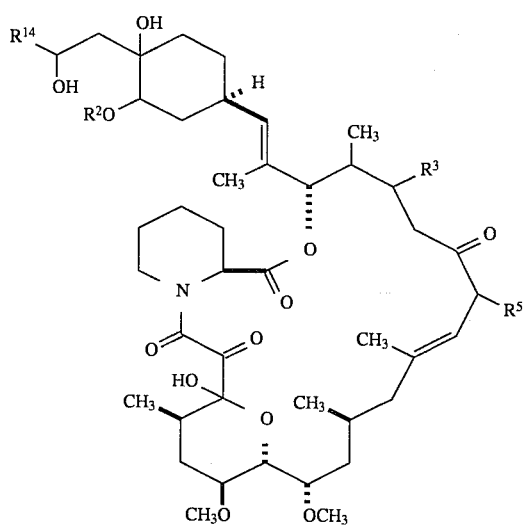
29
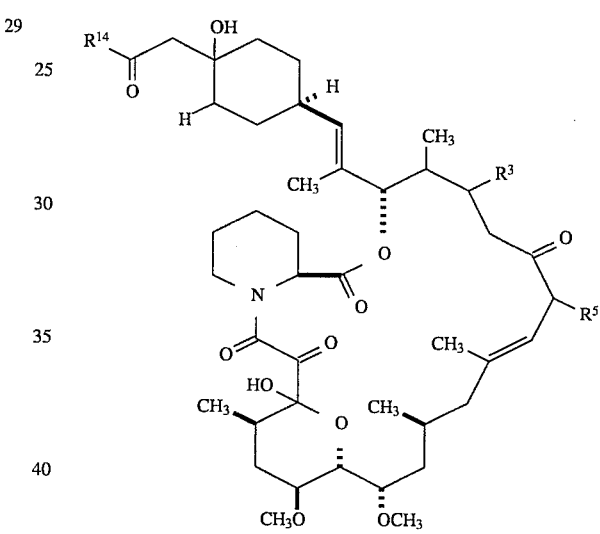
32
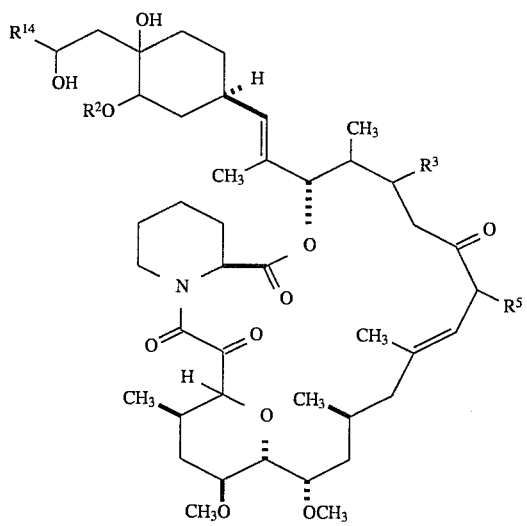
30
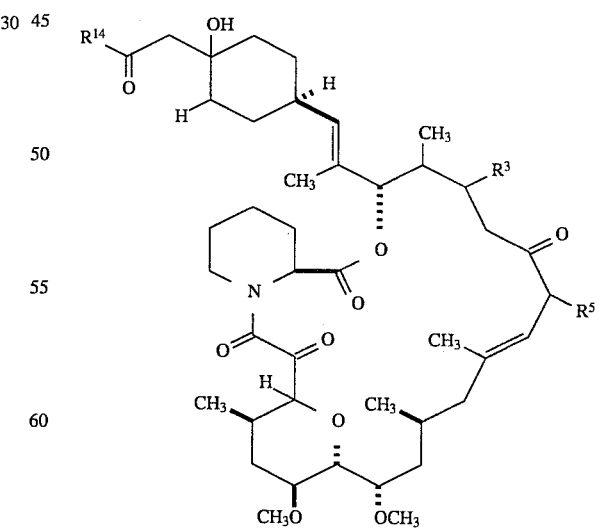
33

34

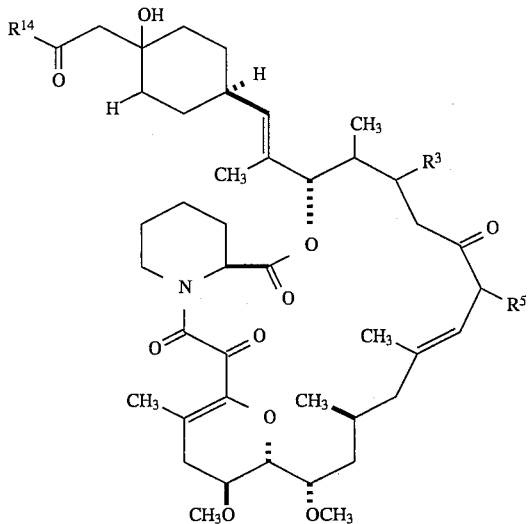

37

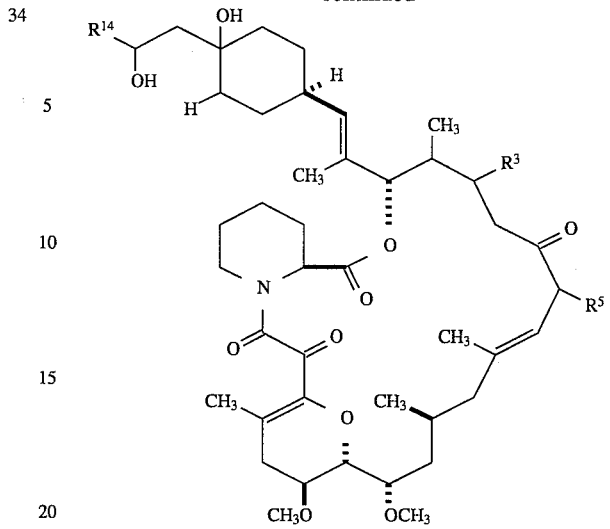

35

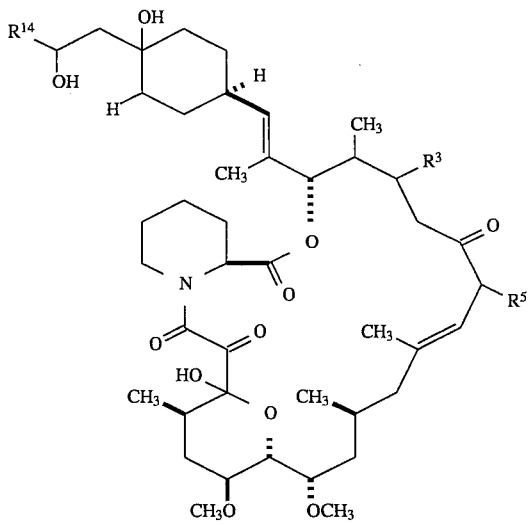

36

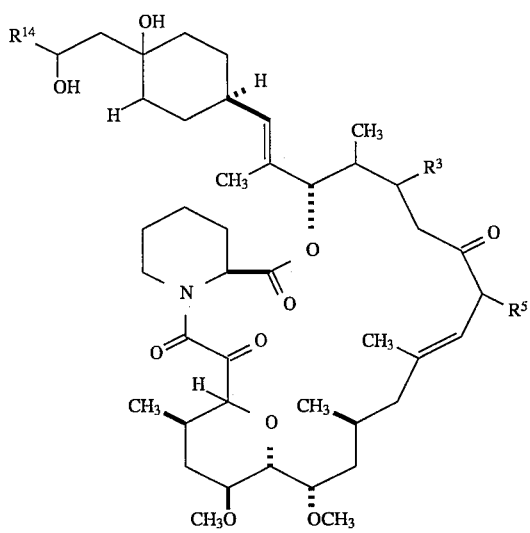

wherein for each of formula 26–37 the definitions of $R^2$, $R^3$, $R^5$, $R^{14}$ are selected from the following groups of substituents:

| $R^{14}$ | $R^2$ | $R^3$ | $R^5$ |
|---|---|---|---|
| $CH_3$ | $CH_3$ | OH | ethyl |
| $CH_3CH_2$ | $CH_3$ | OH | ethyl |
| $CH_2=CHCH_2$ | $CH_3$ | OH | ethyl |
| $CH_3CH_2CH_2$ | $CH_3$ | OH | ethyl |
| $(CH_3)_2CH$ | $CH_3$ | OH | ethyl |
| $HO_2CCH_2CH_2$ | $CH_3$ | OH | ethyl |
| $H_2NCOCH_2CH_2$ | $CH_3$ | OH | ethyl |
| $HOCH_2CH_2$ | $CH_3$ | OH | ethyl |
| $HOCH_2CH_2CH_2$ | $CH_3$ | OH | ethyl |
| $(CH_3)_2CH_2$ | $CH_3$ | OH | ethyl |
| phenyl | $CH_3$ | OH | ethyl |
| 4-pyridyl | $CH_3$ | OH | ethyl |
| 3-pyridyl | $CH_3$ | OH | ethyl |
| 2-pyridyl | $CH_3$ | OH | ethyl |
| 4-pyridylmethyl | $CH_3$ | OH | ethyl |
| 3-pyridylmethyl | $CH_3$ | OH | ethyl |
| 2-pyridylmethyl | $CH_3$ | OH | ethyl |
| benzyl | $CH_3$ | OH | ethyl |
| 4-$HO_2C$-benzyl | $CH_3$ | OH | ethyl |
| 4-$H_2NCO$-benzyl | $CH_3$ | OH | ethyl |
| 4-$CH_3O$-benzyl | $CH_3$ | OH | ethyl |
| 4-HO-benzyl | $CH_3$ | OH | ethyl |
| 4-Cl-benzyl | $CH_3$ | OH | ethyl |
| 4-$(CH_3)_2N$-benzyl | $CH_3$ | OH | ethyl |
| 3-$HO_2C$-benzyl | $CH_3$ | OH | ethyl |
| 3-$H_2NCO$-benzyl | $CH_3$ | OH | ethyl |
| 3-$CH_3O$-benzyl | $CH_3$ | OH | ethyl |
| 3-HO-benzyl | $CH_3$ | OH | ethyl |
| 3-Cl-benzyl | $CH_3$ | OH | ethyl |
| 3-$(CH_3)_2N$-benzyl | $CH_3$ | OH | ethyl |
| 2-$HO_2C$-benzyl | $CH_3$ | OH | ethyl |
| 2-$H_2NCO$-benzyl | $CH_3$ | OH | ethyl |
| 2-$CH_3O$-benzyl | $CH_3$ | OH | ethyl |
| 2-HO-benzyl | $CH_3$ | OH | ethyl |
| 2-Cl-benzyl | $CH_3$ | OH | ethyl |
| 2-$(CH_3)_2N$-benzyl | $CH_3$ | OH | ethyl |
| 2-$O_2N$-benzyl | $CH_3$ | OH | ethyl |
| 3-$O_2N$-benzyl | $CH_3$ | OH | ethyl |
| 4-$O_2N$-benzyl | $CH_3$ | OH | ethyl |
| 2-F-benzyl | $CH_3$ | OH | ethyl |
| 3-F-benzyl | $CH_3$ | OH | ethyl |
| 4-F-benzyl | $CH_3$ | OH | ethyl |
| 2-$F_3C$-benzyl | $CH_3$ | OH | ethyl |
| 3-$F_3C$-benzyl | $CH_3$ | OH | ethyl |
| 4-$F_3C$-benzyl | $CH_3$ | OH | ethyl |
| $CH_3$ | $CH_3$ | H | ethyl |
| $CH_3CH_2$ | $CH_3$ | H | ethyl |

| $R^{14}$ | $R^2$ | $R^3$ | $R^5$ |
|---|---|---|---|
| $CH_2=CHCH_2$ | $CH_3$ | H | ethyl |
| $CH_3CH_2CH_2$ | $CH_3$ | H | ethyl |
| $(CH_3)_2CH$ | $CH_3$ | H | ethyl |
| $HO_2CCH_2CH_2$ | $CH_3$ | H | ethyl |
| $H_2NCOCH_2CH_2$ | $CH_3$ | H | ethyl |
| $HOCH_2CH_2$ | $CH_3$ | H | ethyl |
| $HOCH_2CH_2CH_2$ | $CH_3$ | H | ethyl |
| $(CH_3)_2CH_2$ | $CH_3$ | H | ethyl |
| phenyl | $CH_3$ | H | ethyl |
| 4-pyridyl | $CH_3$ | H | ethyl |
| 3-pyridyl | $CH_3$ | H | ethyl |
| 2-pyridyl | $CH_3$ | H | ethyl |
| 4-pyridylmethyl | $CH_3$ | H | ethyl |
| 3-pyridylmethyl | $CH_3$ | H | ethyl |
| 2-pyridylmethyl | $CH_3$ | H | ethyl |
| benzyl | $CH_3$ | H | ethyl |
| 4-$HO_2C$-benzyl | $CH_3$ | H | ethyl |
| 4-$H_2NCO$-benzyl | $CH_3$ | H | ethyl |
| 4-$CH_3O$-benzyl | $CH_3$ | H | ethyl |
| 4-HO-benzyl | $CH_3$ | H | ethyl |
| 4-Cl-benzyl | $CH_3$ | H | ethyl |
| 4-$(CH_3)_2N$-benzyl | $CH_3$ | H | ethyl |
| 3-$HO_2C$-benzyl | $CH_3$ | H | ethyl |
| 3-$H_2NCO$-benzyl | $CH_3$ | H | ethyl |
| 3-$CH_3O$-benzyl | $CH_3$ | H | ethyl |
| 3-HO-benzyl | $CH_3$ | H | ethyl |
| 3-Cl-benzyl | $CH_3$ | H | ethyl |
| 3-$(CH_3)_2N$-benzyl | $CH_3$ | H | ethyl |
| 2-$HO_2C$-benzyl | $CH_3$ | H | ethyl |
| 2-$H_2NCO$-benzyl | $CH_3$ | H | ethyl |
| 2-$CH_3O$-benzyl | $CH_3$ | H | ethyl |
| 2-HO-benzyl | $CH_3$ | H | ethyl |
| 2-Cl-benzyl | $CH_3$ | H | ethyl |
| 2-$(CH_3)_2N$-benzyl | $CH_3$ | H | ethyl |
| 2-$O_2N$-benzyl | $CH_3$ | H | ethyl |
| 3-$O_2N$-benzyl | $CH_3$ | H | ethyl |
| 4-$O_2N$-benzyl | $CH_3$ | H | ethyl |
| 2-F-benzyl | $CH_3$ | H | ethyl |
| 3-F-benzyl | $CH_3$ | H | ethyl |
| 4-F-benzyl | $CH_3$ | H | ethyl |
| 2-$F_3C$-benzyl | $CH_3$ | H | ethyl |
| 3-$F_3C$-benzyl | $CH_3$ | H | ethyl |
| 4-$F_3C$-benzyl | $CH_3$ | H | ethyl |
| $CH_3$ | $CH_3$ | OH | allyl |
| $CH_3CH_2$ | $CH_3$ | OH | allyl |
| $CH_2=CHCH_2$ | $CH_3$ | OH | allyl |
| $CH_3CH_2CH_2$ | $CH_3$ | OH | allyl |
| $(CH_3)_2CH$ | $CH_3$ | OH | allyl |
| $HO_2CCH_2CH_2$ | $CH_3$ | OH | allyl |
| $H_2NCOCH_2CH_2$ | $CH_3$ | OH | allyl |
| $HOCH_2CH_2$ | $CH_3$ | OH | allyl |
| $HOCH_2CH_2CH_2$ | $CH_3$ | OH | allyl |
| $(CH_3)_2CH_2$ | $CH_3$ | OH | allyl |
| phenyl | $CH_3$ | OH | allyl |
| 4-pyridyl | $CH_3$ | OH | allyl |
| 3-pyridyl | $CH_3$ | OH | allyl |
| 2-pyridyl | $CH_3$ | OH | allyl |
| 4-pyridylmethyl | $CH_3$ | OH | allyl |
| 3-pyridylmethyl | $CH_3$ | OH | allyl |
| 2-pyridylmethyl | $CH_3$ | OH | allyl |
| benzyl | $CH_3$ | OH | allyl |
| 4-$HO_2C$-benzyl | $CH_3$ | OH | allyl |
| 4-$H_2NCO$-benzyl | $CH_3$ | OH | allyl |
| 4-$CH_3O$-benzyl | $CH_3$ | OH | allyl |
| 4-HO-benzyl | $CH_3$ | OH | allyl |
| 4-Cl-benzyl | $CH_3$ | OH | allyl |
| 4-$(CH_3)_2N$-benzyl | $CH_3$ | OH | allyl |
| 3-$HO_2C$-benzyl | $CH_3$ | OH | allyl |
| 3-$H_2NCO$-benzyl | $CH_3$ | OH | allyl |
| 3-$CH_3O$-benzyl | $CH_3$ | OH | allyl |
| 3-HO-benzyl | $CH_3$ | OH | allyl |
| 3-Cl-benzyl | $CH_3$ | OH | allyl |
| 3-$(CH_3)_2N$-benzyl | $CH_3$ | OH | allyl |
| 2-$HO_2C$-benzyl | $CH_3$ | OH | allyl |
| 2-$H_2NCO$-benzyl | $CH_3$ | OH | allyl |
| 2-$CH_3O$-benzyl | $CH_3$ | OH | allyl |
| 2-HO-benzyl | $CH_3$ | OH | allyl |
| 2-Cl-benzyl | $CH_3$ | OH | allyl |
| 2-$(CH_3)_2N$-benzyl | $CH_3$ | OH | allyl. |

12. The compound of claim 1 which is selected from a compound of formula 38–43:

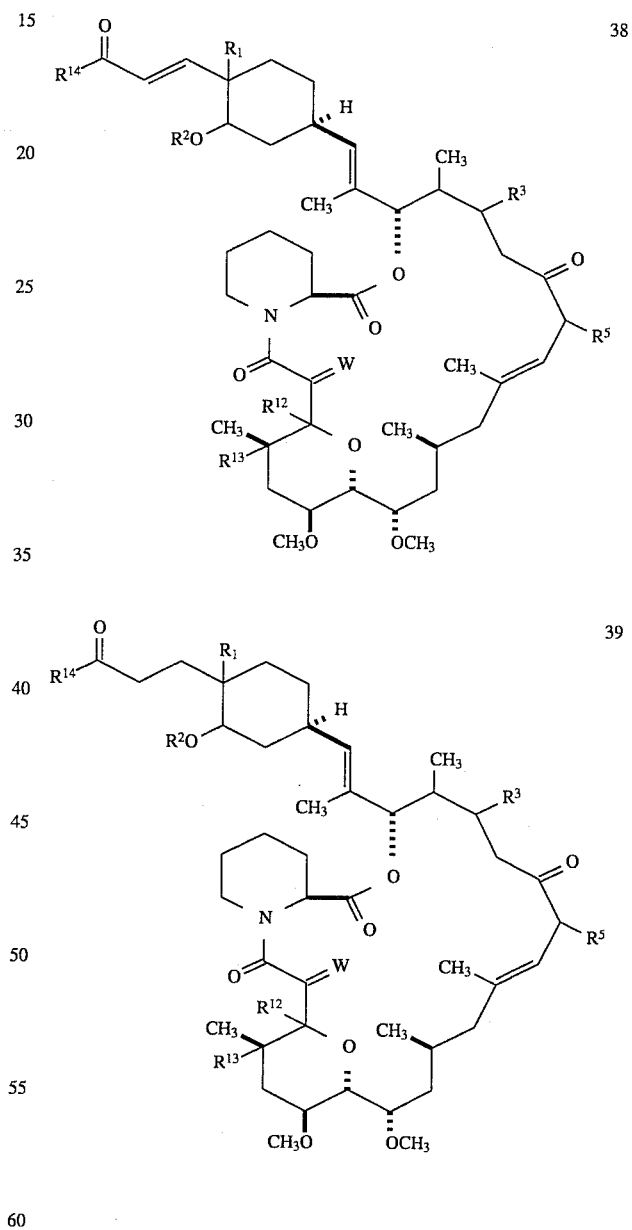

165
-continued

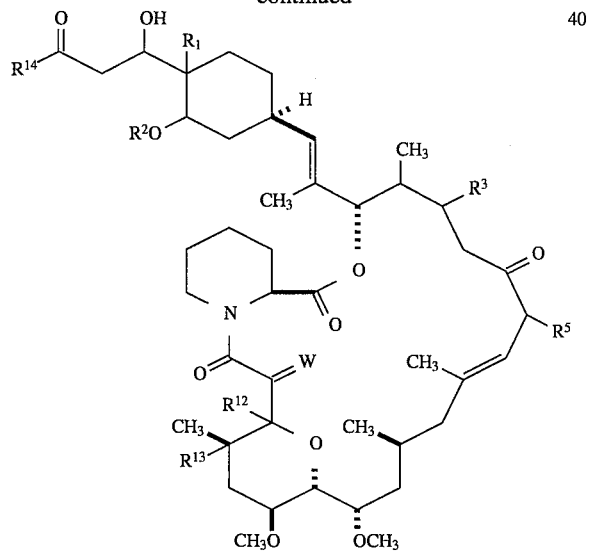

40

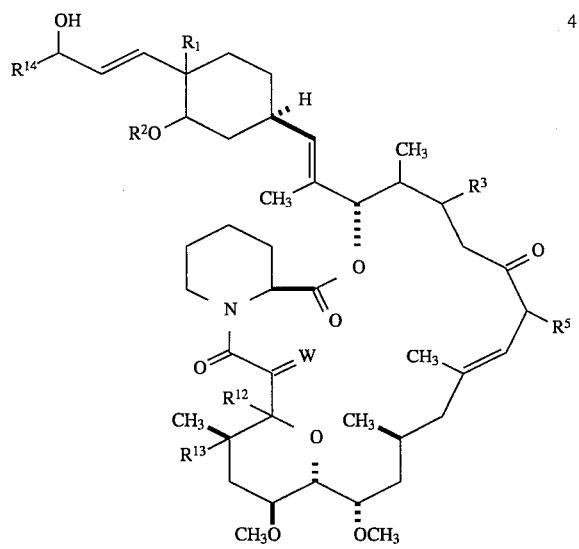

41

166
-continued

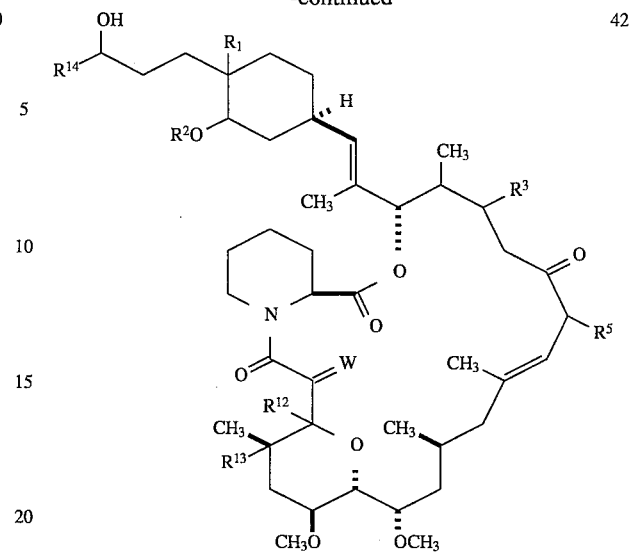

42

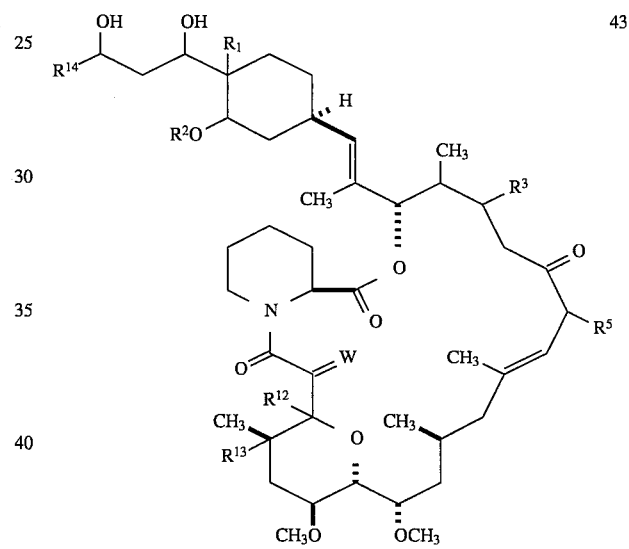

43 wherein for each of formula 38–43 the definitions of $R^1$, $R^2$, $R^3$ and $R^{14}$ are selected from the following groups of substituents and W, $R^{12}$ and $R^{13}$ are as defined in claim 1:

| $R^{14}$ | $R^1$ | $R^2$ | $R^3$ | $R^5$ |
|---|---|---|---|---|
| 4-HO$_2$C-phenyl | OH | CH$_3$ | OH | ethyl |
| 4-H$_2$NCO-phenyl | OH | CH$_3$ | OH | ethyl |
| 4-HO-phenyl | OH | CH$_3$ | OH | ethyl |
| 4-Cl-phenyl | OH | CH$_3$ | OH | ethyl |
| 4-CH$_3$-phenyl | OH | CH$_3$ | OH | ethyl |
| 4-(CH$_3$)$_2$N-phenyl | OH | CH$_3$ | OH | ethyl |
| 3-HO$_2$C-phenyl | OH | CH$_3$ | OH | ethyl |
| 3-H$_2$NCO-phenyl | OH | CH$_3$ | OH | ethyl |
| 3-HO-phenyl | OH | CH$_3$ | OH | ethyl |
| 3-Cl-phenyl | OH | CH$_3$ | OH | ethyl |
| 3-CH$_3$-phenyl | OH | CH$_3$ | OH | ethyl |
| 3-(CH$_3$)$_2$N-phenyl | OH | CH$_3$ | OH | ethyl |
| 3,5-di(CH$_3$)-phenyl | OH | CH$_3$ | OH | ethyl |
| 2-HO$_2$C-phenyl | OH | CH$_3$ | OH | ethyl |
| 2-H$_2$NCO-phenyl | OH | CH$_3$ | OH | ethyl |
| 2-HO-phenyl | OH | CH$_3$ | OH | ethyl |
| 2-Cl-phenyl | OH | CH$_3$ | OH | ethyl |

| R$^{14}$ | R$^1$ | R$^2$ | R$^3$ | R$^5$ |
| --- | --- | --- | --- | --- |
| 2-CH$_3$-phenyl | OH | CH$_3$ | OH | ethyl |
| 2-(CH$_3$)$_2$N-phenyl | OH | CH$_3$ | OH | ethyl |
| 4-pyridyl | OH | CH$_3$ | OH | ethyl |
| 3-pyridyl | OH | CH$_3$ | OH | ethyl |
| 2-pyridyl | OH | CH$_3$ | OH | ethyl |
| 1-naphthyl | OH | CH$_3$ | OH | ethyl |
| 2-naphthyl | OH | CH$_3$ | OH | ethyl |
| 5-indolyl | OH | CH$_3$ | OH | ethyl |
| 6-indolyl | OH | CH$_3$ | OH | ethyl |
| 5-(1-(2-hydroxyethyl)-indolyl)- | OH | CH$_3$ | OH | ethyl |
| 6-(1-(2-hydroxyethyl)-indolyl)- | OH | CH$_3$ | OH | ethyl |
| 2-imidazolyl | OH | CH$_3$ | OH | ethyl |
| 3-imidazolyl | OH | CH$_3$ | OH | ethyl |
| 2-O$_2$N-phenyl | OH | CH$_3$ | OH | ethyl |
| 3-O$_2$N-phenyl | OH | CH$_3$ | OH | ethyl |
| 4-O$_2$N-phenyl | OH | CH$_3$ | OH | ethyl |
| 2-F-phenyl | OH | CH$_3$ | OH | ethyl |
| 3-F-phenyl | OH | CH$_3$ | OH | ethyl |
| 4-F-phenyl | OH | CH$_3$ | OH | ethyl |
| 2-F$_3$C-phenyl | OH | CH$_3$ | OH | ethyl |
| 3-F$_3$C-phenyl | OH | CH$_3$ | OH | ethyl |
| 4-F$_3$C-phenyl | OH | CH$_3$ | OH | ethyl |
| 4-HO$_2$C-phenyl | OH | CH$_3$ | H | ethyl |
| 4-H$_2$NCO-phenyl | OH | CH$_3$ | H | ethyl |
| 4-HO-phenyl | OH | CH$_3$ | H | ethyl |
| 4-Cl-phenyl | OH | CH$_3$ | H | ethyl |
| 4-CH$_3$-phenyl | OH | CH$_3$ | H | ethyl |
| 4-(CH$_3$)$_2$N-phenyl | OH | CH$_3$ | H | ethyl |
| 3-HO$_2$C-phenyl | OH | CH$_3$ | H | ethyl |
| 3-H$_2$NCO-phenyl | OH | CH$_3$ | H | ethyl |
| 3-HO-phenyl | OH | CH$_3$ | H | ethyl |
| 3-Cl-phenyl | OH | CH$_3$ | H | ethyl |
| 3-CH$_3$-phenyl | OH | CH$_3$ | H | ethyl |
| 3-(CH$_3$)$_2$N-phenyl | OH | CH$_3$ | H | ethyl |
| 3,5-di(CH$_3$)-phenyl | OH | CH$_3$ | H | ethyl |
| 2-HO$_2$C-phenyl | OH | CH$_3$ | H | ethyl |
| 2-H$_2$NCO-phenyl | OH | CH$_3$ | H | ethyl |
| 2-HO-phenyl | OH | CH$_3$ | H | ethyl |
| 2-Cl-phenyl | OH | CH$_3$ | H | ethyl |
| 2-CH$_3$-phenyl | OH | CH$_3$ | H | ethyl |
| 2-(CH$_3$)$_2$N-phenyl | OH | CH$_3$ | H | ethyl |
| 4-pyridyl | OH | CH$_3$ | H | ethyl |
| 3-pyridyl | OH | CH$_3$ | H | ethyl |
| 2-pyridyl | OH | CH$_3$ | H | ethyl |
| 1-naphthyl | OH | CH$_3$ | H | ethyl |
| 2-naphthyl | OH | CH$_3$ | H | ethyl |
| 5-indolyl | OH | CH$_3$ | H | ethyl |
| 6-indolyl | OH | CH$_3$ | H | ethyl |
| 5-(1-(2-hydroxyethyl)-indolyl)- | OH | CH$_3$ | H | ethyl |
| 6-(1-(2-hydroxyethyl)-indolyl)- | OH | CH$_3$ | H | ethyl |
| 2-imidazolyl | OH | CH$_3$ | H | ethyl |
| 3-imidazolyl | OH | CH$_3$ | H | ethyl |
| 2-O$_2$N-phenyl | OH | CH$_3$ | H | ethyl |
| 3-O$_2$N-phenyl | OH | CH$_3$ | H | ethyl |
| 4-O$_2$N-phenyl | OH | CH$_3$ | H | ethyl |
| 2-F-phenyl | OH | CH$_3$ | H | ethyl |
| 3-F-phenyl | OH | CH$_3$ | H | ethyl |
| 4-F-phenyl | OH | CH$_3$ | H | ethyl |
| 2-F$_3$C-phenyl | OH | CH$_3$ | H | ethyl |
| 3-F$_3$C-phenyl | OH | CH$_3$ | H | ethyl |
| 4-F$_3$C-phenyl | OH | CH$_3$ | H | ethyl |
| 4-HO$_2$C-phenyl | OH | CH$_3$ | OH | allyl |
| 4-H$_2$NCO-phenyl | OH | CH$_3$ | OH | allyl |
| 4-HO-phenyl | OH | CH$_3$ | OH | allyl |
| 4-Cl-phenyl | OH | CH$_3$ | OH | allyl |
| 4-CH$_3$-phenyl | OH | CH$_3$ | OH | allyl |
| 4-(CH$_3$)$_2$N-phenyl | OH | CH$_3$ | OH | allyl |
| 3-HO$_2$C-phenyl | OH | CH$_3$ | OH | allyl |
| 3-H$_2$NCO-phenyl | OH | CH$_3$ | OH | allyl |
| 3-HO-phenyl | OH | CH$_3$ | OH | allyl |
| 3-Cl-phenyl | OH | CH$_3$ | OH | allyl |
| 3-CH$_3$-phenyl | OH | CH$_3$ | OH | allyl |
| 3-(CH$_3$)$_2$N-phenyl | OH | CH$_3$ | OH | allyl |
| 3,5-di(CH$_3$)-phenyl | OH | CH$_3$ | OH | allyl |
| 2-HO$_2$C-phenyl | OH | CH$_3$ | OH | allyl |
| 2-H$_2$NCO-phenyl | OH | CH$_3$ | OH | allyl |
| 2-HO-phenyl | OH | CH$_3$ | OH | allyl |
| 2-Cl-phenyl | OH | CH$_3$ | OH | allyl |
| 2-CH$_3$-phenyl | OH | CH$_3$ | OH | allyl |
| 2-(CH$_3$)$_2$N-phenyl | OH | CH$_3$ | OH | allyl |
| 4-pyridyl | OH | CH$_3$ | OH | allyl |
| 3-pyridyl | OH | CH$_3$ | OH | allyl |
| 2-pyridyl | OH | CH$_3$ | OH | allyl |
| 1-naphthyl | OH | CH$_3$ | OH | allyl |
| 2-naphthyl | OH | CH$_3$ | OH | allyl |
| 5-indolyl | OH | CH$_3$ | OH | allyl |
| 6-indolyl | OH | CH$_3$ | OH | allyl |
| 5-(1-(2-hydroxyethyl)-indolyl)- | OH | CH$_3$ | OH | allyl |
| 6-(1-(2-hydroxyethyl)-indolyl)- | OH | CH$_3$ | OH | allyl |
| 2-imidazolyl | OH | CH$_3$ | OH | allyl |
| 3-imidazolyl | OH | CH$_3$ | OH | allyl |
| 2-O$_2$N-phenyl | OH | CH$_3$ | OH | allyl |
| 3-O$_2$N-phenyl | OH | CH$_3$ | OH | allyl |
| 4-O$_2$N-phenyl | OH | CH$_3$ | OH | allyl |
| 2-F-phenyl | OH | CH$_3$ | OH | allyl |
| 3-F-phenyl | OH | CH$_3$ | OH | allyl |
| 4-F-phenyl | OH | CH$_3$ | OH | allyl |
| 2-F$_3$C-phenyl | OH | CH$_3$ | OH | allyl |
| 3-F$_3$C-phenyl | OH | CH$_3$ | OH | allyl |
| 4-F$_3$C-phenyl | OH | CH$_3$ | OH | allyl |
| CH$_3$ | H | CH$_3$ | OH | ethyl |
| CH$_3$CH$_2$ | H | CH$_3$ | OH | ethyl |
| CH$_3$CH$_2$CH$_2$ | H | CH$_3$ | OH | ethyl |
| (CH$_3$)$_2$CH | H | CH$_3$ | OH | ethyl |
| HO$_2$CCH$_2$CH$_2$ | H | CH$_3$ | OH | ethyl |
| H$_2$NCOCH$_2$CH$_2$ | H | CH$_3$ | OH | ethyl |
| HOCH$_2$CH$_2$ | H | CH$_3$ | OH | ethyl |
| HOCH$_2$CH$_2$CH$_2$ | H | CH$_3$ | OH | ethyl |
| CH$_3$ | H | CH$_3$ | H | ethyl |
| CH$_3$CH$_2$ | H | CH$_3$ | H | ethyl |
| CH$_3$CH$_2$CH$_2$ | H | CH$_3$ | H | ethyl |
| (CH$_3$)$_2$CH | H | CH$_3$ | H | ethyl |
| HO$_2$CCH$_2$CH$_2$ | H | CH$_3$ | H | ethyl |
| H$_2$NCOCH$_2$CH$_2$ | H | CH$_3$ | H | ethyl |
| HOCH$_2$CH$_2$ | H | CH$_3$ | H | ethyl |
| HOCH$_2$CH$_2$CH$_2$ | H | CH$_3$ | H | ethyl |
| CH$_3$ | H | H | OH | ethyl |
| CH$_3$CH$_2$ | H | H | OH | ethyl |
| CH$_3$CH$_2$CH$_2$ | H | H | OH | ethyl |
| (CH$_3$)$_2$CH | H | H | OH | ethyl |
| HO$_2$CCH$_2$CH$_2$ | H | H | OH | ethyl |
| H$_2$NCOCH$_2$CH$_2$ | H | H | OH | ethyl |
| HOCH$_2$CH$_2$ | H | H | OH | ethyl |
| HOCH$_2$CH$_2$CH$_2$ | H | H | OH | ethyl. |

13. A compound which is selected from the group consisting of:

17-Ethyl-1,14-dihydroxy-12-[2'-(4"-hydroxy-4"-methyl-3"-methoxycyclohexyl)- 1'-methylvinyl]-23,25-dimethoxy-13,19,21,27-tetramethyl- 11,28-dioxa-4-azatricyclo [22.3.1.0$^{4,9}$]octacos-18-ene- 2,3,10,16-tetraone; (#1)

17-Ethyl-1-hydroxy-12-[2'-(4"-hydroxy-4"-methyl-3"-methoxycyclohexyl)- 1'-methylvinyl]-23,25-dimethoxy-13,19,21,27-tetramethyl- 11,28-dioxa-4-azatricyclo [22.3.1.0$^{4,9}$]octacos-18-ene- 2,3,10,16-tetraone; (#2)

17-Allyl-1,14-dihydroxy-12-[2'-(4"-hydroxy-4"-methyl-3"-methoxycyclohexyl)- 1'-methylvinyl]-23,25-dimethoxy-13,19,21,27-tetramethyl- 11,28-dioxa-4-azatricyclo [22.3.1.0$^{4,9}$]octacos-18-ene- 2,3,10,16-tetraone; (#3)

17-Ethyl-1,14-dihydroxy-12-[2'-(4"-hydroxy-4"-phenyl-3"-methoxycyclohexyl)- 1'-methylvinyl]-23,25-dimethoxy-13,19,21,27-tetramethyl- 11,28-dioxa-4-azatricyclo [22.3.1.0$^{4,9}$]octacos-18-ene- 2,3,10,16-tetraone; (#4)

17-Ethyl-1-hydroxy-12-[2'-(4"-hydroxy-4"-phenyl-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#5)

17-Allyl-1,14-dihydroxy-12-[2'-(4"-hydroxy-4"-phenyl-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#6)

17-Ethyl-1,14-dihydroxy-12-[2'-(4"-hydroxy-4"-benzyl-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#7)

17-Ethyl-1-hydroxy-12-[2'-(4"-hydroxy-4"-benzyl-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#8)

17-Allyl-1,14-dihydroxy-12-[2'-(4"-hydroxy-4"-benzyl-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#9)

17-Ethyl-1,14-dihydroxy-12-[2'-(4"-hydroxy-4"-(indol-5-yl)-3"-methoxycyclohexyl)-1'-methylvinyl]-23,25-dimethoxy-13,19,21,27-tetramethyl- 11,28-dioxa-4-azatricyclo[22.3.1.0$^{4,9}$ octacos-18-ene- 2,3,10,16-tetraone; (#10)

17-Ethyl-1-hydroxy-12-[2'-(4"-hydroxy-4"-(indol-5-yl)-3"-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#11)

17-Allyl-1,14-dihydroxy-12-[2'-(4"-hydroxy-4"-(indol-5-yl)-3"-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#12)

17-Ethyl-1,14-dihydroxy-12-[2'-(4"-hydroxy-4"-(indol-5-ylmethyl)-3"-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#13)

17-Ethyl-1-hydroxy-12-[2'-(4"-hydroxy-4"-(indol-5-ylmethyl)-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#14)

17-Allyl-1,14-dihydroxy-12-[2'-(4"-hydroxy-4"-(indol-5-ylmethyl)-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#15)

17-Ethyl-1,14-dihydroxy-12-[2'-(4"-hydroxy-4"-(2-propen-1-yl)-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#16)

17-Ethyl-1-hydroxy-12-[2'-(4"-hydroxy-4"-(2-propen-1-yl)-3"-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#17)

17-Allyl-1,14-dihydroxy-12-[2'-(4"-hydroxy-4"-(2-propen-1-yl)-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#18)

17-Ethyl-1-hydroxy-12-[2'-(4"-hydroxy-4"-(3-phenyl-2-propen-1-yl)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone; (#19)

17-Ethyl-1-hydroxy-12-[2'-(4"-hydroxy-4"-(3-phenyl-2-propen-1-yl)- 3"-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#20)

17-Allyl-1,14-dihydroxy-12-[2'-(4"-hydroxy-4"-(3-phenyl-2-propen-1-yl)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone; (#21)

17-Ethyl-1,14-dihydroxy-12-[2'-(4"-hydroxy-4"-[3-(4-methoxyphenyl)- 2-propen-1-yl]-3"-methoxycyclohexyl)-1'-methylvinyl]-23,25-dimethoxy- 13,19,21,27-tetramethyl-11,28-dioxa-4-azatricyclo- [22.3.1.0$^{4,9}$]octacos-18-ene-2,3,10,16-tetraone; (#22)

17-Ethyl-1-hydroxy-12-[2'-(4"-hydroxy-4"-[3-(4-methoxyphenyl)- 2-propen-1-yl]-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene- 2,3,10,16-tetraone; (#23)

17-Allyl-1,14-dihydroxy-12-[2'-(4"-hydroxy-4"-[3-(4-methoxyphenyl)-2-propen-1-yl]-3"-methoxycyclohexyl)- 1'-methylvinyl]-23,25-dimethoxy- 13,19,21,27-tetramethyl-11,28-dioxa-4-azatricyclo- [22.3.1.0$^{4,9}$]octacos-18-ene-2,3,10,16-tetraone; (#24)

17-Ethyl-1,14-dihydroxy-12-[2'-(4"-hydroxy-4"-[3-(3-methoxyphenyl)- 2-propen-1-yl]-3"-methoxycyclohexyl)-1'-methylvinyl]-23,25-dimethoxy- 13,19,21,27-tetramethyl-11,28-dioxa-4-azatricyclo- [22.3.1.0$^{4,9}$]octacos-18-ene-2,3,10,16-tetraone; (#25)

17-Ethyl-1-hydroxy-12-[2'-(4"-hydroxy-4"-[3-(3-methoxyphenyl)-2-propen-1-yl]-3"-methoxycyclohexyl)-1'-methylvinyl]-23,25-dimethoxy- 13,19,21,27-tetramethyl-11, 28-dioxa-4-azatricyclo[22.3.1.0$^{4,9}$]octacos-18-ene- 2,3,10,16-tetraone; (#26)

17-Allyl-1,14-dihydroxy-12-[2'-(4"-hydroxy-4"-[3-(3-methoxyphenyl)-2-propen-1-yl]-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#27)

17-Ethyl-1,14-dihydroxy-12-[2'-(4"-hydroxy-4"-[3-(3,5-dimethoxyphenyl)- 2-propen-1-yl]-3"-methoxycyclohexyl)-1'-methylvinyl]- 13,19,21,27-tetramethyl-11,28-dioxa-4-azatricyclo[22.3.1.04, 9]octacos-18-ene-2,3,10,16-tetraone; (#28)

17-Ethyl-1-hydroxy-12-[2'-(4"-hydroxy-4"-[3-(3,5-dimethoxyphenyl)- 2-propen-1-yl]-3"-methoxycyclohexyl)-1'-methylvinyl]-23,25-dimethoxy- 13,19,21,27-tetramethyl-11,28-dioxa-4-azatricyclo[22.3.1.0$^{4,9}$] octacos-18-ene-2,3,10,16-tetraone; (#29)

17-Allyl-1,14-dihydroxy-12-[2'-(4"-hydroxy-4"-[3-(3,5-dimethoxyphenyl)- 2-propen-1-yl]-3"-methoxycyclohexyl)-1'-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone; (#30)

17-Ethyl-1,14-dihydroxy-12-[2'-(4"-hydroxy-4"-(penta-2,4-dien-1-yl)- 3"-methoxycyclohexyl)-1'-methylvinyl]-23, 25-dimethoxy-13,19,21,27-tetramethyl- 11,28-dioxa-4-azatricyclo[22.3.1.0$^{4,9}$]octacos-18-ene- 2,3,10,16-tetraone; (#31)

17-Ethyl-1-hydroxy-12-[2'-(4"-hydroxy-4"-(penta-2,4-dien-1-yl)-3"-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#32)

17-Allyl-1,14-dihydroxy-12-[2'-(4"-hydroxy-4"-(penta-2,4-dien-1-yl)- 3"-methoxycyclohexyl)-1'-methylvinyl]-23, 25-dimethoxy-13,19,21,27-tetramethyl- 11,28-dioxa-4-azatricyclo[22.3.1.0$^{4,9}$]octacos-18-ene- 2,3,10,16-tetraone; (#33)

17-Ethyl-1,14-dihydroxy-12-[2'-(4"-hydroxy-4"-(5-phenylpenta-2,4-dien- 1-yl)-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#34)

17-Ethyl-1-hydroxy-12-[2'-(4"-hydroxy-4"-(5-phenylpenta-2,4-dien-1 -yl)-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone; (#35)

17-Allyl-1,14-dihydroxy-12-[2'-(4"-hydroxy-4"-(5-phenylpenta-2,4-dien- 1-yl)-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#36)

17-Ethyl-1,14-dihydroxy-12-[2'-(4"-hydroxy-4"-[5-(4-methoxyphenyl)-penta- 2,4-dien-1-yl]-3"-methoxycyclohexyl)-1'-methylvinyl]- 23,25-dimethoxy-13,19,21,27-tetramethyl-11,28-dioxa-4-azatricyclo[2.3.1.0$^{4,9}$]octacos-18-ene-2,3,10,16-tetraone; (#37)

17-Ethyl-1-hydroxy-12-[2'-(4"-hydroxy-4"-[5-(4-methoxyphenyl)-penta- 2,4-dien-1-yl]-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#38)

17-Allyl-1,14-dihydroxy-12-[2'-(4"-hydroxy-4"-[5-(4-methoxyphenyl)-penta- 2,4-dien-1-yl]-3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone; (#39)

17-Ethyl-1,14-dihydroxy-12-[2'-(4"-hydroxy-4"-[5-(3-methoxyphenyl)-penta- 2,4-dien-1-yl]-3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone; (#40)

17-Ethyl-1-hydroxy-12-[2'-(4"-hydroxy-4"-[5-(3-methoxyphenyl)-penta- 2,4-dien-1-yl]-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#41)

17-Allyl-1,14-dihydroxy-12-[2'-(4"-hydroxy-4"-[5-(3-methoxyphenyl)-penta- 2,4-dien-1-yl]-3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone; (#42)

17-Ethyl-1,14-dihydroxy-12-[2'-(4"-hydroxy-4"-[5-(3,5-dimethoxyphenyl)-penta-2,4-dien-1-yl]-3"-methoxycyclohexyl)-1'-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone; (#43)

17-Ethyl-1-hydroxy-12-[2'-(4"-hydroxy-4"-[5-(3,5-dimethoxyphenyl)-penta- 2,4-dien-1-yl]-3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#44)

17-Allyl-1,14-dihydroxy-12-[2'-(4"-hydroxy-4"-[5-(3,5-dimethoxyphenyl)-penta-2,4-dien-1-yl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#45)

17-Ethyl-1,14-dihydroxy-12-[2'-(4"-(2-carboxymethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone; (#46)

17-Ethyl-1-hydroxy-12-[2'-(4"-(2-carboxymethylidene)-3"-methoxycyclohexyl)- 1'-methylvinyl]-23,25-dimethoxy- 13,19,21,27-tetramethyl- 11,28-dioxa-4-azatricyclo[22.3.1.0$^{4,9}$]octacos-18-ene- 2,3,10,16-tetraone; (#47)

17-Allyl-1,14-dihydroxy-12-[2'-(4"-(2-carboxymethylidene)-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#48)

17-Ethyl-1,14-dihydroxy-12-[2'-(4"-(2-methoxycarbonylmethylidene)- 3"-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#49)

17-Ethyl-1-hydroxy-12-[2'-(4"-(2-methoxycarbonylmethylidene)-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#50)

17-Allyl-1,14-dihydroxy-12-[2'-(4"-(2-methoxycarbonyl methylidene)- 3"-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#51)

17-Ethyl-1,14-dihydroxy-12-[2'-(4"-(2-benzyloxycarbonylmethylidene)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone; (#52)

17-Ethyl-1-hydroxy-12-[2'-(4"-hydroxy-4"-(2-benzyloxycarbonylmethylidene)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone; (#53)

17-Allyl-1,14-dihydroxy-12-[2'-(4"-hydroxy-4"-(2-benzyloxycarbonylmethylidene)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone; (#54)

17-Ethyl-1,14-dihydroxy-12-[2'-(4"-hydroxy-4"-(2-benzylaminocarbonylmethylidene)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#55)

17-Ethyl-1-hydroxy-12-[2'-(4"-hydroxy-4"-(2-benzylaminocarbonylmethylidene)-3"-methoxycyclohexyl)-1'-methylvinyl]-23,25-dimethoxy-13,19,21,27-tetramethyl-11, 28-dioxa-4-azatricyclo[22.3.1.0$^{4,9}$]octacos-18-ene-2,3,10,16-tetraone; (#56)

17-Allyl-1,14-dihydroxy-12-[2'-(4"-hydroxy-4"-(2-benzylaminocarbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#57)

17-Ethyl-1,14-dihydroxy-12-[2'-(4"-(2-carboxymethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#58)

17-Ethyl-1-hydroxy-12-[2'-(4"-(2-carboxymethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18ene-2,3,10,16-tetraone; (#59)

17-Allyl-1,14-dihydroxy-12-[2'-(4"-(2-carboxymethylenyl)-3"-methoxycyclohexyl)- 1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#60)

17-Ethyl-1,14-dihydroxy-12-[2'-(4"-(2-methoxycarbonylmethylenyl-3 "-methoxycyclohexyl)-1'-methylvinyl]-23,25-dimethoxy-13,19,21,27-tetramethyl- 11,28-dioxa-4-azatricyclo[22.3.1.0$^{4,9}$]octacos-18-ene- 2,3,10,16-tetraone; (#61)

17-Ethyl-1-hydroxy-12-[2'-(4"-(2-methoxycarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#62)

17-Allyl-1,14-dihydroxy-12-[2'-(4"-(2-methoxycarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#63)

17-Ethyl-1,14-dihydroxy-12-[2'-(4"-(2-benzyloxycarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#64)

17-Ethyl-1-hydroxy-12-[2'-(4"-hydroxy-4"-(2-benzyloxycarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#65)

17-Allyl-1,14-dihydroxy-12-[2'-(4"-hydroxy-4"-(2-benzyloxycarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#66)

17-Ethyl-1,14-dihydroxy-12-[2'-(4"-hydroxy-4"-(2-benzylaminocarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#67)

17-Ethyl-1-hydroxy-12-[2'-(4"-hydroxy-4"-(2-benzylaminocarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#68)

17-Allyl-1,14-dihydroxy-12-[2'-(4"-hydroxy-4"-(2-benzylaminocarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#69)

17-Ethyl-1,14-dihydroxy-12-[2'-(4"-(2-methylcarbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#70)

17-Ethyl-1-hydroxy-12-[2'-(4"-(2-methylcarbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#71)

17-Allyl-1,14-dihydroxy-12-[2'-(4"-(2-methylcarbonylmethylidene)-3"-methoxycyclohexyl-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#72)

17-Ethyl-1,14-dihydroxy-12-[2'-(4"-(2-phenylcarbonylmethylidene-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#73)

17-Ethyl-1-hydroxy-12-[2'-(4"-(2-phenylcarbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#74)

17-Allyl-1,14-dihydroxy-12-[2'-(4"-(2-phenylcarbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#75)

17-Ethyl-1,14-dihydroxy-12-[2'-(4"-(2-(3-methoxyphenyl)-carbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#76)

17-Ethyl-1-hydroxy-12-[2'-(4"-hydroxy-4"-(2-(3-methoxyphenyl)-carbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#77)

17-Allyl-1,14-dihydroxy-12-[2'-(4"-hydroxy-4"-(2-(3-methoxyphenyl)-carbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#78)

17-Ethyl-1,14-dihydroxy-12-[2'-(4"-hydroxy-4"-(2-(4-methoxyphenyl)-carbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#79)

17-Ethyl-1-hydroxy-12-[2'-(4"-hydroxy-4"-(2-(4-methoxyphenyl)-carbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#80)

17-Allyl-1,14-dihydroxy-12-[2'-(4"-hydroxy-4"-(2-(4-methoxyphenyl)-carbonylmethylidene)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#81)

17-Ethyl-1,14-dihydroxy-12-[2'(4"-(2-methylcarbonylmethyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#82)

17Ethyl-1-hydroxy-12-[2'-(4"-(2-methylcarbonylmethylenyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#83)

17-Allyl-1,14-dihydroxy-12-[2'-(4"-(2-methylcarbonylmethyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#84)

17-Ethyl-1,14-dihydroxy-12-[2'-(4"-(2-phenylcarbonylmethyl-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#85)

17-Ethyl-1-hydroxy-12-[2'-(4"-(2-phenylcarbonylmethyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#86)

17-Allyl-1,14-dihydroxy-12-[2'-(4"-(2-phenylcarbonylmethyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#87)

17-Ethyl-1,14-dihydroxy-12-[2'-(4"-(2-(3-methoxyphenyl)-carbonylmethyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#88)

17-Ethyl-1-hydroxy-12-[2'-(4"-(2-(3-methoxyphenyl)-carbonylmethyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#89)

17-Allyl-1,14-dihydroxy-12-[2'-(4"-(2-(3-methoxyphenyl)-carbonylmethyl)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#90)

17-Ethyl-1,14-dihydroxy-12-[2'-(4"-(2-(4-methoxyphenyl)-carbonylmethyl)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos-18-ene-2,3,10,16-tetraone; (#91)

17-Ethyl-1-hydroxy-12-[2'-(4"-(3-methoxyphenyl)carbonylmethylenyl)- 3"-methoxycyclohexyl)-1'-methylvinyl]-23,25-dimethoxy- 13,19,21,27-tetramethyl-11,28-dioxa-4-azatricyclo[22.3.1.0$^{4,9}$]octacos- 18-ene-2,3,10,16-tetraone; (#92)

17-Allyl-1,14-dihydroxy-12-[2'-(4"-hydroxy-4"-(3-methoxyphenyl)-carbonylmethyl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#93)

17-Ethyl-1,14-dihydroxy-12-[2'-(4"-hydroxy-4"-[3-(3,5-dimethylphenyl)-3-hydroxypropyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#94)

17-Ethyl-1,14-dihydroxy-12-[2'-(4"-hydroxy-4"-[3-(3-fluorophenyl)-3 -hydroxypropyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2, 3,10,16-tetraone; (#95)

17-Ethyl-1,14-dihydroxy-12-[2'-(4"-hydroxy-4"-[3-(2benzo[b]thienyl)-3-hydroxypropyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#96)

17-Ethyl-1,14-dihydroxy-12-[2'-(4"-hydroxy-4"-[3-(2-naphthyl)-3 -hydroxypropyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#97)

17-Ethyl-1,14-dihydroxy-12-[2'-(4"-hydroxy-4"-[3-(3-methylphenyl)-3 -hydroxypropyl]-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#98)

or a pharmaceutically acceptable salt thereof.

* * * * *